US007939083B2

(12) United States Patent
Dey et al.

(10) Patent No.: US 7,939,083 B2
(45) Date of Patent: May 10, 2011

(54) SOLUBLE, STABILIZED, PROTEOLYTICALLY CLEAVED, TRIMERIC HIV-1 GP140 PROTEINS COMPRISING MODIFICATIONS IN THE N-TERMINUS OF THE GP41 ECTODOMAIN

(75) Inventors: Antu K. Dey, Auburndale, MA (US); John P. Moore, New York, NY (US); William C. Olson, Yorktown Heights, NY (US); Sai Prasad N. Iyer, East Elmhurst, NY (US); Yun (Kenneth) Kang, Livingston, NJ (US); Michael Franti, Cambridge, MA (US)

(73) Assignee: Progenics Pharmaceuticals Inc., Tarrytown, NY (US)

( * ) Notice: Subject to any disclaimer, the term of this patent is extended or adjusted under 35 U.S.C. 154(b) by 0 days.

(21) Appl. No.: 12/312,016

(22) PCT Filed: Oct. 17, 2007

(86) PCT No.: PCT/US2007/022227
§ 371 (c)(1),
(2), (4) Date: Oct. 7, 2009

(87) PCT Pub. No.: WO03/087757
PCT Pub. Date: Oct. 23, 2003

(65) Prior Publication Data
US 2010/0041875 A1    Feb. 18, 2010

Related U.S. Application Data

(60) Provisional application No. 60/854,034, filed on Oct. 23, 2006, provisional application No. 60/855,236, filed on Oct. 30, 2006.

(51) Int. Cl.
*A61K 39/21* (2006.01)
*A61K 39/12* (2006.01)
(52) U.S. Cl. ............ 424/208.1; 424/188.1; 424/199.1
(58) Field of Classification Search ............. None
See application file for complete search history.

(56) References Cited

U.S. PATENT DOCUMENTS

| | | | |
|---|---|---|---|
| 5,474,914 | A | 12/1995 | Spaete |
| 5,886,163 | A | 3/1999 | Hasel et al. |
| 5,935,579 | A | 8/1999 | Habeshaw et al. |
| 6,171,596 | B1 | 1/2001 | Warl et al. |
| 6,602,705 | B1 | 8/2003 | Barnett et al. |
| 6,710,173 | B1 | 3/2004 | Binley et al. |
| 6,911,205 | B2 | 6/2005 | Sodroski et al. |
| 7,022,324 | B2 | 4/2006 | Binley et al. |
| 7,105,655 | B2 | 9/2006 | Sodroski et al. |
| 7,479,553 | B2 | 1/2009 | Binley et al. |
| 2004/0191269 | A1 | 9/2004 | Lu et al. |
| 2004/0224308 | A1 | 11/2004 | Binley et al. |
| 2004/0259075 | A1 | 12/2004 | Dimitrov et al. |
| 2005/0089526 | A1 | 4/2005 | Moore et al. |
| 2006/0051373 | A1 | 3/2006 | Olson et al. |
| 2006/0094049 | A1 | 5/2006 | Binley et al. |

FOREIGN PATENT DOCUMENTS

| | | |
|---|---|---|
| WO | WO 01/00648 A1 | 1/2001 |
| WO | WO 03/022869 | 3/2003 |
| WO | WO 03/087757 | 10/2003 |
| WO | WO 2004/087201 A2 | 10/2004 |
| WO | WO 2006/002079 | 1/2006 |
| WO | WO 2006/002079 A2 | 1/2006 |

OTHER PUBLICATIONS

Gerhardt, M., et al., 2005, In-depth, longitudinal analysis of viral quasispecies from an individual triply infected with late-stage human immunodeficiency virus type 1, using a multiple PCR primer approach, J. Virol. 79(13):8249-8261.*
Charpentier, C., et al., 2006, Extensive recombination among human immunodeficiency virus type 1 quasispecies makes an important contribution to viral diversity in individual patients, J. Virol. 80(5):2472-2482.*
Holland, J. J., et al., 1992, RNA virus populations as quasispecies, Curr. Topics Microbiol. Immunol. 176:1-20.*
Beddows, S., et al., 2006, Construction and characterization of soluble, cleaved, and stabilized trimeric Env proteins based on HIV type 1 Env subtype A, AIDS Res. Human Retrovir. 22(6):569-79.*
Dowling, W. E., et al., 2002, Forty-one near full-length HIV-1 sequences from Kenya reveal an epidemic of subtype A and A-containing recombinants, AIDS 16:1809-1820.*
International Search Report issued by the International Searching Authority (ISA/US) on Sep. 15, 2008 in connection with International Application No. PCT/US2007/022227.
Written Opinion of the International Searching Authority issued by the International Searching Authority (ISA/US) on Sep. 15, 2008 in connection with International Application No. PCT/US2007/022227.
U.S. Appl. No. 09/340,992, filed Jun. 25, 1999, Binley et al.
U.S. Appl. No. 10/117,366, filed Apr. 5, 2002, Binley et al.
U.S. Appl. No. 60/141,168, filed Jun. 25, 1999, Binley et al.
U.S. Appl. No. 60/370,410, filed Apr. 5, 2002, Binley et al.
U.S. Appl. No. 60/317,775, filed Sep. 6, 2001, Moore et al.

(Continued)

*Primary Examiner* — Jeffrey S. Parkin
(74) *Attorney, Agent, or Firm* — John P. White; Cooper & Dunham LLP

(57) ABSTRACT

This invention provides a modified gp140 envelope polypeptide of an HIV-1 isolate comprising a gp120 polypeptide portion comprising consecutive amino acids and a gp41 ectodomain polypeptide portion comprising consecutive amino acids, said gp41 ectodomain polypeptide portion being modified to comprise isoleucine (I) at an amino acid position equivalent to amino acid position 535; glutamine (Q) at an amino acid position equivalent to amino acid position 543; serine (S) at an amino acid position equivalent to amino acid position 553; lysine (K) at an amino acid position equivalent to amino acid position 567; and arginine (R) at an amino acid position equivalent to amino acid position 588, the amino acid positions being numbered by reference to the HIV-1 isolate KNH1144. This invention also provides nucleic acids encoding such a polypeptide, vectors, host cells, trimeric complexes and compositions thereof. Also provided are antibodies generated against the modified polypeptides and trimeric complexes, and methods of using the modified polypeptides, compositions and trimeric complexes.

21 Claims, 29 Drawing Sheets

OTHER PUBLICATIONS

Figure 1:
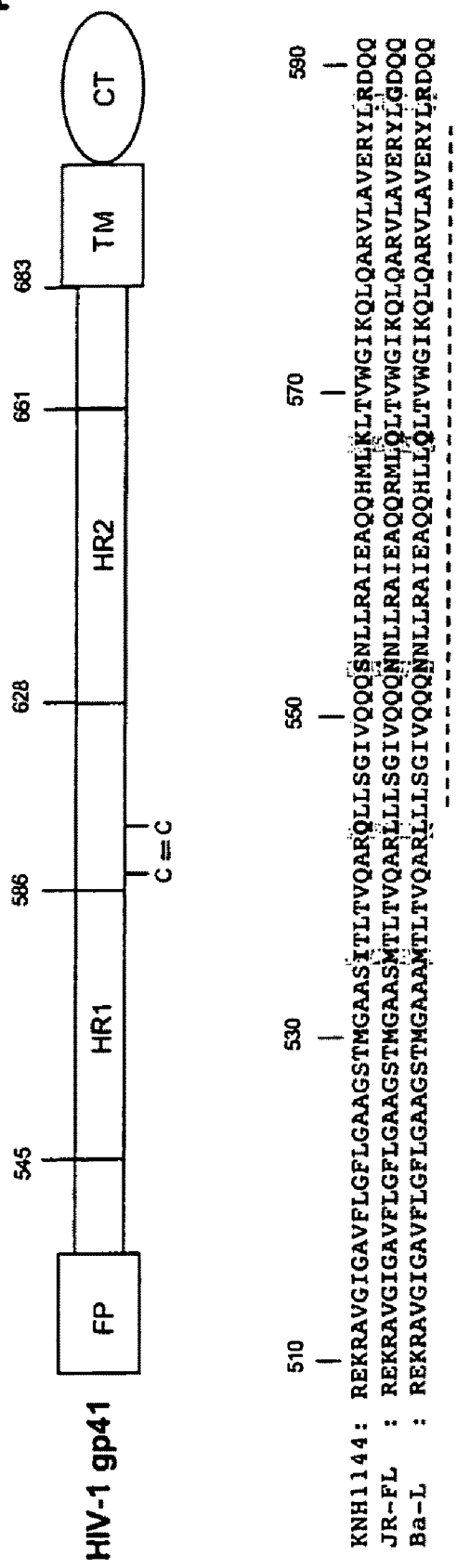

U.S. Appl. No. 60/370,264, filed Apr. 5, 2000, Moore et al.
U.S. Appl. No. 60/317,910, filed Sep. 6, 2001, Moore et al.
U.S. Appl. No. 60/317,909, filed Sep. 6, 2001, Binley et al.
U.S. Appl. No. 60/317,764, filed Sep. 6, 2001, Binley et al.
U.S. Appl. No. 60/580,229, filed Mar. 5, 2004, Schülke and Olson.
Atwell, et al. (1997) "Stable Heterodimers From Remodeling the Domain Interface of a Homodimer Using a Phage Display Library" J. Mol. Biol. 270:26-35.
Barouch, D.H. et al. (2002) "Eventual AIDS Vaccine Failure in the Rhesus Monkey by Viral Escape From Cytotoxic T Lymphocytes" Nature 415:335-339.
Barouch, D.H. et al. (2000) "DNA Vaccination for HIV-1 and SIV" Intervirol. 4:282-287.
Binley, J.M. et al. (2002) "Enhancing the Proteolytic Maturation of Human Immunodeficiency Virus Type 1 Envelope Glycoproteins." J. of Virology, 76 (6): 2606-2616.
Binley, J.M. et al. (2000) "A Recombinant Human Immunodeficiency Virus Type 1 Envelope Glycoprotein Complex Stabilized by an Intermolecular Disulfide Bond Between the gp120 and gp41 Subunits Is an Antigenic Mimic of the Trimeric Viron-Associated Structure" J. Virol. 627-643.
Burton, D.R. et al. (1994) "Efficient Neutralization of Primary Isolates of HIV-1 by a Recombinant Human Monoclonal Antibody" Science 266:1024-1027.
Burton, D.R. et al. (1998) Why Do We Not Have an HIV Vaccine and How Can We Make One? Nature Med. Vaccine Suppl. 4(5):495-498.
Cao, J. et al. (1993) "Effects of Amino Acid Changes in the Extracellular Domain of the Human Immunodeficiency Virus Type 1 Gp41 Envelope Glycoprotein" J. Virol. 67(5):2747-2755.
Cao, et al. (1997) "Replication and Neutralization of Human Immunodeficiency Virus Type 1 Lacking the V1 and V2 Variable Loops of the gp120 Envelope Glycoprotein" J. Virol. 71:9808-9812.
Chen, S. (1993) "Mutational Analysis of the Leucine Zipper-Like Motif of the Human Immunodeficiency Virus Type 1 Envelope Transmembrane Glycoprotein." J. of Virology 67 (6):3615-3619.
Creson, J. (1999) "The Mode and Duration of Anti-CD28 Costimulation Determine Resistance to Infection by Macrophage-Tropic Strains of Human Immunodeficiency Virus Type 1 In Vitro." J. of Virology 73(11):9337-9347.
Ditzel H J et al. (1997) "Mapping the Protein Surface of Human Immunodeficiency Virus Type 1 gp 120 Using Human Monoclonal Antibodies From Phage Display Libraries" J. of Molecular Biology, 267 (3):684-695.
Edinger, et al. (1999) "Functional Dissection of CCR5 Coreceptor Function Through the Use of CD4-Independent Simian Immunodeficiency Virus Strains" J. Virol. 73:4062-4073.
Farzan, M. et al. (1998) "Stabilization of Human Immunodeficiency Virus Type 1 Envelope Glycoprotein Trimers by Disulfide Bonds Introduced Into the gp 41 Glycoprotein Ectodomain" J. Virol. 72:7620-7625.
Fouts, et al. (1998) "Interactions of Polyclonal and Monoclonal Anti-Glycoprotein 120 Antibodies With Oligomeric Glycoprotein 120-Glycoprotein 41 Complexes of a Primary HIV Type 1 Isolate: Relationship to Neutralization" AIDS Res Human Retrovir. 14:591-597.
Fouts, et al. (1997) "Neutralization of the Human Immunodeficiency Virus Type 1 Primary Isolate JR-FL by Human Monoclonal Antibodies Correlates With Antibody Binding to the Oligomeric Form of the Envelope Glycoprotein Complex" J. Virol. 71:2779-2785.
Gallaher, et al. (1995) "A General Model for the Surface Glycoproteins of HIV and Other Retroviruses" AIDS Res. Human Retrovir. 11:191-202.
Haynes, B.F. (1996) "Update on the Issues of HIV Vaccine Development" Ann. Med. 28:39-41.
Haynes, B.F. (1996) "HIV Vaccines: Where Are We and We Are We Going?" Lancet 348:933-937.
Helseth, E. et al. (1991) "Human Immunodeficiency Virus Type 1 gp120 Envelope Glycoprotein Regions Important for Association With the gp41 Transmembrane Glycoprotein" J. Virol. 65(4):2119-2123.
Ishikawa et al. (1998) "Rapid Formation of the Immune Complexes on Solid Phase in the Immune Complex Transfer Enzyme Immunoassays for HIV-1 P24 Antigen and Antibody IiFfs to HIV-1" J. of Virol. 12:227-237.
Johnston, M.I. et al. (2001) "Progress in HIV Vaccine Develoment" Curr. Op. Pharmacol. 1(5):504-510.
Josephson, et al. (1999) "High-Efficiency Intracellurlar Magnetic Labeling With Novel Superpapamagnetic-Tat Peptide Conjugates" *Bioconjugate Chemistry*, vol. 10 pp. 186-191.
Joy, A.K. et al. (1999) Can HIV Infection Be Prevented With a Vaccine? Drugs R&D 6:431-440.
Labranche, C. et al. (1994) "ERRATUM Biological, Molecular, and Structural Analysis of a Cytopathic Variant From a Molecularly Cloned Simian Immunodeficiency Virus" J. Virol. 68:7665-7667.
Labranche, C. et al. (1994) "Biological, Molecular, and Structural Analysis of a Cytopathic Variant From a Molecularly Cloned Simian Immunodeficiency Virus" J. Virol. 68:5509-5522.
Letvin, N. L. (1998) "Progress in the Development of an HIV-1 Vaccine" Science 280:1875-1880.
Maerz, A.L. eta l. (2001) "Functional Analysis of the Disulfide-Bonded Loop/Chain Reversal Region of Human Immunodeficiency Virus Type 1 gp41 Reveals a Critical Role in gp120-gp41 Association" J. Virol. 75(14):6635-6644.
McInerney, T. et al. (1998) "Mutation-Directed Chemical Cross-Linking of Human Immunodeficiency Virus Type 1 gp41 Oligomers" J. Virol. 72:1523-1533.
Mitchell, et al. (1998) "Inactivation of a Common Epitope Responsible for the Induction of Antibody-Dependent Enhancement of HIV" AIDS 12:147-156.
Moore, et al. (1994) "Probing the Structure of the Human Immunodeficiency Virus Surface Glycoprotein Gp120 With a Panel of Monoclonal Antibodies" J. Virol. 68:469-484.
Moore, et al. (1994b) "Immunological Evidence for Interactions Between the First, Second, and Fifth Conserved Domains to the Gp120 Surface Glycoprotein of Human Immunodeficiency Virus Type 1" J. Virol. 68(11):6836-6847.
Murphy, F.A. (1996) in Fields Virology, 3rd Edition, Fileds, B.N. et al. eds., Lippincott-Raven Publishers, Philadelphia, 40-41.
Nakashe, J. et al., (2001) "Rectal Immunization With Antigen-Containing Microspheres Induces Stronger Th2 Responses Than Oral Immunization: A New Method for Vaccination" Vaccine, Butterworth Scientific Guildford, GB, 20 (3-4):377-384.
Parker, Carole, et al. (2001) "Fine Definition of the Epitope on the Gp41 Glycoprotein of Human Immunodeficiency Virus Type 1 for the Neutralizing Monoclonal Antibody 2F5" J. of Virol. 75 (22):10906-10911.
Parren, et al. (1997) "HIV-1 Antibody—Debris or Virion?" Nat. Med. 3:366-367.
Parren, et al. (1998) "Neutralization of Human Immunodeficiency Virus Type 1 by Antibody to gp120 Is Determined Primarily by Occupancy of Sites on the Virion Irrespective of Epitope Specificity" J. Virol. 72:3512-3519.
Reitter, et al. (1998) "A Role for Carbohydrates in Immune Evasion in AIDS" Nat. Med. 4:679-684.
Rickman et al. (1991) "Use of Adjuvant Containing Mycobacterial Cell Wall Skeleton, Monophosphoryl Lipid A, and Aqualene in Malaria Circumporozoite Proein Vaccine" *The Lancet*, vol. 337, pp. 998-1001.
Sanders R. et al., (2002) "Stabilization of the Soluble, Cleaved, Trimeric Form of the Envelope Glycoprotein Complex of Human Immunodeficiency Virus Type 1" Journal of Virology, 76 (17):8875-8889.
Sanders, R. (2000) "Variable-Loop-Deleted Variants of the Human Immunodeficiency Virus Type 1 Envelope Glycoprotein Can Be Stabilized by an Intermolecular Disulfide Bond Between the Gp120 and Gp41 Subunits." J. of Virol. 74(11):5091-5100.
Schulke et al. (2002) "Oligomeric and Conformational Properties of a Proteolytically Mature, Disulfide-Stabilized Human Immunodeficiency Virus Type 1 gp140 Envelope Glycoprotein" J. of Virology, 76 (15):7760-7776.
Schulz, et al. (1992) "Conserved Structural Features in the Interaction Between Retroviral Surface and Transmembrane Glycoproteins?" AIDS Res. Hum. Retrovirus 8(9):1571-1580.

Stamatatos, L. et al. (1994) "Differential Regulation of Cellular Tropism and Sensitivity to Soluble CD4 Neutralization by the Envelope gp120 of Human Immunodeficiency Virus Type 1" J. Virol. 68:4973-4979.

Trkola A. et al. (1996) "Human Monoclonal Antibody 2g12 Defines a Distinctive Neutralization Epitope on the gp120 Glycoprotein of Human Immunodeficiency Virus Type 1" J. Virol.70:1100-1108.

Sep. 7, 2000 International Search Report for Application No. PCT/US00/17267, filed Jun. 23, 2000.

Jan. 23, 2002 International Preliminary Examination Report for Application No. PCT/US00/17267, filed Jun. 23, 2000.

Mar. 5, 2003 Supplementary European Search Report for Application No. EP 00 94 4801.

Jun. 11, 2003 Supplementary European Search Report for App. No. EP00944801.

Apr. 15, 2004 International Search Report for International PCT Application No. PCT/US02/28331, filed Sep. 6, 2002.

May 12, 2004 International Search Report for International PCT Application No. PCT/US02/28332, filed Sep. 6, 2002.

Aug. 22, 2006 Supplementary European Search Report for Application No. EP/02770472.

Aug. 31, 2006 Supplementary European Search Report for Application No. EP/02770473.

Dec. 27, 2006 International Search Report for App. No. PCT/US05/21091, filed Jun. 15, 2005.

Feb. 1, 2007 International Preliminary Report for PCT/US2005/021091, filed Jun. 15, 2005.

PCT International Preliminary Examination Report issued Mar. 20, 2003 for International Application Publication No. WO 03/022869 A2.

PCT International Preliminary Examination Report issued Oct. 23, 2003 for International Application Publication No. WO 03/087757 A2.

PCT International Preliminary Examination Report issued Jun. 17, 2004 for International Application Publication No. WO 2004/050856.

Barnett, S.W. et al., (2001). "The Ability of an Oligomeric Human Immunodeficiency Virus Type 1 (HIV-1) Envelope Antigen to Elicit Neutralizing Antibodies against Primary HIV-1 Isolates Is Improved following Partial Deletion of the Second Hypervariable Region," J. of Virology, 75(12):5526-5540.

Binley, J.M. et al., (2003). "Redox-Triggered Infection by Disfulfide-Shackled Human Immunodeficiency Virus Type 1 Pseudovirions," J. of Virology, 77(10):5678-5684.

Binley, J.M. et al. (2004). "Comprehensive Cross-Clade Neutralization Analysis of a Panel of Anti-Human Immunodeficiency Virus Type 1 Monoclonal Antibodies," J. of Virology, 78(23):13232-13252.

Buckner, C. et al., (2003). "Priming B cell-mediated anti-HIV envelope responses by vaccination allows for the long-term control of infection in macaques exposed to a R5-tropic SHIV," Virology, 320:167-180.

Letvin, N. et al., (1997). "Potent, protective anti-HIV immune generated by bimodal HIV envelope DNA plus protein vaccination," PNAS, 94:9378-9383.

Leung, L. et al., (2003). "Immunogenicity of HIV-1 and Gag in baboons using a DNA prime/protein boost regimen," AIDS, 18:991-1001.

Sanders, R.W. et al., (2004). "Evolution of the HIV-1 envelope glycoproteins with a disulfide bond between gp120 and gp41," Retrovirology, 1:3.

Schuelke N. et al., (2004). "Immunogenicity of Disulfide-stabilized HIV-1 envelope trimers," Int. Conf. AIDS, abstract No. ThPpA2084.

Sep. 7, 2005 Non-Final Office Action issued in connection with U.S. Appl. No. 10/489,040.

Apr. 24, 2006 Non-Final Office Action issued in connection with U.S. Appl. No. 10/510,268.

May 19, 2006 Non-Final Office Action issued in connection with U.S. Appl. No. 10/489,040.

Oct. 5, 2006 Non-Final Office Action issued in connection with U.S. Appl. No. 10/510,268.

Oct. 5, 2006 Non-Final Office Action issued in connection with U.S. Appl. No. 10/780,993.

Mar. 9, 2007 Non-Final Office Action issued in connection with U.S. Appl. No. 10/780,993.

Mar. 23, 2007 Non-Final Office Action issued in connection with U.S. Appl. No. 10/489,040.

Jul. 7, 2008 Final Office Action issued in connection with U.S. Appl. No. 10/489,040.

Sanders et al. (2002) "The Mannose-Dependent Epitope for Neutralizing Antibody 2G12 on Human Immunodeficiency Virus Type 1 Glycoprotein gp120," Journal of Virology, pp. 7293-7305.

Notification of Transmittal of the International Search Report and the Written Opinion of the International Searching Authority, or the Declaration issued Sep. 12, 2008 in connection with PCT International Application No. PCT/US07/14389.

Iyer et al. "Purified, Proteolytically Mature HIV Type 1 SOSIP gp140 Envelope Trimers," AIDS Research and Human Retroviruses (2007) 23(6):817-828.

Notification of Transmittal of the International Search Report and the Written Opinion of the International Searching Authority, or the Declaration issued Sep. 12, 2008 in connection with PCT International Application No. PCT/US08/02325.

Notification of Transmittal of the International Search Report and the Written Opinion of the International Searching Authority, or the Declaration, including the International Search Report and the Written Opinion, issued Sep. 15, 2008 in connection with PCT International Application No. PCT/US07/22227.

Official Action issued Oct. 14, 2008 in connection with Japanese Application No. 2003-5269342 (English translation).

Cameron et al. (2000) "Polyarginines Are Potent Furin Inhibitors" 275:47, pp. 36741-36749.

Dec. 1, 2008 Final Office Action issued in connection with U.S. Appl. No. 11/261,390.

Nov. 17, 2008 Office Action issued in connection with U.S. Appl. No. 10/489,040.

Notification Concerning Transmittal of International Preliminary Report on Patentability issued Jan. 8, 2009 including an International Preliminary Report on Patentability dated Dec. 22, 2008 in connection with International Publication No. PCT/US2007/014388.

Notification Concerning Transmittal of International Preliminary Report on Patentability issued Jan. 8, 2009 including an International Preliminary Report on Patentability dated Dec. 22, 2008 in connection with PCT International Publication No. PCT/US2007/014389.

Notification Concerning Transmittal of International Preliminary Report on Patentability issued May 7, 2009 including an International Preliminary Report on Patentability dated Apr. 28, 2009 in connection with PCT International Publication No. PCT/US2007/022227.

Jun. 15, 2009 Office Action issued in connection with U.S. Appl. No. 10/489,040.

May 13, 2009 Notice of Allowance and Fees Due, including a Notice of Allowability, issued in connection with U.S. Appl. No. 11/261,390.

Final Office Action issued Mar. 4, 2010 in connection with U.S. Appl. No. 10/489,040.

European Search Report and European Search Opinion issued Sep. 28, 2010 in connection with related European Patent Application No. 07870794.0.

Dowling et al., "Forty-One Near Full-Length HIV-1 Sequences from Kenya Reveal an Epidemic of Subtype A and A-Containing Recombinants," vol. 16, No. 13, Sep. 6, 2002, pp. 1809-1820.

Brown et al., "Biological and Genetic Characterization of a Panel of Sixty Human Immunodeficiency Virus Type 1 (Hiv-1) Isolates, Representing Clades A, B, C, D, CRF01_AE and CRF02_AG, for the Development and Assessment of Candidate Vaccines," Sep. 27, 2005 (Abstract Only).

Sanders et al., "Stabilization of the Soluble, Cleaved, Trimeric Form of the Envelope Glycoprotein Complex of Human Immunodeficiency Virus Type 1," Journal of Virology, vol. 76, No. 17, Sep. 1, 2002, pp. 8875-8889.

Currier et al., "CTL Epitope Distribution Patterns in the Gag and Nef Proteins of HIV-1 from Subtype A Infected Subjects in Kenya: Use of Multiple Peptide Sets Increases the Detectable Breadth of the CTL Response," BMC Immunology, vol. 7, No. 1, Apr. 18, 2006, p. 8.

Yang et al., "Characterization of Stable, Soluble Trimers Containing Complete Ectodomains of Human Immunodeficiency Virus Type 1 Envelope Glycoproteins," Journal of Virology, vol. 74, No. 12, Jun. 1, 2009, pp. 5716-5725.

Dong et al., "N- and C-Domains of HIV-1 GP41: Mutation, Structure and Functions," Immunology Letters, vol. 75, Feb. 1, 2001, pp. 215-220.

Beddows et al., "Construction and Characterization of Soluble, Cleaved and Stabilized Trimeric Env Proteins Based on HIV Type 1 Env Subtype A," Aids Research and Human Retroviruses, vol. 22, No. 6, Jun. 1, 2006, pp. 575-577.

Dey et al., "N-Terminal Substitutions in HIV-1 GP41 Reduce the Expression of Non-Trimeric Envelope Glycoproteins on the Virus," Virology, vol. 371, Nov. 26, 2007, pp. 187-200.

European Search Report and European Search Opinion issued Jul. 23, 2010 in connection with related European Patent Application No. 07809721.9.

Dey et al., "Specific Amino Acids in the N-Terminus of the GP41 Ectodomain Contribute to the Stabilization of a Soluble, Cleaved GP140 Envelope Glycoprotein from Human Immunodeficiency Virus Type 1," Virology, Academic Press, vol. 360, No. 1, Feb. 28, 2007, pp. 199-208.

Beddows et al., "Evaluating the Immunogenicity of a Disulfide-Stabilized, Cleaved, Trimeric Form of the Envelope Glycoprotein Complex of Human Immunodeficiency Virus Type 1," Journal of Virology, vol. 79, No. 14, Jul. 2005, pp. 8812-8827.

Sanders et al., "Evolution of the HIV-1 Envelope Glycoproteins with a Disulfide Bond Between GP120 and GP41," Retrovirology, vol. 1, No. 1, Mar. 9, 2004, p. 3.

Schülke et al., "Oligomeric and Conformational Properties of a Proteolytically Mature, Disulfide-Stabilized Human Immunodeficiency virus Type 1 GP140 Envelope Glycoprotein," Journal of Virology, vol. 76, No. 15, Aug. 1, 2002, pp. 7760-7776.

Sanders et al., "Variable-Loop-Deleted Variants of the Human Immunodeficiency Virus Type 1 Envelope Glycoprotein Can Be Stabilized by an Intermolecular Disulfide Bond Between the GP120 and GP41 Subunits," Journal of Virology, vol. 74, No. 11, Jun. 1, 2000, pp. 5091-5100.

Binley et al, "A Recombinant Human Immunodeficiency Virus Type 1 Envelope Glycoprotein Complex Stabilized by an Intermolecular Disulfide Bond Between the GP120 and GP41 Subunits is an Antigenic Mimic of the Trimeric Virion-Associated Structure," Journal of Virology, vol. 74, No. 2, Jan. 1, 2000, pp. 627-643.

* cited by examiner (A)

(B)

Figure 8A
Figure 8B
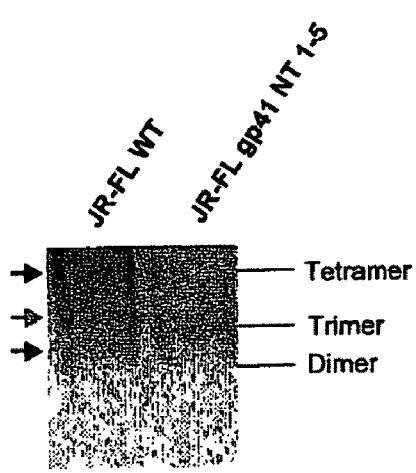
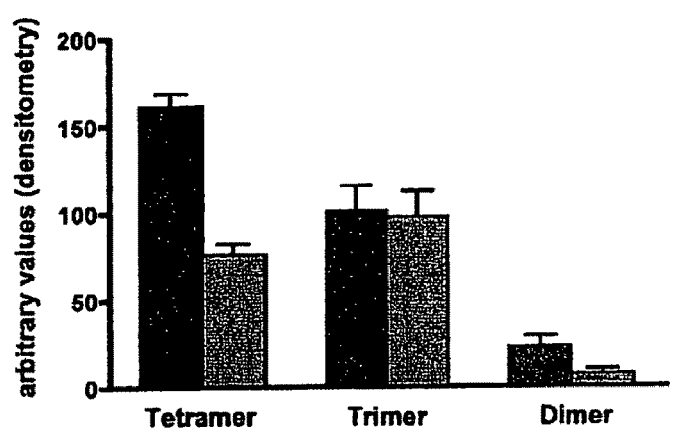

■ JR-FL WT    △ JR-FL gp41 NT 1-5

Figure 13A
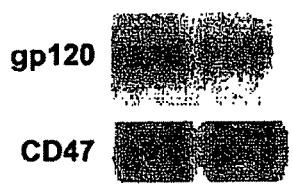
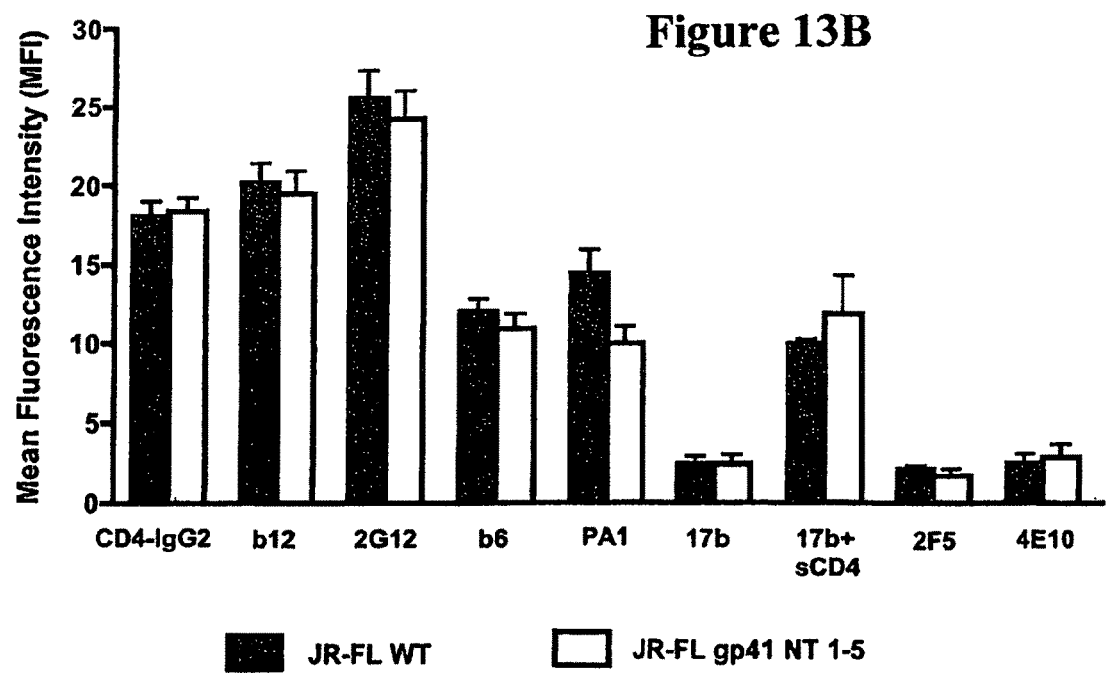
Figure 13B

A.

B.

SEQUENCE LISTING

<160> NUMBER OF SEQ ID NOS: 39

<210> SEQ ID NO 1
<211> LENGTH: 84
<212> TYPE: PRT
<213> ORGANISM: Artificial Sequence
<220> FEATURE:
<223> OTHER INFORMATION: KNH1144 gp41

<400> SEQUENCE: 1

Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Ile Thr Leu Thr Val
                20                  25                  30

Gln Ala Arg Gln Leu Leu Ser Gly Ile Val Gln Gln Gln Ser Asn Leu
            35                  40                  45

Leu Arg Ala Ile Glu Ala Gln Gln His Met Leu Lys Leu Thr Val Trp
        50                  55                  60

Gly Ile Lys Gln Leu Gln Ala Arg Val Leu Ala Val Glu Arg Tyr Leu
65                  70                  75                  80

Arg Asp Gln Gln

<210> SEQ ID NO 2
<211> LENGTH: 84
<212> TYPE: PRT
<213> ORGANISM: Artificial Sequence
<220> FEATURE:
<223> OTHER INFORMATION: JRFL gp41

<400> SEQUENCE: 2

Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Met Thr Leu Thr Val
                20                  25                  30

Gln Ala Arg Leu Leu Leu Ser Gly Ile Val Gln Gln Gln Asn Asn Leu
            35                  40                  45

Leu Arg Ala Ile Glu Ala Gln Gln Arg Met Leu Gln Leu Thr Val Trp
        50                  55                  60

Gly Ile Lys Gln Leu Gln Ala Arg Val Leu Ala Val Glu Arg Tyr Leu
65                  70                  75                  80

Gly Asp Gln Gln

<210> SEQ ID NO 3
<211> LENGTH: 84
<212> TYPE: PRT
<213> ORGANISM: Artificial Sequence
<220> FEATURE:
<223> OTHER INFORMATION: Ba-L gp41

<400> SEQUENCE: 3

Arg Glu Lys Arg Ala Val Gly Ile Gly Ala Val Phe Leu Gly Phe Leu
1               5                   10                  15

Gly Ala Ala Gly Ser Thr Met Gly Ala Ala Met Thr Leu Thr Val
                20                  25                  30

Gln Ala Arg Leu Leu Leu Ser Gly Ile Val Gln Gln Gln Asn Asn Leu
            35                  40                  45

Leu Arg Ala Ile Glu Ala Gln Gln His Leu Leu Gln Leu Thr Val Trp
        50                  55                  60

-continued

Gly Ile Lys Gln Leu Gln Ala Arg Val Leu Ala Val Glu Arg Tyr Leu
65                  70                  75                  80

Arg Asp Gln Gln

<210> SEQ ID NO 4
<211> LENGTH: 39
<212> TYPE: DNA
<213> ORGANISM: Artificial Sequence
<220> FEATURE:
<223> OTHER INFORMATION: T7 Translation Initiation Sequence

<400> SEQUENCE: 4
tctagaaata attttgttta actttaagaa ggagatata                          39

<210> SEQ ID NO 5
<211> LENGTH: 863
<212> TYPE: PRT
<213> ORGANISM: Artificial Sequence
<220> FEATURE:
<223> OTHER INFORMATION: KNH1144 with 5 trimer stability enhancing amino
      acids

<400> SEQUENCE: 5

Met Ile Val Met Gly Thr Gln Arg Asn Tyr Gln His Leu Leu Arg Trp
1               5                   10                  15

Gly Thr Met Ile Leu Gly Leu Ile Ile Cys Ser Ala Ala Asp Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile Pro Leu Glu Asn Val Thr Glu Glu Phe Asn Met Trp Lys
                85                  90                  95

Asn Lys Met Val Glu Gln Met His Thr Asp Ile Ile Ser Leu Trp Asp
            100                 105                 110

Gln Ser Leu Gln Pro Cys Val Lys Leu Thr Pro Leu Cys Val Thr Leu
        115                 120                 125

Asn Cys Thr Asp Ala Thr Asn Gly Thr Ile Gly Asn Ile Thr Asp Glu
    130                 135                 140

Met Lys Gly Glu Ile Lys Asn Cys Ser Phe Asn Ile Thr Thr Glu Ile
145                 150                 155                 160

Arg Asp Lys Lys Gln Lys Val Tyr Ser Leu Phe Tyr Arg Leu Asp Val
                165                 170                 175

Val Pro Ile Glu Pro Asp Ser Ser Asn Ser Ser Arg Asn Ser Ser Glu
            180                 185                 190

Tyr Arg Leu Ile Asn Cys Asn Thr Ser Ala Ile Thr Gln Ala Cys Pro
        195                 200                 205

Lys Val Ser Phe Glu Pro Ile Pro Ile His Tyr Cys Ala Pro Ala Gly
    210                 215                 220

Phe Ala Ile Leu Lys Cys Arg Asp Lys Glu Phe Asn Gly Thr Gly Lys
225                 230                 235                 240

Cys Lys Asn Val Ser Thr Val Gln Cys Thr His Gly Ile Lys Pro Val
                245                 250                 255

Val Ser Thr Gln Leu Leu Leu Asn Gly Ser Leu Ala Glu Gly Glu Val
            260                 265                 270

Arg Ile Arg Ser Glu Asn Ile Thr Asn Asn Ala Lys Thr Ile Ile Val

```
                275                 280                 285
Gln Leu Val Glu Pro Val Arg Ile Asn Cys Thr Arg Pro Asn Asn Asn
    290                 295                 300

Thr Arg Glu Ser Val Arg Ile Gly Pro Gly Gln Ala Phe Phe Ala Thr
305                 310                 315                 320

Gly Asp Ile Ile Gly Asp Ile Arg Gln Ala His Cys Asn Val Ser Arg
                325                 330                 335

Ser Gln Trp Asn Lys Thr Leu Gln Gln Val Ala Ala Gln Leu Gly Glu
                340                 345                 350

His Phe Lys Asn Lys Ala Ile Thr Phe Asn Ser Ser Ser Gly Gly Asp
        355                 360                 365

Leu Glu Ile Thr Thr His Ser Phe Asn Cys Gly Gly Glu Phe Phe Tyr
    370                 375                 380

Cys Asn Thr Ser Gly Leu Phe Asn Ser Thr Trp Lys Ala Asn Asn Gly
385                 390                 395                 400

Thr Trp Lys Ala Asn Ile Ser Glu Ser Asn Asn Thr Glu Ile Thr Leu
                405                 410                 415

Gln Cys Arg Ile Lys Gln Ile Ile Asn Met Trp Gln Arg Thr Gly Gln
                420                 425                 430

Ala Ile Tyr Ala Pro Pro Ile Gln Gly Val Ile Arg Cys Glu Ser Asn
        435                 440                 445

Ile Thr Gly Leu Leu Leu Thr Arg Asp Gly Gly Glu Gly Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Arg Ala Arg Arg Val Val Gly Arg Glu Lys Arg Ala
                500                 505                 510

Val Gly Ile Gly Ala Val Phe Leu Gly Phe Leu Gly Ala Ala Gly Ser
        515                 520                 525

Thr Met Gly Ala Ala Ser Ile Thr Leu Thr Val Gln Ala Arg Gln Leu
    530                 535                 540

Leu Ser Gly Ile Val Gln Gln Ser Asn Leu Leu Arg Ala Ile Glu
545                 550                 555                 560

Ala Gln Gln His Met Leu Lys Leu Thr Val Trp Gly Ile Lys Gln Leu
                565                 570                 575

Gln Ala Arg Val Leu Ala Val Glu Arg Tyr Leu Arg Asp Gln Gln Leu
        580                 585                 590

Leu Gly Ile Trp Gly Cys Ser Gly Lys Leu Ile Cys Thr Thr Asn Val
    595                 600                 605

Pro Trp Asn Ser Ser Trp Ser Asn Lys Ser His Asp Glu Ile Trp Asn
    610                 615                 620

Asn Met Thr Trp Leu Gln Trp Asp Lys Glu Ile Ser Asn Tyr Thr Asn
625                 630                 635                 640

Leu Ile Tyr Ser Leu Ile Glu Glu Ser Gln Asn Gln Gln Glu Lys Asn
                645                 650                 655

Glu Gln Asp Leu Leu Ala Leu Asp Lys Trp Ala Ser Leu Trp Asn Trp
        660                 665                 670

Phe Asp Ile Ser Lys Trp Leu Trp Tyr Ile Lys Ile Phe Ile Met Ile
    675                 680                 685

Val Gly Gly Leu Ile Gly Leu Arg Ile Val Phe Ala Val Leu Ala Val
    690                 695                 700
```

Ile Lys Arg Val Arg Gln Gly Tyr Ser Pro Val Ser Phe Gln Ile His
705                 710                 715                 720

Asn Pro Asn Pro Gly Leu Asp Arg Pro Gly Arg Ile Glu Glu Glu
            725                 730                 735

Gly Gly Glu Pro Gly Arg Gly Arg Ser Ile Arg Leu Val Ser Gly Phe
            740                 745                 750

Leu Ala Leu Ala Trp Asp Asp Leu Arg Asn Leu Cys Leu Phe Ser Tyr
        755                 760                 765

His Arg Leu Arg Asp Phe Ala Leu Ile Val Ala Arg Thr Val Glu Leu
    770                 775                 780

Leu Gly His Ser Ser Leu Lys Gly Leu Arg Leu Gly Trp Glu Gly Leu
785                 790                 795                 800

Lys Tyr Leu Trp Asn Leu Leu Val Tyr Trp Ser Gln Glu Leu Lys Thr
            805                 810                 815

Ser Ala Ile Asn Leu Val Asp Thr Ile Ala Ile Ala Val Ala Gly Trp
        820                 825                 830

Thr Asp Arg Val Ile Glu Ile Gly Gln Gly Ile Gly Arg Ala Phe Leu
    835                 840                 845

His Ile Pro Arg Arg Ile Arg Gln Gly Leu Glu Arg Ala Leu Leu
850                 855                 860

<210> SEQ ID NO 6
<211> LENGTH: 863
<212> TYPE: PRT
<213> ORGANISM: Artificial Sequence
<220> FEATURE:
<223> OTHER INFORMATION: KNH1144 gp160 with I559P mutation

<400> SEQUENCE: 6

Met Ile Val Met Gly Thr Gln Arg Asn Tyr Gln His Leu Leu Arg Trp
1               5                   10                  15

Gly Thr Met Ile Leu Gly Leu Ile Ile Ile Cys Ser Ala Ala Asp Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile Pro Leu Glu Asn Val Thr Glu Glu Phe Asn Met Trp Lys
            85                  90                  95

Asn Lys Met Val Glu Gln Met His Thr Asp Ile Ile Ser Leu Trp Asp
            100                 105                 110

Gln Ser Leu Gln Pro Cys Val Lys Leu Thr Pro Leu Cys Val Thr Leu
        115                 120                 125

Asn Cys Thr Asp Ala Thr Asn Gly Thr Ile Gly Asn Ile Thr Asp Glu
130                 135                 140

Met Lys Gly Glu Ile Lys Asn Cys Ser Phe Asn Ile Thr Thr Glu Ile
145                 150                 155                 160

Arg Asp Lys Lys Gln Lys Val Tyr Ser Leu Phe Tyr Arg Leu Asp Val
            165                 170                 175

Val Pro Ile Glu Pro Asp Ser Ser Asn Ser Ser Arg Asn Ser Ser Glu
        180                 185                 190

Tyr Arg Leu Ile Asn Cys Asn Thr Ser Ala Ile Thr Gln Ala Cys Pro
    195                 200                 205

Lys Val Ser Phe Glu Pro Ile Pro Ile His Tyr Cys Ala Pro Ala Gly

```
              210                 215                 220
Phe Ala Ile Leu Lys Cys Arg Asp Lys Glu Phe Asn Gly Thr Gly Lys
225                 230                 235                 240

Cys Lys Asn Val Ser Thr Val Gln Cys Thr His Gly Ile Lys Pro Val
            245                 250                 255

Val Ser Thr Gln Leu Leu Leu Asn Gly Ser Leu Ala Glu Gly Glu Val
            260                 265                 270

Arg Ile Arg Ser Glu Asn Ile Thr Asn Asn Ala Lys Thr Ile Ile Val
        275                 280                 285

Gln Leu Val Glu Pro Val Arg Ile Asn Cys Thr Arg Pro Asn Asn Asn
    290                 295                 300

Thr Arg Glu Ser Val Arg Ile Gly Pro Gly Gln Ala Phe Phe Ala Thr
305                 310                 315                 320

Gly Asp Ile Ile Gly Asp Ile Arg Gln Ala His Cys Asn Val Ser Arg
            325                 330                 335

Ser Gln Trp Asn Lys Thr Leu Gln Gln Val Ala Ala Gln Leu Gly Glu
            340                 345                 350

His Phe Lys Asn Lys Ala Ile Thr Phe Asn Ser Ser Gly Gly Asp
        355                 360                 365

Leu Glu Ile Thr Thr His Ser Phe Asn Cys Gly Gly Glu Phe Phe Tyr
    370                 375                 380

Cys Asn Thr Ser Gly Leu Phe Asn Ser Thr Trp Lys Ala Asn Asn Gly
385                 390                 395                 400

Thr Trp Lys Ala Asn Ile Ser Glu Ser Asn Asn Thr Glu Ile Thr Leu
            405                 410                 415

Gln Cys Arg Ile Lys Gln Ile Ile Asn Met Trp Gln Arg Thr Gly Gln
        420                 425                 430

Ala Ile Tyr Ala Pro Pro Ile Gln Gly Val Ile Arg Cys Glu Ser Asn
    435                 440                 445

Ile Thr Gly Leu Leu Leu Thr Arg Asp Gly Gly Glu Gly Asn Asn Glu
        450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
            485                 490                 495

Ala Pro Thr Arg Ala Arg Arg Val Val Gly Arg Glu Lys Arg Ala
            500                 505                 510

Val Gly Ile Gly Ala Val Phe Leu Gly Phe Leu Gly Ala Ala Gly Ser
        515                 520                 525

Thr Met Gly Ala Ala Ser Ile Thr Leu Thr Val Gln Ala Arg Gln Leu
    530                 535                 540

Leu Ser Gly Ile Val Gln Gln Gln Ser Asn Leu Leu Arg Ala Pro Glu
545                 550                 555                 560

Ala Gln Gln His Met Leu Lys Leu Thr Val Trp Gly Ile Lys Gln Leu
            565                 570                 575

Gln Ala Arg Val Leu Ala Val Glu Arg Tyr Leu Arg Asp Gln Gln Leu
            580                 585                 590

Leu Gly Ile Trp Gly Cys Ser Gly Lys Leu Ile Cys Thr Thr Asn Val
        595                 600                 605

Pro Trp Asn Ser Ser Trp Ser Asn Lys Ser His Asp Glu Ile Trp Asn
    610                 615                 620

Asn Met Thr Trp Leu Gln Trp Asp Lys Glu Ile Ser Asn Tyr Thr Asn
625                 630                 635                 640
```

-continued

```
Leu Ile Tyr Ser Leu Ile Glu Glu Ser Gln Asn Gln Gln Glu Lys Asn
            645                 650                 655
Glu Gln Asp Leu Leu Ala Leu Asp Lys Trp Ala Ser Leu Trp Asn Trp
        660                 665                 670
Phe Asp Ile Ser Lys Trp Leu Trp Tyr Ile Lys Ile Phe Ile Met Ile
    675                 680                 685
Val Gly Gly Leu Ile Gly Leu Arg Ile Val Phe Ala Val Leu Ala Val
690                 695                 700
Ile Lys Arg Val Arg Gln Gly Tyr Ser Pro Val Ser Phe Gln Ile His
705                 710                 715                 720
Asn Pro Asn Pro Gly Gly Leu Asp Arg Pro Gly Arg Ile Glu Glu Glu
                725                 730                 735
Gly Gly Glu Pro Gly Arg Gly Arg Ser Ile Arg Leu Val Ser Gly Phe
            740                 745                 750
Leu Ala Leu Ala Trp Asp Asp Leu Arg Asn Leu Cys Leu Phe Ser Tyr
        755                 760                 765
His Arg Leu Arg Asp Phe Ala Leu Ile Val Ala Arg Thr Val Glu Leu
    770                 775                 780
Leu Gly His Ser Ser Leu Lys Gly Leu Arg Leu Gly Trp Glu Gly Leu
785                 790                 795                 800
Lys Tyr Leu Trp Asn Leu Leu Val Tyr Trp Ser Gln Glu Leu Lys Thr
                805                 810                 815
Ser Ala Ile Asn Leu Val Asp Thr Ile Ala Ile Ala Val Ala Gly Trp
            820                 825                 830
Thr Asp Arg Val Ile Glu Ile Gly Gln Gly Ile Gly Arg Ala Phe Leu
        835                 840                 845
His Ile Pro Arg Arg Ile Arg Gln Gly Leu Glu Arg Ala Leu Leu
    850                 855                 860

<210> SEQ ID NO 7
<211> LENGTH: 863
<212> TYPE: PRT
<213> ORGANISM: Artificial Sequence
<220> FEATURE:
<223> OTHER INFORMATION: KNH1144 gp160 with I535M mutation

<400> SEQUENCE: 7

Met Ile Val Met Gly Thr Gln Arg Asn Tyr Gln His Leu Leu Arg Trp
1               5                   10                  15
Gly Thr Met Ile Leu Gly Leu Ile Ile Ile Cys Ser Ala Ala Asp Asn
            20                  25                  30
Leu Trp Val Thr Val Tyr Tyr Gly Val Pro Val Trp Lys Asp Ala Glu
        35                  40                  45
Thr Thr Leu Phe Cys Ala Ser Asp Ala Lys Ala Tyr Glu Thr Glu Lys
    50                  55                  60
His Asn Val Trp Ala Thr His Ala Cys Val Pro Thr Asp Pro Asn Pro
65                  70                  75                  80
Gln Glu Ile Pro Leu Glu Asn Val Thr Glu Glu Phe Asn Met Trp Lys
                85                  90                  95
Asn Lys Met Val Glu Gln Met His Thr Asp Ile Ile Ser Leu Trp Asp
            100                 105                 110
Gln Ser Leu Gln Pro Cys Val Lys Leu Thr Pro Leu Cys Val Thr Leu
        115                 120                 125
Asn Cys Thr Asp Ala Thr Asn Gly Thr Ile Gly Asn Ile Thr Asp Glu
    130                 135                 140
Met Lys Gly Glu Ile Lys Asn Cys Ser Phe Asn Ile Thr Thr Glu Ile
```

-continued

```
                145                 150                 155                 160
Arg Asp Lys Lys Gln Lys Val Tyr Ser Leu Phe Tyr Arg Leu Asp Val
                    165                 170                 175

Val Pro Ile Glu Pro Asp Ser Ser Asn Ser Arg Asn Ser Ser Glu
            180                 185                 190

Tyr Arg Leu Ile Asn Cys Asn Thr Ser Ala Ile Thr Gln Ala Cys Pro
                195                 200                 205

Lys Val Ser Phe Glu Pro Ile Pro Ile His Tyr Cys Ala Pro Ala Gly
            210                 215                 220

Phe Ala Ile Leu Lys Cys Arg Asp Lys Glu Phe Asn Gly Thr Gly Lys
225                 230                 235                 240

Cys Lys Asn Val Ser Thr Val Gln Cys Thr His Gly Ile Lys Pro Val
                    245                 250                 255

Val Ser Thr Gln Leu Leu Leu Asn Gly Ser Leu Ala Glu Gly Glu Val
                260                 265                 270

Arg Ile Arg Ser Glu Asn Ile Thr Asn Asn Ala Lys Thr Ile Ile Val
            275                 280                 285

Gln Leu Val Glu Pro Val Arg Ile Asn Cys Thr Arg Pro Asn Asn Asn
    290                 295                 300

Thr Arg Glu Ser Val Arg Ile Gly Pro Gly Gln Ala Phe Phe Ala Thr
305                 310                 315                 320

Gly Asp Ile Ile Gly Asp Ile Arg Gln Ala His Cys Asn Val Ser Arg
                    325                 330                 335

Ser Gln Trp Asn Lys Thr Leu Gln Gln Val Ala Ala Gln Leu Gly Glu
                340                 345                 350

His Phe Lys Asn Lys Ala Ile Thr Phe Asn Ser Ser Ser Gly Gly Asp
            355                 360                 365

Leu Glu Ile Thr Thr His Ser Phe Asn Cys Gly Gly Glu Phe Phe Tyr
    370                 375                 380

Cys Asn Thr Ser Gly Leu Phe Asn Ser Thr Trp Lys Ala Asn Asn Gly
385                 390                 395                 400

Thr Trp Lys Ala Asn Ile Ser Glu Ser Asn Asn Thr Glu Ile Thr Leu
                    405                 410                 415

Gln Cys Arg Ile Lys Gln Ile Ile Asn Met Trp Gln Arg Thr Gly Gln
                420                 425                 430

Ala Ile Tyr Ala Pro Pro Ile Gln Gly Val Ile Arg Cys Glu Ser Asn
            435                 440                 445

Ile Thr Gly Leu Leu Leu Thr Arg Asp Gly Gly Glu Gly Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                    485                 490                 495

Ala Pro Thr Arg Ala Arg Arg Arg Val Val Gly Arg Glu Lys Arg Ala
                500                 505                 510

Val Gly Ile Gly Ala Val Phe Leu Gly Phe Leu Gly Ala Ala Gly Ser
            515                 520                 525

Thr Met Gly Ala Ala Ser Met Thr Leu Thr Val Gln Ala Arg Gln Leu
    530                 535                 540

Leu Ser Gly Ile Val Gln Gln Gln Ser Asn Leu Leu Arg Ala Ile Glu
545                 550                 555                 560

Ala Gln Gln His Met Leu Lys Leu Thr Val Trp Gly Ile Lys Gln Leu
                    565                 570                 575
```

Gln Ala Arg Val Leu Ala Val Glu Arg Tyr Leu Arg Asp Gln Gln Leu
    580                 585                 590

Leu Gly Ile Trp Gly Cys Ser Gly Lys Leu Ile Cys Thr Thr Asn Val
    595                 600                 605

Pro Trp Asn Ser Ser Trp Ser Asn Lys Ser His Asp Glu Ile Trp Asn
    610                 615                 620

Asn Met Thr Trp Leu Gln Trp Asp Lys Glu Ile Ser Asn Tyr Thr Asn
625                 630                 635                 640

Leu Ile Tyr Ser Leu Ile Glu Glu Ser Gln Asn Gln Gln Glu Lys Asn
                645                 650                 655

Glu Gln Asp Leu Leu Ala Leu Asp Lys Trp Ala Ser Leu Trp Asn Trp
            660                 665                 670

Phe Asp Ile Ser Lys Trp Leu Trp Tyr Ile Lys Ile Phe Ile Met Ile
        675                 680                 685

Val Gly Gly Leu Ile Gly Leu Arg Ile Val Phe Ala Val Leu Ala Val
    690                 695                 700

Ile Lys Arg Val Arg Gln Gly Tyr Ser Pro Val Ser Phe Gln Ile His
705                 710                 715                 720

Asn Pro Asn Pro Gly Gly Leu Asp Arg Pro Gly Arg Ile Glu Glu Glu
                725                 730                 735

Gly Gly Glu Pro Gly Arg Gly Arg Ser Ile Arg Leu Val Ser Gly Phe
            740                 745                 750

Leu Ala Leu Ala Trp Asp Asp Leu Arg Asn Leu Cys Leu Phe Ser Tyr
        755                 760                 765

His Arg Leu Arg Asp Phe Ala Leu Ile Val Ala Arg Thr Val Glu Leu
    770                 775                 780

Leu Gly His Ser Ser Leu Lys Gly Leu Arg Leu Gly Trp Glu Gly Leu
785                 790                 795                 800

Lys Tyr Leu Trp Asn Leu Leu Val Tyr Trp Ser Gln Glu Leu Lys Thr
                805                 810                 815

Ser Ala Ile Asn Leu Val Asp Thr Ile Ala Ile Ala Val Ala Gly Trp
            820                 825                 830

Thr Asp Arg Val Ile Glu Ile Gly Gln Gly Ile Gly Arg Ala Phe Leu
        835                 840                 845

His Ile Pro Arg Arg Ile Arg Gln Gly Leu Glu Arg Ala Leu Leu
    850                 855                 860

<210> SEQ ID NO 8
<211> LENGTH: 863
<212> TYPE: PRT
<213> ORGANISM: Artificial Sequence
<220> FEATURE:
<223> OTHER INFORMATION: KNH1144 gp160 with I535M and I559P mutations

<400> SEQUENCE: 8

Met Ile Val Met Gly Thr Gln Arg Asn Tyr Gln His Leu Leu Arg Trp
1               5                   10                  15

Gly Thr Met Ile Leu Gly Leu Ile Ile Ile Cys Ser Ala Ala Asp Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile Pro Leu Glu Asn Val Thr Glu Glu Phe Asn Met Trp Lys

-continued

```
                    85                  90                  95
Asn Lys Met Val Gln Met His Thr Asp Ile Ile Ser Leu Trp Asp
                100                 105                 110

Gln Ser Leu Gln Pro Cys Val Lys Leu Thr Pro Leu Cys Val Thr Leu
                115                 120                 125

Asn Cys Thr Asp Ala Thr Asn Gly Thr Ile Gly Asn Ile Thr Asp Glu
                130                 135                 140

Met Lys Gly Glu Ile Lys Asn Cys Ser Phe Asn Ile Thr Thr Glu Ile
145                 150                 155                 160

Arg Asp Lys Lys Gln Lys Val Tyr Ser Leu Phe Tyr Arg Leu Asp Val
                165                 170                 175

Val Pro Ile Glu Pro Asp Ser Ser Asn Ser Ser Arg Asn Ser Ser Glu
                180                 185                 190

Tyr Arg Leu Ile Asn Cys Asn Thr Ser Ala Ile Thr Gln Ala Cys Pro
                195                 200                 205

Lys Val Ser Phe Glu Pro Ile Pro Ile His Tyr Cys Ala Pro Ala Gly
                210                 215                 220

Phe Ala Ile Leu Lys Cys Arg Asp Lys Glu Phe Asn Gly Thr Gly Lys
225                 230                 235                 240

Cys Lys Asn Val Ser Thr Val Gln Cys Thr His Gly Ile Lys Pro Val
                245                 250                 255

Val Ser Thr Gln Leu Leu Leu Asn Gly Ser Leu Ala Glu Gly Glu Val
                260                 265                 270

Arg Ile Arg Ser Glu Asn Ile Thr Asn Asn Ala Lys Thr Ile Ile Val
                275                 280                 285

Gln Leu Val Glu Pro Val Arg Ile Asn Cys Thr Arg Pro Asn Asn Asn
                290                 295                 300

Thr Arg Glu Ser Val Arg Ile Gly Pro Gly Gln Ala Phe Phe Ala Thr
305                 310                 315                 320

Gly Asp Ile Ile Gly Asp Ile Arg Gln Ala His Cys Asn Val Ser Arg
                325                 330                 335

Ser Gln Trp Asn Lys Thr Leu Gln Gln Val Ala Ala Gln Leu Gly Glu
                340                 345                 350

His Phe Lys Asn Lys Ala Ile Thr Phe Asn Ser Ser Ser Gly Gly Asp
                355                 360                 365

Leu Glu Ile Thr Thr His Ser Phe Asn Cys Gly Gly Glu Phe Phe Tyr
                370                 375                 380

Cys Asn Thr Ser Gly Leu Phe Asn Ser Thr Trp Lys Ala Asn Asn Gly
385                 390                 395                 400

Thr Trp Lys Ala Asn Ile Ser Glu Ser Asn Asn Thr Glu Ile Thr Leu
                405                 410                 415

Gln Cys Arg Ile Lys Gln Ile Ile Asn Met Trp Gln Arg Thr Gly Gln
                420                 425                 430

Ala Ile Tyr Ala Pro Pro Ile Gln Gly Val Ile Arg Cys Glu Ser Asn
                435                 440                 445

Ile Thr Gly Leu Leu Leu Thr Arg Asp Gly Gly Glu Gly Asn Asn Glu
                450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Arg Ala Arg Arg Arg Val Val Gly Arg Glu Lys Arg Ala
                500                 505                 510
```

```
Val Gly Ile Gly Ala Val Phe Leu Gly Phe Leu Gly Ala Ala Gly Ser
            515                 520                 525

Thr Met Gly Ala Ala Ser Met Thr Leu Thr Val Gln Ala Arg Gln Leu
        530                 535                 540

Leu Ser Gly Ile Val Gln Gln Gln Ser Asn Leu Leu Arg Ala Pro Glu
545                 550                 555                 560

Ala Gln Gln His Met Leu Lys Leu Thr Val Trp Gly Ile Lys Gln Leu
                565                 570                 575

Gln Ala Arg Val Leu Ala Val Glu Arg Tyr Leu Arg Asp Gln Gln Leu
            580                 585                 590

Leu Gly Ile Trp Gly Cys Ser Gly Lys Leu Ile Cys Thr Thr Asn Val
        595                 600                 605

Pro Trp Asn Ser Ser Trp Ser Asn Lys Ser His Asp Glu Ile Trp Asn
610                 615                 620

Asn Met Thr Trp Leu Gln Trp Asp Lys Glu Ile Ser Asn Tyr Thr Asn
625                 630                 635                 640

Leu Ile Tyr Ser Leu Ile Glu Glu Ser Gln Asn Gln Gln Glu Lys Asn
                645                 650                 655

Glu Gln Asp Leu Leu Ala Leu Asp Lys Trp Ala Ser Leu Trp Asn Trp
            660                 665                 670

Phe Asp Ile Ser Lys Trp Leu Trp Tyr Ile Lys Ile Phe Ile Met Ile
        675                 680                 685

Val Gly Gly Leu Ile Gly Leu Arg Ile Val Phe Ala Val Leu Ala Val
690                 695                 700

Ile Lys Arg Val Arg Gln Gly Tyr Ser Pro Val Ser Phe Gln Ile His
705                 710                 715                 720

Asn Pro Asn Pro Gly Gly Leu Asp Arg Pro Gly Arg Ile Glu Glu Glu
                725                 730                 735

Gly Gly Glu Pro Gly Arg Gly Arg Ser Ile Arg Leu Val Ser Gly Phe
            740                 745                 750

Leu Ala Leu Ala Trp Asp Asp Leu Arg Asn Leu Cys Leu Phe Ser Tyr
        755                 760                 765

His Arg Leu Arg Asp Phe Ala Leu Ile Val Ala Arg Thr Val Glu Leu
770                 775                 780

Leu Gly His Ser Ser Leu Lys Gly Leu Arg Leu Gly Trp Glu Gly Leu
785                 790                 795                 800

Lys Tyr Leu Trp Asn Leu Leu Val Tyr Trp Ser Gln Glu Leu Lys Thr
                805                 810                 815

Ser Ala Ile Asn Leu Val Asp Thr Ile Ala Ile Ala Val Ala Gly Trp
            820                 825                 830

Thr Asp Arg Val Ile Glu Ile Gly Gln Gly Ile Gly Arg Ala Phe Leu
        835                 840                 845

His Ile Pro Arg Arg Ile Arg Gln Gly Leu Glu Arg Ala Leu Leu
850                 855                 860

<210> SEQ ID NO 9
<211> LENGTH: 847
<212> TYPE: PRT
<213> ORGANISM: Artificial Sequence
<220> FEATURE:
<223> OTHER INFORMATION: JRFL gp160

<400> SEQUENCE: 9

Met Arg Val Lys Gly Ile Arg Lys Ser Tyr Gln Tyr Leu Trp Lys Gly
1               5                   10                  15

Gly Thr Leu Leu Leu Gly Ile Leu Met Ile Cys Ser Ala Val Glu Lys
```

```
                 20                  25                  30
Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
 50                  55                  60

His Asn Val Trp Ala Thr His Ala Cys Val Pro Thr Asp Pro Asn Pro
 65                  70                  75                  80

Gln Glu Val Val Leu Glu Asn Val Thr Glu His Phe Asn Met Trp Lys
                85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Lys Asp Val Asn Ala Thr Asn Thr Thr Asn Asp Ser Glu Gly
        130                 135                 140

Thr Met Glu Arg Gly Glu Ile Lys Asn Cys Ser Phe Asn Ile Thr Thr
145                 150                 155                 160

Ser Ile Arg Asp Glu Val Gln Lys Glu Tyr Ala Leu Phe Tyr Lys Leu
                165                 170                 175

Asp Val Val Pro Ile Asp Asn Asn Asn Thr Ser Tyr Arg Leu Ile Ser
            180                 185                 190

Cys Asp Thr Ser Val Ile Thr Gln Ala Cys Pro Lys Ile Ser Phe Glu
        195                 200                 205

Pro Ile Pro Ile His Tyr Cys Ala Pro Ala Gly Phe Ala Ile Leu Lys
        210                 215                 220

Cys Asn Asp Lys Thr Phe Asn Gly Lys Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Glu Val Ile Arg Ser Asp
            260                 265                 270

Asn Phe Thr Asn Asn Ala Lys Thr Ile Ile Val Gln Leu Lys Glu Ser
        275                 280                 285

Val Glu Ile Asn Cys Thr Arg Pro Asn Asn Asn Thr Arg Lys Ser Ile
        290                 295                 300

His Ile Gly Pro Gly Arg Ala Phe Tyr Thr Thr Gly Glu Ile Ile Gly
305                 310                 315                 320

Asp Ile Arg Gln Ala His Cys Asn Ile Ser Arg Ala Lys Trp Asn Asp
                325                 330                 335

Thr Leu Lys Gln Ile Val Ile Lys Leu Arg Glu Gln Phe Glu Asn Lys
            340                 345                 350

Thr Ile Val Phe Asn His Ser Ser Gly Gly Asp Pro Glu Ile Val Met
        355                 360                 365

His Ser Phe Asn Cys Gly Gly Glu Phe Phe Tyr Cys Asn Ser Thr Gln
        370                 375                 380

Leu Phe Asn Ser Thr Trp Asn Asn Asn Thr Glu Gly Ser Asn Asn Thr
385                 390                 395                 400

Glu Gly Asn Thr Ile Thr Leu Pro Cys Arg Ile Lys Gln Ile Ile Asn
                405                 410                 415

Met Trp Gln Glu Val Gly Lys Ala Met Tyr Ala Pro Pro Ile Arg Gly
            420                 425                 430

Gln Ile Arg Cys Ser Ser Asn Ile Thr Gly Leu Leu Leu Thr Arg Asp
        435                 440                 445
```

```
Gly Gly Ile Asn Glu Asn Gly Thr Glu Ile Phe Arg Pro Gly Gly Gly
        450                 455                 460

Asp Met Arg Asp Asn Trp Arg Ser Glu Leu Tyr Lys Tyr Lys Val Val
465                 470                 475                 480

Lys Ile Glu Pro Leu Gly Val Ala Pro Thr Lys Ala Lys Arg Arg Val
                485                 490                 495

Val Gln Arg Glu Lys Arg Ala Val Gly Ile Gly Ala Val Phe Leu Gly
            500                 505                 510

Phe Leu Gly Ala Ala Gly Ser Thr Met Gly Ala Ala Ser Met Thr Leu
        515                 520                 525

Thr Val Gln Ala Arg Leu Leu Leu Ser Gly Ile Val Gln Gln Gln Asn
    530                 535                 540

Asn Leu Leu Arg Ala Ile Glu Ala Gln Gln Arg Met Leu Gln Leu Thr
545                 550                 555                 560

Val Trp Gly Ile Lys Gln Leu Gln Ala Arg Val Leu Ala Val Glu Arg
                565                 570                 575

Tyr Leu Gly Asp Gln Gln Leu Leu Gly Ile Trp Gly Cys Ser Gly Lys
            580                 585                 590

Leu Ile Cys Thr Thr Ala Val Pro Trp Asn Ala Ser Trp Ser Asn Lys
        595                 600                 605

Ser Leu Asp Arg Ile Trp Asn Asn Met Thr Trp Met Glu Trp Glu Arg
    610                 615                 620

Glu Ile Asp Asn Tyr Thr Ser Glu Ile Tyr Thr Leu Ile Glu Glu Ser
625                 630                 635                 640

Gln Asn Gln Gln Glu Lys Asn Glu Gln Glu Leu Leu Glu Leu Asp Lys
                645                 650                 655

Trp Ala Ser Leu Trp Asn Trp Phe Asp Ile Thr Lys Trp Leu Trp Tyr
            660                 665                 670

Ile Lys Ile Phe Ile Met Ile Val Gly Gly Leu Val Gly Leu Arg Leu
        675                 680                 685

Val Phe Thr Val Leu Ser Ile Val Asn Arg Val Arg Gln Gly Tyr Ser
    690                 695                 700

Pro Leu Ser Phe Gln Thr Leu Leu Pro Ala Pro Arg Gly Pro Asp Arg
705                 710                 715                 720

Pro Glu Gly Ile Glu Glu Gly Gly Glu Arg Asp Arg Asp Arg Ser
                725                 730                 735

Gly Arg Leu Val Asn Gly Phe Leu Ala Leu Ile Trp Val Asp Leu Arg
            740                 745                 750

Ser Leu Cys Leu Phe Ser Tyr His Arg Leu Arg Asp Leu Leu Leu Thr
        755                 760                 765

Val Thr Arg Ile Val Glu Leu Leu Gly Arg Arg Gly Trp Glu Val Leu
    770                 775                 780

Lys Tyr Trp Trp Asn Leu Leu Gln Tyr Trp Ser Gln Glu Leu Lys Asn
785                 790                 795                 800

Ser Ala Val Ser Leu Leu Asn Ala Thr Ala Ile Ala Val Ala Glu Gly
                805                 810                 815

Thr Asp Arg Ile Ile Glu Ala Leu Gln Arg Thr Tyr Arg Ala Ile Leu
            820                 825                 830

His Ile Pro Thr Arg Ile Arg Gln Gly Leu Glu Arg Ala Leu Leu
        835                 840                 845

<210> SEQ ID NO 10
<211> LENGTH: 847
<212> TYPE: PRT
<213> ORGANISM: Artificial Sequence
```

```
<220> FEATURE:
<223> OTHER INFORMATION: JRFL with P mutation at position equivalent to
      position 559 in KNH1144

<400> SEQUENCE: 10

Met Arg Val Lys Gly Ile Arg Lys Ser Tyr Gln Tyr Leu Trp Lys Gly
1               5                   10                  15

Gly Thr Leu Leu Leu Gly Ile Leu Met Ile Cys Ser Ala Val Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
50                  55                  60

His Asn Val Trp Ala Thr His Ala Cys Val Pro Thr Asp Pro Asn Pro
65                  70                  75                  80

Gln Glu Val Val Leu Glu Asn Val Thr Glu His Phe Asn Met Trp Lys
                85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Lys Asp Val Asn Ala Thr Asn Thr Thr Asn Asp Ser Glu Gly
130                 135                 140

Thr Met Glu Arg Gly Glu Ile Lys Asn Cys Ser Phe Asn Ile Thr Thr
145                 150                 155                 160

Ser Ile Arg Asp Glu Val Gln Lys Glu Tyr Ala Leu Phe Tyr Lys Leu
                165                 170                 175

Asp Val Val Pro Ile Asp Asn Asn Asn Thr Ser Tyr Arg Leu Ile Ser
            180                 185                 190

Cys Asp Thr Ser Val Ile Thr Gln Ala Cys Pro Lys Ile Ser Phe Glu
        195                 200                 205

Pro Ile Pro Ile His Tyr Cys Ala Pro Ala Gly Phe Ala Ile Leu Lys
210                 215                 220

Cys Asn Asp Lys Thr Phe Asn Gly Lys Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Val Val Ile Arg Ser Asp
            260                 265                 270

Asn Phe Thr Asn Asn Ala Lys Thr Ile Ile Val Gln Leu Lys Glu Ser
            275                 280                 285

Val Glu Ile Asn Cys Thr Arg Pro Asn Asn Thr Arg Lys Ser Ile
290                 295                 300

His Ile Gly Pro Gly Arg Ala Phe Tyr Thr Thr Gly Glu Ile Ile Gly
305                 310                 315                 320

Asp Ile Arg Gln Ala His Cys Asn Ile Ser Arg Ala Lys Trp Asn Asp
                325                 330                 335

Thr Leu Lys Gln Ile Val Ile Lys Leu Arg Glu Gln Phe Glu Asn Lys
            340                 345                 350

Thr Ile Val Phe Asn His Ser Ser Gly Gly Asp Pro Glu Ile Val Met
        355                 360                 365

His Ser Phe Asn Cys Gly Gly Glu Phe Phe Tyr Cys Asn Ser Thr Gln
370                 375                 380

Leu Phe Asn Ser Thr Trp Asn Asn Asn Thr Glu Gly Ser Asn Asn Thr
385                 390                 395                 400
```

```
Glu Gly Asn Thr Ile Thr Leu Pro Cys Arg Ile Lys Gln Ile Ile Asn
                405                 410                 415
Met Trp Gln Glu Val Gly Lys Ala Met Tyr Ala Pro Pro Ile Arg Gly
                420                 425                 430
Gln Ile Arg Cys Ser Ser Asn Ile Thr Gly Leu Leu Leu Thr Arg Asp
                435                 440                 445
Gly Gly Ile Asn Glu Asn Gly Thr Glu Ile Phe Arg Pro Gly Gly Gly
            450                 455                 460
Asp Met Arg Asp Asn Trp Arg Ser Glu Leu Tyr Lys Tyr Lys Val Val
465                 470                 475                 480
Lys Ile Glu Pro Leu Gly Val Ala Pro Thr Lys Ala Lys Arg Arg Val
                485                 490                 495
Val Gln Arg Glu Lys Arg Ala Val Gly Ile Gly Ala Val Phe Leu Gly
                500                 505                 510
Phe Leu Gly Ala Ala Gly Ser Thr Met Gly Ala Ala Ser Met Thr Leu
            515                 520                 525
Thr Val Gln Ala Arg Leu Leu Leu Ser Gly Ile Val Gln Gln Gln Asn
            530                 535                 540
Asn Leu Leu Arg Ala Pro Glu Ala Gln Gln Arg Met Leu Gln Leu Thr
545                 550                 555                 560
Val Trp Gly Ile Lys Gln Leu Gln Ala Arg Val Leu Ala Val Glu Arg
                565                 570                 575
Tyr Leu Gly Asp Gln Gln Leu Leu Gly Ile Trp Gly Cys Ser Gly Lys
                580                 585                 590
Leu Ile Cys Thr Thr Ala Val Pro Trp Asn Ala Ser Trp Ser Asn Lys
            595                 600                 605
Ser Leu Asp Arg Ile Trp Asn Asn Met Thr Trp Met Glu Trp Glu Arg
            610                 615                 620
Glu Ile Asp Asn Tyr Thr Ser Glu Ile Tyr Thr Leu Ile Glu Glu Ser
625                 630                 635                 640
Gln Asn Gln Gln Glu Lys Asn Glu Gln Glu Leu Leu Glu Leu Asp Lys
                645                 650                 655
Trp Ala Ser Leu Trp Asn Trp Phe Asp Ile Thr Lys Trp Leu Trp Tyr
                660                 665                 670
Ile Lys Ile Phe Ile Met Ile Val Gly Gly Leu Val Gly Leu Arg Leu
            675                 680                 685
Val Phe Thr Val Leu Ser Ile Val Asn Arg Val Arg Gln Gly Tyr Ser
            690                 695                 700
Pro Leu Ser Phe Gln Thr Leu Leu Pro Ala Pro Arg Gly Pro Asp Arg
705                 710                 715                 720
Pro Glu Gly Ile Glu Glu Glu Gly Gly Glu Arg Asp Arg Asp Arg Ser
                725                 730                 735
Gly Arg Leu Val Asn Gly Phe Leu Ala Leu Ile Trp Val Asp Leu Arg
            740                 745                 750
Ser Leu Cys Leu Phe Ser Tyr His Arg Leu Arg Asp Leu Leu Leu Thr
            755                 760                 765
Val Thr Arg Ile Val Glu Leu Leu Gly Arg Arg Gly Trp Glu Val Leu
            770                 775                 780
Lys Tyr Trp Trp Asn Leu Leu Gln Tyr Trp Ser Gln Glu Leu Lys Asn
785                 790                 795                 800
Ser Ala Val Ser Leu Leu Asn Ala Thr Ala Ile Ala Val Ala Glu Gly
                805                 810                 815
Thr Asp Arg Ile Ile Glu Ala Leu Gln Arg Thr Tyr Arg Ala Ile Leu
```

```
                        820                 825                 830
His Ile Pro Thr Arg Ile Arg Gln Gly Leu Glu Arg Ala Leu Leu
            835                 840                 845

<210> SEQ ID NO 11
<211> LENGTH: 847
<212> TYPE: PRT
<213> ORGANISM: Artificial Sequence
<220> FEATURE:
<223> OTHER INFORMATION: JRFL gp160 modified to contain P at position
      equivalent to position 559 in KNH1144 and the 5 trimer stability
      enhancing amino acids

<400> SEQUENCE: 11

Met Arg Val Lys Gly Ile Arg Lys Ser Tyr Gln Tyr Leu Trp Lys Gly
1               5                   10                  15

Gly Thr Leu Leu Leu Gly Ile Leu Met Ile Cys Ser Ala Val Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu His Phe Asn Met Trp Lys
                85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Lys Asp Val Asn Ala Thr Asn Thr Thr Asn Asp Ser Glu Gly
    130                 135                 140

Thr Met Glu Arg Gly Glu Ile Lys Asn Cys Ser Phe Asn Ile Thr Thr
145                 150                 155                 160

Ser Ile Arg Asp Glu Val Gln Lys Glu Tyr Ala Leu Phe Tyr Lys Leu
                165                 170                 175

Asp Val Val Pro Ile Asp Asn Asn Asn Thr Ser Tyr Arg Leu Ile Ser
            180                 185                 190

Cys Asp Thr Ser Val Ile Thr Gln Ala Cys Pro Lys Ile Ser Phe Glu
        195                 200                 205

Pro Ile Pro Ile His Tyr Cys Ala Pro Ala Gly Phe Ala Ile Leu Lys
    210                 215                 220

Cys Asn Asp Lys Thr Phe Asn Gly Lys Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Val Val Ile Arg Ser Asp
            260                 265                 270

Asn Phe Thr Asn Asn Ala Lys Thr Ile Ile Val Gln Leu Lys Glu Ser
        275                 280                 285

Val Glu Ile Asn Cys Thr Arg Pro Asn Asn Asn Thr Arg Lys Ser Ile
    290                 295                 300

His Ile Gly Pro Gly Arg Ala Phe Tyr Thr Thr Gly Glu Ile Ile Gly
305                 310                 315                 320

Asp Ile Arg Gln Ala His Cys Asn Ile Ser Arg Ala Lys Trp Asn Asp
                325                 330                 335
```

-continued

```
Thr Leu Lys Gln Ile Val Ile Lys Leu Arg Glu Gln Phe Glu Asn Lys
            340                 345                 350

Thr Ile Val Phe Asn His Ser Gly Gly Asp Pro Glu Ile Val Met
        355                 360                 365

His Ser Phe Asn Cys Gly Gly Glu Phe Phe Tyr Cys Asn Ser Thr Gln
370                 375                 380

Leu Phe Asn Ser Thr Trp Asn Asn Thr Glu Gly Ser Asn Asn Thr
385                 390                 395                 400

Glu Gly Asn Thr Ile Thr Leu Pro Cys Arg Ile Lys Gln Ile Ile Asn
                405                 410                 415

Met Trp Gln Glu Val Gly Lys Ala Met Tyr Ala Pro Pro Ile Arg Gly
            420                 425                 430

Gln Ile Arg Cys Ser Ser Asn Ile Thr Gly Leu Leu Leu Thr Arg Asp
            435                 440                 445

Gly Gly Ile Asn Glu Asn Gly Thr Glu Ile Phe Arg Pro Gly Gly Gly
        450                 455                 460

Asp Met Arg Asp Asn Trp Arg Ser Glu Leu Tyr Lys Tyr Lys Val Val
465                 470                 475                 480

Lys Ile Glu Pro Leu Gly Val Ala Pro Thr Lys Ala Lys Arg Arg Val
                485                 490                 495

Val Gln Arg Glu Lys Arg Ala Val Gly Ile Gly Ala Val Phe Leu Gly
            500                 505                 510

Phe Leu Gly Ala Ala Gly Ser Thr Met Gly Ala Ala Ser Ile Thr Leu
        515                 520                 525

Thr Val Gln Ala Arg Gln Leu Leu Ser Gly Ile Val Gln Gln Ser
    530                 535                 540

Asn Leu Leu Arg Ala Pro Glu Ala Gln Gln Arg Met Leu Lys Leu Thr
545                 550                 555                 560

Val Trp Gly Ile Lys Gln Leu Gln Ala Arg Val Leu Ala Val Glu Arg
                565                 570                 575

Tyr Leu Arg Asp Gln Gln Leu Leu Gly Ile Trp Gly Cys Ser Gly Lys
            580                 585                 590

Leu Ile Cys Thr Thr Ala Val Pro Trp Asn Ala Ser Trp Ser Asn Lys
        595                 600                 605

Ser Leu Asp Arg Ile Trp Asn Asn Met Thr Trp Met Glu Trp Glu Arg
610                 615                 620

Glu Ile Asp Asn Tyr Thr Ser Glu Ile Tyr Thr Leu Ile Glu Glu Ser
625                 630                 635                 640

Gln Asn Gln Gln Glu Lys Asn Glu Gln Glu Leu Leu Glu Leu Asp Lys
                645                 650                 655

Trp Ala Ser Leu Trp Asn Trp Phe Asp Ile Thr Lys Trp Leu Trp Tyr
            660                 665                 670

Ile Lys Ile Phe Ile Met Ile Val Gly Gly Leu Val Gly Leu Arg Leu
        675                 680                 685

Val Phe Thr Val Leu Ser Ile Val Asn Arg Val Arg Gln Gly Tyr Ser
    690                 695                 700

Pro Leu Ser Phe Gln Thr Leu Leu Pro Ala Pro Arg Gly Pro Asp Arg
705                 710                 715                 720

Pro Glu Gly Ile Glu Glu Glu Gly Gly Glu Arg Asp Arg Asp Arg Ser
                725                 730                 735

Gly Arg Leu Val Asn Gly Phe Leu Ala Leu Ile Trp Val Asp Leu Arg
            740                 745                 750

Ser Leu Cys Leu Phe Ser Tyr His Arg Leu Arg Asp Leu Leu Leu Thr
        755                 760                 765
```

Val Thr Arg Ile Val Glu Leu Leu Gly Arg Arg Gly Trp Glu Val Leu
            770                 775                 780

Lys Tyr Trp Trp Asn Leu Leu Gln Tyr Trp Ser Gln Glu Leu Lys Asn
785                 790                 795                 800

Ser Ala Val Ser Leu Leu Asn Ala Thr Ala Ile Ala Val Ala Glu Gly
                805                 810                 815

Thr Asp Arg Ile Ile Glu Ala Leu Gln Arg Thr Tyr Arg Ala Ile Leu
            820                 825                 830

His Ile Pro Thr Arg Ile Arg Gln Gly Leu Glu Arg Ala Leu Leu
            835                 840                 845

<210> SEQ ID NO 12
<211> LENGTH: 853
<212> TYPE: PRT
<213> ORGANISM: Artificial Sequence
<220> FEATURE:
<223> OTHER INFORMATION: Ba-L gp160
<220> FEATURE:
<221> NAME/KEY: MISC_FEATURE
<222> LOCATION: (23)..(830)
<223> OTHER INFORMATION: X=any AA

<400> SEQUENCE: 12

Met Arg Val Thr Glu Ile Arg Lys Ser Tyr Gln His Trp Trp Arg Trp
1               5                   10                  15

Gly Ile Met Leu Leu Gly Xaa Leu Met Ile Cys Asn Ala Glu Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
50                  55                  60

His Asn Val Trp Ala Thr His Ala Cys Val Pro Thr Asp Pro Asn Pro
65                  70                  75                  80

Gln Glu Val Xaa Xaa Xaa Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Xaa Xaa Asn Xaa Thr Xaa Thr
130                 135                 140

Thr Ser Ser Ser Arg Gly Met Val Gly Gly Gly Glu Xaa Lys Asn Cys
145                 150                 155                 160

Ser Phe Asn Ile Thr Thr Xaa Ile Arg Gly Lys Val Gln Lys Glu Tyr
                165                 170                 175

Ala Leu Phe Tyr Glu Leu Asp Ile Val Pro Ile Asp Asn Xaa Ile Asp
            180                 185                 190

Arg Tyr Arg Leu Ile Ser Cys Asn Thr Ser Val Ile Thr Gln Ala Cys
        195                 200                 205

Pro Lys Val Ser Phe Glu Pro Ile Pro Ile His Tyr Cys Ala Pro Ala
210                 215                 220

Gly Phe Ala Ile Leu Lys Cys Lys Asp Lys Lys Phe Asn Gly Lys Gly
225                 230                 235                 240

Pro Cys Xaa Asn Val Ser Thr Val Gln Cys Thr His Gly Ile Arg Pro
                245                 250                 255

Val Val Ser Thr Gln Leu Leu Leu Asn Gly Ser Leu Ala Glu Glu Glu
            260                 265                 270

```
Val Val Ile Arg Ser Xaa Asn Phe Xaa Asx Asn Ala Lys Xaa Ile Ile
            275                 280                 285
Val Gln Leu Asn Glu Ser Val Glu Ile Asn Cys Thr Arg Pro Asn Asn
        290                 295                 300
Asn Thr Arg Lys Ser Ile His Ile Gly Pro Gly Arg Ala Phe Tyr Thr
305                 310                 315                 320
Thr Gly Glu Ile Ile Gly Asp Ile Arg Gln Ala His Cys Asn Leu Ser
                325                 330                 335
Arg Ala Lys Trp Asn Asp Thr Leu Asn Lys Ile Val Xaa Lys Leu Arg
            340                 345                 350
Glu Gln Phe Gly Asn Lys Thr Ile Val Phe Lys His Ser Ser Gly Gly
        355                 360                 365
Asp Pro Glu Ile Val Thr His Ser Phe Asn Cys Gly Gly Glu Phe Phe
    370                 375                 380
Tyr Cys Asn Ser Thr Gln Leu Phe Asn Ser Thr Trp Asn Val Thr Glu
385                 390                 395                 400
Glu Ser Asn Asn Thr Val Glu Asn Asn Thr Ile Thr Leu Pro Cys Arg
                405                 410                 415
Ile Lys Gln Ile Ile Asn Met Trp Gln Xaa Val Gly Arg Ala Met Tyr
            420                 425                 430
Ala Pro Pro Ile Arg Gly Gln Ile Arg Cys Ser Ser Asn Ile Thr Gly
        435                 440                 445
Leu Leu Leu Thr Arg Asp Gly Gly Pro Glu Asp Asn Lys Thr Glu Val
    450                 455                 460
Phe Arg Pro Gly Gly Gly Asp Met Arg Asp Asn Trp Arg Ser Glu Leu
465                 470                 475                 480
Tyr Lys Tyr Lys Val Val Lys Ile Glu Pro Leu Gly Val Ala Pro Thr
                485                 490                 495
Lys Ala Lys Arg Arg Val Val Gln Arg Glu Lys Arg Ala Val Gly Ile
            500                 505                 510
Gly Ala Val Phe Leu Gly Phe Leu Gly Ala Ala Gly Ser Thr Met Gly
        515                 520                 525
Ala Ala Ser Met Thr Leu Thr Val Gln Ala Arg Leu Leu Leu Ser Gly
    530                 535                 540
Ile Val Gln Gln Gln Asn Asn Leu Leu Arg Ala Ile Glu Ala Gln Gln
545                 550                 555                 560
His Leu Leu Gln Leu Thr Val Trp Gly Ile Lys Gln Leu Gln Ala Arg
                565                 570                 575
Val Leu Ala Val Glu Arg Tyr Leu Arg Asp Gln Gln Leu Leu Gly Ile
            580                 585                 590
Trp Gly Cys Ser Gly Lys Leu Ile Cys Thr Thr Ala Val Pro Trp Asn
        595                 600                 605
Ala Ser Trp Ser Asn Lys Ser Leu Asn Lys Ile Trp Asp Asn Met Thr
    610                 615                 620
Trp Met Glu Trp Asp Arg Glu Ile Asn Asn Tyr Thr Ser Ile Ile Tyr
625                 630                 635                 640
Ser Leu Ile Glu Glu Ser Gln Asn Gln Gln Glu Lys Asn Glu Gln Glu
                645                 650                 655
Leu Leu Glu Leu Asp Lys Trp Ala Ser Leu Trp Asn Trp Phe Asp Ile
            660                 665                 670
Thr Xaa Trp Leu Trp Tyr Ile Lys Ile Phe Ile Met Ile Val Gly Gly
        675                 680                 685
Leu Ile Gly Leu Arg Ile Val Phe Ser Val Leu Ser Ile Val Asn Arg
```

```
                    690                 695                 700
Val Arg Gln Gly Tyr Ser Pro Leu Ser Phe Gln Thr His Leu Pro Ala
705                 710                 715                 720

Ser Arg Gly Pro Asp Arg Pro Gly Ile Glu Glu Glu Gly Glu
                725                 730                 735

Arg Asp Arg Asp Arg Ser Gly Pro Leu Val Asn Gly Phe Leu Xaa Leu
                740                 745                 750

Ile Trp Val Asp Leu Arg Ser Leu Xaa Leu Phe Ser Tyr His Arg Leu
                755                 760                 765

Arg Asp Leu Leu Leu Ile Val Thr Arg Ile Val Glu Leu Leu Gly Arg
                770                 775                 780

Arg Gly Trp Glu Val Leu Lys Tyr Trp Trp Xaa Leu Leu Gln Tyr Trp
785                 790                 795                 800

Ser Gln Glu Leu Lys Asn Ser Ala Val Ser Leu Leu Asn Xaa Xaa Ala
                805                 810                 815

Xaa Ala Val Ala Glu Gly Thr Asp Arg Val Ile Glu Val Xaa Gln Arg
                820                 825                 830

Ala Val Arg Ala Ile Leu His Ile Pro Arg Arg Ile Arg Gln Gly Leu
                835                 840                 845

Glu Arg Ala Leu Leu
                850

<210> SEQ ID NO 13
<211> LENGTH: 853
<212> TYPE: PRT
<213> ORGANISM: Artificial Sequence
<220> FEATURE:
<223> OTHER INFORMATION: Ba-L containing mutation to P at position
      equivalent to position 559 in KNH1144
<220> FEATURE:
<221> NAME/KEY: MISC_FEATURE
<222> LOCATION: (23)..(830)
<223> OTHER INFORMATION: X=Any AA

<400> SEQUENCE: 13

Met Arg Val Thr Glu Ile Arg Lys Ser Tyr Gln His Trp Trp Arg Trp
1               5                   10                  15

Gly Ile Met Leu Leu Gly Xaa Leu Met Ile Cys Asn Ala Glu Glu Lys
                20                  25                  30

Leu Trp Val Thr Val Tyr Tyr Gly Val Pro Val Trp Lys Glu Ala Thr
                35                  40                  45

Thr Thr Leu Phe Cys Ala Ser Asp Ala Lys Ala Tyr Asp Thr Glu Val
                50                  55                  60

His Asn Val Trp Ala Thr His Ala Cys Val Pro Thr Asp Pro Asn Pro
65                  70                  75                  80

Gln Glu Val Xaa Xaa Xaa Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
                115                 120                 125

Asn Cys Thr Asp Leu Arg Asn Ala Thr Xaa Xaa Asn Xaa Thr Xaa Thr
                130                 135                 140

Thr Ser Ser Ser Arg Gly Met Val Gly Gly Gly Glu Xaa Lys Asn Cys
145                 150                 155                 160

Ser Phe Asn Ile Thr Thr Xaa Ile Arg Gly Lys Val Gln Lys Glu Tyr
                165                 170                 175
```

-continued

```
Ala Leu Phe Tyr Glu Leu Asp Ile Val Pro Ile Asp Asn Xaa Ile Asp
            180                 185                 190

Arg Tyr Arg Leu Ile Ser Cys Asn Thr Ser Val Ile Thr Gln Ala Cys
        195                 200                 205

Pro Lys Val Ser Phe Glu Pro Ile Pro Ile His Tyr Cys Ala Pro Ala
    210                 215                 220

Gly Phe Ala Ile Leu Lys Cys Lys Asp Lys Lys Phe Asn Gly Lys Gly
225                 230                 235                 240

Pro Cys Xaa Asn Val Ser Thr Val Gln Cys Thr His Gly Ile Arg Pro
            245                 250                 255

Val Val Ser Thr Gln Leu Leu Leu Asn Gly Ser Leu Ala Glu Glu
            260                 265                 270

Val Val Ile Arg Ser Xaa Asn Phe Xaa Asx Asn Ala Lys Xaa Ile Ile
            275                 280                 285

Val Gln Leu Asn Glu Ser Val Glu Ile Asn Cys Thr Arg Pro Asn Asn
    290                 295                 300

Asn Thr Arg Lys Ser Ile His Ile Gly Pro Gly Arg Ala Phe Tyr Thr
305                 310                 315                 320

Thr Gly Glu Ile Ile Gly Asp Ile Arg Gln Ala His Cys Asn Leu Ser
            325                 330                 335

Arg Ala Lys Trp Asn Asp Thr Leu Asn Lys Ile Val Xaa Lys Leu Arg
        340                 345                 350

Glu Gln Phe Gly Asn Lys Thr Ile Val Phe Lys His Ser Ser Gly Gly
    355                 360                 365

Asp Pro Glu Ile Val Thr His Ser Phe Asn Cys Gly Gly Glu Phe Phe
370                 375                 380

Tyr Cys Asn Ser Thr Gln Leu Phe Asn Ser Thr Trp Asn Val Thr Glu
385                 390                 395                 400

Glu Ser Asn Asn Thr Val Glu Asn Asn Thr Ile Thr Leu Pro Cys Arg
            405                 410                 415

Ile Lys Gln Ile Ile Asn Met Trp Gln Xaa Val Gly Arg Ala Met Tyr
        420                 425                 430

Ala Pro Pro Ile Arg Gly Gln Ile Arg Cys Ser Ser Asn Ile Thr Gly
    435                 440                 445

Leu Leu Leu Thr Arg Asp Gly Gly Pro Glu Asp Asn Lys Thr Glu Val
450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
            485                 490                 495

Lys Ala Lys Arg Arg Val Val Gln Arg Glu Lys Arg Ala Val Gly Ile
        500                 505                 510

Gly Ala Val Phe Leu Gly Phe Leu Gly Ala Ala Gly Ser Thr Met Gly
    515                 520                 525

Ala Ala Ser Met Thr Leu Thr Val Gln Ala Arg Leu Leu Leu Ser Gly
530                 535                 540

Ile Val Gln Gln Gln Asn Asn Leu Leu Arg Ala Pro Glu Ala Gln Gln
545                 550                 555                 560

His Leu Leu Gln Leu Thr Val Trp Gly Ile Lys Gln Leu Gln Ala Arg
            565                 570                 575

Val Leu Ala Val Glu Arg Tyr Leu Arg Asp Gln Gln Leu Leu Gly Ile
        580                 585                 590

Trp Gly Cys Ser Gly Lys Leu Ile Cys Thr Thr Ala Val Pro Trp Asn
    595                 600                 605
```

```
Ala Ser Trp Ser Asn Lys Ser Leu Asn Lys Ile Trp Asp Asn Met Thr
    610                 615                 620

Trp Met Glu Trp Asp Arg Glu Ile Asn Asn Tyr Thr Ser Ile Ile Tyr
625                 630                 635                 640

Ser Leu Ile Glu Glu Ser Gln Asn Gln Gln Glu Lys Asn Glu Gln Glu
                645                 650                 655

Leu Leu Glu Leu Asp Lys Trp Ala Ser Leu Trp Asn Trp Phe Asp Ile
            660                 665                 670

Thr Xaa Trp Leu Trp Tyr Ile Lys Ile Phe Ile Met Ile Val Gly Gly
        675                 680                 685

Leu Ile Gly Leu Arg Ile Val Phe Ser Val Leu Ser Ile Val Asn Arg
690                 695                 700

Val Arg Gln Gly Tyr Ser Pro Leu Ser Phe Gln Thr His Leu Pro Ala
705                 710                 715                 720

Ser Arg Gly Pro Asp Arg Pro Gly Gly Ile Glu Glu Glu Gly Gly Glu
                725                 730                 735

Arg Asp Arg Asp Arg Ser Gly Pro Leu Val Asn Gly Phe Leu Xaa Leu
            740                 745                 750

Ile Trp Val Asp Leu Arg Ser Leu Xaa Leu Phe Ser Tyr His Arg Leu
        755                 760                 765

Arg Asp Leu Leu Leu Ile Val Thr Arg Ile Val Glu Leu Leu Gly Arg
770                 775                 780

Arg Gly Trp Glu Val Leu Lys Tyr Trp Trp Xaa Leu Leu Gln Tyr Trp
785                 790                 795                 800

Ser Gln Glu Leu Lys Asn Ser Ala Val Ser Leu Leu Asn Xaa Xaa Ala
                805                 810                 815

Xaa Ala Val Ala Glu Gly Thr Asp Arg Val Ile Glu Val Xaa Gln Arg
            820                 825                 830

Ala Val Arg Ala Ile Leu His Ile Pro Arg Arg Ile Arg Gln Gly Leu
        835                 840                 845

Glu Arg Ala Leu Leu
    850

<210> SEQ ID NO 14
<211> LENGTH: 853
<212> TYPE: PRT
<213> ORGANISM: Artificial Sequence
<220> FEATURE:
<223> OTHER INFORMATION: Ba-L gp160 modified to contain P at position
      equivalent to position 559 in KNH1144 and the 5 trimer mutations
<220> FEATURE:
<221> NAME/KEY: MISC_FEATURE
<222> LOCATION: (23)..(830)
<223> OTHER INFORMATION: X=Any AA

<400> SEQUENCE: 14

Met Arg Val Thr Glu Ile Arg Lys Ser Tyr Gln His Trp Trp Arg Trp
1               5                   10                  15

Gly Ile Met Leu Leu Gly Xaa Leu Met Ile Cys Asn Ala Glu Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Xaa Xaa Xaa Asn Val Thr Glu Asn Phe Asn Met Trp Lys
```

```
                    85                  90                  95
Asn Asn Met Val Glu Gln Met His Glu Asp Ile Ile Ser Leu Trp Asp
            100                 105                 110
Gln Ser Leu Lys Pro Cys Val Lys Leu Thr Pro Leu Cys Val Thr Leu
            115                 120                 125
Asn Cys Thr Asp Leu Arg Asn Ala Thr Xaa Xaa Asn Xaa Thr Xaa Thr
            130                 135                 140
Thr Ser Ser Ser Arg Gly Met Val Gly Gly Glu Xaa Lys Asn Cys
145                 150                 155                 160
Ser Phe Asn Ile Thr Thr Xaa Ile Arg Gly Lys Val Gln Lys Glu Tyr
                165                 170                 175
Ala Leu Phe Tyr Glu Leu Asp Ile Val Pro Ile Asp Asn Xaa Ile Asp
                180                 185                 190
Arg Tyr Arg Leu Ile Ser Cys Asn Thr Ser Val Ile Thr Gln Ala Cys
                195                 200                 205
Pro Lys Val Ser Phe Glu Pro Ile Pro Ile His Tyr Cys Ala Pro Ala
            210                 215                 220
Gly Phe Ala Ile Leu Lys Cys Lys Asp Lys Lys Phe Asn Gly Lys Gly
225                 230                 235                 240
Pro Cys Xaa Asn Val Ser Thr Val Gln Cys Thr His Gly Ile Arg Pro
                245                 250                 255
Val Val Ser Thr Gln Leu Leu Leu Asn Gly Ser Leu Ala Glu Glu Glu
                260                 265                 270
Val Val Ile Arg Ser Xaa Asn Phe Xaa Asx Asn Ala Lys Xaa Ile Ile
                275                 280                 285
Val Gln Leu Asn Glu Ser Val Glu Ile Asn Cys Thr Arg Pro Asn Asn
            290                 295                 300
Asn Thr Arg Lys Ser Ile His Ile Gly Pro Gly Arg Ala Phe Tyr Thr
305                 310                 315                 320
Thr Gly Glu Ile Ile Gly Asp Ile Arg Gln Ala His Cys Asn Leu Ser
                325                 330                 335
Arg Ala Lys Trp Asn Asp Thr Leu Asn Lys Ile Val Xaa Lys Leu Arg
                340                 345                 350
Glu Gln Phe Gly Asn Lys Thr Ile Val Phe Lys His Ser Ser Gly Gly
            355                 360                 365
Asp Pro Glu Ile Val Thr His Ser Phe Asn Cys Gly Gly Glu Phe Phe
            370                 375                 380
Tyr Cys Asn Ser Thr Gln Leu Phe Asn Ser Thr Trp Asn Val Thr Glu
385                 390                 395                 400
Glu Ser Asn Asn Thr Val Glu Asn Asn Thr Ile Thr Leu Pro Cys Arg
                405                 410                 415
Ile Lys Gln Ile Ile Asn Met Trp Gln Xaa Val Gly Arg Ala Met Tyr
            420                 425                 430
Ala Pro Pro Ile Arg Gly Gln Ile Arg Cys Ser Ser Asn Ile Thr Gly
            435                 440                 445
Leu Leu Leu Thr Arg Asp Gly Gly Pro Glu Asp Asn Lys Thr Glu Val
            450                 455                 460
Phe Arg Pro Gly Gly Gly Asp Met Arg Asp Asn Trp Arg Ser Glu Leu
465                 470                 475                 480
Tyr Lys Tyr Lys Val Val Lys Ile Glu Pro Leu Gly Val Ala Pro Thr
                485                 490                 495
Lys Ala Lys Arg Arg Val Val Gln Arg Glu Lys Arg Ala Val Gly Ile
            500                 505                 510
```

```
Gly Ala Val Phe Leu Gly Phe Leu Gly Ala Ala Gly Ser Thr Met Gly
            515                 520                 525

Ala Ala Ser Ile Thr Leu Thr Val Gln Ala Arg Gln Leu Leu Ser Gly
            530                 535                 540

Ile Val Gln Gln Gln Ser Asn Leu Leu Arg Ala Pro Glu Ala Gln Gln
545                 550                 555                 560

His Leu Leu Lys Leu Thr Val Trp Gly Ile Lys Gln Leu Gln Ala Arg
            565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Ala Val Pro Trp Asn
            595                 600                 605

Ala Ser Trp Ser Asn Lys Ser Leu Asn Lys Ile Trp Asp Asn Met Thr
            610                 615                 620

Trp Met Glu Trp Asp Arg Glu Ile Asn Asn Tyr Thr Ser Ile Ile Tyr
625                 630                 635                 640

Ser Leu Ile Glu Glu Ser Gln Asn Gln Gln Lys Asn Glu Gln Glu
            645                 650                 655

Leu Leu Glu Leu Asp Lys Trp Ala Ser Leu Trp Asn Trp Phe Asp Ile
            660                 665                 670

Thr Xaa Trp Leu Trp Tyr Ile Lys Ile Phe Ile Met Ile Val Gly Gly
            675                 680                 685

Leu Ile Gly Leu Arg Ile Val Phe Ser Val Leu Ser Ile Val Asn Arg
            690                 695                 700

Val Arg Gln Gly Tyr Ser Pro Leu Ser Phe Gln Thr His Leu Pro Ala
705                 710                 715                 720

Ser Arg Gly Pro Asp Arg Pro Gly Gly Ile Glu Glu Glu Gly Gly Glu
            725                 730                 735

Arg Asp Arg Asp Arg Ser Gly Pro Leu Val Asn Gly Phe Leu Xaa Leu
            740                 745                 750

Ile Trp Val Asp Leu Arg Ser Leu Xaa Leu Phe Ser Tyr His Arg Leu
            755                 760                 765

Arg Asp Leu Leu Leu Ile Val Thr Arg Ile Val Glu Leu Leu Gly Arg
            770                 775                 780

Arg Gly Trp Glu Val Leu Lys Tyr Trp Trp Xaa Leu Leu Gln Tyr Trp
785                 790                 795                 800

Ser Gln Glu Leu Lys Asn Ser Ala Val Ser Leu Leu Asn Xaa Xaa Ala
            805                 810                 815

Xaa Ala Val Ala Glu Gly Thr Asp Arg Val Ile Glu Val Xaa Gln Arg
            820                 825                 830

Ala Val Arg Ala Ile Leu His Ile Pro Arg Arg Ile Arg Gln Gly Leu
            835                 840                 845

Glu Arg Ala Leu Leu
    850

<210> SEQ ID NO 15
<211> LENGTH: 748
<212> TYPE: PRT
<213> ORGANISM: Artificial Sequence
<220> FEATURE:
<223> OTHER INFORMATION: AAA76668 gp160

<400> SEQUENCE: 15

Met Arg Val Lys Glu Lys Tyr Gln His Leu Arg Arg Trp Gly Trp Arg
1               5                   10                  15

Trp Gly Thr Met Leu Leu Gly Met Leu Met Ile Cys Ser Ala Thr Glu
```

-continued

```
            20                  25                  30
Lys Leu Trp Val Thr Val Tyr Tyr Gly Val Pro Val Trp Lys Glu Ala
            35                  40                  45
Thr Thr Thr Leu Phe Cys Ala Ser Asp Ala Lys Ala Tyr Asp Thr Glu
        50                  55                  60
Val His Asn Val Trp Ala Thr His Ala Cys Val Pro Thr Asp Pro Asn
65                  70                  75                  80
Pro Gln Glu Val Val Leu Val Asn Val Thr Glu Asn Phe Asn Met Trp
                85                  90                  95
Lys Asn Asp Met Val Glu Gln Met His Glu Asp Ile Ile Ser Leu Trp
            100                 105                 110
Asp Gln Ser Leu Lys Pro Cys Val Lys Leu Thr Pro Leu Cys Val Ser
        115                 120                 125
Leu Lys Cys Thr Asp Leu Lys Asn Asp Thr Asn Thr Asn Ser Ser Ser
    130                 135                 140
Gly Gly Met Ile Met Glu Lys Gly Glu Ile Lys Asn Cys Ser Phe Asn
145                 150                 155                 160
Ile Ser Thr Ser Ile Arg Gly Lys Val Gln Lys Glu Tyr Ala Phe Phe
                165                 170                 175
Tyr Lys Leu Asp Ile Ile Pro Ile Asp Asn Asp Thr Thr Ser Tyr Thr
            180                 185                 190
Leu Thr Ser Cys Asn Thr Ser Val Ile Thr Gln Ala Cys Pro Lys Val
        195                 200                 205
Ser Phe Glu Pro Ile Pro Ile His Tyr Cys Ala Pro Ala Gly Phe Ala
    210                 215                 220
Ile Leu Lys Cys Asn Asn Lys Thr Phe Asn Gly Thr Gly Pro Cys Thr
225                 230                 235                 240
Asn Val Ser Thr Val Gln Cys Thr His Gly Ile Arg Pro Val Val Ser
                245                 250                 255
Thr Gln Leu Leu Leu Asn Gly Ser Leu Ala Glu Glu Val Val Ile
            260                 265                 270
Arg Ser Ala Asn Phe Thr Asp Asn Val Lys Thr Ile Ile Val Gln Leu
        275                 280                 285
Asn Gln Ser Val Glu Ile Asn Cys Thr Lys Pro Asn Asn Asn Thr Gly
    290                 295                 300
Lys Arg Ile Arg Ile Gln Arg Gly Pro Gly Arg Thr Phe Val Thr Ile
305                 310                 315                 320
Gly Lys Ile Gly Asn Met Arg Gln Ala His Cys Asn Ile Ser Arg Ala
                325                 330                 335
Lys Trp Asn Asn Thr Leu Lys Gln Ile Ala Ser Lys Leu Arg Glu Gln
            340                 345                 350
Tyr Gly Asn Asn Lys Thr Ile Ile Phe Lys Gln Ser Ser Gly Gly Asp
        355                 360                 365
Leu Glu Ile Val Thr His Ser Phe Asn Cys Gly Gly Glu Phe Phe Tyr
    370                 375                 380
Cys Asn Ser Thr Gln Leu Phe Asn Ser Thr Trp Phe Asn Ser Thr Gly
385                 390                 395                 400
Ser Asn Asn Thr Glu Gly Ser Asp Thr Ile Thr Leu Pro Cys Arg Ile
                405                 410                 415
Lys Gln Ile Ile Asn Met Trp Gln Glu Val Gly Lys Ala Met Tyr Ala
            420                 425                 430
Pro Pro Ile Ser Gly Gln Ile Arg Cys Ser Ser Asn Ile Thr Gly Leu
        435                 440                 445
```

Leu Leu Thr Arg Asp Gly Gly Asn Asn Asn Gly Ser Glu Ile Phe
450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Lys
                485                 490                 495

Ala Lys Arg Arg Val Val Gln Arg Glu Lys Arg Ala Val Gly Ile Gly
            500                 505                 510

Ala Leu Phe Leu Gly Phe Leu Gly Ala Ala Gly Ser Thr Met Gly Ala
        515                 520                 525

Ala Ser Met Thr Leu Thr Val Gln Ala Arg Gln Leu Leu Ser Gly Ile
    530                 535                 540

Val Gln Gln Gln Asn Asn Leu Leu Arg Ala Ile Glu Ala Gln Gln His
545                 550                 555                 560

Leu Leu Gln Leu Thr Val Trp Gly Ile Lys Gln Leu Gln Ala Arg Ile
                565                 570                 575

Leu Ala Val Glu Arg Tyr Leu Lys Asp Gln Gln Leu Leu Gly Ile Trp
            580                 585                 590

Gly Cys Ser Gly Lys Leu Ile Cys Thr Thr Ala Val Pro Trp Asn Ala
        595                 600                 605

Ser Trp Ser Asn Lys Ser Leu Glu Arg Ile Trp Asn His Thr Thr Trp
    610                 615                 620

Met Glu Trp Asp Arg Glu Ile Asn Asn Tyr Thr Ser Leu Ile His Ser
625                 630                 635                 640

Leu Ile Glu Glu Ser Gln Asn Gln Gln Glu Lys Asn Glu Gln Glu Leu
                645                 650                 655

Leu Glu Leu Asp Lys Trp Ala Ser Leu Trp Asn Trp Phe Asn Ile Thr
            660                 665                 670

Asn Trp Leu Trp Tyr Val Lys Ile Phe Ile Met Ile Val Gly Gly Leu
        675                 680                 685

Val Gly Leu Arg Ile Val Phe Ala Val Leu Ser Ile Val Asn Arg Val
    690                 695                 700

Arg Gln Gly Tyr Ser Pro Leu Ser Phe Gln Thr His Leu Pro Thr Pro
705                 710                 715                 720

Gly Gly Pro Asp Arg Pro Glu Gly Ile Glu Glu Gly Gly Glu Arg
                725                 730                 735

Asp Arg Asp Arg Ser Ile Arg Leu Val Asn Gly Ser
            740                 745

<210> SEQ ID NO 16
<211> LENGTH: 748
<212> TYPE: PRT
<213> ORGANISM: Artificial Sequence
<220> FEATURE:
<223> OTHER INFORMATION: AAA76668 gp160 containing mutation to P at
      position equivalent to position 559 in KNH1144

<400> SEQUENCE: 16

Met Arg Val Lys Glu Lys Tyr Gln His Leu Arg Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60

```
Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
                 85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Gly Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Thr
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Ala Asn Phe Thr Asp Asn Val Lys Thr Ile Ile Val Gln Leu
    275                 280                 285

Asn Gln Ser Val Glu Ile Asn Cys Thr Lys Pro Asn Asn Asn Thr Gly
290                 295                 300

Lys Arg Ile Arg Ile Gln Arg Gly Pro Gly Arg Thr Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Tyr Gly Asn Asn Lys Thr Ile Ile Phe Lys Gln Ser Ser Gly Gly Asp
        355                 360                 365

Leu Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Gly
385                 390                 395                 400

Ser Asn Asn Thr Glu Gly Ser Asp Thr Ile Thr Leu Pro Cys Arg Ile
                405                 410                 415

Lys Gln Ile Ile Asn Met Trp Gln Glu Val Gly Lys Ala Met Tyr Ala
            420                 425                 430

Pro Pro Ile Ser Gly Gln Ile Arg Cys Ser Ser Asn Ile Thr Gly Leu
        435                 440                 445

Leu Leu Thr Arg Asp Gly Gly Asn Asn Asn Gly Ser Glu Ile Phe
    450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Lys
                485                 490                 495
```

Ala Lys Arg Arg Val Val Gln Arg Glu Lys Arg Ala Val Gly Ile Gly
            500                 505                 510

Ala Leu Phe Leu Gly Phe Leu Gly Ala Ala Gly Ser Thr Met Gly Ala
            515                 520                 525

Ala Ser Met Thr Leu Thr Val Gln Ala Arg Gln Leu Leu Ser Gly Ile
            530                 535                 540

Val Gln Gln Asn Asn Leu Leu Arg Ala Pro Glu Ala Gln Gln His
545                 550                 555                 560

Leu Leu Gln Leu Thr Val Trp Gly Ile Lys Gln Leu Gln Ala Arg Ile
            565                 570                 575

Leu Ala Val Glu Arg Tyr Leu Lys Asp Gln Gln Leu Leu Gly Ile Trp
            580                 585                 590

Gly Cys Ser Gly Lys Leu Ile Cys Thr Thr Ala Val Pro Trp Asn Ala
            595                 600                 605

Ser Trp Ser Asn Lys Ser Leu Glu Arg Ile Trp Asn His Thr Thr Trp
            610                 615                 620

Met Glu Trp Asp Arg Glu Ile Asn Asn Tyr Thr Ser Leu Ile His Ser
625                 630                 635                 640

Leu Ile Glu Glu Ser Gln Asn Gln Gln Glu Lys Asn Glu Gln Glu Leu
            645                 650                 655

Leu Glu Leu Asp Lys Trp Ala Ser Leu Trp Asn Trp Phe Asn Ile Thr
            660                 665                 670

Asn Trp Leu Trp Tyr Val Lys Ile Phe Ile Met Ile Val Gly Gly Leu
            675                 680                 685

Val Gly Leu Arg Ile Val Phe Ala Val Leu Ser Ile Val Asn Arg Val
            690                 695                 700

Arg Gln Gly Tyr Ser Pro Leu Ser Phe Gln Thr His Leu Pro Thr Pro
705                 710                 715                 720

Gly Gly Pro Asp Arg Pro Glu Gly Ile Glu Glu Glu Gly Gly Glu Arg
            725                 730                 735

Asp Arg Asp Arg Ser Ile Arg Leu Val Asn Gly Ser
            740                 745

<210> SEQ ID NO 17
<211> LENGTH: 748
<212> TYPE: PRT
<213> ORGANISM: Artificial Sequence
<220> FEATURE:
<223> OTHER INFORMATION: AAA76668 gp160 modified to contain proline (P)
      at position equivalent to amino acid position 559 in KNH1144 and
      the 5 trimer stability enhancing amino acids

<400> SEQUENCE: 17

Met Arg Val Lys Glu Lys Tyr Gln His Leu Arg Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
            50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
            85                  90                  95

Lys Asn Asp Met Val Glu Gln Met His Glu Asp Ile Ile Ser Leu Trp

```
                100             105             110
Asp Gln Ser Leu Lys Pro Cys Val Lys Leu Thr Pro Leu Cys Val Ser
            115                 120                 125
Leu Lys Cys Thr Asp Leu Lys Asn Asp Thr Asn Thr Asn Ser Ser Ser
        130                 135                 140
Gly Gly Met Ile Met Glu Lys Gly Glu Ile Lys Asn Cys Ser Phe Asn
145                 150                 155                 160
Ile Ser Thr Ser Ile Arg Gly Lys Val Gln Lys Glu Tyr Ala Phe Phe
                165                 170                 175
Tyr Lys Leu Asp Ile Ile Pro Ile Asp Asn Asp Thr Thr Ser Tyr Thr
            180                 185                 190
Leu Thr Ser Cys Asn Thr Ser Val Ile Thr Gln Ala Cys Pro Lys Val
        195                 200                 205
Ser Phe Glu Pro Ile Pro Ile His Tyr Cys Ala Pro Ala Gly Phe Ala
    210                 215                 220
Ile Leu Lys Cys Asn Asn Lys Thr Phe Asn Gly Thr Gly Pro Cys Thr
225                 230                 235                 240
Asn Val Ser Thr Val Gln Cys Thr His Gly Ile Arg Pro Val Val Ser
                245                 250                 255
Thr Gln Leu Leu Leu Asn Gly Ser Leu Ala Glu Glu Val Val Ile
            260                 265                 270
Arg Ser Ala Asn Phe Thr Asp Asn Val Lys Thr Ile Ile Val Gln Leu
        275                 280                 285
Asn Gln Ser Val Glu Ile Asn Cys Thr Lys Pro Asn Asn Asn Thr Gly
    290                 295                 300
Lys Arg Ile Arg Ile Gln Arg Gly Pro Gly Arg Thr Phe Val Thr Ile
305                 310                 315                 320
Gly Lys Ile Gly Asn Met Arg Gln Ala His Cys Asn Ile Ser Arg Ala
                325                 330                 335
Lys Trp Asn Asn Thr Leu Lys Gln Ile Ala Ser Lys Leu Arg Glu Gln
            340                 345                 350
Tyr Gly Asn Asn Lys Thr Ile Ile Phe Lys Gln Ser Ser Gly Gly Asp
        355                 360                 365
Leu Glu Ile Val Thr His Ser Phe Asn Cys Gly Gly Glu Phe Phe Tyr
    370                 375                 380
Cys Asn Ser Thr Gln Leu Phe Asn Ser Thr Trp Phe Asn Ser Thr Gly
385                 390                 395                 400
Ser Asn Asn Thr Glu Gly Ser Asp Thr Ile Thr Leu Pro Cys Arg Ile
                405                 410                 415
Lys Gln Ile Ile Asn Met Trp Gln Glu Val Gly Lys Ala Met Tyr Ala
            420                 425                 430
Pro Pro Ile Ser Gly Gln Ile Arg Cys Ser Ser Asn Ile Thr Gly Leu
        435                 440                 445
Leu Leu Thr Arg Asp Gly Gly Asn Asn Asn Gly Ser Glu Ile Phe
    450                 455                 460
Arg Pro Gly Gly Gly Asp Met Arg Asp Asn Trp Arg Ser Glu Leu Tyr
465                 470                 475                 480
Lys Tyr Lys Val Val Lys Ile Glu Pro Leu Gly Val Ala Pro Thr Lys
                485                 490                 495
Ala Lys Arg Arg Val Val Gln Arg Glu Lys Arg Ala Val Gly Ile Gly
            500                 505                 510
Ala Leu Phe Leu Gly Phe Leu Gly Ala Ala Gly Ser Thr Met Gly Ala
        515                 520                 525
```

```
Ala Ser Ile Thr Leu Thr Val Gln Ala Arg Gln Leu Leu Ser Gly Ile
            530                 535                 540

Val Gln Gln Gln Ser Asn Leu Leu Arg Ala Pro Glu Ala Gln Gln His
545                 550                 555                 560

Leu Leu Lys Leu Thr Val Trp Gly Ile Lys Gln Leu Gln Ala Arg Ile
                565                 570                 575

Leu Ala Val Glu Arg Tyr Leu Arg Asp Gln Gln Leu Leu Gly Ile Trp
            580                 585                 590

Gly Cys Ser Gly Lys Leu Ile Cys Thr Thr Ala Val Pro Trp Asn Ala
        595                 600                 605

Ser Trp Ser Asn Lys Ser Leu Glu Arg Ile Trp Asn His Thr Thr Trp
610                 615                 620

Met Glu Trp Asp Arg Glu Ile Asn Asn Tyr Thr Ser Leu Ile His Ser
625                 630                 635                 640

Leu Ile Glu Glu Ser Gln Asn Gln Gln Glu Lys Asn Glu Gln Glu Leu
                645                 650                 655

Leu Glu Leu Asp Lys Trp Ala Ser Leu Trp Asn Trp Phe Asn Ile Thr
            660                 665                 670

Asn Trp Leu Trp Tyr Val Lys Ile Phe Ile Met Ile Val Gly Gly Leu
        675                 680                 685

Val Gly Leu Arg Ile Val Phe Ala Val Leu Ser Ile Val Asn Arg Val
    690                 695                 700

Arg Gln Gly Tyr Ser Pro Leu Ser Phe Gln Thr His Leu Pro Thr Pro
705                 710                 715                 720

Gly Gly Pro Asp Arg Pro Glu Gly Ile Glu Glu Glu Gly Gly Glu Arg
                725                 730                 735

Asp Arg Asp Arg Ser Ile Arg Leu Val Asn Gly Ser
            740                 745
```

<210> SEQ ID NO 18
<211> LENGTH: 356
<212> TYPE: PRT
<213> ORGANISM: Artificial Sequence
<220> FEATURE:
<223> OTHER INFORMATION: KNH1144 gp41

<400> SEQUENCE: 18

```
Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Ile Thr Leu Thr Val
            20                  25                  30

Gln Ala Arg Gln Leu Leu Ser Gly Ile Val Gln Gln Gln Ser Asn Leu
        35                  40                  45

Leu Arg Ala Ile Glu Ala Gln Gln His Met Leu Lys Leu Thr Val Trp
    50                  55                  60

Gly Ile Lys Gln Leu Gln Ala Arg Val Leu Ala Val Glu Arg Tyr Leu
65                  70                  75                  80

Arg Asp Gln Gln Leu Leu Gly Ile Trp Gly Cys Ser Gly Lys Leu Ile
                85                  90                  95

Cys Thr Thr Asn Val Pro Trp Asn Ser Ser Trp Ser Asn Lys Ser His
            100                 105                 110

Asp Glu Ile Trp Asn Asn Met Thr Trp Leu Gln Trp Asp Lys Glu Ile
        115                 120                 125

Ser Asn Tyr Thr Asn Leu Ile Tyr Ser Leu Ile Glu Glu Ser Gln Asn
    130                 135                 140

Gln Gln Glu Lys Asn Glu Gln Asp Leu Leu Ala Leu Asp Lys Trp Ala
```

-continued

```
                145                 150                 155                 160
Ser Leu Trp Asn Trp Phe Asp Ile Ser Lys Trp Leu Trp Tyr Ile Lys
                165                 170                 175

Ile Phe Ile Met Ile Val Gly Gly Leu Ile Gly Leu Arg Ile Val Phe
            180                 185                 190

Ala Val Leu Ala Val Ile Lys Arg Val Arg Gln Gly Tyr Ser Pro Val
            195                 200                 205

Ser Phe Gln Ile His Asn Pro Asn Pro Gly Gly Leu Asp Arg Pro Gly
    210                 215                 220

Arg Ile Glu Glu Glu Gly Gly Glu Pro Gly Arg Gly Arg Ser Ile Arg
225                 230                 235                 240

Leu Val Ser Gly Phe Leu Ala Leu Ala Trp Asp Asp Leu Arg Asn Leu
                245                 250                 255

Cys Leu Phe Ser Tyr His Arg Leu Arg Asp Phe Ala Leu Ile Val Ala
                260                 265                 270

Arg Thr Val Glu Leu Leu Gly His Ser Ser Leu Lys Gly Leu Arg Leu
            275                 280                 285

Gly Trp Glu Gly Leu Lys Tyr Leu Trp Asn Leu Leu Val Tyr Trp Ser
            290                 295                 300

Gln Glu Leu Lys Thr Ser Ala Ile Asn Leu Val Asp Thr Ile Ala Ile
305                 310                 315                 320

Ala Val Ala Gly Trp Thr Asp Arg Val Ile Glu Ile Gly Gln Gly Ile
                325                 330                 335

Gly Arg Ala Phe Leu His Ile Pro Arg Arg Ile Arg Gln Gly Leu Glu
                340                 345                 350

Arg Ala Leu Leu
        355

<210> SEQ ID NO 19
<211> LENGTH: 356
<212> TYPE: PRT
<213> ORGANISM: Artificial Sequence
<220> FEATURE:
<223> OTHER INFORMATION: KNH1144 gp41 containing mutation to proline (P)
      at position equivalent to amino acid position 559 in KNH1144

<400> SEQUENCE: 19

Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Ile Thr Leu Thr Val
            20                  25                  30

Gln Ala Arg Gln Leu Leu Ser Gly Ile Val Gln Gln Gln Ser Asn Leu
        35                  40                  45

Leu Arg Ala Pro Glu Ala Gln Gln His Met Leu Lys Leu Thr Val Trp
    50                  55                  60

Gly Ile Lys Gln Leu Gln Ala Arg Val Leu Ala Val Glu Arg Tyr Leu
65                  70                  75                  80

Arg Asp Gln Gln Leu Leu Gly Ile Trp Gly Cys Ser Gly Lys Leu Ile
                85                  90                  95

Cys Thr Thr Asn Val Pro Trp Asn Ser Ser Trp Ser Asn Lys Ser His
            100                 105                 110

Asp Glu Ile Trp Asn Asn Met Thr Trp Leu Gln Trp Asp Lys Glu Ile
        115                 120                 125

Ser Asn Tyr Thr Asn Leu Ile Tyr Ser Leu Ile Glu Glu Ser Gln Asn
    130                 135                 140

Gln Gln Glu Lys Asn Glu Gln Asp Leu Leu Ala Leu Asp Lys Trp Ala
```

-continued

```
                145                 150                 155                 160
Ser Leu Trp Asn Trp Phe Asp Ile Ser Lys Trp Leu Trp Tyr Ile Lys
                    165                 170                 175

Ile Phe Ile Met Ile Val Gly Gly Leu Ile Gly Leu Arg Ile Val Phe
                180                 185                 190

Ala Val Leu Ala Val Ile Lys Arg Val Arg Gln Gly Tyr Ser Pro Val
            195                 200                 205

Ser Phe Gln Ile His Asn Pro Asn Pro Gly Gly Leu Asp Arg Pro Gly
        210                 215                 220

Arg Ile Glu Glu Glu Gly Gly Glu Pro Gly Arg Gly Arg Ser Ile Arg
225                 230                 235                 240

Leu Val Ser Gly Phe Leu Ala Leu Ala Trp Asp Asp Leu Arg Asn Leu
                245                 250                 255

Cys Leu Phe Ser Tyr His Arg Leu Arg Asp Phe Ala Leu Ile Val Ala
                260                 265                 270

Arg Thr Val Glu Leu Leu Gly His Ser Ser Leu Lys Gly Leu Arg Leu
            275                 280                 285

Gly Trp Glu Gly Leu Lys Tyr Leu Trp Asn Leu Leu Val Tyr Trp Ser
        290                 295                 300

Gln Glu Leu Lys Thr Ser Ala Ile Asn Leu Val Asp Thr Ile Ala Ile
305                 310                 315                 320

Ala Val Ala Gly Trp Thr Asp Arg Val Ile Glu Ile Gly Gln Gly Ile
                325                 330                 335

Gly Arg Ala Phe Leu His Ile Pro Arg Arg Ile Arg Gln Gly Leu Glu
            340                 345                 350

Arg Ala Leu Leu
        355

<210> SEQ ID NO 20
<211> LENGTH: 356
<212> TYPE: PRT
<213> ORGANISM: Artificial Sequence
<220> FEATURE:
<223> OTHER INFORMATION: KNH1144 gp41 containing I535M mutation

<400> SEQUENCE: 20

Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Ile Thr Leu Thr Val
                20                  25                  30

Gln Ala Arg Gln Leu Leu Ser Gly Ile Val Gln Gln Gln Ser Asn Leu
            35                  40                  45

Leu Arg Ala Ile Glu Ala Gln Gln His Met Leu Lys Leu Thr Val Trp
        50                  55                  60

Gly Ile Lys Gln Leu Gln Ala Arg Val Leu Ala Val Glu Arg Tyr Leu
65                  70                  75                  80

Arg Asp Gln Gln Leu Leu Gly Ile Trp Gly Cys Ser Gly Lys Leu Ile
                85                  90                  95

Cys Thr Thr Asn Val Pro Trp Asn Ser Ser Trp Ser Asn Lys Ser His
                100                 105                 110

Asp Glu Ile Trp Asn Asn Met Thr Trp Leu Gln Trp Asp Lys Glu Ile
            115                 120                 125

Ser Asn Tyr Thr Asn Leu Ile Tyr Ser Leu Ile Glu Glu Ser Gln Asn
        130                 135                 140

Gln Gln Glu Lys Asn Glu Gln Asp Leu Leu Ala Leu Asp Lys Trp Ala
145                 150                 155                 160
```

```
Ser Leu Trp Asn Trp Phe Asp Ile Ser Lys Trp Leu Trp Tyr Ile Lys
            165                 170                 175

Ile Phe Ile Met Ile Val

```
                    145                 150                 155                 160
Ser Leu Trp Asn Trp Phe Asp Ile Ser Lys Trp Leu Trp Tyr Ile Lys
                165                 170                 175

Ile Phe Ile Met Ile Val Gly Gly Leu Ile Gly Leu Arg Ile Val Phe
            180                 185                 190

Ala Val Leu Ala Val Ile Lys Arg Val Arg Gln Gly Tyr Ser Pro Val
        195                 200                 205

Ser Phe Gln Ile His Asn Pro Asn Pro Gly Gly Leu Asp Arg Pro Gly
    210                 215                 220

Arg Ile Glu Glu Glu Gly Gly Glu Pro Gly Arg Gly Arg Ser Ile Arg
225                 230                 235                 240

Leu Val Ser Gly Phe Leu Ala Leu Ala Trp Asp Asp Leu Arg Asn Leu
                245                 250                 255

Cys Leu Phe Ser Tyr His Arg Leu Arg Asp Phe Ala Leu Ile Val Ala
            260                 265                 270

Arg Thr Val Glu Leu Leu Gly His Ser Ser Leu Lys Gly Leu Arg Leu
        275                 280                 285

Gly Trp Glu Gly Leu Lys Tyr Leu Trp Asn Leu Leu Val Tyr Trp Ser
    290                 295                 300

Gln Glu Leu Lys Thr Ser Ala Ile Asn Leu Val Asp Thr Ile Ala Ile
305                 310                 315                 320

Ala Val Ala Gly Trp Thr Asp Arg Val Ile Glu Ile Gly Gln Gly Ile
                325                 330                 335

Gly Arg Ala Phe Leu His Ile Pro Arg Arg Ile Arg Gln Gly Leu Glu
            340                 345                 350

Arg Ala Leu Leu
        355

<210> SEQ ID NO 22
<211> LENGTH: 349
<212> TYPE: PRT
<213> ORGANISM: Artificial Sequence
<220> FEATURE:
<223> OTHER INFORMATION: JR-FL gp41

<400> SEQUENCE: 22

Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Met Thr Leu Thr Val
            20                  25                  30

Gln Ala Arg Leu Leu Leu Ser Gly Ile Val Gln Gln Asn Asn Leu
        35                  40                  45

Leu Arg Ala Ile Glu Ala Gln Gln Arg Met Leu Gln Leu Thr Val Trp
    50                  55                  60

Gly Ile Lys Gln Leu Gln Ala Arg Val Leu Ala Val Glu Arg Tyr Leu
65                  70                  75                  80

Gly Asp Gln Gln Leu Leu Gly Ile Trp Gly Cys Ser Gly Lys Leu Ile
                85                  90                  95

Cys Thr Thr Ala Val Pro Trp Asn Ala Ser Trp Ser Asn Lys Ser Leu
            100                 105                 110

Asp Arg Ile Trp Asn Asn Met Thr Trp Met Glu Trp Glu Arg Glu Ile
        115                 120                 125

Asp Asn Tyr Thr Ser Glu Ile Tyr Thr Leu Ile Glu Glu Ser Gln Asn
    130                 135                 140

Gln Gln Glu Lys Asn Glu Gln Glu Leu Leu Glu Leu Asp Lys Trp Ala
145                 150                 155                 160
```

Ser Leu Trp Asn Trp Phe Asp Ile Thr Lys Trp Leu Trp Tyr Ile Lys
            165                 170                 175

Ile Phe Ile Met Ile Val Gly Gly Leu Val Gly Leu Arg Leu Val Phe
            180                 185                 190

Thr Val Leu Ser Ile Val Asn Arg Val Arg Gln Gly Tyr Ser Pro Leu
            195                 200                 205

Ser Phe Gln Thr Leu Leu Pro Ala Pro Arg Gly Pro Asp Arg Pro Glu
    210                 215                 220

Gly Ile Glu Glu Glu Gly Gly Glu Arg Asp Arg Asp Arg Ser Gly Arg
225                 230                 235                 240

Leu Val Asn Gly Phe Leu Ala Leu Ile Trp Val Asp Leu Arg Ser Leu
                245                 250                 255

Cys Leu Phe Ser Tyr His Arg Leu Arg Asp Leu Leu Leu Thr Val Thr
                260                 265                 270

Arg Ile Val Glu Leu Leu Gly Arg Arg Gly Trp Glu Val Leu Lys Tyr
            275                 280                 285

Trp Trp Asn Leu Leu Gln Tyr Trp Ser Gln Glu Leu Lys Asn Ser Ala
    290                 295                 300

Val Ser Leu Leu Asn Ala Thr Ala Ile Ala Val Ala Glu Gly Thr Asp
305                 310                 315                 320

Arg Ile Ile Glu Ala Leu Gln Arg Thr Tyr Arg Ala Ile Leu His Ile
                325                 330                 335

Pro Thr Arg Ile Arg Gln Gly Leu Glu Arg Ala Leu Leu
                340                 345

<210> SEQ ID NO 23
<211> LENGTH: 349
<212> TYPE: PRT
<213> ORGANISM: Artificial Sequence
<220> FEATURE:
<223> OTHER INFORMATION: JR-FL gp41 containing mutation to proline (P)
      at position equivalent to amino acid position 559 in KNH1144

<400> SEQUENCE: 23

Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Met Thr Leu Thr Val
            20                  25                  30

Gln Ala Arg Leu Leu Leu Ser Gly Ile Val Gln Gln Gln Asn Asn Leu
        35                  40                  45

Leu Arg Ala Pro Glu Ala Gln Gln Arg Met Leu Gln Leu Thr Val Trp
    50                  55                  60

Gly Ile Lys Gln Leu Gln Ala Arg Val Leu Ala Val Glu Arg Tyr Leu
65                  70                  75                  80

Gly Asp Gln Gln Leu Leu Gly Ile Trp Gly Cys Ser Gly Lys Leu Ile
                85                  90                  95

Cys Thr Thr Ala Val Pro Trp Asn Ala Ser Trp Ser Asn Lys Ser Leu
            100                 105                 110

Asp Arg Ile Trp Asn Asn Met Thr Trp Met Glu Trp Glu Arg Glu Ile
        115                 120                 125

Asp Asn Tyr Thr Ser Glu Ile Tyr Thr Leu Ile Glu Glu Ser Gln Asn
    130                 135                 140

Gln Gln Glu Lys Asn Glu Gln Glu Leu Leu Glu Leu Asp Lys Trp Ala
145                 150                 155                 160

Ser Leu Trp Asn Trp Phe Asp Ile Thr Lys Trp Leu Trp Tyr Ile Lys
                165                 170                 175

```
Ile Phe Ile Met Ile Val Gly Gly Leu Val Gly Leu Arg Leu Val Phe
                180                 185                 190

Thr Val Leu Ser Ile Val Asn Arg Val Arg Gln Gly Tyr Ser Pro Leu
            195                 200                 205

Ser Phe Gln Thr Leu Leu Pro Ala Pro Arg Gly Pro Asp Arg Pro Glu
        210                 215                 220

Gly Ile Glu Glu Glu Gly Gly Glu Arg Asp Arg Asp Arg Ser Gly Arg
225                 230                 235                 240

Leu Val Asn Gly Phe Leu Ala Leu Ile Trp Val Asp Leu Arg Ser Leu
                245                 250                 255

Cys Leu Phe Ser Tyr His Arg Leu Arg Asp Leu Leu Leu Thr Val Thr
            260                 265                 270

Arg Ile Val Glu Leu Leu Gly Arg Arg Gly Trp Glu Val Leu Lys Tyr
        275                 280                 285

Trp Trp Asn Leu Leu Gln Tyr Trp Ser Gln Glu Leu Lys Asn Ser Ala
290                 295                 300

Val Ser Leu Leu Asn Ala Thr Ala Ile Ala Val Ala Glu Gly Thr Asp
305                 310                 315                 320

Arg Ile Ile Glu Ala Leu Gln Arg Thr Tyr Arg Ala Ile Leu His Ile
                325                 330                 335

Pro Thr Arg Ile Arg Gln Gly Leu Glu Arg Ala Leu Leu
            340                 345

<210> SEQ ID NO 24
<211> LENGTH: 349
<212> TYPE: PRT
<213> ORGANISM: Artificial Sequence
<220> FEATURE:
<223> OTHER INFORMATION: JR-FL gp41 containing mutation to proline (P)
      at position equivalent to amino acid position 559 in KNH1144 and
      the 5 trimer stability enhancing amino acids of the invention

<400> SEQUENCE: 24

Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Ile Thr Leu Thr Val
                20                  25                  30

Gln Ala Arg Gln Leu Leu Ser Gly Ile Val Gln Gln Gln Ser Asn Leu
            35                  40                  45

Leu Arg Ala Pro Glu Ala Gln Gln Arg Met Leu Lys Leu Thr Val Trp
        50                  55                  60

Gly Ile Lys Gln Leu Gln Ala Arg Val Leu Ala Val Glu Arg Tyr Leu
65                  70                  75                  80

Arg Asp Gln Gln Leu Leu Gly Ile Trp Gly Cys Ser Gly Lys Leu Ile
                85                  90                  95

Cys Thr Thr Ala Val Pro Trp Asn Ala Ser Trp Ser Asn Lys Ser Leu
            100                 105                 110

Asp Arg Ile Trp Asn Asn Met Thr Trp Met Glu Trp Glu Arg Glu Ile
        115                 120                 125

Asp Asn Tyr Thr Ser Glu Ile Tyr Thr Leu Ile Glu Glu Ser Gln Asn
130                 135                 140

Gln Gln Glu Lys Asn Glu Gln Glu Leu Leu Glu Leu Asp Lys Trp Ala
145                 150                 155                 160

Ser Leu Trp Asn Trp Phe Asp Ile Thr Lys Trp Leu Trp Tyr Ile Lys
                165                 170                 175

Ile Phe Ile Met Ile Val Gly Gly Leu Val Gly Leu Arg Leu Val Phe
```

```
                180             185             190
Thr Val Leu Ser Ile Val Asn Arg Val Arg Gln Gly Tyr Ser Pro Leu
            195                 200                 205
Ser Phe Gln Thr Leu Leu Pro Ala Pro Arg Gly Pro Asp Arg Pro Glu
        210                 215                 220
Gly Ile Glu Glu Glu Gly Glu Arg Asp Arg Asp Arg Ser Gly Arg
225                 230                 235                 240
Leu Val Asn Gly Phe Leu Ala Leu Ile Trp Val Asp Leu Arg Ser Leu
                245                 250                 255
Cys Leu Phe Ser Tyr His Arg Leu Arg Asp Leu Leu Leu Thr Val Thr
            260                 265                 270
Arg Ile Val Glu Leu Leu Gly Arg Arg Gly Trp Glu Val Leu Lys Tyr
            275                 280                 285
Trp Trp Asn Leu Leu Gln Tyr Trp Ser Gln Glu Leu Lys Asn Ser Ala
        290                 295                 300
Val Ser Leu Leu Asn Ala Thr Ala Ile Ala Val Ala Glu Gly Thr Asp
305                 310                 315                 320
Arg Ile Ile Glu Ala Leu Gln Arg Thr Tyr Arg Ala Ile Leu His Ile
                325                 330                 335
Pro Thr Arg Ile Arg Gln Gly Leu Glu Arg Ala Leu Leu
                340                 345

<210> SEQ ID NO 25
<211> LENGTH: 349
<212> TYPE: PRT
<213> ORGANISM: Artificial Sequence
<220> FEATURE:
<223> OTHER INFORMATION: Ba-L gp41
<220> FEATURE:
<221> NAME/KEY: MISC_FEATURE
<222> LOCATION: (170)..(326)
<223> OTHER INFORMATION: X=Any AA

<400> SEQUENCE: 25

Arg Glu Lys Arg Ala Val Gly Ile Gly Ala Val Phe Leu Gly Phe Leu
1               5                   10                  15
Gly Ala Ala Gly Ser Thr Met Gly Ala Ala Ser Met Thr Leu Thr Val
            20                  25                  30
Gln Ala Arg Leu Leu Leu Ser Gly Ile Val Gln Gln Gln Asn Asn Leu
        35                  40                  45
Leu Arg Ala Ile Glu Ala Gln Gln His Leu Leu Gln Leu Thr Val Trp
    50                  55                  60
Gly Ile Lys Gln Leu Gln Ala Arg Val Leu Ala Val Glu Arg Tyr Leu
65                  70                  75                  80
Arg Asp Gln Gln Leu Leu Gly Ile Trp Gly Cys Ser Gly Lys Leu Ile
                85                  90                  95
Cys Thr Thr Ala Val Pro Trp Asn Ala Ser Trp Ser Asn Lys Ser Leu
            100                 105                 110
Asn Lys Ile Trp Asp Asn Met Thr Trp Met Glu Trp Asp Arg Glu Ile
        115                 120                 125
Asn Asn Tyr Thr Ser Ile Ile Tyr Ser Leu Ile Glu Glu Ser Gln Asn
    130                 135                 140
Gln Gln Glu Lys Asn Glu Gln Glu Leu Leu Glu Leu Asp Lys Trp Ala
145                 150                 155                 160
Ser Leu Trp Asn Trp Phe Asp Ile Thr Xaa Trp Leu Trp Tyr Ile Lys
                165                 170                 175
Ile Phe Ile Met Ile Val Gly Gly Leu Ile Gly Leu Arg Ile Val Phe
```

-continued

```
                        180                 185                 190
Ser Val Leu Ser Ile Val Asn Arg Val Arg Gln

-continued

```
Ile Phe Ile Met Ile Val Gly Gly Leu Ile Gly Leu Arg Ile Val Phe
                180                 185                 190
Ser Val Leu Ser Ile Val Asn Arg Val Arg Gln Gly Tyr Ser Pro Leu
            195                 200                 205
Ser Phe Gln Thr His Leu Pro Ala Ser Arg Gly Pro Asp Arg Pro Gly
        210                 215                 220
Gly Ile Glu Glu Glu Gly Gly Glu Arg Asp Arg Asp Arg Ser Gly Pro
225                 230                 235                 240
Leu Val Asn Gly Phe Leu Xaa Leu Ile Trp Val Asp Leu Arg Ser Leu
                245                 250                 255
Xaa Leu Phe Ser Tyr His Arg Leu Arg Asp Leu Leu Leu Ile Val Thr
            260                 265                 270
Arg Ile Val Glu Leu Leu Gly Arg Arg Gly Trp Glu Val Leu Lys Tyr
        275                 280                 285
Trp Trp Xaa Leu Leu Gln Tyr Trp Ser Gln Glu Leu Lys Asn Ser Ala
                290                 295                 300
Val Ser Leu Leu Asn Xaa Xaa Ala Xaa Ala Val Ala Glu Gly Thr Asp
305                 310                 315                 320
Arg Val Ile Glu Val Xaa Gln Arg Ala Val Arg Ala Ile Leu His Ile
                325                 330                 335
Pro Arg Arg Ile Arg Gln Gly Leu Glu Arg Ala Leu Leu
            340                 345
```

<210> SEQ ID NO 27
<211> LENGTH: 349
<212> TYPE: PRT
<213> ORGANISM: Artificial Sequence
<220> FEATURE:
<223> OTHER INFORMATION: Ba-L gp41 containing mutation to proline (P) at
      position equivalent to amino acid position 559 in KNH1144 and the
      5 trimer stability enhancing amino acids of the invention
<220> FEATURE:
<221> NAME/KEY: MISC_FEATURE
<222> LOCATION: (170)..(326)
<223> OTHER INFORMATION: X=Any AA

<400> SEQUENCE: 27

```
Arg Glu Lys Arg Ala Val Gly Ile Gly Ala Val Phe Leu Gly Phe Leu
1               5                   10                  15
Gly Ala Ala Gly Ser Thr Met Gly Ala Ala Ser Ile Thr Leu Thr Val
                20                  25                  30
Gln Ala Arg Gln Leu Leu Ser Gly Ile Val Gln Gln Ser Asn Leu
            35                  40                  45
Leu Arg Ala Pro Glu Ala Gln Gln His Leu Leu Lys Leu Thr Val Trp
    50                  55                  60
Gly Ile Lys Gln Leu Gln Ala Arg Val Leu Ala Val Glu Arg Tyr Leu
65                  70                  75                  80
Arg Asp Gln Gln Leu Leu Gly Ile Trp Gly Cys Ser Gly Lys Leu Ile
                85                  90                  95
Cys Thr Thr Ala Val Pro Trp Asn Ala Ser Trp Ser Asn Lys Ser Leu
            100                 105                 110
Asn Lys Ile Trp Asp Asn Met Thr Trp Met Glu Trp Asp Arg Glu Ile
        115                 120                 125
Asn Asn Tyr Thr Ser Ile Ile Tyr Ser Leu Ile Glu Glu Ser Gln Asn
    130                 135                 140
Gln Gln Glu Lys Asn Glu Gln Glu Leu Leu Glu Leu Asp Lys Trp Ala
145                 150                 155                 160
Ser Leu Trp Asn Trp Phe Asp Ile Thr Xaa Trp Leu Trp Tyr Ile Lys
```

```
                165                 170                 175
Ile Phe Ile Met Ile Val Gly Gly Leu Ile Gly Leu Arg Ile Val Phe
            180                 185                 190

Ser Val Leu Ser Ile Val Asn Arg Val Arg Gln Gly Tyr Ser Pro Leu
            195                 200                 205

Ser Phe Gln Thr His Leu Pro Ala Ser Arg Gly Pro Asp Arg Pro Gly
        210                 215                 220

Gly Ile Glu Glu Gly Gly Glu Arg Asp Arg Asp Arg Ser Gly Pro
225                 230                 235                 240

Leu Val Asn Gly Phe Leu Xaa Leu Ile Trp Val Asp Leu Arg Ser Leu
                245                 250                 255

Xaa Leu Phe Ser Tyr His Arg Leu Arg Asp Leu Leu Leu Ile Val Thr
            260                 265                 270

Arg Ile Val Glu Leu Leu Gly Arg Arg Gly Trp Glu Val Leu Lys Tyr
            275                 280                 285

Trp Trp Xaa Leu Leu Gln Tyr Trp Ser Gln Glu Leu Lys Asn Ser Ala
            290                 295                 300

Val Ser Leu Leu Asn Xaa Xaa Ala Xaa Ala Val Ala Glu Gly Thr Asp
305                 310                 315                 320

Arg Val Ile Glu Val Xaa Gln Arg Ala Val Arg Ala Ile Leu His Ile
                325                 330                 335

Pro Arg Arg Ile Arg Gln Gly Leu Glu Arg Ala Leu Leu
            340                 345

<210> SEQ ID NO 28
<211> LENGTH: 358
<212> TYPE: PRT
<213> ORGANISM: Artificial Sequence
<220> FEATURE:
<223> OTHER INFORMATION: S21998 gp41
<220> FEATURE:
<221> NAME/KEY: MISC_FEATURE
<222> LOCATION: (349)..(349)
<223> OTHER INFORMATION: X=Any AA

<400> SEQUENCE: 28

Lys Ala Lys Arg Arg Val Val Gln Arg Glu Lys Arg Ala Val Gly Met
1               5                   10                  15

Gly Ala Ala Phe Phe Leu Gly Phe Leu Gly Ala Ala Gly Ser Thr Met
            20                  25                  30

Gly Ala Ala Ser Leu Thr Leu Thr Val Gln Ala Arg Leu Leu Leu Ser
        35                  40                  45

Gly Ile Val Gln Gln Gln Asn Asn Leu Leu Arg Ala Ile Glu Ala His
    50                  55                  60

Glu His Leu Leu Gln Leu Thr Val Trp Gly Ile Lys Gln Leu Gln Ala
65                  70                  75                  80

Arg Ile Leu Ala Val Glu Arg Tyr Leu Lys Asp Gln Gln Leu Leu Gly
                85                  90                  95

Ile Trp Gly Cys Ser Gly Lys Leu Ile Cys Thr Thr Thr Val Pro Trp
            100                 105                 110

Asn Ala Ser Trp Ser Asn Lys Ser Leu Asp Lys Ile Trp Asn Asn Met
        115                 120                 125

Thr Trp Met Glu Trp Asp Arg Glu Ile Asn Asn Tyr Thr Ser Leu Ile
    130                 135                 140

Tyr Thr Leu Ile Glu Gln Ser Gln Asn Gln Glu Lys Asn Glu Gln
145                 150                 155                 160

Glu Leu Leu Glu Leu Asp Lys Trp Ala Ser Leu Trp Asn Trp Phe Asp
```

```
                        165                 170                 175
Ile Thr Gln Trp Leu Trp Tyr Ile Lys Ile Phe Ile Met Ile Val Gly
                180                 185                 190

Gly Leu Ile Gly Leu Arg Ile Val Phe Thr Val Leu Ser Ile Val Asn
            195                 200                 205

Arg Val Arg Gln Gly Tyr Ser Pro Leu Ser Phe Gln Thr Arg Arg Pro
        210                 215                 220

Ala Arg Arg Gly Pro Asp Arg Pro Glu Gly Ile Glu Glu Gly Gly
225                 230                 235                 240

Glu Arg Asp Arg Asp Arg Ser Gly Arg Leu Val Asn Gly Phe Leu Ala
                245                 250                 255

Leu Ile Trp Asp Asp Leu Arg Ser Leu Cys Leu Phe Ser Tyr His Arg
            260                 265                 270

Leu Arg Asp Leu Leu Leu Ile Val Thr Arg Ile Val Glu Leu Leu Gly
        275                 280                 285

Arg Arg Gly Trp Glu Val Leu Lys Tyr Leu Trp Asn Leu Leu Gln Tyr
    290                 295                 300

Trp Ser Gln Glu Leu Lys Asn Ser Ala Val Ser Leu Leu Asn Ala Thr
305                 310                 315                 320

Ala Ile Ala Val Ala Glu Gly Thr Asp Arg Val Ile Glu Leu Leu Gln
                325                 330                 335

Arg Ala Phe Arg Ala Ile Leu His Ile Pro Arg Arg Xaa Arg Gln Gly
            340                 345                 350

Leu Glu Arg Ala Leu Leu
        355

<210> SEQ ID NO 29
<211> LENGTH: 358
<212> TYPE: PRT
<213> ORGANISM: Artificial Sequence
<220> FEATURE:
<223> OTHER INFORMATION: S21998 gp41 containing mutation to proline (P)
      at position equivalent to amino acid position 559 in KNH1144
<220> FEATURE:
<221> NAME/KEY: MISC_FEATURE
<222> LOCATION: (349)..(349)
<223> OTHER INFORMATION: X=Any AA

<400> SEQUENCE: 29

Lys Ala Lys Arg Arg Val Val Gln Arg Glu Lys Arg Ala Val Gly Met
1               5                   10                  15

Gly Ala Ala Phe Phe Leu Gly Phe Leu Gly Ala Ala Gly Ser Thr Met
            20                  25                  30

Gly Ala Ala Ser Leu Thr Leu Thr Val Gln Ala Arg Leu Leu Leu Ser
        35                  40                  45

Gly Ile Val Gln Gln Gln Asn Asn Leu Leu Arg Ala Pro Glu Ala His
    50                  55                  60

Glu His Leu Leu Gln Leu Thr Val Trp Gly Ile Lys Gln Leu Gln Ala
65                  70                  75                  80

Arg Ile Leu Ala Val Glu Arg Tyr Leu Lys Asp Gln Gln Leu Leu Gly
                85                  90                  95

Ile Trp Gly Cys Ser Gly Lys Leu Ile Cys Thr Thr Val Pro Trp
            100                 105                 110

Asn Ala Ser Trp Ser Asn Lys Ser Leu Asp Lys Ile Trp Asn Asn Met
        115                 120                 125

Thr Trp Met Glu Trp Asp Arg Glu Ile Asn Asn Tyr Thr Ser Leu Ile
    130                 135                 140
```

```
Tyr Thr Leu Ile Glu Gln Ser Gln Asn Gln Gln Lys Asn Glu Gln
145                 150                 155                 160

Glu Leu Leu Glu Leu Asp Lys Trp Ala Ser Leu Trp Asn Trp Phe Asp
            165                 170                 175

Ile Thr Gln Trp Leu Trp Tyr Ile Lys Ile Phe Ile Met Ile Val Gly
            180                 185                 190

Gly Leu Ile Gly Leu Arg Ile Val Phe Thr Val Leu Ser Ile Val Asn
            195                 200                 205

Arg Val Arg Gln Gly Tyr Ser Pro Leu Ser Phe Gln Thr Arg Arg Pro
210                 215                 220

Ala Arg Arg Gly Pro Asp Arg Pro Glu Gly Ile Glu Glu Gly Gly
225                 230                 235                 240

Glu Arg Asp Arg Asp Arg Ser Gly Arg Leu Val Asn Gly Phe Leu Ala
                245                 250                 255

Leu Ile Trp Asp Asp Leu Arg Ser Leu Cys Leu Phe Ser Tyr His Arg
            260                 265                 270

Leu Arg Asp Leu Leu Leu Ile Val Thr Arg Ile Val Glu Leu Leu Gly
            275                 280                 285

Arg Arg Gly Trp Glu Val Leu Lys Tyr Leu Trp Asn Leu Leu Gln Tyr
290                 295                 300

Trp Ser Gln Glu Leu Lys Asn Ser Ala Val Ser Leu Leu Asn Ala Thr
305                 310                 315                 320

Ala Ile Ala Val Ala Glu Gly Thr Asp Arg Val Ile Glu Leu Leu Gln
                325                 330                 335

Arg Ala Phe Arg Ala Ile Leu His Ile Pro Arg Arg Xaa Arg Gln Gly
            340                 345                 350

Leu Glu Arg Ala Leu Leu
        355

<210> SEQ ID NO 30
<211> LENGTH: 358
<212> TYPE: PRT
<213> ORGANISM: Artificial Sequence
<220> FEATURE:
<223> OTHER INFORMATION: S21998 gp41 containing mutation to proline (P)
      at position equivalent to amino acid position 559 in KNH1144 and
      the 5 trimer stability enhancing amino acids of the invention
<220> FEATURE:
<221> NAME/KEY: MISC_FEATURE
<222> LOCATION: (349)..(349)
<223> OTHER INFORMATION: X=Any AA

<400> SEQUENCE: 30

Lys Ala Lys Arg Arg Val Val Gln Arg Glu Lys Arg Ala Val Gly Met
1               5                   10                  15

Gly Ala Ala Phe Phe Leu Gly Phe Leu Gly Ala Ala Gly Ser Thr Met
            20                  25                  30

Gly Ala Ala Ser Ile Thr Leu Thr Val Gln Ala Arg Gln Leu Leu Ser
            35                  40                  45

Gly Ile Val Gln Gln Gln Ser Asn Leu Leu Arg Ala Pro Glu Ala His
        50                  55                  60

Glu His Leu Leu Lys Leu Thr Val Trp Gly Ile Lys Gln Leu Gln Ala
65                  70                  75                  80

Arg Ile Leu Ala Val Glu Arg Tyr Leu Arg Asp Gln Gln Leu Leu Gly
                85                  90                  95

Ile Trp Gly Cys Ser Gly Lys Leu Ile Cys Thr Thr Thr Val Pro Trp
            100                 105                 110

Asn Ala Ser Trp Ser Asn Lys Ser Leu Asp Lys Ile Trp Asn Asn Met
```

```
            115                 120                 125
Thr Trp Met Glu Trp Asp Arg Glu Ile Asn Asn Tyr Thr Ser Leu Ile
130                 135                 140

Tyr Thr Leu Ile Glu Gln Ser Gln Asn Gln Gln Glu Lys Asn Glu Gln
145                 150                 155                 160

Glu Leu Leu Glu Leu Asp Lys Trp Ala Ser Leu Trp Asn Trp Phe Asp
                165                 170                 175

Ile Thr Gln Trp Leu Trp Tyr Ile Lys Ile Phe Ile Met Ile Val Gly
            180                 185                 190

Gly Leu Ile Gly Leu Arg Ile Val Phe Thr Val Leu Ser Ile Val Asn
        195                 200                 205

Arg Val Arg Gln Gly Tyr Ser Pro Leu Ser Phe Gln Thr Arg Arg Pro
    210                 215                 220

Ala Arg Arg Gly Pro Asp Arg Pro Glu Gly Ile Glu Glu Glu Gly Gly
225                 230                 235                 240

Glu Arg Asp Arg Asp Arg Ser Gly Arg Leu Val Asn Gly Phe Leu Ala
                245                 250                 255

Leu Ile Trp Asp Asp Leu Arg Ser Leu Cys Leu Phe Ser Tyr His Arg
            260                 265                 270

Leu Arg Asp Leu Leu Leu Ile Val Thr Arg Ile Val Glu Leu Leu Gly
        275                 280                 285

Arg Arg Gly Trp Glu Val Leu Lys Tyr Leu Trp Asn Leu Leu Gln Tyr
    290                 295                 300

Trp Ser Gln Glu Leu Lys Asn Ser Ala Val Ser Leu Leu Asn Ala Thr
305                 310                 315                 320

Ala Ile Ala Val Ala Glu Gly Thr Asp Arg Val Ile Glu Leu Leu Gln
                325                 330                 335

Arg Ala Phe Arg Ala Ile Leu His Ile Pro Arg Arg Xaa Arg Gln Gly
            340                 345                 350

Leu Glu Arg Ala Leu Leu
        355

<210> SEQ ID NO 31
<211> LENGTH: 847
<212> TYPE: PRT
<213> ORGANISM: Artificial Sequence
<220> FEATURE:
<223> OTHER INFORMATION: JR-FL gp160, "double mutant" containing A492C
      and T596C mutations

<400> SEQUENCE: 31

Met Arg Val Lys Gly Ile Arg Lys Ser Tyr Gln Tyr Leu Trp Lys Gly
1               5                   10                  15

Gly Thr Leu Leu Leu Gly Ile Leu Met Ile Cys Ser Ala Val Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Glu Asn Val Thr Glu His Phe Asn Met Trp Lys
                85                  90                  95

Asn Asn Met Val Glu Gln Met Gln Glu Asp Ile Ile Ser Leu Trp Asp
                100                 105                 110

Gln Ser Leu Lys Pro Cys Val Lys Leu Thr Pro Leu Cys Val Thr Leu
```

-continued

```
                115                 120                 125
Asn Cys Lys Asp Val Asn Ala Thr Asn Thr Asn Asp Ser Glu Gly
        130                 135                 140
Thr Met Glu Arg Gly Glu Ile Lys Asn Cys Ser Phe Asn Ile Thr Thr
145                 150                 155                 160
Ser Ile Arg Asp Glu Val Gln Lys Glu Tyr Ala Leu Phe Tyr Lys Leu
                165                 170                 175
Asp Val Val Pro Ile Asp Asn Asn Thr Ser Tyr Arg Leu Ile Ser
                180                 185                 190
Cys Asp Thr Ser Val Ile Thr Gln Ala Cys Pro Lys Ile Ser Phe Glu
                195                 200                 205
Pro Ile Pro Ile His Tyr Cys Ala Pro Ala Gly Phe Ala Ile Leu Lys
            210                 215                 220
Cys Asn Asp Lys Thr Phe Asn Gly Lys Gly Pro Cys Lys Asn Val Ser
225                 230                 235                 240
Thr Val Gln Cys Thr His Gly Ile Arg Pro Val Val Ser Thr Gln Leu
                    245                 250                 255
Leu Leu Asn Gly Ser Leu Ala Glu Glu Val Val Ile Arg Ser Asp
            260                 265                 270
Asn Phe Thr Asn Asn Ala Lys Thr Ile Ile Val Gln Leu Lys Glu Ser
            275                 280                 285
Val Glu Ile Asn Cys Thr Arg Pro Asn Asn Asn Thr Arg Lys Ser Ile
            290                 295                 300
His Ile Gly Pro Gly Arg Ala Phe Tyr Thr Thr Gly Glu Ile Ile Gly
305                 310                 315                 320
Asp Ile Arg Gln Ala His Cys Asn Ile Ser Arg Ala Lys Trp Asn Asp
                    325                 330                 335
Thr Leu Lys Gln Ile Val Ile Lys Leu Arg Glu Gln Phe Glu Asn Lys
                340                 345                 350
Thr Ile Val Phe Asn His Ser Ser Gly Gly Asp Pro Glu Ile Val Met
                355                 360                 365
His Ser Phe Asn Cys Gly Gly Glu Phe Phe Tyr Cys Asn Ser Thr Gln
370                 375                 380
Leu Phe Asn Ser Thr Trp Asn Asn Asn Thr Glu Gly Ser Asn Asn Thr
385                 390                 395                 400
Glu Gly Asn Thr Ile Thr Leu Pro Cys Arg Ile Lys Gln Ile Ile Asn
                    405                 410                 415
Met Trp Gln Glu Val Gly Lys Ala Met Tyr Ala Pro Pro Ile Arg Gly
                420                 425                 430
Gln Ile Arg Cys Ser Ser Asn Ile Thr Gly Leu Leu Leu Thr Arg Asp
                435                 440                 445
Gly Gly Ile Asn Glu Asn Gly Thr Glu Ile Phe Arg Pro Gly Gly Gly
            450                 455                 460
Asp Met Arg Asp Asn Trp Arg Ser Glu Leu Tyr Lys Tyr Lys Val Val
465                 470                 475                 480
Lys Ile Glu Pro Leu Gly Val Ala Pro Thr Lys Cys Lys Arg Arg Val
                    485                 490                 495
Val Gln Arg Glu Lys Arg Ala Val Gly Ile Gly Ala Val Phe Leu Gly
                500                 505                 510
Phe Leu Gly Ala Ala Gly Ser Thr Met Gly Ala Ala Ser Met Thr Leu
            515                 520                 525
Thr Val Gln Ala Arg Leu Leu Leu Ser Gly Ile Val Gln Gln Gln Asn
            530                 535                 540
```

```
Asn Leu Leu Arg Ala Ile Glu Ala Gln Gln Arg Met Leu Gln Leu Thr
545                 550                 555                 560

Val Trp Gly Ile Lys Gln Leu Gln Ala Arg Val Leu Ala Val Glu Arg
                565                 570                 575

Tyr Leu Gly Asp Gln Gln Leu Leu Gly Ile Trp Gly Cys Ser Gly Lys
            580                 585                 590

Leu Ile Cys Cys Thr Ala Val Pro Trp Asn Ala Ser Trp Ser Asn Lys
        595                 600                 605

Ser Leu Asp Arg Ile Trp Asn Asn Met Thr Trp Met Glu Trp Glu Arg
610                 615                 620

Glu Ile Asp Asn Tyr Thr Ser Glu Ile Tyr Thr Leu Ile Glu Glu Ser
625                 630                 635                 640

Gln Asn Gln Gln Glu Lys Asn Glu Gln Glu Leu Leu Glu Leu Asp Lys
                645                 650                 655

Trp Ala Ser Leu Trp Asn Trp Phe Asp Ile Thr Lys Trp Leu Trp Tyr
            660                 665                 670

Ile Lys Ile Phe Ile Met Ile Val Gly Gly Leu Val Gly Leu Arg Leu
        675                 680                 685

Val Phe Thr Val Leu Ser Ile Val Asn Arg Val Arg Gln Gly Tyr Ser
690                 695                 700

Pro Leu Ser Phe Gln Thr Leu Leu Pro Ala Pro Arg Gly Pro Asp Arg
705                 710                 715                 720

Pro Glu Gly Ile Glu Glu Gly Gly Glu Arg Asp Arg Asp Arg Ser
                725                 730                 735

Gly Arg Leu Val Asn Gly Phe Leu Ala Leu Ile Trp Val Asp Leu Arg
            740                 745                 750

Ser Leu Cys Leu Phe Ser Tyr His Arg Leu Arg Asp Leu Leu Leu Thr
        755                 760                 765

Val Thr Arg Ile Val Glu Leu Leu Gly Arg Arg Gly Trp Glu Val Leu
770                 775                 780

Lys Tyr Trp Trp Asn Leu Leu Gln Tyr Trp Ser Gln Glu Leu Lys Asn
785                 790                 795                 800

Ser Ala Val Ser Leu Leu Asn Ala Thr Ala Ile Ala Val Ala Glu Gly
                805                 810                 815

Thr Asp Arg Ile Ile Glu Ala Leu Gln Arg Thr Tyr Arg Ala Ile Leu
            820                 825                 830

His Ile Pro Thr Arg Ile Arg Gln Gly Leu Glu Arg Ala Leu Leu
        835                 840                 845

<210> SEQ ID NO 32
<211> LENGTH: 498
<212> TYPE: PRT
<213> ORGANISM: Artificial Sequence
<220> FEATURE:
<223> OTHER INFORMATION: JR-FL gp120 containing A492C mutation

<400> SEQUENCE: 32

Met Arg Val Lys Gly Ile Arg Lys Ser Tyr Gln Tyr Leu Trp Lys Gly
1               5                   10                  15

Gly Thr Leu Leu Leu Gly Ile Leu Met Ile Cys Ser Ala Val Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
```

```
                65                  70                  75                  80
Gln Glu Val Val Leu Glu Asn Val Thr Glu His Phe Asn Met Trp Lys
                            85                  90                  95
Asn Asn Met Val Glu Gln Met Gln Glu Asp Ile Ile Ser Leu Trp Asp
                100                 105                 110
Gln Ser Leu Lys Pro Cys Val Lys Leu Thr Pro Leu Cys Val Thr Leu
                115                 120                 125
Asn Cys Lys Asp Val Asn Ala Thr Asn Thr Thr Asn Asp Ser Glu Gly
            130                 135                 140
Thr Met Glu Arg Gly Glu Ile Lys Asn Cys Ser Phe Asn Ile Thr Thr
145                 150                 155                 160
Ser Ile Arg Asp Glu Val Gln Lys Glu Tyr Ala Leu Phe Tyr Lys Leu
                165                 170                 175
Asp Val Val Pro Ile Asp Asn Asn Thr Ser Tyr Arg Leu Ile Ser
                180                 185                 190
Cys Asp Thr Ser Val Ile Thr Gln Ala Cys Pro Lys Ile Ser Phe Glu
            195                 200                 205
Pro Ile Pro Ile His Tyr Cys Ala Pro Ala Gly Phe Ala Ile Leu Lys
            210                 215                 220
Cys Asn Asp Lys Thr Phe Asn Gly Lys Gly Pro Cys Lys Asn Val Ser
225                 230                 235                 240
Thr Val Gln Cys Thr His Gly Ile Arg Pro Val Val Ser Thr Gln Leu
                245                 250                 255
Leu Leu Asn Gly Ser Leu Ala Glu Glu Glu Val Val Ile Arg Ser Asp
                260                 265                 270
Asn Phe Thr Asn Asn Ala Lys Thr Ile Ile Val Gln Leu Lys Glu Ser
                275                 280                 285
Val Glu Ile Asn Cys Thr Arg Pro Asn Asn Asn Thr Arg Lys Ser Ile
            290                 295                 300
His Ile Gly Pro Gly Arg Ala Phe Tyr Thr Thr Gly Glu Ile Ile Gly
305                 310                 315                 320
Asp Ile Arg Gln Ala His Cys Asn Ile Ser Arg Ala Lys Trp Asn Asp
                325                 330                 335
Thr Leu Lys Gln Ile Val Ile Lys Leu Arg Glu Gln Phe Glu Asn Lys
                340                 345                 350
Thr Ile Val Phe Asn His Ser Ser Gly Gly Asp Pro Glu Ile Val Met
            355                 360                 365
His Ser Phe Asn Cys Gly Gly Glu Phe Phe Tyr Cys Asn Ser Thr Gln
            370                 375                 380
Leu Phe Asn Ser Thr Trp Asn Asn Thr Glu Gly Ser Asn Asn Thr
385                 390                 395                 400
Glu Gly Asn Thr Ile Thr Leu Pro Cys Arg Ile Lys Gln Ile Ile Asn
                405                 410                 415
Met Trp Gln Glu Val Gly Lys Ala Met Tyr Ala Pro Pro Ile Arg Gly
                420                 425                 430
Gln Ile Arg Cys Ser Ser Asn Ile Thr Gly Leu Leu Leu Thr Arg Asp
            435                 440                 445
Gly Gly Ile Asn Glu Asn Gly Thr Glu Ile Phe Arg Pro Gly Gly Gly
            450                 455                 460
Asp Met Arg Asp Asn Trp Arg Ser Glu Leu Tyr Lys Tyr Lys Val Val
465                 470                 475                 480
Lys Ile Glu Pro Leu Gly Val Ala Pro Thr Lys Cys Lys Arg Arg Val
                485                 490                 495
```

Val Gln

<210> SEQ ID NO 33
<211> LENGTH: 349
<212> TYPE: PRT
<213> ORGANISM: Artificial Sequence
<220> FEATURE:
<223> OTHER INFORMATION: JR-FL gp41 containing T596C mutation

<400> SEQUENCE: 33

Arg Glu Lys Arg Ala Val Gly Ile Gly Ala Val Phe Leu Gly Phe Leu
1               5                   10                  15

Gly Ala Ala Gly Ser Thr Met Gly Ala Ser Met Thr Leu Thr Val
                20                  25                  30

Gln Ala Arg Leu Leu Leu Ser Gly Ile Val Gln Gln Gln Asn Asn Leu
            35                  40                  45

Leu Arg Ala Ile Glu Ala Gln Gln Arg Met Leu Gln Leu Thr Val Trp
        50                  55                  60

Gly Ile Lys Gln Leu Gln Ala Arg Val Leu Ala Val Glu Arg Tyr Leu
65                  70                  75                  80

Gly Asp Gln Gln Leu Leu Gly Ile Trp Gly Cys Ser Gly Lys Leu Ile
                85                  90                  95

Cys Cys Thr Ala Val Pro Trp Asn Ala Ser Trp Ser Asn Lys Ser Leu
            100                 105                 110

Asp Arg Ile Trp Asn Asn Met Thr Trp Met Glu Trp Glu Arg Glu Ile
        115                 120                 125

Asp Asn Tyr Thr Ser Glu Ile Tyr Thr Leu Ile Glu Glu Ser Gln Asn
130                 135                 140

Gln Gln Glu Lys Asn Glu Gln Glu Leu Leu Glu Leu Asp Lys Trp Ala
145                 150                 155                 160

Ser Leu Trp Asn Trp Phe Asp Ile Thr Lys Trp Leu Trp Tyr Ile Lys
                165                 170                 175

Ile Phe Ile Met Ile Val Gly Gly Leu Val Gly Leu Arg Leu Val Phe
            180                 185                 190

Thr Val Leu Ser Ile Val Asn Arg Val Arg Gln Gly Tyr Ser Pro Leu
        195                 200                 205

Ser Phe Gln Thr Leu Leu Pro Ala Pro Arg Gly Pro Asp Arg Pro Glu
210                 215                 220

Gly Ile Glu Glu Glu Gly Gly Glu Arg Asp Arg Asp Arg Ser Gly Arg
225                 230                 235                 240

Leu Val Asn Gly Phe Leu Ala Leu Ile Trp Val Asp Leu Arg Ser Leu
                245                 250                 255

Cys Leu Phe Ser Tyr His Arg Leu Arg Asp Leu Leu Leu Thr Val Thr
            260                 265                 270

Arg Ile Val Glu Leu Leu Gly Arg Arg Gly Trp Glu Val Leu Lys Tyr
        275                 280                 285

Trp Trp Asn Leu Leu Gln Tyr Trp Ser Gln Glu Leu Lys Asn Ser Ala
290                 295                 300

Val Ser Leu Leu Asn Ala Thr Ala Ile Ala Val Ala Glu Gly Thr Asp
305                 310                 315                 320

Arg Ile Ile Glu Ala Leu Gln Arg Thr Tyr Arg Ala Ile Leu His Ile
                325                 330                 335

Pro Thr Arg Ile Arg Gln Gly Leu Glu Arg Ala Leu Leu
            340                 345

<210> SEQ ID NO 34

<211> LENGTH: 863
<212> TYPE: PRT
<213> ORGANISM: Artificial Sequence
<220> FEATURE:
<223> OTHER INFORMATION: KNH1144 gp160 modified to contain cysteines at positions equivalent to 492 and 596 in JR-FL

<400> SEQUENCE: 34

```
Met Ile Val Met Gly Thr Gln Arg Asn Tyr Gln His Leu Leu Arg Trp
1               5                   10                  15

Gly Thr Met Ile Leu Gly Leu Ile Ile Cys Ser Ala Ala Asp Asn
            20                  25                  30

Leu Trp Val Thr Val Tyr Gly Val Pro Val Trp Lys Asp Ala Glu
            35                  40                  45

Thr Thr Leu Phe Cys Ala Ser Asp Ala Lys Ala Tyr Glu Thr Glu Lys
50                  55                  60

His Asn Val Trp Ala Thr His Ala Cys Val Pro Thr Asp Pro Asn Pro
65                  70                  75                  80

Gln Glu Ile Pro Leu Glu Asn Val Thr Glu Glu Phe Asn Met Trp Lys
                85                  90                  95

Asn Lys Met Val Glu Gln Met His Thr Asp Ile Ile Ser Leu Trp Asp
            100                 105                 110

Gln Ser Leu Gln Pro Cys Val Lys Leu Thr Pro Leu Cys Val Thr Leu
        115                 120                 125

Asn Cys Thr Asp Ala Thr Asn Gly Thr Ile Gly Asn Ile Thr Asp Glu
130                 135                 140

Met Lys Gly Glu Ile Lys Asn Cys Ser Phe Asn Ile Thr Thr Glu Ile
145                 150                 155                 160

Arg Asp Lys Lys Gln Lys Val Tyr Ser Leu Phe Tyr Arg Leu Asp Val
                165                 170                 175

Val Pro Ile Glu Pro Asp Ser Ser Asn Ser Ser Arg Asn Ser Ser Glu
            180                 185                 190

Tyr Arg Leu Ile Asn Cys Asn Thr Ser Ala Ile Thr Gln Ala Cys Pro
        195                 200                 205

Lys Val Ser Phe Glu Pro Ile Pro Ile His Tyr Cys Ala Pro Ala Gly
210                 215                 220

Phe Ala Ile Leu Lys Cys Arg Asp Lys Glu Phe Asn Gly Thr Gly Lys
225                 230                 235                 240

Cys Lys Asn Val Ser Thr Val Gln Cys Thr His Gly Ile Lys Pro Val
                245                 250                 255

Val Ser Thr Gln Leu Leu Leu Asn Gly Ser Leu Ala Glu Gly Glu Val
            260                 265                 270

Arg Ile Arg Ser Glu Asn Ile Thr Asn Asn Ala Lys Thr Ile Ile Val
        275                 280                 285

Gln Leu Val Glu Pro Val Arg Ile Asn Cys Thr Arg Pro Asn Asn Asn
290                 295                 300

Thr Arg Glu Ser Val Arg Ile Gly Pro Gly Gln Ala Phe Phe Ala Thr
305                 310                 315                 320

Gly Asp Ile Ile Gly Asp Ile Arg Gln Ala His Cys Asn Val Ser Arg
                325                 330                 335

Ser Gln Trp Asn Lys Thr Leu Gln Gln Val Ala Ala Gln Leu Gly Glu
            340                 345                 350

His Phe Lys Asn Lys Ala Ile Thr Phe Asn Ser Ser Ser Gly Gly Asp
        355                 360                 365

Leu Glu Ile Thr Thr His Ser Phe Asn Cys Gly Gly Glu Phe Phe Tyr
370                 375                 380
```

-continued

```
Cys Asn Thr Ser Gly Leu Phe Asn Ser Thr Trp Lys Ala Asn Asn Gly
385                 390                 395                 400

Thr Trp Lys Ala Asn Ile Ser Glu Ser Asn Asn Thr Glu Ile Thr Leu
                405                 410                 415

Gln Cys Arg Ile Lys Gln Ile Ile Asn Met Trp Gln Arg Thr Gly Gln
                420                 425                 430

Ala Ile Tyr Ala Pro Pro Ile Gln Gly Val Ile Arg Cys Glu Ser Asn
            435                 440                 445

Ile Thr Gly Leu Leu Thr Arg Asp Gly Gly Glu Gly Asn Asn Glu
        450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Arg Cys Arg Arg Val Val Gly Arg Glu Lys Arg Ala
            500                 505                 510

Val Gly Ile Gly Ala Val Phe Leu Gly Phe Leu Gly Ala Ala Gly Ser
        515                 520                 525

Thr Met Gly Ala Ala Ser Ile Thr Leu Thr Val Gln Ala Arg Gln Leu
        530                 535                 540

Leu Ser Gly Ile Val Gln Gln Gln Ser Asn Leu Leu Arg Ala Ile Glu
545                 550                 555                 560

Ala Gln Gln His Met Leu Lys Leu Thr Val Trp Gly Ile Lys Gln Leu
                565                 570                 575

Gln Ala Arg Val Leu Ala Val Glu Arg Tyr Leu Arg Asp Gln Gln Leu
            580                 585                 590

Leu Gly Ile Trp Gly Cys Ser Gly Lys Leu Ile Cys Cys Thr Asn Val
        595                 600                 605

Pro Trp Asn Ser Ser Trp Ser Asn Lys Ser His Asp Glu Ile Trp Asn
        610                 615                 620

Asn Met Thr Trp Leu Gln Trp Asp Lys Glu Ile Ser Asn Tyr Thr Asn
625                 630                 635                 640

Leu Ile Tyr Ser Leu Ile Glu Glu Ser Gln Asn Gln Gln Glu Lys Asn
                645                 650                 655

Glu Gln Asp Leu Leu Ala Leu Asp Lys Trp Ala Ser Leu Trp Asn Trp
            660                 665                 670

Phe Asp Ile Ser Lys Trp Leu Trp Tyr Ile Lys Ile Phe Ile Met Ile
        675                 680                 685

Val Gly Gly Leu Ile Gly Leu Arg Ile Val Phe Ala Val Leu Ala Val
690                 695                 700

Ile Lys Arg Val Arg Gln Gly Tyr Ser Pro Val Ser Phe Gln Ile His
705                 710                 715                 720

Asn Pro Asn Pro Gly Gly Leu Asp Arg Pro Gly Arg Ile Glu Glu Glu
                725                 730                 735

Gly Gly Glu Pro Gly Arg Gly Arg Ser Ile Arg Leu Val Ser Gly Phe
            740                 745                 750

Leu Ala Leu Ala Trp Asp Asp Leu Arg Asn Leu Cys Leu Phe Ser Tyr
        755                 760                 765

His Arg Leu Arg Asp Phe Ala Leu Ile Val Ala Arg Thr Val Glu Leu
        770                 775                 780

Leu Gly His Ser Ser Leu Lys Gly Leu Arg Leu Gly Trp Glu Gly Leu
785                 790                 795                 800

Lys Tyr Leu Trp Asn Leu Leu Val Tyr Trp Ser Gln Glu Leu Lys Thr
```

```
                    805                 810                 815
Ser Ala Ile Asn Leu Val Asp Thr Ile Ala Ile Ala Val Ala Gly Trp
            820                 825                 830

Thr Asp Arg Val Ile Glu Ile Gly Gln Gly Ile Gly Arg Ala Phe Leu
            835                 840                 845

His Ile Pro Arg Arg Ile Arg Gln Gly Leu Glu Arg Ala Leu Leu
            850                 855                 860

<210> SEQ ID NO 35
<211> LENGTH: 507
<212> TYPE: PRT
<213> ORGANISM: Artificial Sequence
<220> FEATURE:
<223> OTHER INFORMATION: KNH1144 gp120 modified to contain cysteine at
      position equivalent to 492 in JR-FL

<400> SEQUENCE: 35

Met Ile Val Met Gly Thr Gln Arg Asn Tyr Gln His Leu Leu Arg Trp
1               5                   10                  15

Gly Thr Met Ile Leu Gly Leu Ile Ile Cys Ser Ala Ala Asp Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile Pro Leu Glu Asn Val Thr Glu Glu Phe Asn Met Trp Lys
                85                  90                  95

Asn Lys Met Val Glu Gln Met His Thr Asp Ile Ile Ser Leu Trp Asp
            100                 105                 110

Gln Ser Leu Gln Pro Cys Val Lys Leu Thr Pro Leu Cys Val Thr Leu
        115                 120                 125

Asn Cys Thr Asp Ala Thr Asn Gly Thr Ile Gly Asn Ile Thr Asp Glu
    130                 135                 140

Met Lys Gly Glu Ile Lys Asn Cys Ser Phe Asn Ile Thr Thr Glu Ile
145                 150                 155                 160

Arg Asp Lys Lys Gln Lys Val Tyr Ser Leu Phe Tyr Arg Leu Asp Val
                165                 170                 175

Val Pro Ile Glu Pro Asp Ser Ser Asn Ser Ser Arg Asn Ser Ser Glu
            180                 185                 190

Tyr Arg Leu Ile Asn Cys Asn Thr Ser Ala Ile Thr Gln Ala Cys Pro
        195                 200                 205

Lys Val Ser Phe Glu Pro Ile Pro Ile His Tyr Cys Ala Pro Ala Gly
    210                 215                 220

Phe Ala Ile Leu Lys Cys Arg Asp Lys Glu Phe Asn Gly Thr Gly Lys
225                 230                 235                 240

Cys Lys Asn Val Ser Thr Val Gln Cys Thr His Gly Ile Lys Pro Val
                245                 250                 255

Val Ser Thr Gln Leu Leu Leu Asn Gly Ser Leu Ala Glu Gly Glu Val
            260                 265                 270

Arg Ile Arg Ser Glu Asn Ile Thr Asn Asn Ala Lys Thr Ile Ile Val
        275                 280                 285

Gln Leu Val Glu Pro Val Arg Ile Asn Cys Thr Arg Pro Asn Asn Asn
    290                 295                 300

Thr Arg Glu Ser Val Arg Ile Gly Pro Gly Gln Ala Phe Phe Ala Thr
```

```
                    305                 310                 315                 320
Gly Asp Ile Ile Gly Asp Ile Arg Gln Ala His Cys Asn Val Ser Arg
                325                 330                 335
Ser Gln Trp Asn Lys Thr Leu Gln Gln Val Ala Ala Gln Leu Gly Glu
                340                 345                 350
His Phe Lys Asn Lys Ala Ile Thr Phe Asn Ser Ser Ser Gly Gly Asp
                355                 360                 365
Leu Glu Ile Thr Thr His Ser Phe Asn Cys Gly Gly Glu Phe Phe Tyr
            370                 375                 380
Cys Asn Thr Ser Gly Leu Phe Asn Ser Thr Trp Lys Ala Asn Asn Gly
385                 390                 395                 400
Thr Trp Lys Ala Asn Ile Ser Glu Ser Asn Asn Thr Glu Ile Thr Leu
                405                 410                 415
Gln Cys Arg Ile Lys Gln Ile Ile Asn Met Trp Gln Arg Thr Gly Gln
                420                 425                 430
Ala Ile Tyr Ala Pro Pro Ile Gln Gly Val Ile Arg Cys Glu Ser Asn
                435                 440                 445
Ile Thr Gly Leu Leu Leu Thr Arg Asp Gly Gly Glu Gly Asn Asn Glu
            450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Arg Cys Arg Arg Arg Val Val Gly
                500                 505

<210> SEQ ID NO 36
<211> LENGTH: 356
<212> TYPE: PRT
<213> ORGANISM: Artificial Sequence
<220> FEATURE:
<223> OTHER INFORMATION: KNH1144 gp41 modified to contain cysteine at
      position equivalent to 596 in JR-FL

<400> SEQUENCE: 36

Arg Glu Lys Arg Ala Val Gly Ile Gly Ala Val Phe Leu Gly Phe Leu
1               5                   10                  15
Gly Ala Ala Gly Ser Thr Met Gly Ala Ala Ser Ile Thr Leu Thr Val
                20                  25                  30
Gln Ala Arg Gln Leu Leu Ser Gly Ile Val Gln Gln Gln Ser Asn Leu
            35                  40                  45
Leu Arg Ala Ile Glu Ala Gln Gln His Met Leu Lys Leu Thr Val Trp
        50                  55                  60
Gly Ile Lys Gln Leu Gln Ala Arg Val Leu Ala Val Glu Arg Tyr Leu
65                  70                  75                  80
Arg Asp Gln Gln Leu Leu Gly Ile Trp Gly Cys Ser Gly Lys Leu Ile
                85                  90                  95
Cys Cys Thr Asn Val Pro Trp Asn Ser Ser Trp Ser Asn Lys Ser His
                100                 105                 110
Asp Glu Ile Trp Asn Asn Met Thr Trp Leu Gln Trp Asp Lys Glu Ile
            115                 120                 125
Ser Asn Tyr Thr Asn Leu Ile Tyr Ser Leu Ile Glu Glu Ser Gln Asn
        130                 135                 140
Gln Gln Glu Lys Asn Glu Gln Asp Leu Leu Ala Leu Asp Lys Trp Ala
145                 150                 155                 160
Ser Leu Trp Asn Trp Phe Asp Ile Ser Lys Trp Leu Trp Tyr Ile Lys
```

-continued

```
                165                 170                 175
Ile Phe Ile Met Ile Val Gly Gly Leu Ile Gly Leu Arg Ile Val Phe
            180                 185                 190

Ala Val Leu Ala Val Ile Lys Arg Val Arg Gln Gly Tyr Ser Pro Val
            195                 200                 205

Ser Phe Gln Ile His Asn Pro Asn Pro Gly Gly Leu Asp Arg Pro Gly
            210                 215                 220

Arg Ile Glu Glu Gly Gly Glu Pro Gly Arg Gly Arg Ser Ile Arg
225                 230                 235                 240

Leu Val Ser Gly Phe Leu Ala Leu Ala Trp Asp Asp Leu Arg Asn Leu
                245                 250                 255

Cys Leu Phe Ser Tyr His Arg Leu Arg Asp Phe Ala Leu Ile Val Ala
                260                 265                 270

Arg Thr Val Glu Leu Leu Gly His Ser Ser Leu Lys Gly Leu Arg Leu
            275                 280                 285

Gly Trp Glu Gly Leu Lys Tyr Leu Trp Asn Leu Leu Val Tyr Trp Ser
            290                 295                 300

Gln Glu Leu Lys Thr Ser Ala Ile Asn Leu Val Asp Thr Ile Ala Ile
305                 310                 315                 320

Ala Val Ala Gly Trp Thr Asp Arg Val Ile Glu Ile Gly Gln Gly Ile
                325                 330                 335

Gly Arg Ala Phe Leu His Ile Pro Arg Arg Ile Arg Gln Gly Leu Glu
                340                 345                 350

Arg Ala Leu Leu
        355

<210> SEQ ID NO 37
<211> LENGTH: 853
<212> TYPE: PRT
<213> ORGANISM: Artificial Sequence
<220> FEATURE:
<223> OTHER INFORMATION: Ba-L gp160 modified to contain cysteines at
      positions equivalent to 492 and 596 in JR-FL
<220> FEATURE:
<221> NAME/KEY: MISC_FEATURE
<222> LOCATION: (23)..(830)
<223> OTHER INFORMATION: X=Any AA

<400> SEQUENCE: 37

Met Arg Val Thr Glu Ile Arg Lys Ser Tyr Gln His Trp Trp Arg Trp
1               5                   10                  15

Gly Ile Met Leu Leu Gly Xaa Leu Met Ile Cys Asn Ala Glu Glu Lys
            20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Xaa Xaa Xaa Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
            115                 120                 125

Asn Cys Thr Asp Leu Arg Asn Ala Thr Xaa Xaa Asn Xaa Thr Xaa Thr
    130                 135                 140
```

-continued

Thr Ser Ser Ser Arg Gly Met Val Gly Gly Glu Xaa Lys Asn Cys
145                 150                 155                 160

Ser Phe Asn Ile Thr Thr Xaa Ile Arg Gly Lys Val Gln Lys Glu Tyr
            165                 170                 175

Ala Leu Phe Tyr Glu Leu Asp Ile Val Pro Ile Asp Asn Xaa Ile Asp
            180                 185                 190

Arg Tyr Arg Leu Ile Ser Cys Asn Thr Ser Val Ile Thr Gln Ala Cys
            195                 200                 205

Pro Lys Val Ser Phe Glu Pro Ile Pro Ile His Tyr Cys Ala Pro Ala
            210                 215                 220

Gly Phe Ala Ile Leu Lys Cys Lys Asp Lys Lys Phe Asn Gly Lys Gly
225                 230                 235                 240

Pro Cys Xaa Asn Val Ser Thr Val Gln Cys Thr His Gly Ile Arg Pro
            245                 250                 255

Val Val Ser Thr Gln Leu Leu Leu Asn Gly Ser Leu Ala Glu Glu Glu
            260                 265                 270

Val Val Ile Arg Ser Xaa Asn Phe Xaa Asx Asn Ala Lys Xaa Ile Ile
            275                 280                 285

Val Gln Leu Asn Glu Ser Val Glu Ile Asn Cys Thr Arg Pro Asn Asn
290                 295                 300

Asn Thr Arg Lys Ser Ile His Ile Gly Pro Gly Arg Ala Phe Tyr Thr
305                 310                 315                 320

Thr Gly Glu Ile Ile Gly Asp Ile Arg Gln Ala His Cys Asn Leu Ser
            325                 330                 335

Arg Ala Lys Trp Asn Asp Thr Leu Asn Lys Ile Val Xaa Lys Leu Arg
            340                 345                 350

Glu Gln Phe Gly Asn Lys Thr Ile Val Phe Lys His Ser Ser Gly Gly
            355                 360                 365

Asp Pro Glu Ile Val Thr His Ser Phe Asn Cys Gly Gly Glu Phe Phe
            370                 375                 380

Tyr Cys Asn Ser Thr Gln Leu Phe Asn Ser Thr Trp Asn Val Thr Glu
385                 390                 395                 400

Glu Ser Asn Asn Thr Val Glu Asn Asn Thr Ile Thr Leu Pro Cys Arg
            405                 410                 415

Ile Lys Gln Ile Ile Asn Met Trp Gln Xaa Val Gly Arg Ala Met Tyr
            420                 425                 430

Ala Pro Pro Ile Arg Gly Gln Ile Arg Cys Ser Ser Asn Ile Thr Gly
            435                 440                 445

Leu Leu Leu Thr Arg Asp Gly Gly Pro Glu Asp Asn Lys Thr Glu Val
            450                 455                 460

Phe Arg Pro Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
            485                 490                 495

Lys Cys Lys Arg Arg Val Val Gln Arg Glu Lys Arg Ala Val Gly Ile
            500                 505                 510

Gly Ala Val Phe Leu Gly Phe Leu Gly Ala Ala Gly Ser Thr Met Gly
            515                 520                 525

Ala Ala Ser Met Thr Leu Thr Val Gln Ala Arg Leu Leu Leu Ser Gly
530                 535                 540

Ile Val Gln Gln Gln Asn Asn Leu Leu Arg Ala Ile Glu Ala Gln Gln
545                 550                 555                 560

His Leu Leu Gln Leu Thr Val Trp Gly Ile Lys Gln Leu Gln Ala Arg
            565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Cys Thr Ala Val Pro Trp Asn
        595                 600                 605

Ala Ser Trp Ser Asn Lys Ser Leu Asn Lys Ile Trp Asp Asn Met Thr
    610                 615                 620

Trp Met Glu Trp Asp Arg Glu Ile Asn Asn Tyr Thr Ser Ile Ile Tyr
625                 630                 635                 640

Ser Leu Ile Glu Glu Ser Gln Asn Gln Gln Glu Lys Asn Glu Gln Glu
                645                 650                 655

Leu Leu Glu Leu Asp Lys Trp Ala Ser Leu Trp Asn Trp Phe Asp Ile
            660                 665                 670

Thr Xaa Trp Leu Trp Tyr Ile Lys Ile Phe Ile Met Ile Val Gly Gly
        675                 680                 685

Leu Ile Gly Leu Arg Ile Val Phe Ser Val Leu Ser Ile Val Asn Arg
    690                 695                 700

Val Arg Gln Gly Tyr Ser Pro Leu Ser Phe Gln Thr His Leu Pro Ala
705                 710                 715                 720

Ser Arg Gly Pro Asp Arg Pro Gly Gly Ile Glu Glu Glu Gly Gly Glu
                725                 730                 735

Arg Asp Arg Asp Arg Ser Gly Pro Leu Val Asn Gly Phe Leu Xaa Leu
            740                 745                 750

Ile Trp Val Asp Leu Arg Ser Leu Xaa Leu Phe Ser Tyr His Arg Leu
        755                 760                 765

Arg Asp Leu Leu Leu Ile Val Thr Arg Ile Val Glu Leu Leu Gly Arg
    770                 775                 780

Arg Gly Trp Glu Val Leu Lys Tyr Trp Trp Xaa Leu Leu Gln Tyr Trp
785                 790                 795                 800

Ser Gln Glu Leu Lys Asn Ser Ala Val Ser Leu Leu Asn Xaa Xaa Ala
                805                 810                 815

Xaa Ala Val Ala Glu Gly Thr Asp Arg Val Ile Glu Val Xaa Gln Arg
            820                 825                 830

Ala Val Arg Ala Ile Leu His Ile Pro Arg Arg Ile Arg Gln Gly Leu
        835                 840                 845

Glu Arg Ala Leu Leu
    850

<210> SEQ ID NO 38
<211> LENGTH: 504
<212> TYPE: PRT
<213> ORGANISM: Artificial Sequence
<220> FEATURE:
<223> OTHER INFORMATION: Ba-L gp120 modified to contain cysteine at
      position equivalent to 492 in JR-FL
<220> FEATURE:
<221> NAME/KEY: MISC_FEATURE
<222> LOCATION: (23)..(426)
<223> OTHER INFORMATION: X=Any AA

<400> SEQUENCE: 38

Met Arg Val Thr Glu Ile Arg Lys Ser Tyr Gln His Trp Trp Arg Trp
1               5                   10                  15

Gly Ile Met Leu Leu Gly Xaa Leu Met Ile Cys Asn Ala Glu Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val

```
                50                  55                  60
His Asn Val Trp Ala Thr His Ala Cys Val Pro Thr Asp Pro Asn Pro
 65                  70                  75                  80

Gln Glu Val Xaa Xaa Xaa Asn Val Thr Glu Asn Phe Asn Met Trp Lys
                     85                  90                  95

Asn Asn Met Val Glu Gln Met His Glu Asp Ile Ile Ser Leu Trp Asp
                    100                 105                 110

Gln Ser Leu Lys Pro Cys Val Lys Leu Thr Pro Leu Cys Val Thr Leu
                115                 120                 125

Asn Cys Thr Asp Leu Arg Asn Ala Thr Xaa Xaa Asn Xaa Thr Xaa Thr
130                 135                 140

Thr Ser Ser Ser Arg Gly Met Val Gly Gly Gly Glu Xaa Lys Asn Cys
145                 150                 155                 160

Ser Phe Asn Ile Thr Thr Xaa Ile Arg Gly Lys Val Gln Lys Glu Tyr
                    165                 170                 175

Ala Leu Phe Tyr Glu Leu Asp Ile Val Pro Ile Asp Asn Xaa Ile Asp
                180                 185                 190

Arg Tyr Arg Leu Ile Ser Cys Asn Thr Ser Val Ile Thr Gln Ala Cys
                195                 200                 205

Pro Lys Val Ser Phe Glu Pro Ile Pro Ile His Tyr Cys Ala Pro Ala
210                 215                 220

Gly Phe Ala Ile Leu Lys Cys Lys Asp Lys Phe Asn Gly Lys Gly
225                 230                 235                 240

Pro Cys Xaa Asn Val Ser Thr Val Gln Cys Thr His Gly Ile Arg Pro
                    245                 250                 255

Val Val Ser Thr Gln Leu Leu Leu Asn Gly Ser Leu Ala Glu Glu Glu
                260                 265                 270

Val Val Ile Arg Ser Xaa Asn Phe Xaa Asx Asn Ala Lys Xaa Ile Ile
                275                 280                 285

Val Gln Leu Asn Glu Ser Val Glu Ile Asn Cys Thr Arg Pro Asn Asn
290                 295                 300

Asn Thr Arg Lys Ser Ile His Ile Gly Pro Gly Arg Ala Phe Tyr Thr
305                 310                 315                 320

Thr Gly Glu Ile Ile Gly Asp Ile Arg Gln Ala His Cys Asn Leu Ser
                    325                 330                 335

Arg Ala Lys Trp Asn Asp Thr Leu Asn Lys Ile Val Xaa Lys Leu Arg
                340                 345                 350

Glu Gln Phe Gly Asn Lys Thr Ile Val Phe Lys His Ser Ser Gly Gly
                355                 360                 365

Asp Pro Glu Ile Val Thr His Ser Phe Asn Cys Gly Gly Glu Phe Phe
370                 375                 380

Tyr Cys Asn Ser Thr Gln Leu Phe Asn Ser Thr Trp Asn Val Thr Glu
385                 390                 395                 400

Glu Ser Asn Asn Thr Val Glu Asn Thr Ile Thr Leu Pro Cys Arg
                    405                 410                 415

Ile Lys Gln Ile Ile Asn Met Trp Gln Xaa Val Gly Arg Ala Met Tyr
                420                 425                 430

Ala Pro Pro Ile Arg Gly Gln Ile Arg Cys Ser Ser Asn Ile Thr Gly
                435                 440                 445

Leu Leu Leu Thr Arg Asp Gly Gly Pro Glu Asp Asn Lys Thr Glu Val
    450                 455                 460

Phe Arg Pro Gly Gly Gly Asp Met Arg Asp Asn Trp Arg Ser Glu Leu
465                 470                 475                 480
```

-continued

```
Tyr Lys Tyr Lys Val Lys Ile Glu Pro Leu Gly Val Ala Pro Thr
                485                 490                 495

Lys Cys Lys Arg Arg Val Val Gln
            500
```

<210> SEQ ID NO 39
<211> LENGTH: 349
<212> TYPE: PRT
<213> ORGANISM: Artificial Sequence
<220> FEATURE:
<223> OTHER INFORMATION: Ba-L gp41 modified to contain cysteine at
      position equivalent to 596 in JR-FL
<220> FEATURE:
<221> NAME/KEY: MISC_FEATURE
<222> LOCATION: (170)..(326)
<223> OTHER INFORMATION: X=Any AA

<400> SEQUENCE: 39

```
Arg Glu Lys Arg Ala Val Gly Ile Gly Ala Val Phe Leu Gly Phe Leu
1               5                   10                  15

Gly Ala Ala Gly Ser Thr Met Gly Ala Ala Ser Met Thr Leu Thr Val
                20                  25                  30

Gln Ala Arg Leu Leu Leu Ser Gly Ile Val Gln Gln Gln Asn Asn Leu
            35                  40                  45

Leu Arg Ala Ile Glu Ala Gln Gln His Leu Leu Gln Leu Thr Val Trp
    50                  55                  60

Gly Ile Lys Gln Leu Gln Ala Arg Val Leu Ala Val Glu Arg Tyr Leu
65                  70                  75                  80

Arg Asp Gln Gln Leu Leu Gly Ile Trp Gly Cys Ser Gly Lys Leu Ile
                85                  90                  95

Cys Cys Thr Ala Val Pro Trp Asn Ala Ser Trp Ser Asn Lys Ser Leu
            100                 105                 110

Asn Lys Ile Trp Asp Asn Met Thr Trp Met Glu Trp Asp Arg Glu Ile
        115                 120                 125

Asn Asn Tyr Thr Ser Ile Ile Tyr Ser Leu Ile Glu Glu Ser Gln Asn
    130                 135                 140

Gln Gln Glu Lys Asn Glu Gln Glu Leu Leu Glu Leu Asp Lys Trp Ala
145                 150                 155                 160

Ser Leu Trp Asn Trp Phe Asp Ile Thr Xaa Trp Leu Trp Tyr Ile Lys
                165                 170                 175

Ile Phe Ile Met Ile Val Gly Gly Leu Ile Gly Leu Arg Ile Val Phe
            180                 185                 190

Ser Val Leu Ser Ile Val Asn Arg Val Arg Gln Gly Tyr Ser Pro Leu
        195                 200                 205

Ser Phe Gln Thr His Leu Pro Ala Ser Arg Gly Pro Asp Arg Pro Gly
    210                 215                 220

Gly Ile Glu Glu Glu Gly Gly Glu Arg Asp Arg Asp Arg Ser Gly Pro
225                 230                 235                 240

Leu Val Asn Gly Phe Leu Xaa Leu Ile Trp Val Asp Leu Arg Ser Leu
                245                 250                 255

Xaa Leu Phe Ser Tyr His Arg Leu Arg Asp Leu Leu Leu Ile Val Thr
            260                 265                 270

Arg Ile Val Glu Leu Leu Gly Arg Arg Gly Trp Glu Val Leu Lys Tyr
        275                 280                 285

Trp Trp Xaa Leu Leu Gln Tyr Trp Ser Gln Glu Leu Lys Asn Ser Ala
    290                 295                 300

Val Ser Leu Leu Asn Xaa Xaa Ala Xaa Ala Val Ala Glu Gly Thr Asp
305                 310                 315                 320
```

```
Arg Val Ile Glu Val Xaa Gln Arg Ala Val Arg Ala Ile Leu His Ile
                325                 330                 335

Pro Arg Arg Ile Arg Gln Gly Leu Glu Arg Ala Leu Leu
                340                 345
```

SOLUBLE, STABILIZED, PROTEOLYTICALLY CLEAVED, TRIMERIC HIV-1 GP140 PROTEINS COMPRISING MODIFICATIONS IN THE N-TERMINUS OF THE GP41 ECTODOMAIN

This application is a §371 national stage of PCT International Application No. PCT/US2007/022227, filed Oct. 17, 2007, and claims the benefit of U.S. Provisional Applications Nos. 60/855,236, filed Oct. 30, 2006 and 60/854,034, filed Oct. 23, 2006, the contents of all of which are hereby incorporated by reference into this application.

This invention was made with support under Grant Nos. AI 36082 and AI 45463 and NIH contract N01 AI 30030 from the National Institutes of Health, U.S. Department of Health and Human Services. Accordingly, the United States Government has certain rights in the subject invention.

Throughout this application, certain publications are referenced. Full citations for these publications may be found immediately preceding the claims. The disclosures of these publications in their entireties are hereby incorporated by reference into this application in order to more fully describe the state of the art to which this invention relates.

BACKGROUND OF THE INVENTION

The ability of human immunodeficiency virus type 1 (HIV-1) to enter its target cell and establish an infection is dependent on interactions between functional HIV envelope glycoprotein (Env) complexes on the virus and receptors on the host cell. The HIV-1 Env complex is initially synthesized as the polyprotein precursor gp160, which undergoes oligomerization, disulfide bond formation and extensive glycosylation in the endoplasmic reticulum (Earl, Moss, and Doms, 1991) and is then proteolytically cleaved into the surface (gp120) and transmembrane (gp41) subunits by furin-like endo-proteases in the Golgi network (Fields, 1996; Hunter and Swanstrom, 1990). The resulting Env complex is a trimer, with three gp120 proteins associated non-covalently with three gp41 subunits.

During the entry process, gp120 interacts with the CD4 receptor, which triggers conformational changes that facilitate gp120 binding to a coreceptor, CCR5 or CXCR4 (Berger, Murphy, and Farber, 1999; Rizzuto et al., 1998). These interactions promote extensive conformational changes in the gp41 subunit that drive the insertion of the hydrophobic gp41 N-terminal region (fusion peptide) into the host cell membrane. Subsequently, formation of the six-helix bundle configuration of the three gp41 ectodomains forces the juxtaposition of the viral and cell membranes, promoting their fusion (Doms and Moore, 2000; Jones, Korte, and Blumenthal, 1998; Melikyan et al., 2000; Moore and Doms, 2003; Sattentau and Moore, 1991; Sullivan et al., 1998; Wu et al., 1996; Zhang et al., 1999).

The trimeric nature of the Env complex has been confirmed by various lines of evidence (Blacklow, Lu, and Kim, 1995; Center et al., 2002; Center et al., 2001; Chan et al., 1997; Chan and Kim, 1998; Lu, Blacklow, and Kim, 1995; Zhu et al., 2003), most recently by cryo-electron microscopy (Zanetti et al., 2006; Zhu et al., 2006). The trimer is held together by labile, non-covalent inter-subunit interactions. The weak interactions between gp120 and gp41, and between individual gp41 subunits, are probably necessary to permit the conformational changes that are necessary for the process of virus-cell fusion to proceed efficiently, but such instability of the Env complexes complicates the generation of soluble forms of Env trimers that are suitable for vaccine research and structural studies. To obtain soluble Env trimers, the transmembrane (TM) region and the cytoplasmic tail (CT) are routinely deleted from gp41 to create gp140 proteins that contain gp120 and the gp41 ectodomain (gp41ECTO). Attempts to stabilize the non-covalent inter-subunit interactions have included mutating the cleavage site within gp140 to make uncleaved oligomers (Chakrabarti et al., 2002; Srivastava et al., 2002; Yang et al., 2000; Yang et al., 2002; Zhang et al., 2001) and engineering of an inter-subunit disulfide bond (Binley et al., 2000) between gp120 and gp41 and an isoleucine to proline substitution at position 559 (I559P) in the N-terminal heptad region of gp41 ectodomain (SOSIP) (Sanders et al., 2002) to promote gp41-gp41 association.

Despite the efforts to stabilize the naturally unstable Env complexes, problems with the stability of the complexes still exist. For example, gp120 rapidly dissociates from gp41 when soluble forms of gp140 proteins are expressed, and trimeric gp140 proteins can degrade into dimers and monomers, or associate into tetramers (dimers of dimers) and aggregates (Earl et al., 1994; Schulke et al., 2002; Staropoli et al., 2000). Similarly, monomeric and oligomeric gp120-gp41 structures are found to be present on cells that express Env proteins, as are both gp41 stumps from which gp120 has been shed and uncleaved proteins that have evaded the host cell proteases that typically process gp160 (Herrera et al., 2005; Kuznetsov et al., 2003; Moore et al., 2006; Thomas et al., 1991; Wyatt and Sodroski, 1998; Zhu et al., 2003).

Thus, stable, Env-based vaccines that mimic the native trimer conformation of the native Env structure and that remain stable when used as immunogenns and vaccines are needed in the art to combat infection by HIV and its devastating consequences.

SUMMARY OF THE INVENTION

Described herein are the molecular determinants of enhanced trimer stability. These lie within the N-terminal region of gp41$_{ECTO}$, an area with a well-documented role in gp41-gp41 interactions (Center, Kemp, and Poumbourios, 1997; Poumbourios et al., 1997; Shugars et al., 1996). Specifically, five amino acid changes based on the KNH1144 sequence have a trimer-stabilizing effect on heterologous gp140 proteins. The introduction of these changes does not impair the exposure of various neutralizing antibody epitopes on the resulting gp140 proteins, leaving the overall antigenic structure of the trimer not adversely affected.

The present invention provides a modified gp140 envelope polypeptide of an HIV-1 isolate comprising a gp120 polypeptide portion comprising consecutive amino acids and a gp41 ectodomain polypeptide portion comprising consecutive amino acids, the gp41 ectodomain polypeptide portion being modified to comprise glutamine (Q) at an amino acid position equivalent to amino acid position 543 (Q543); serine (S) at an amino acid position equivalent to amino acid position 553 (S553); and lysine (K) at an amino acid position equivalent to amino acid position 567 (K567); and optionally being modified to comprise isoleucine (I) at an amino acid position equivalent to amino acid position 535 (I535) and arginine (R) at an amino acid position equivalent to amino acid position 588 (R588), wherein the amino acid positions are numbered by reference to the HIV-1 isolate KNH1144.

This invention provides a modified gp140 envelope polypeptide of an HIV-1 isolate comprising a gp120 polypeptide portion comprising consecutive amino acids and a gp41 ectodomain polypeptide portion comprising consecutive amino acids, the gp41 ectodomain polypeptide portion being modified to comprise isoleucine (I) at an amino acid position equivalent to amino acid position 535 (I535); glutamine (Q) at an amino acid position equivalent to amino acid position 543 (Q543); serine (S) at an amino acid position equivalent to amino acid position 553 (S553); lysine (K) at an amino acid position equivalent to amino acid position 567 (K567); and arginine (R) at an amino acid position equivalent to amino acid position 588 (R588), wherein the amino acid positions are numbered by reference to the HIV-1 isolate KNH1144.

The invention also provides a modified gp140 envelope polypeptide of an HIV-1 isolate comprising a gp120 polypeptide portion comprising consecutive amino acids and a gp41 ectodomain polypeptide portion comprising consecutive amino acids, the gp41 ectodomain polypeptide portion being modified to comprise isoleucine (I) at amino acid position 535; glutamine (Q) at amino acid position 543; serine (S) at amino acid position 553; lysine (K) at amino acid position 567; and arginine (R) at amino acid position 588, wherein the amino acid positions are numbered by reference to the HIV-1 isolate KNH1144.

This invention also provides a modified gp140 envelope polypeptide of an HIV-1 isolate, wherein a first portion of the gp140 polypeptide corresponds to a modified gp120 polypeptide and a second portion of the gp140 polypeptide corresponds to a modified gp41 ectodomain polypeptide, wherein the modified gp120 polypeptide comprises an A→C mutation at amino acid position 492, numbered by reference to the HIV-1 isolate JR-FL, and the modified gp41 ectodomain polypeptide comprises (i) a T→C mutation at amino acid position 596, numbered by reference to the HIV-1 isolate JR-FL; and (ii) isoleucine (I) at amino acid position 535; glutamine (Q) at amino acid position 543; serine (S) at amino acid position 553; lysine (K) at amino acid position 567; and arginine (R) at amino acid position 588, wherein amino acid positions 535, 543, 553, 567 and 588 are numbered by reference to the HIV-1 isolate KNH1144.

In an embodiment, the gp120 polypeptide portion of the above described modified gp140 envelope polypeptides is modified to comprise a cysteine (C) residue at an amino acid position equivalent to amino acid position 492, numbered by reference to the HIV isolate JR-FL. In an embodiment, the gp41 ectodomain polypeptide portion of the above described modified gp140 envelope polypeptide is modified to comprise a cysteine (C) residue at an amino acid position equivalent to amino acid position 596, numbered by reference to the HIV-1 isolate JR-FL. In an embodiment, the gp41 ectodomain polypeptide portion of the above described modified gp140 envelope polypeptide is modified to comprise a proline (P) residue at an amino acid position equivalent to amino acid position 559, numbered by reference to the HIV-1 isolate KNH1144. In an embodiment, in the above described modified gp140 polypeptides, the isoleucine (I) at the amino acid position equivalent to amino acid position 535 is the result of an M535I mutation; the glutamine (Q) at the amino acid position equivalent to amino acid position 543 is the result of an L543Q mutation; the serine (S) at the amino acid position equivalent to amino acid position 553 is the result of an N553S mutation; the lysine (K) at the amino acid position equivalent to amino acid position 567 is the result of a Q567K mutation; and the arginine (R) at the amino acid position equivalent to amino acid position 588 is the result of a G588R mutation, wherein the amino acid positions 535, 543, 553, 567 and 588 are numbered by reference to the HIV-1 isolate KNH1144.

The invention provides a modified gp140 envelope polypeptide of an HIV-1 isolate, wherein a first portion of the gp140 polypeptide corresponds to a modified gp120 polypeptide and a second portion of the gp140 polypeptide corresponds to a modified gp41 ectodomain polypeptide, wherein the modified gp120 polypeptide comprises an cysteine (C) at an amino acid position equivalent to amino acid position 492 of the HIV-1 isolate JR-FL, and the modified gp41 ectodomain polypeptide comprises (i) a cysteine (C) at an amino acid position equivalent to amino acid position 596 of the HIV-1 isolate JR-FL; (ii) a proline (P) at an amino acid position equivalent to amino acid 559 of the HIV-1 isolate KNH1144; and (iii) isoleucine (I) at an amino acid position equivalent to amino acid position 535 (I535); glutamine (Q) at an amino acid position equivalent to amino acid position 543 (Q543); serine (S) at an amino acid position equivalent to amino acid position 553 (S553); lysine (K) at an amino acid position equivalent to amino acid position 567 (K567); and arginine (R) at an amino acid position equivalent to amino acid position 588 (R588), wherein the amino positions of (iii) are numbered by reference to the HIV-1 isolate KNH1144.

The invention further provides a modified gp140 envelope polypeptide of an HIV-1 isolate, wherein a first portion of the gp140 polypeptide corresponds to a modified gp120 polypeptide and a second portion of the gp140 polypeptide corresponds to a modified gp41 ectodomain polypeptide, wherein the modified gp120 polypeptide comprises an A→C mutation at amino acid position 492, numbered by reference to the HIV-1 isolate JR-FL, and the modified gp41 ectodomain polypeptide comprises (i) a T→C mutation at amino acid position 596, numbered by reference to the HIV-1 isolate JR-FL; and (ii) isoleucine (I) at amino acid position 535; glutamine (Q) at amino acid position 543; serine (S) at amino acid position 553; lysine (K) at amino acid position 567; and arginine (R) at amino acid position 588, wherein the 535, 543, 553, 567 and 588 amino acid positions are numbered by reference to the HIV-1 isolate KNH1144. In an embodiment, the modified gp140 envelope polypeptide also contains an I→P mutation at amino acid position 559, numbered by reference to the HIV-1 isolate KNH1144.

The present invention also provides a modified gp140 envelope polypeptide of an HIV-1 isolate, wherein a first portion of the gp140 polypeptide corresponds to a modified gp120 polypeptide and a second portion of the gp140 polypeptide corresponds to a modified gp41 ectodomain polypeptide, wherein the modified gp120 polypeptide comprises a cysteine (C) residue at an amino acid position equivalent to amino acid position 492 of the HIV-1 isolate JR-FL, and the modified gp41 ectodomain polypeptide comprises (i) a cysteine (C) residue at an amino acid position equivalent to amino acid position 596 of the HIV-1 isolate JR-FL; (ii) a proline (P) residue at an amino acid position equivalent to amino acid position 559 of the HIV-1 isolate KNH1144; and (iii) glutamine (Q) at an amino acid position equivalent to amino acid position 543 (Q543); serine (S) at an amino acid position equivalent to amino acid position 553 (S553); and lysine (K) at an amino acid position equivalent to amino acid position 567 (K567); and optionally comprises isoleucine (I) at an amino acid position equivalent to amino acid position 535 (I535) and arginine (R) at an amino acid position equivalent to amino acid position 588 (R588), wherein the amino acid positions of (iii) are numbered by reference to the HIV-1 isolate KNH1144.

The invention provides an isolated nucleic acid encoding a modified form of an HIV-1 gp120 and gp41 polypeptide complex, wherein the modification in gp120 comprises a mutation of a non-cysteine amino acid to cysteine (C) at an amino acid position equivalent to amino acid position 492 of the HIV-1 isolate JR-FL; and the modifications in gp41 comprise a mutation of a non-cysteine amino acid to cysteine (C) at an amino acid position equivalent to amino acid position 596 of the HIV-1 isolate JR-FL, a mutation of a non-isoleucine amino acid to isoleucine (I) at an amino acid position equivalent to amino acid position 535 of the HIV-1 isolate KNH1144, a mutation of a non-glutamine amino acid to glutamine (Q) at an amino acid position equivalent to amino acid position 543 of the HIV-1 isolate KNH1144, a mutation of a non-serine amino acid to serine (S) at an amino acid position equivalent to amino acid position 553 of the HIV-1 isolate KNH1144, a mutation of a non-lysine amino acid to lysine (K) at an amino acid position equivalent to amino acid position 567 of the HIV-1 isolate KNH1144, and a mutation of a non-arginine amino acid to arginine (R) at an amino acid position equivalent to amino acid position 588 of the HIV-1 isolate KNH1144. In an embodiment, the modifications in gp41 encoded by the isolated nucleic acid further comprise a mutation of a non-proline amino acid to proline (P) at an amino acid position equivalent to amino acid position 559 of the HIV-1 isolate KNH1144. In an embodiment, the isolated nucleic acid is DNA, cDNA, or RNA. In an embodiment, an expression vector, which may contain an expression cassette, contains the above-described nucleic acid. In an embodiment, a eukaryotic or prokaryotic host cell contains the expression vector.

This invention further provides an isolated nucleic acid encoding a modified form of an HIV-1 gp120 and gp41 polypeptide complex, wherein the modification in gp120 comprises an A492C mutation and the modifications in gp41 comprise a T596C mutation, an M535I mutation; an L543Q mutation; an N553S mutation; a Q567K mutation and a G588R mutation, wherein the A492C and T596C mutations are numbered by reference to the HIV-1 isolate JR-FL, and the M535I, L543Q, N553S, Q567K and G588R mutations are numbered by reference to the HIV-1 isolate KNH1144.

This invention also provides a method for eliciting an immune response against HIV-1 or an HIV-1 infected cell in a subject comprising administering to the subject an amount of the composition of the invention effective to elicit the immune response in the subject.

This invention provides a method for eliciting an immune response against HIV-1 or an HIV-1 infected cell in a subject comprising administering to the subject an amount of the trimeric complex of the invention effective to elicit the immune response in the subject.

This invention also provides a method for preventing a subject from becoming infected with HIV-1, comprising administering to the subject an amount of the composition of the invention effective to prevent the subject from becoming infected with HIV-1.

This invention further provides a method for reducing the likelihood of a subject becoming infected with HIV-1, comprising administering to the subject an amount of the composition of of the invention effective to reduce the likelihood of the subject becoming infected with HIV-1.

This invention also provides a method for delaying the onset of, or slowing the rate of progression of, an HIV-1-related disease in an HIV-1-infected subject, which comprises administering to the subject an amount of an isolated nucleic acid encoding a modified form of an HIV-1 gp120 and gp41 polypeptide complex, wherein the modification in gp120 comprises an A492C mutation and the modifications in gp41 comprise a T596C mutation, an M535I mutation; an L543Q mutation; an N553S mutation, a Q567K mutation and a G588R mutation, wherein the A492C and T596C mutations are numbered by reference to the HIV-1 isolate JR-FL, and the M535I, L543Q, N553S, Q567K and G588R mutations are numbered by reference to the HIV-1 isolate KNH1144 effective to delay the onset of, or slow the rate of progression of, the HIV-1-related disease in the subject.

This invention also provides a method of stabilizing HIV-1 trimer complexes which comprise non-covalently associated gp120 and gp41 envelope polypeptides, which polypeptides comprise consecutive amino acids, said method comprising: introducing into the gp41 ectodomain polypeptide an isoleucine (I) at an amino acid position equivalent to amino acid position 535; a glutamine (Q) at an amino acid position equivalent to amino acid position 543; a serine (S) at an amino acid position equivalent to amino acid position 553; a lysine (K) at an amino acid position equivalent to amino acid position 567; and an arginine (R) at an amino acid position equivalent to amino acid position 588, wherein the amino acid positions are numbered by reference to the HIV-1 isolate KNH1144.

The invention provides a chimeric gp140 polypeptide comprising (i) a gp120 envelope polypeptide of a lade B subtype of an HIV-1 isolate and (ii) a gp41 ectodomain polypeptide of the HIV-1 isolate KNH1144, said polypeptides comprising consecutive amino acids, wherein the KNH1144 gp41 ectodomain polypeptide comprises isoleucine (I) at amino acid position 535; glutamine (Q) at amino acid position 543; serine (S) at amino acid position 553; lysine (K) at amino acid position 567; and arginine (R) at amino acid position 588; and wherein the amino acid positions are numbered by reference to the HIV-1 isolate KNH1144.

The invention further provides a chimeric gp140 polypeptide comprising (i) a gp120 envelope polypeptide of a clade B subtype of an HIV-1 isolate and (ii) a gp41 ectodomain polypeptide of the HIV-1 isolate KNH1144, said polypeptides comprising consecutive amino acids, wherein the KNH1144 gp41 ectodomain polypeptide comprises the sequence as set forth in SEQ ID NO:1 or SEQ ID NO:18.

The invention further provides a chimeric gp140 polypeptide comprising (i) a gp120 envelope polypeptide of a clade B subtype of an HIV-1 isolate and (ii) a gp41 ectodomain polypeptide of the HIV-1 isolate KNH1144, said polypeptides comprising consecutive amino acids, wherein the KNH1144 gp41 ectodomain polypeptide comprises an amino acid sequence as set forth in SEQ ID NO:20 or SEQ ID NO:21, or the gp41 ectodomain polypeptide portion of the gp160 polypeptide as set forth in any one of SEQ ID NOS:5-8.

This invention provides a gp41 ectodomain polypeptide which comprises the consecutive amino acid sequence as set forth in any one of SEQ ID NO:1, SEQ ID NO:18, SEQ ID NO:2, SEQ ID NO:22, SEQ ID NO:3, SEQ ID NO:25, or SEQ ID NO:28, which sequences contain or are modified to contain one or more of the trimer stabilizing amino acid residues described herein. In an embodiment, the gp41 ectodomain polypeptide contains at least three of the trimer stabilizing amino acid residues.

The invention further provides a modified gp41 ectodomain polypeptide which comprises the consecutive amino acid sequence as set forth in any one of SEQ ID NO:20, SEQ ID NO:21, SEQ ID NO:24, SEQ ID NO:27, or SEQ ID NO:30.

The invention also provides a modified gp160 polypeptide, which comprises a consecutive amino acid sequence as set forth in any one of SEQ ID NO:7, SEQ ID NO:8, SEQ ID NO:11, SEQ ID NO:14, or SEQ ID NO:17.

The invention further provides a gp160 polypeptide which comprises the consecutive amino acid sequence as set forth in any one of SEQ ID NO:9, SEQ ID NO:12, or SEQ ID NO:15, which sequences are modified to contain one or more of the trimer stabilizing amino acid residues described herein. In an embodiment, the modified gp160 polypeptides contain at least three of the trimer stabilizing amino acid residues.

Also provided are the gp120 and gp41 portions of the modified gp160 polypeptides, which can complex to form stabilized trimers of the invention. In an embodiment, the trimers further comprise a non-ionic detergent as described herein.

The present invention further provides an antibody, or a portion of the antibody, generated by immunizing an animal with a modified gp140 polypeptide as described herein; an antibody, or a portion of the antibody, generated by immunizing an animal with a trimeric complex as described herein; an antibody, or a portion of the antibody, generated by immunizing an animal with a composition as described herein; an antibody, or a portion of the antibody, generated by immunizing an animal with a modified gp41 ectodomain polypeptide as described herein; or an antibody, or a portion of the antibody, generated by immunizing an animal with the modified gp160 polypeptide or a portion thereof, e.g., gp120 polypeptide and/or gp41 ectodomain polypeptide, as described herein. In an embodiment, the antibody is a monoclonal antibody, or a portion of the monoclonal antibody. In an embodiment, the antibody is a humanized antibody, or a portion of the humanized antibody.

This invention also provides trimeric complexes and compositions as described herein, further comprising a non-ionic detergent.

The invention further provides a use of a modified gp140 polypeptide, a trimeric complex, a composition, a modified gp41 ectodomain polypeptide, or a modified gp160 polypeptide, or portion thereof, e.g., gp120 polypeptide and/or gp41 ectodomain polypeptide, for the preparation of a medicament for the treatment or prevention of infection by human immunodeficiency virus (HIV).

BRIEF DESCRIPTIONS OF THE FIGURES

FIGS. 1A and 1B: (A) Schematic view of gp41 region showing the location of the fusion peptide (FP), heptad repeat regions 1 and 2 (HR1 and HR2), the transmembrane region (TM) and the cytoplasmic tail (CT). The intramolecular disulfide bond is also shown. (B) Alignment of the N-terminus regions of KNH1144, JR-FL and Ba-L gp41, highlighting the 5 amino acids (bold and shaded) in and near the HR1 region (underlined) that differ in JR-FL and B-aL when compared to KNH1144.

Figure 2:
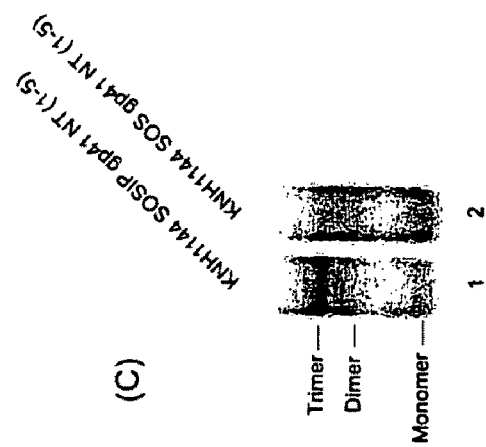
Figure 2:
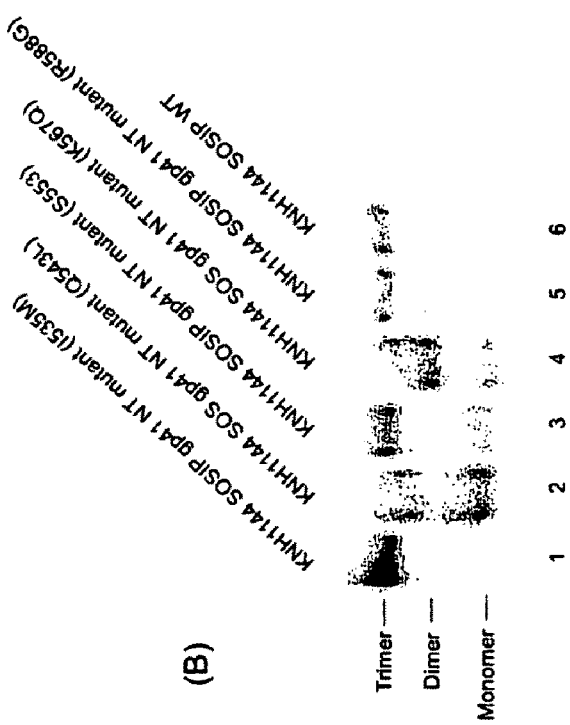
Figure 2:
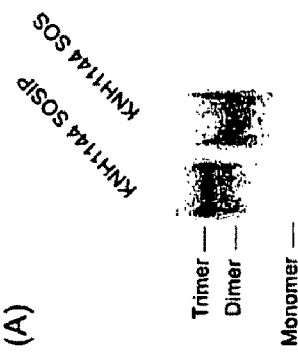

FIGS. 2A-2C: Trimer formation by cleaved, wild-type and mutant KNH1144 gp140 proteins. (A) SOS and SOSIP versions of KNH1144 gp140 proteins. (B) KNH1144 SOSIP gp140 mutants containing the indicated single residue substitutions in the gp41 N-terminal region, compared with the wild-type KNH1144 SOSIP gp140. (C) KNH1144 SOSIP and SOS mutant gp140s, as indicated. Each panel shows a BN-PAGE analysis, followed by western blotting using MAb CA13.

Figure 3:
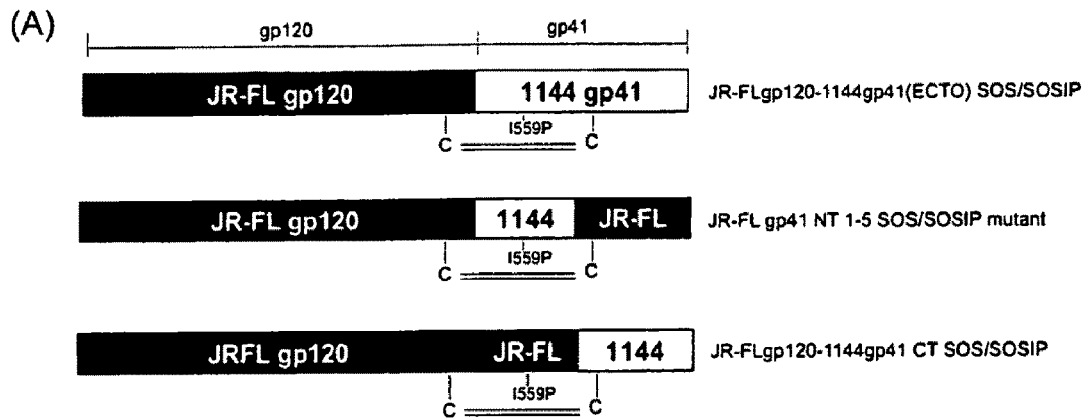
Figure 3:
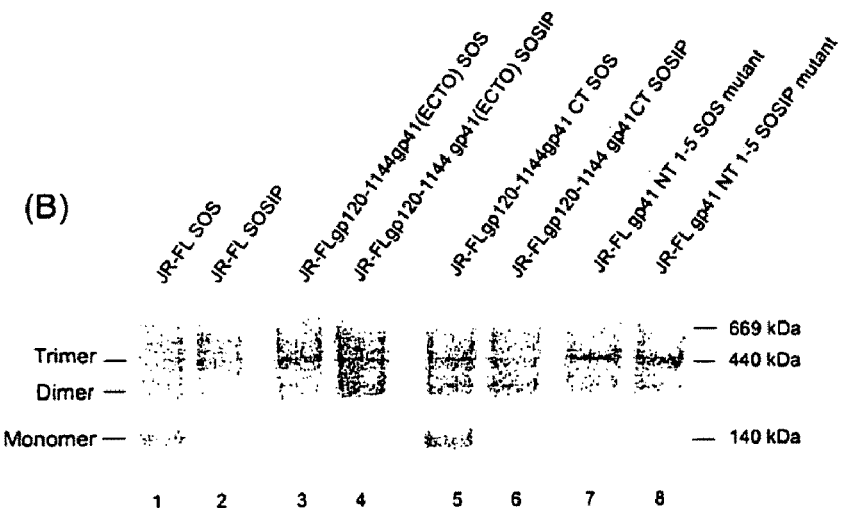
Figure 3:
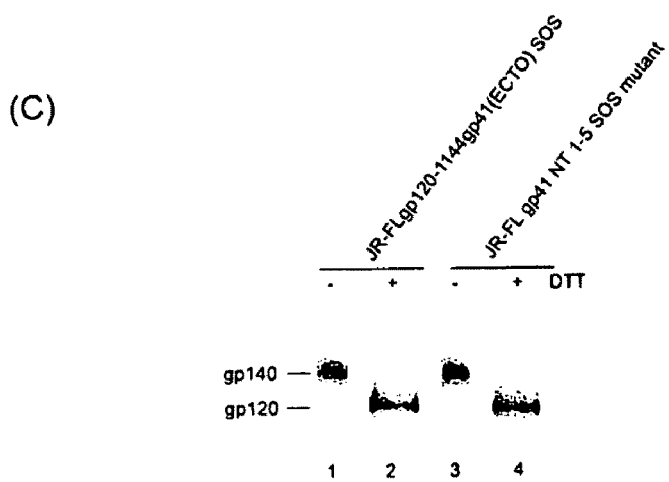

FIGS. 3A-3C: Trimer formation by cleaved, wild-type and mutant JR-FL SOS gp140 proteins. (A) Design of various chimeric and mutant JR-FL gp140s. The intermolecular disulfide bond (SOS) and the Ile to Pro substitution at position 559 (I559P; SOSIP) are shown. (B) The indicated wild-type and mutant/chimeric gp140 proteins were analyzed using BN-PAGE and western blotting with MAb CA13. The designation NT 1-5 refers to substitution of the 5 amino acids M535I, L543Q, N553S, Q567K and G588R, in the gp41 N-terminus region. (C) The JR-FLgp120-1144gp41(ECTO) SOS gp140 chimera and the JR-FL gp41 NT 1-5 SOS gp140 mutant were analyzed by SDS-PAGE and western blotting, followed by detection with MAb B13. The − and + symbols indicate the absence and presence of DTT.

FIGS. 4A and 4B: (A) The wild-type JR-FL SOS gp140 and (B) the JR-FL gp41 NT 1-5 SOS gp140 mutant were analyzed by size-exclusion chromatography followed by BN-PAGE and western blotting with MAb CA13. The mutant protein is predominantly trimeric, the wild-type protein mostly monomeric.

Figure 5:
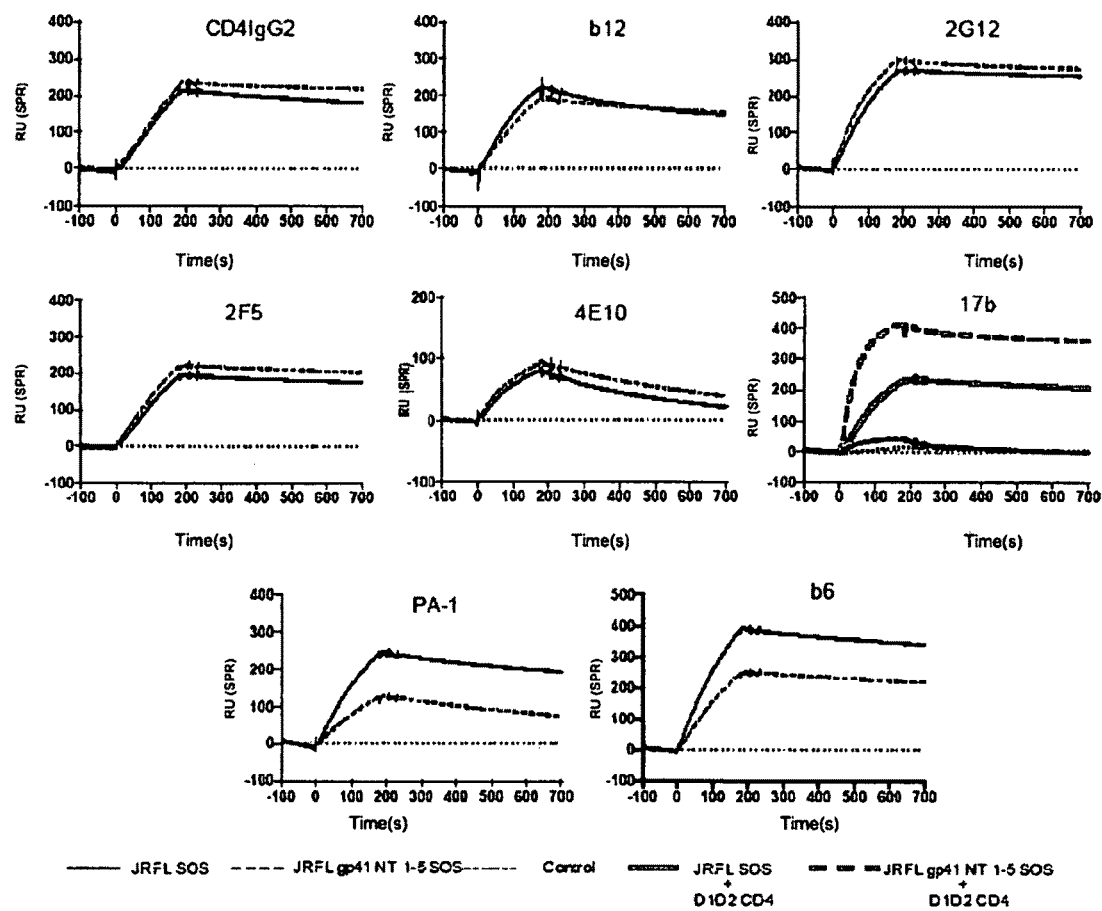
Figure 5:
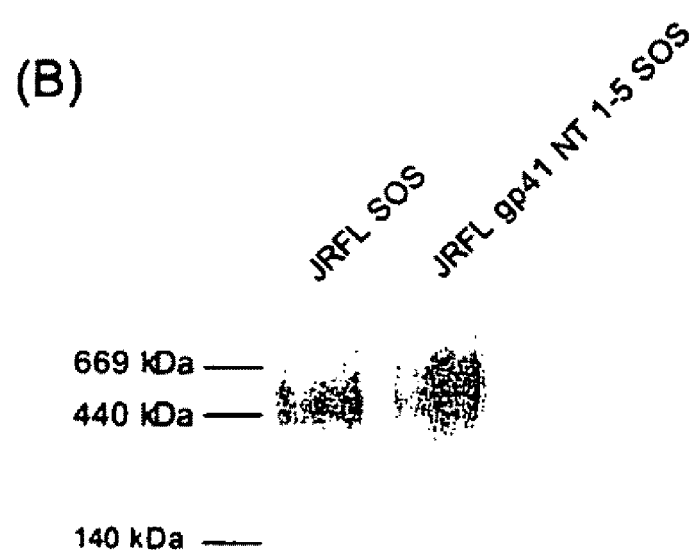

FIGS. 5A and 5B: (A) Representative SPR analysis of the binding of MAbs to the JR-FL SOS gp140 and the gp41 NT 1-5 SOS gp140 mutant to the following test agents were: (I) CD4IgG2, (II) b12, (III) 2G12, (IV) 2F5, (V) 4E10, (VI) PA-1, (VII) b6 and (VIII) 17b −/+ D1D2-CD4. The y-axis shows the SPR response unit (RU), the x-axis the time in seconds (s). (B) Injected samples from the BIAcore machine were manually collected after the ligand binding analysis, then analyzed by BN-PAGE. The wild-type JR-FL SOS gp140 and the gp41 NT 1-5 SOS gp140 mutant proteins are shown, from a representative experiment, one using the PA-1 mAb.

Figure 6:
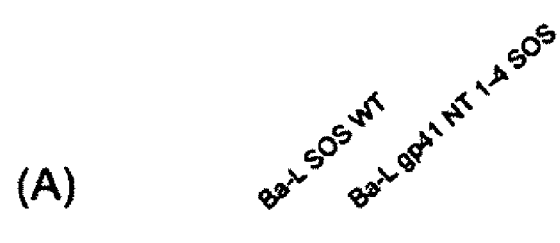
Figure 6:
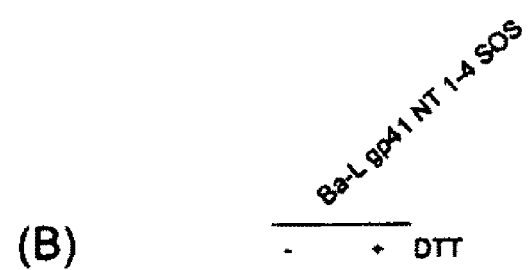
Figure 6:

FIGS. 6A and 6B: Stabilizing cleaved Ba-L SOS gp140 trimers. (A) The wild-type Ba-L SOS gp140 and the mutant Ba-L gp41 NT 1-4 SOS gp140 proteins were analyzed by BN-PAGE and western blotting with MAb CA13. (B) The same proteins were analyzed by SDS-PAGE and western blotting, followed by detection with MAb B13. The − and + symbols indicate the absence and presence of DTT.

Figure 7:
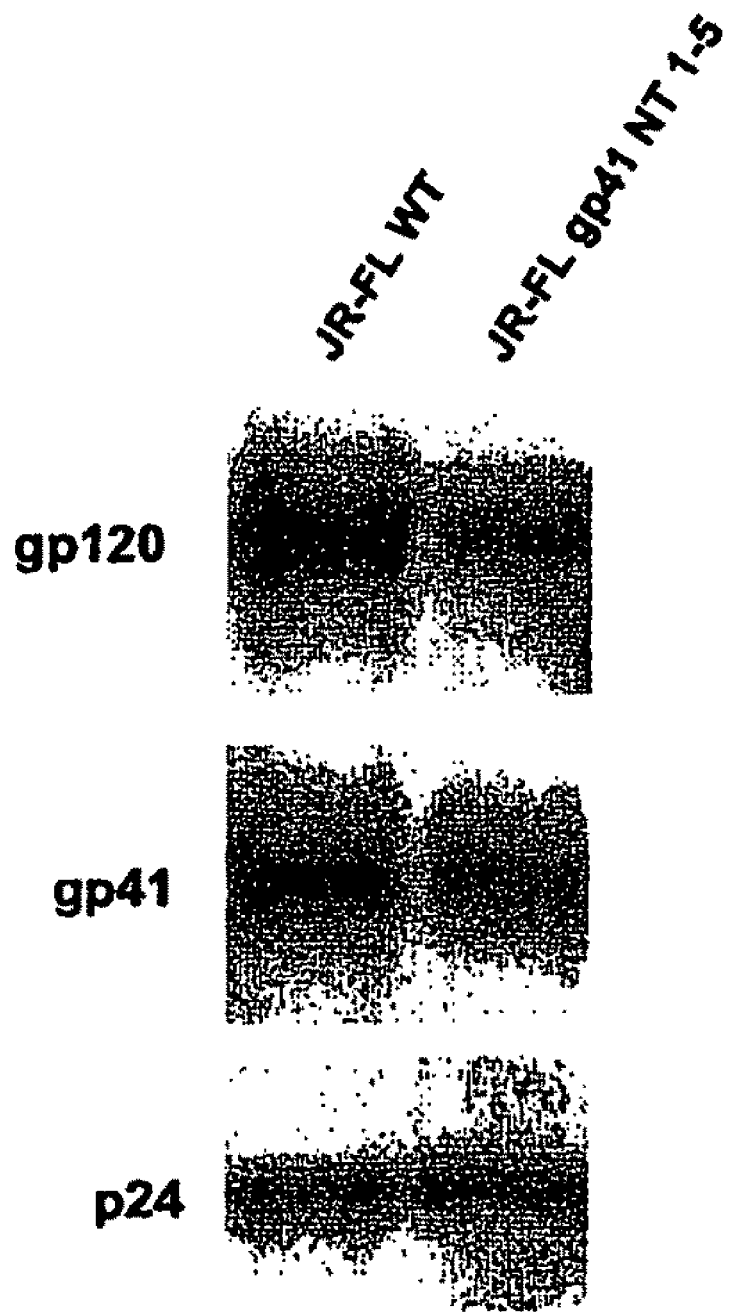

FIG. 7: Effect of gp41 N-terminus substitutions on Env incorporation into pseudovirions. The JR-FL WT and gp41 NT 1-5 mutant viruses were produced by transfection of HEK 293T cells and pelleted from clarified supernatants. The gp120, gp41 and p24 proteins wree resolved by SDS-PAGE and analyzed by Western blotting with the appropriate antibodies.

FIGS. 8A and 8B: Effect of gp41 N-terminal changes on the Env forms present on pseudovirions. FIG. 8A: Virions, normalized for p24 content and expressing either the JR-FL WT Env glycoprotein, or the gp41 NT 1-5 mutant Env glycoprotein, were solubilized and analyzed under native conditions on a 4-12% Bis-Tris NuPAGE gel and Western blotted with the anti-gp12-MAb ARP43119. Env tetramers and dimers are highlighted with black arrows; trimers are indicated with a gray arrow. FIG. 8B: The histogram shows the relative proportions of the different Env forms present on the WT (black bars) and mutant (gray bars) pseudovirions. The densitometric data represents the Mean±Standard Deviation of values from four independent experiments.

Figure 9A:
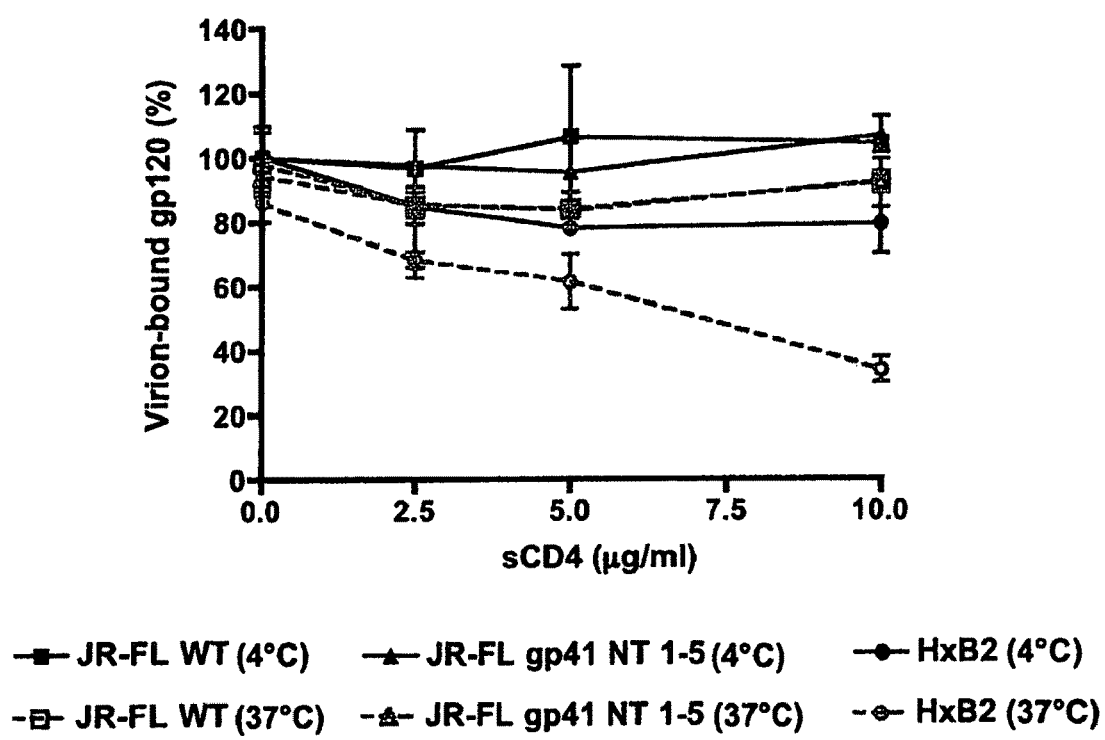
Figure 9B:
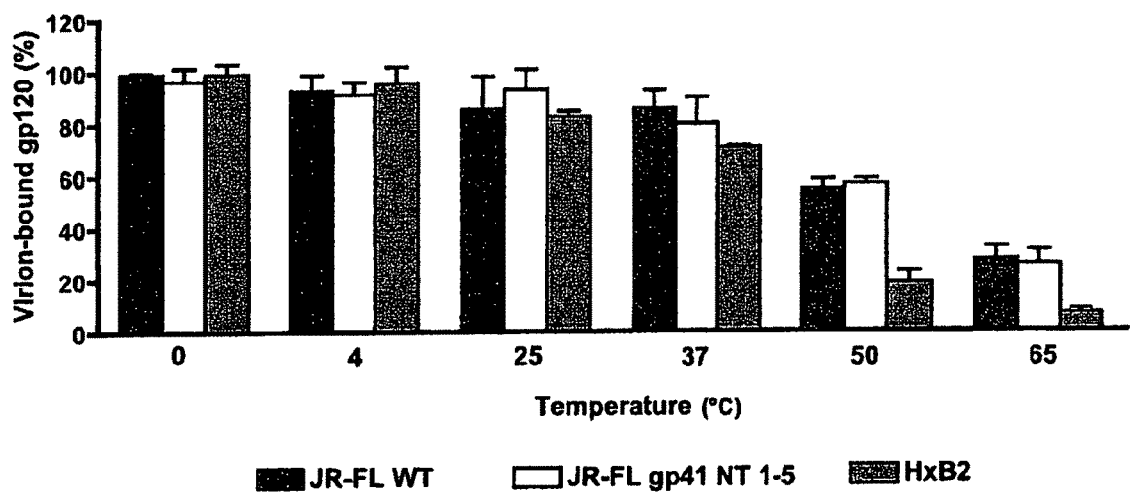

FIGS. 9A and 9B: Effect of gp41 N-terminal substitutions on soluble CD4- and temperature-induced gp120 shedding from pseudovirions. FIG. 9A: Pseudovirions expressing the JR-FL WT Env or gp41 NT 1-5 mutant Env were incubated for 2 hours with sCD4 at the concentrations indicated, at either 4° C. or 37° C. FIG. 9B: The pseudovirions were incubated for 2 hours at the temperatures indicated in the absence of sCD4. In both experiments, the HxB2 Env-pseudotyped virus served as a reference standard. The amount of virion-bound Env is expressed relative to that present on each virus in the absence of sCD4 at 4° C. (=100%).

Figure 10:
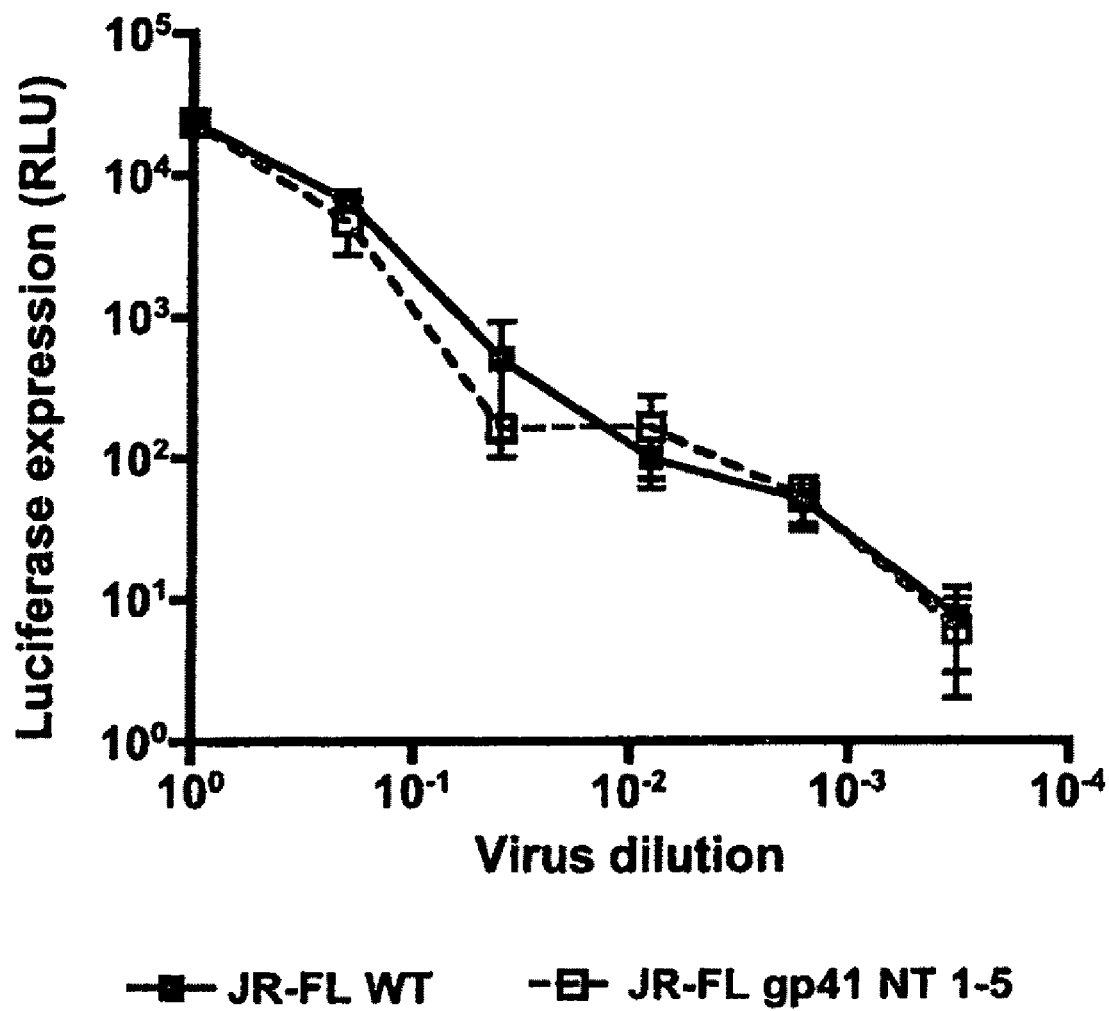

FIG. 10: Effect of gp41 N-terminal substitutions on Env-pseudotyped virus infectivity. Pseudovirions containing normalized amounts of p24 antigen and bearing the WT or mutant forms of JR-FL Env were serially diluted and used to infect U87.CD4.CCR5 cells. Infectivity was quantified by measuring luciferase activity four days post infection.

Figure 11A:
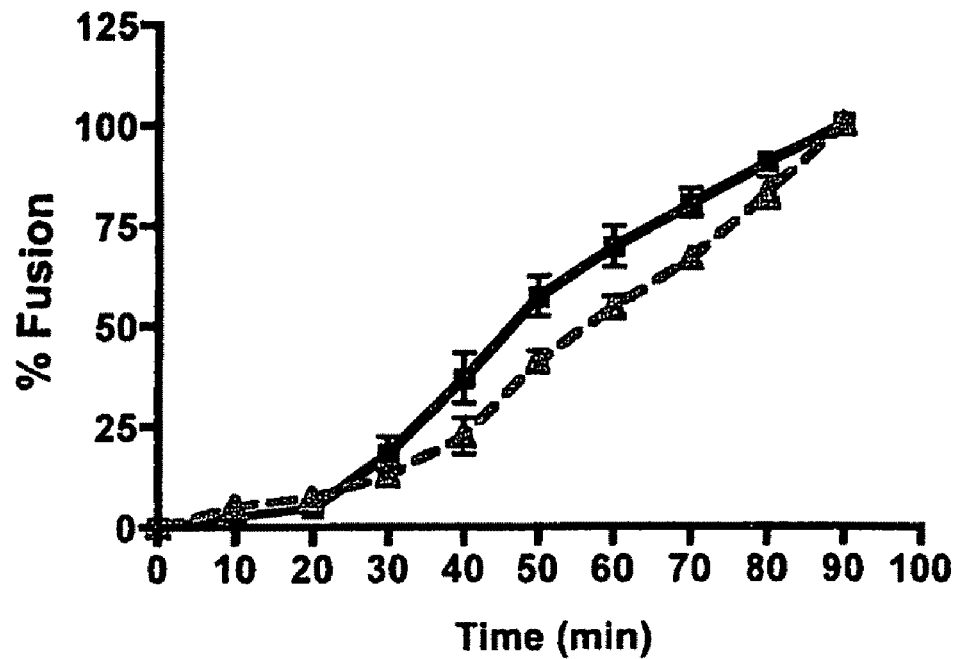
Figure 11B:
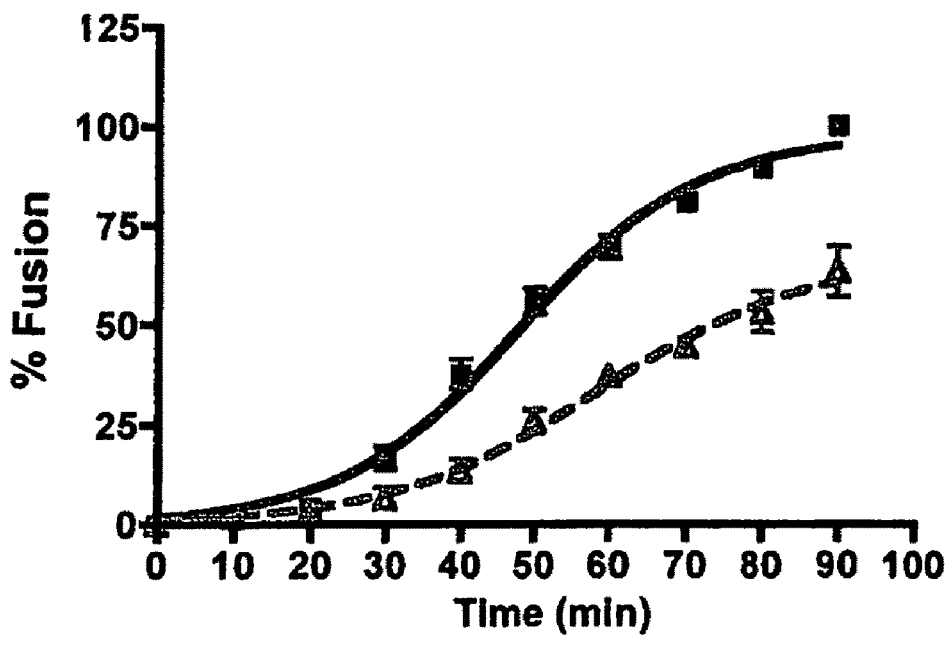

FIGS. 11A and 11B: Effect of gp41 N-terminal substitutions on Env-mediated cell-cell fusion. The kinetics of fusion mediated by the WT (black squares) and mutant (gray triangles) forms of JR-FL Env were determined in a β-lactamase reporter assay using HeLa-CD4/CCR5 (RC49) cells. The extent of fusion is expressed as the percentage of the maximal fusion mediated by each Env (FIG. 11A), or the maximal fusion mediated by the WT Env (FIG. 11B). The data represent the Mean±Standard Errors of three independent experiments. The various kinetic parameters are described in Table 3.

Figure 12A:
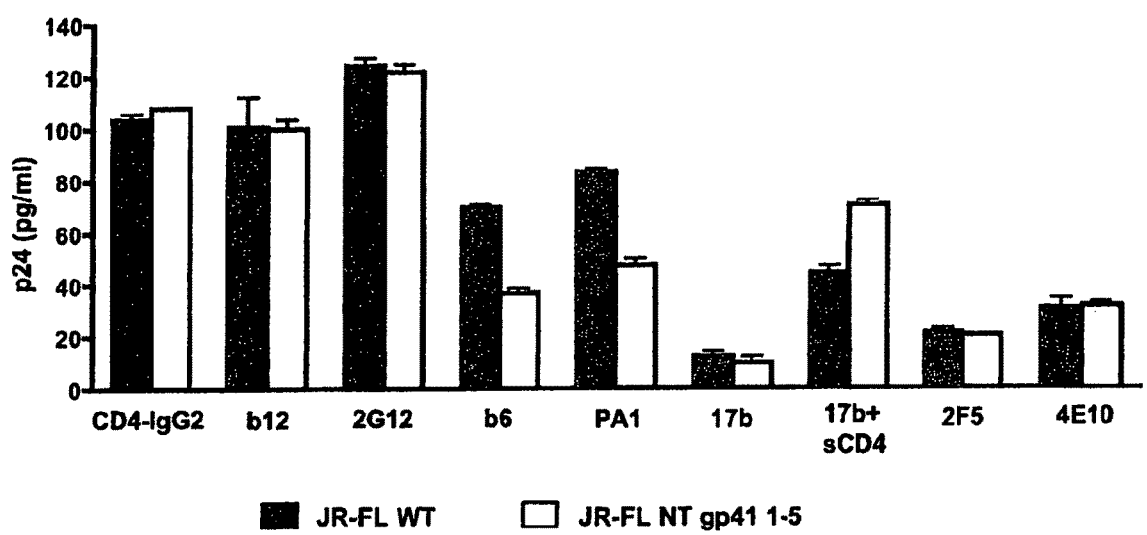
Figure 12B:
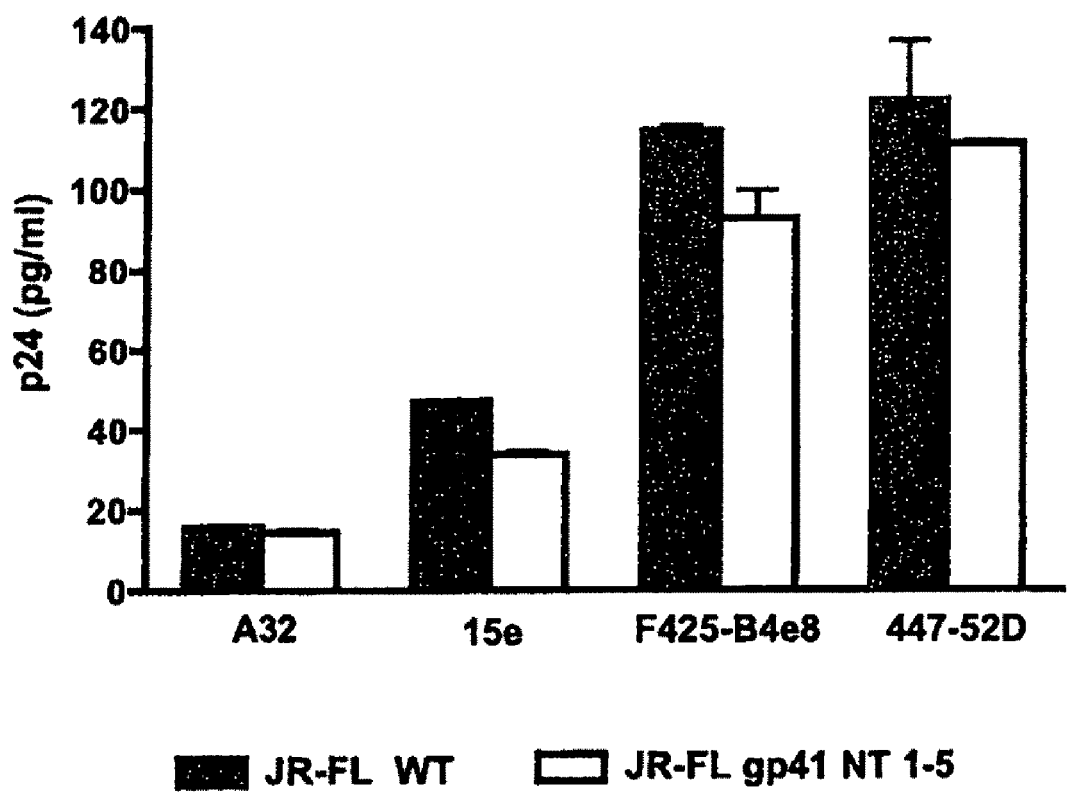

FIGS. 12A and 12B: Effect of gp41 N-terminal substitutions on the binding of MAbs to pseudovirions. Equal amounts (judged by p24 antigen content) of virions expressing either the WT (black bars) or mutant (white bars) forms of JR-FL Env were tested in a virus capture assay. The amount of p24 antigen captured by each of the indicated MAbs is recorded.

FIGS. 13A and 13B: Cell-surface expression of wild-type and gp41 mutant Env glycoproteins and their reactivity with CD4-IgG2 and MAbs. FIG. 13A: Cell surface-expressed Envs were biotinylated, avidin-precipitated and detected using MAb ARP3119. Cell surface expressed CD47 served as a loading control (lower panel). FIG. 13B: The WT and gp41 NT mutant Env glycoproteins were stained with 10 μg/ml of biotinylated MAbs, followed by streptavidin-PE. Background fluorescence due to the secondary antibody was determined using isotype-matched controls; background values were subtracted from experimental values. The MFI (mean fluorescence intensity) values are shown as Mean±Standard Deviation from a representative experiment performed in triplicate.

Figure 14:
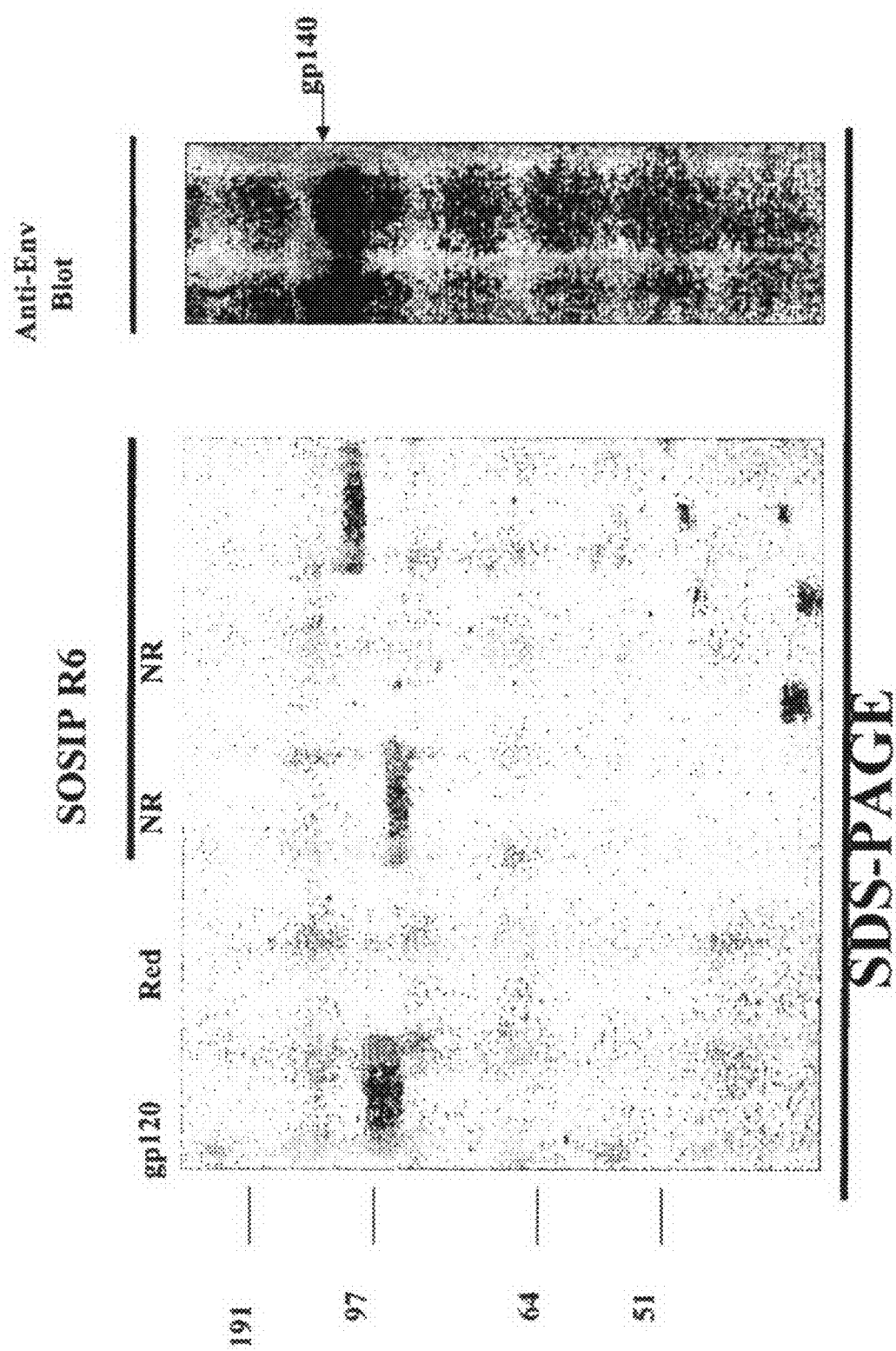
Figure 14:
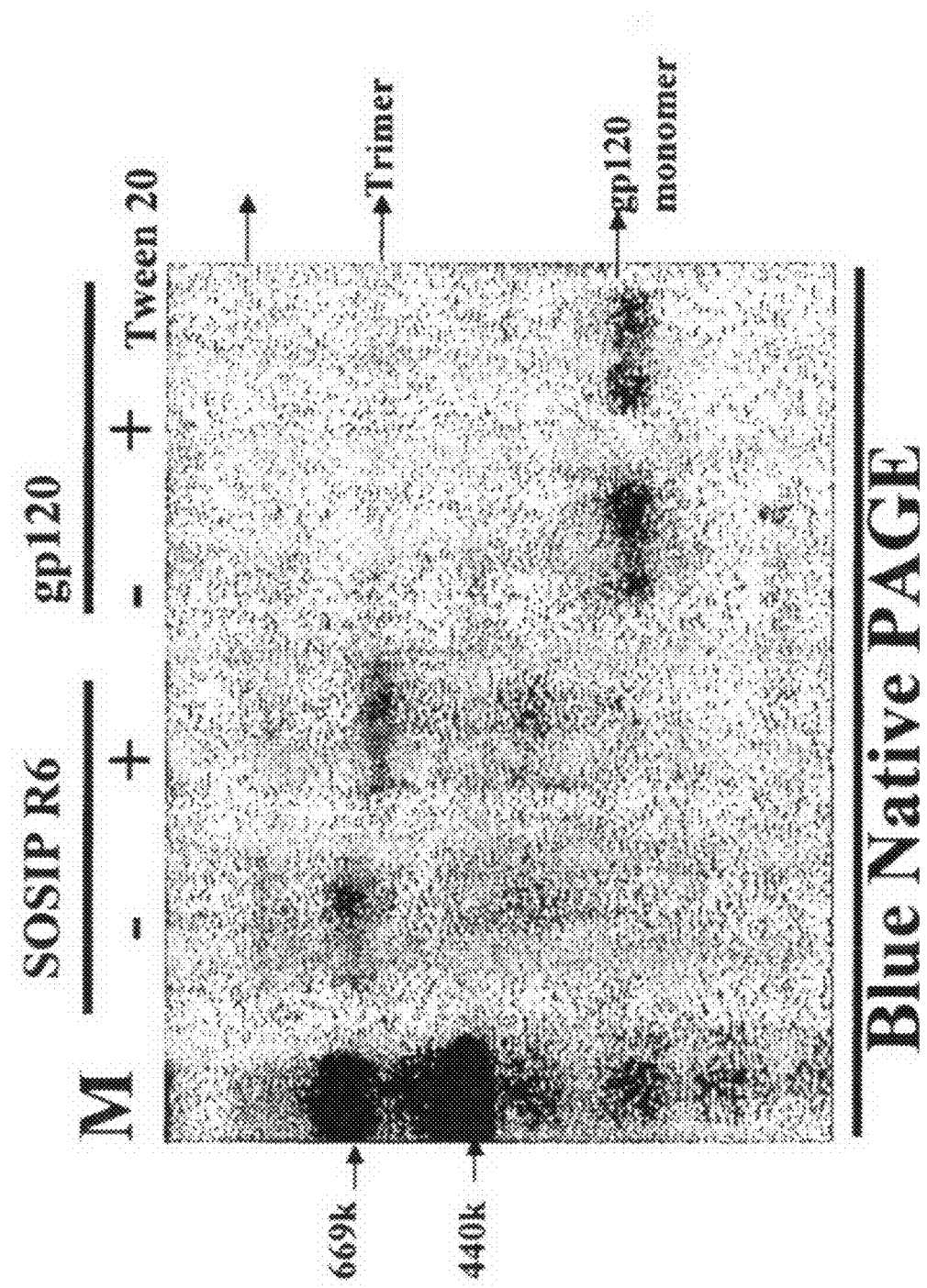

FIG. 14: Analysis of purified KNH1144 SOSIP R6 gp140 trimer and gp120 monomer. Purified KNH1144 gp120 monomer (left panel, gp120) and SOSIP R6 gp140 trimer were analyzed by reducing (left panel, SOSIP R6, Red) and non-reducing SDS-PAGE (left panel, SOSIP R6, NR). Proteins were visualized by Coomassie G-250 stain. Purified trimer was also analyzed via ARP3119 western blot on non-reducing SDS-PAGE to examine presence of SDS-insoluble aggregates (middle panel, Anti-Env blot). The numbers on the left represent the migratory positions of the molecular weight standard proteins. The right panel shows BN-PAGE analysis of purified trimer, either untreated or treated with Tween® 20 (SOSIPR6, −/+ lanes) and purified gp120 monomer in absence or presence of Tween® 20 treatment (gp120, −/+ lanes). Arrows indicate high molecular weight (HMW) aggregate, trimer and gp120 monomer species. M stands for the 669k thyroglobulin and 440k ferritin molecular weight protein standards.

FIGS. 15A-15D: Tween® 20 conversion experiments. (A) Dose response: Purified KNH1144 SOSIP R6 gp140 trimer was incubated with 0 (no detergent control), or 0.1, 0.05, 0.01, 0.001, or 0.0001% Tween® 20 and analyzed by BN-PAGE and Coomassie G-250 stain. Arrows point to HMW aggregate and trimer species. M stands for the 669k thyroglobulin and 440k ferritin molecular weight protein standards. (B) Time course: Purified KNH1144 SOSIP R6 gp140 trimer was incubated with Tween® 20 for 5 min (left panel) or 10 min (right panel). Trimer was either untreated (−lane) or Tween® 20 treated (+lane). Arrows indicate trimer and HMW aggregate bands. (C) Temperature effect: Purified KNH1144 SOSIP R6 gp140 trimer was either untreated (−lane) or treated with Tween® 20 at on ice (0), room temperature (RT) or 37° C. Reactions were analyzed by BN-PAGE and Coomassie G-250 stain. Arrows indicate HMW aggregate and trimer proteins. (D) Tween® 20 effect on HMW aggregate and dimer fractions: A preparation composed predominantly of HMW aggregate (>80%) was untreated (left panel, −lane), or incubated with Tween® 20 (left panel, +lane), and analyzed by BN-PAGE and Coomassie G-250 stain. Solid arrows indicate HMW aggregate and trimer proteins. Preparations composed of HMW aggregate, dimers and monomers were untreated (right panel, −lane) or incubated with Tween® 20 (right panel, +lane) and analyzed by BN-PAGE and Coomassie G-250 stain. Arrows on the right hand side point to aggregate, trimer, dimer and monomer species.

Figure 16:
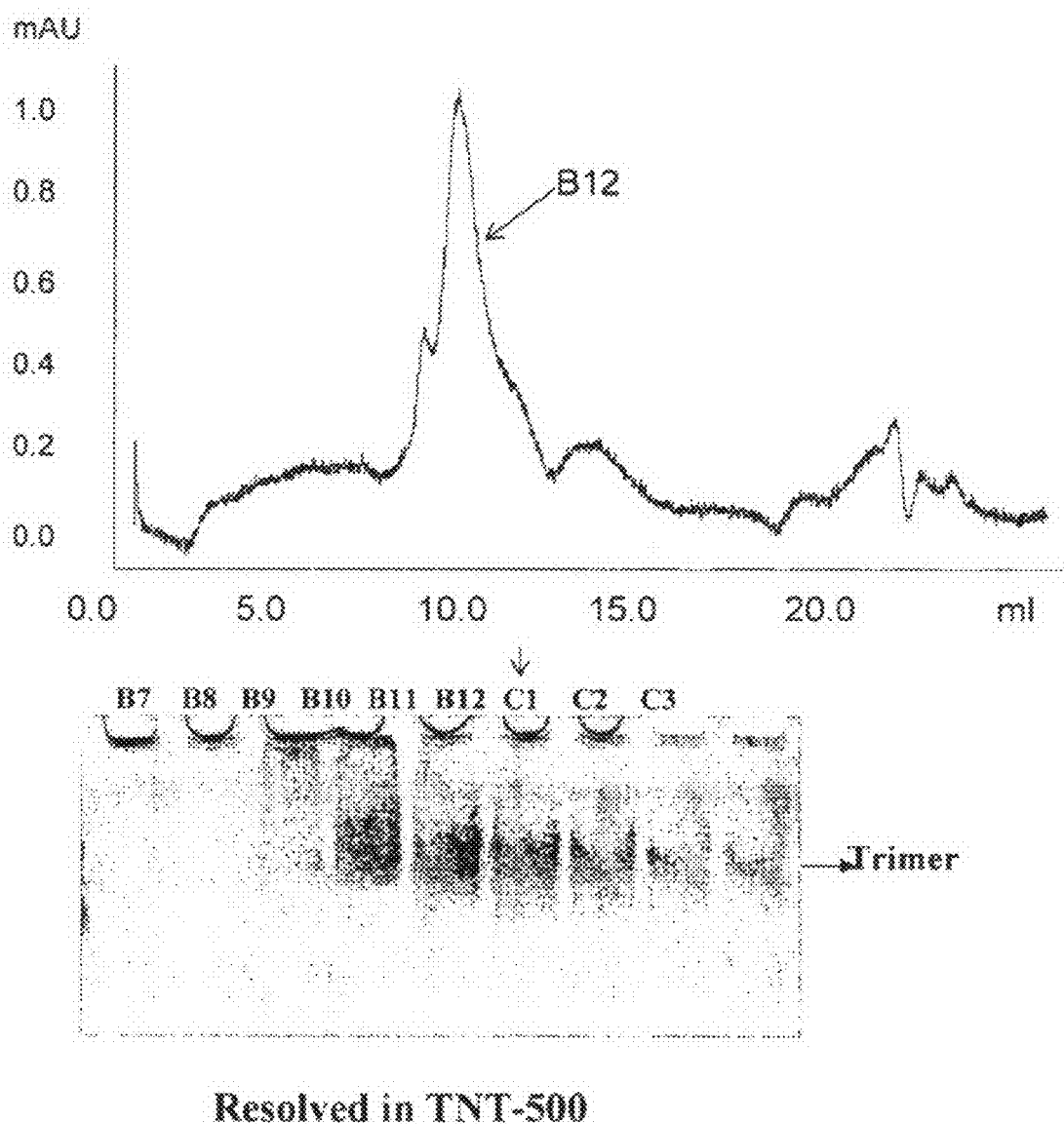

FIG. 16: Size Exchange Chromatography (SEC) analysis of KNH1144 SOSIP R6 gp140 trimer. KNH1144 SOSIP R6 gp140 trimer was resolved on a Superdex 200 10/300 GL column in TN-500 buffer containing 0.05% Tween® 20 (TNT-500). The $A_{280}$ protein profile of the run is shown in the middle panel. Fractions B7-C3 from the run were analyzed by BN-PAGE, followed by silver stain (bottom panel). Arrows to the side of the BN-PAGE image point to the trimer. The vertical arrow in the BN-PAGE indicates the peak signal of the trimer in fraction B12. The arrow in the middle chromatograph corresponds to fraction B12.

Figure 17A:
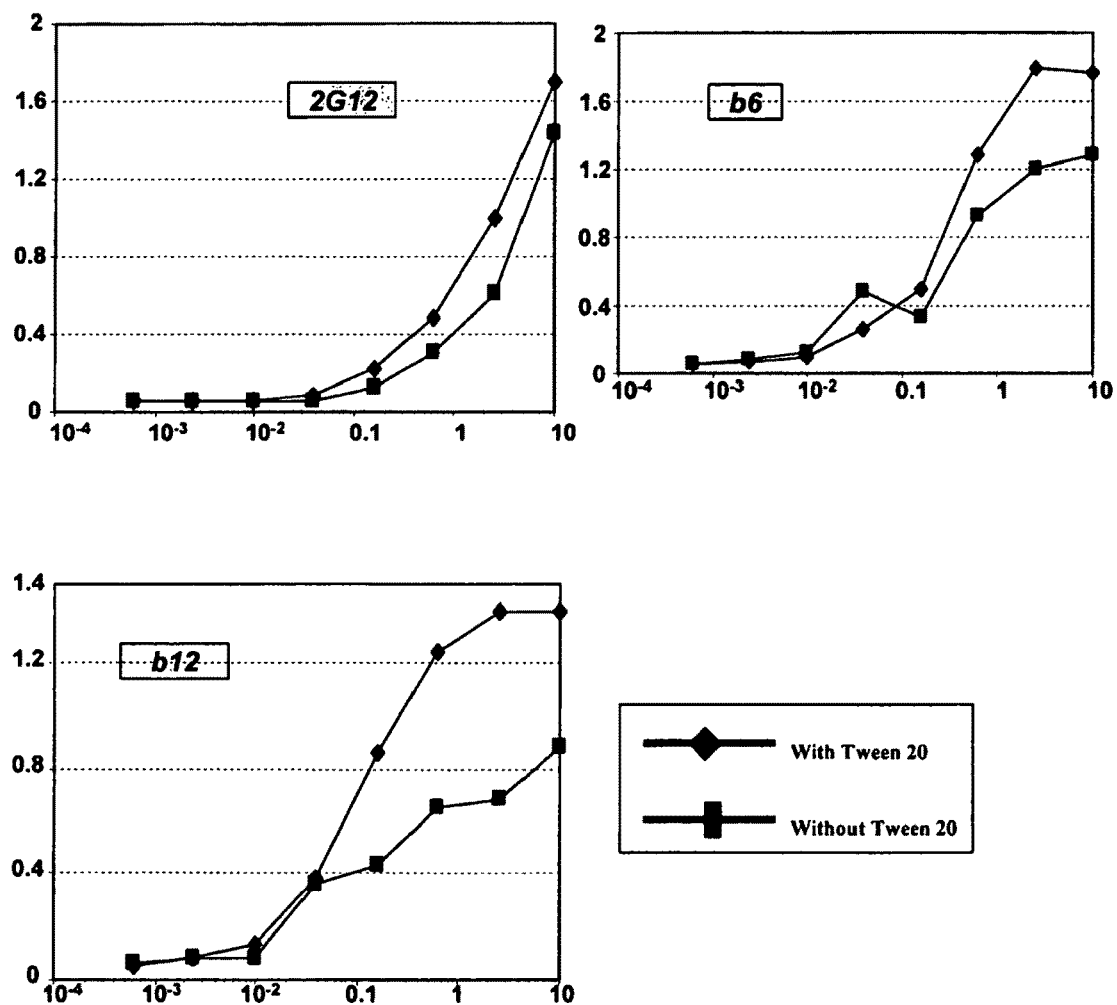
Figure 17A:
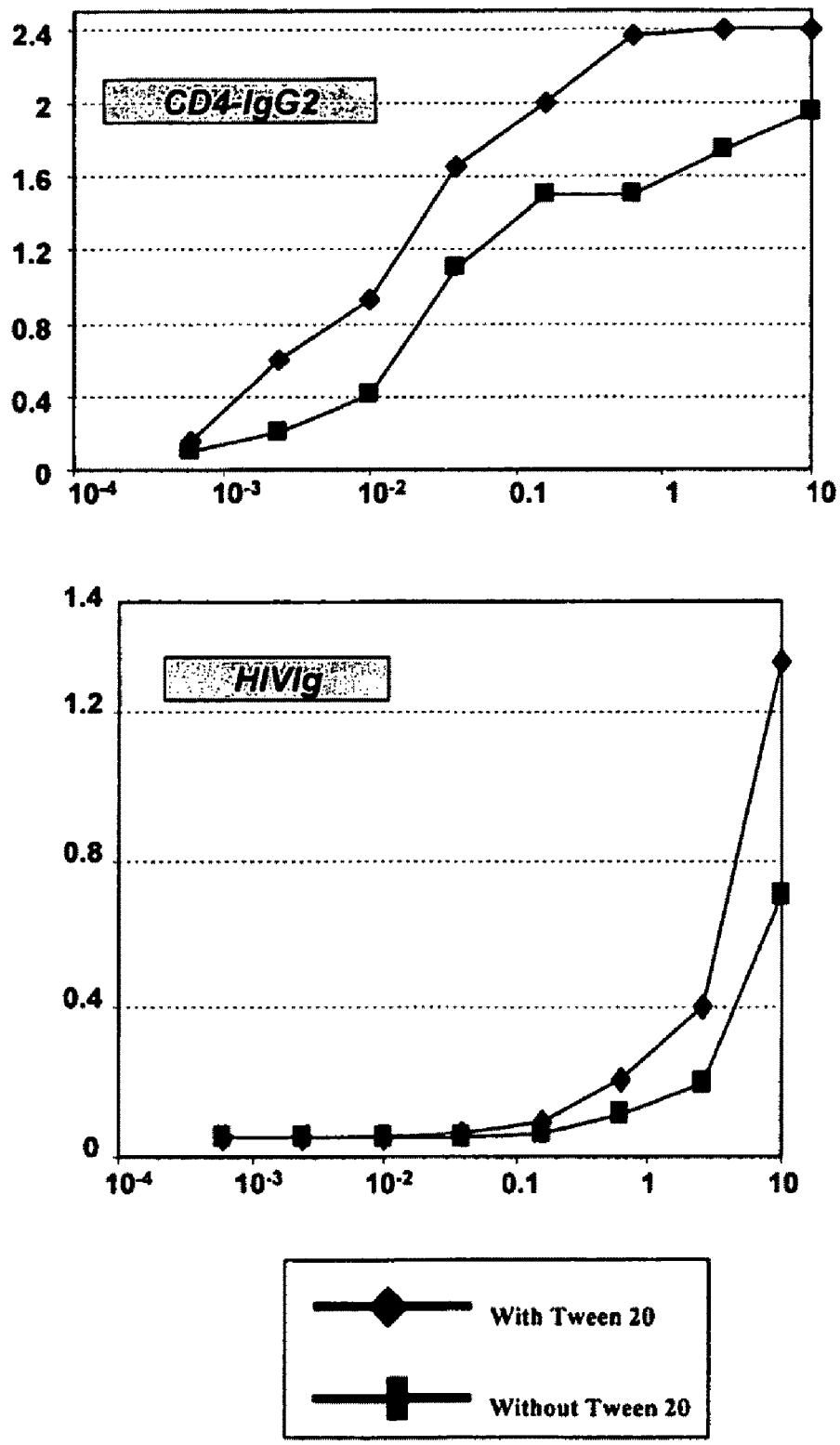
Figure 17B:
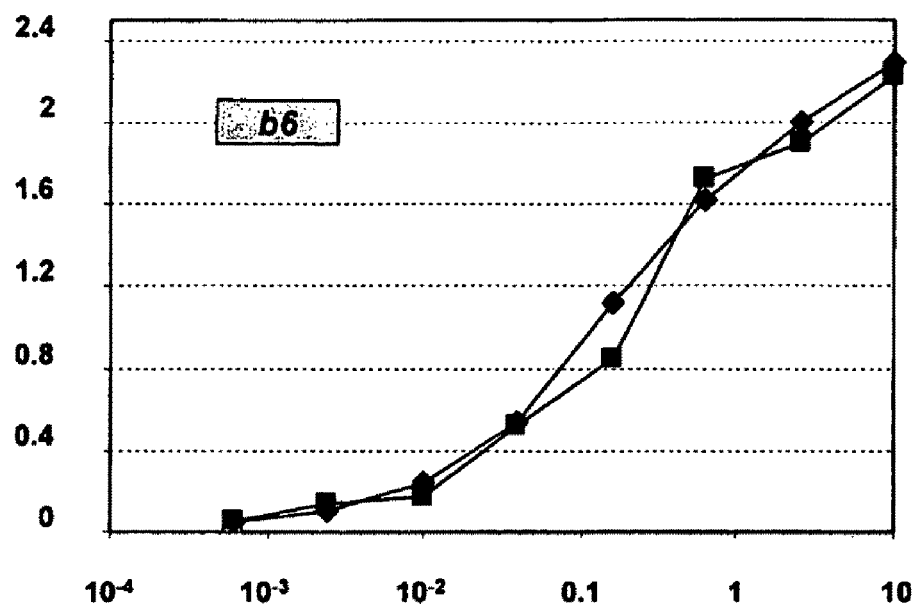
Figure 17B:
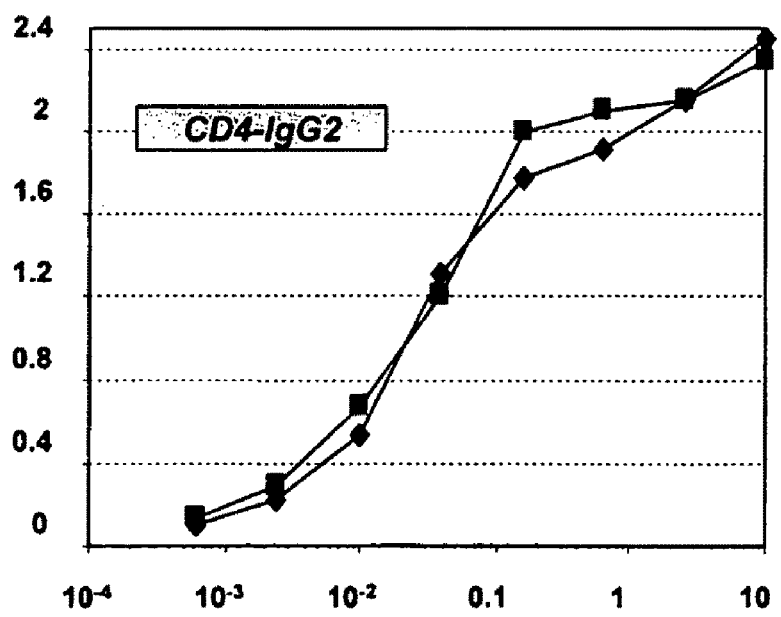
Figure 17B:
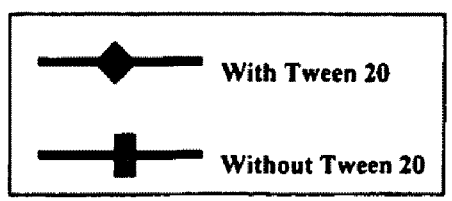
Figure 17B:
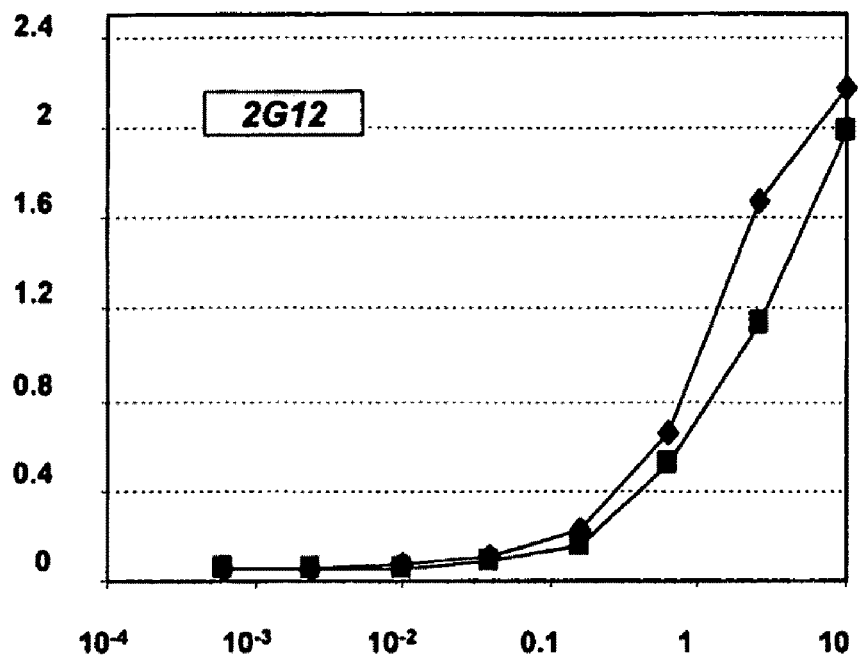
Figure 17B:
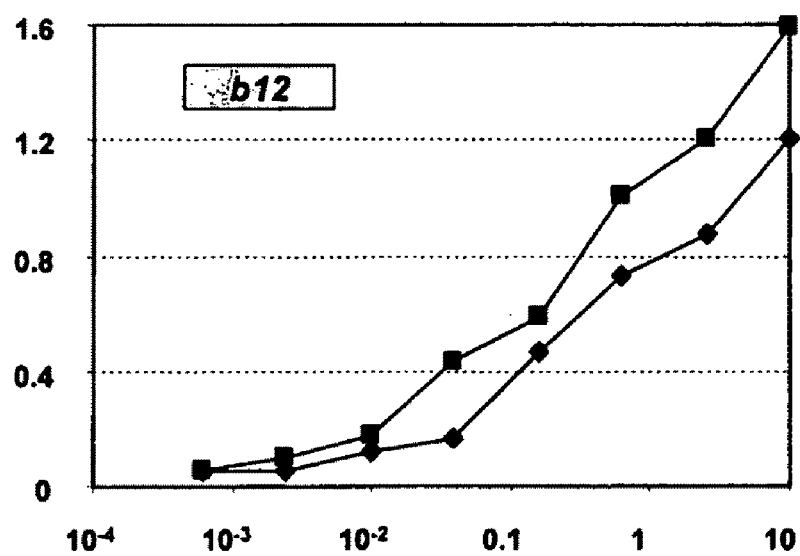
Figure 17B:
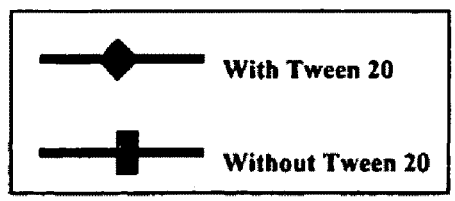

FIGS. 17A and 17B: Effect of Tween® 20 treatment on KNH1144 SOSIP R6 HMW aggregate antigenicity. (A) Lectin ELISA of untreated and Tween® 20 treated KNH1144 SOSIP R6 HMW aggregate: Untreated or Tween® 20-treated HMW aggregate were bound to GNA lectin coated ELISA plates and probed with 2G12, b6, b12, CD4-IgG2, and HIVIg. The panels represent their respective binding curves. Antibody affinity to the untreated HMW aggregate is represented by the curve having diamond lines. Affinity to the Tween® 20 treated HMW aggregate is represented by curve having square lines. The Y-axis represents the calorimetric signal at OD492 and the X-axis represents antibody concentration in [ug/ml]. (B) Lectin ELISA of untreated and Tween® 20-treated KNH1144 SOSIP R6 gp140 trimer: Untreated or Tween® 20 treated trimer (containing 10-15% HMW aggregate) were bound to GNA lectin coated ELISA plates and probed with 2G12, b6, b12, and CD4-IgG2. The panels represent their respective binding curves. Antibody affinity to the untreated trimer is represented by the curve having diamond lines. Affinity to the Tween® 20 treated trimer is represented by the curve having square lines. The Y-axis represents the calorimetric signal at OD492 and the X-axis represents antibody concentration in [ug/ml].

Figure 18:
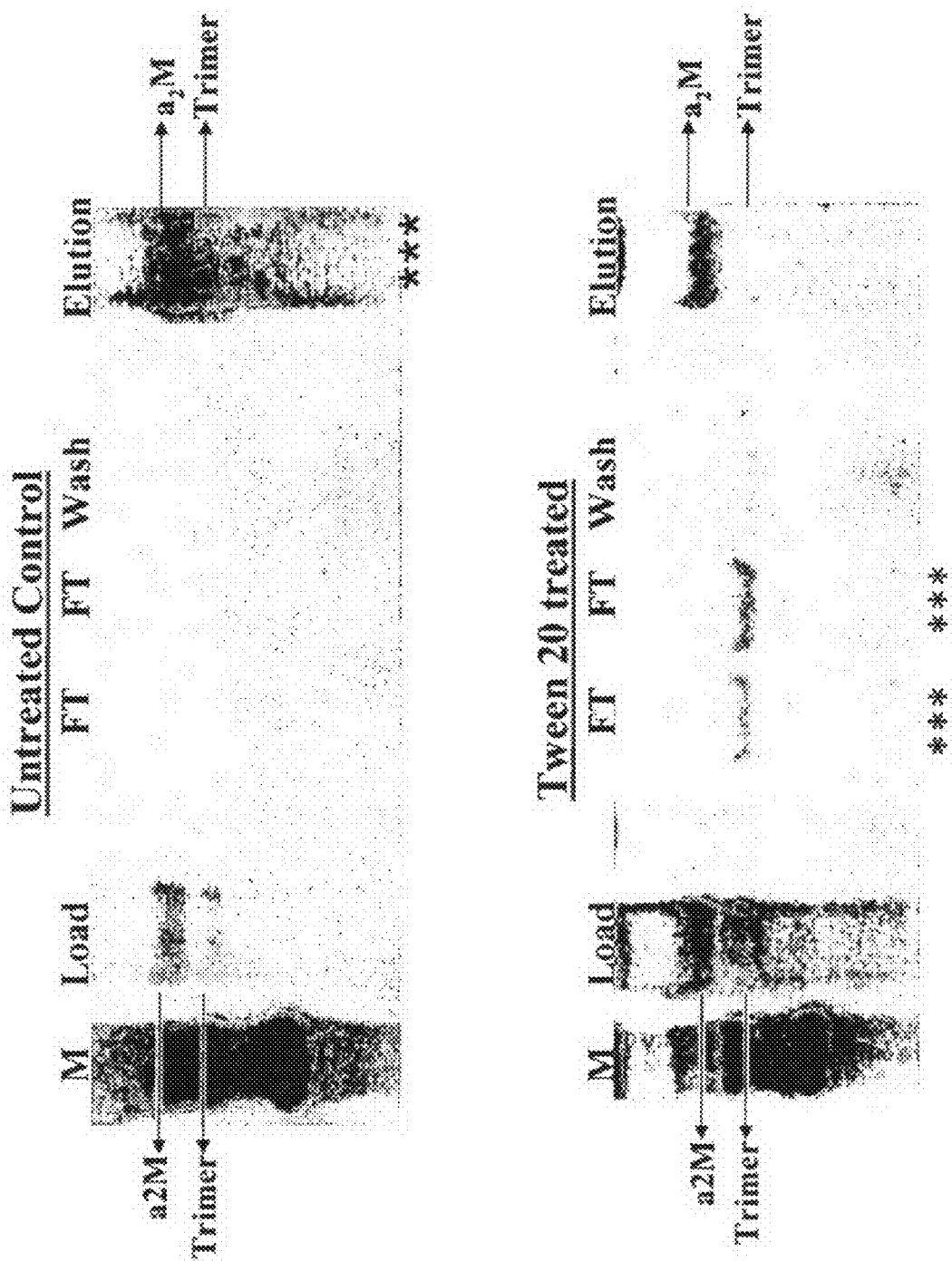

FIG. 18: Effect of Tween® 20 treatment on KNH1144 SOSIP R6 gp140 trimer binding to DEAE anion exchange column. Purified KNH1144 SOSIP R6 gp140 trimer, spiked with alpha-2 macroglobulin ($a_2M$) contaminant, was either untreated or treated with Tween® 20. Following treatment, sample was applied over an anion exchange column (DEAE HiTrap FF 1 ml column) (Load). Flow through (FT) fractions were collected and the column was washed (Wash). The column was eluted (Elution) and fractions were analyzed over BN-PAGE, followed by Coomassie G-250 stain. The top panel shows fractions analyzed from the untreated control trimer DEAE application. The bottom panel shows fractions analyzed from the Tween® 20 treated trimer DEAE application. Arrows point to trimer and $a_2M$ contaminant proteins. M stands for the 669k thyroglobulin and 440k ferritin molecular weight protein standards. Asterisks highlight the fraction where the trimer is found.

Figure 19:
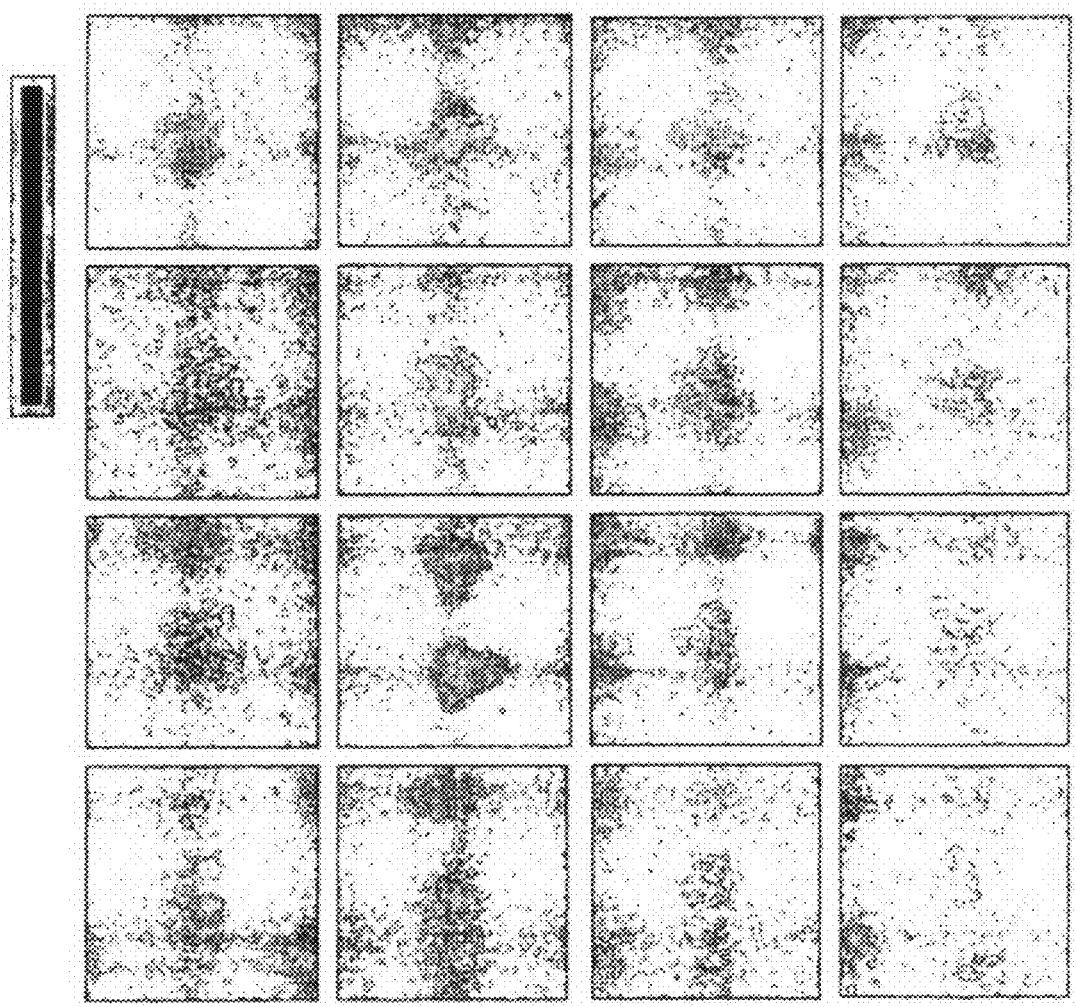

FIG. 19: Negative stain electron micrographs of KNH1144 SOSIP R6 gp140 trimers. KNH1144 SOSIP R6 gp140 trimers were analyzed by negative stain electron microscopy. A gallery of 19 selected trimeric proteins in deeper stain is shown. Bar=50 nm.

Figure 20:
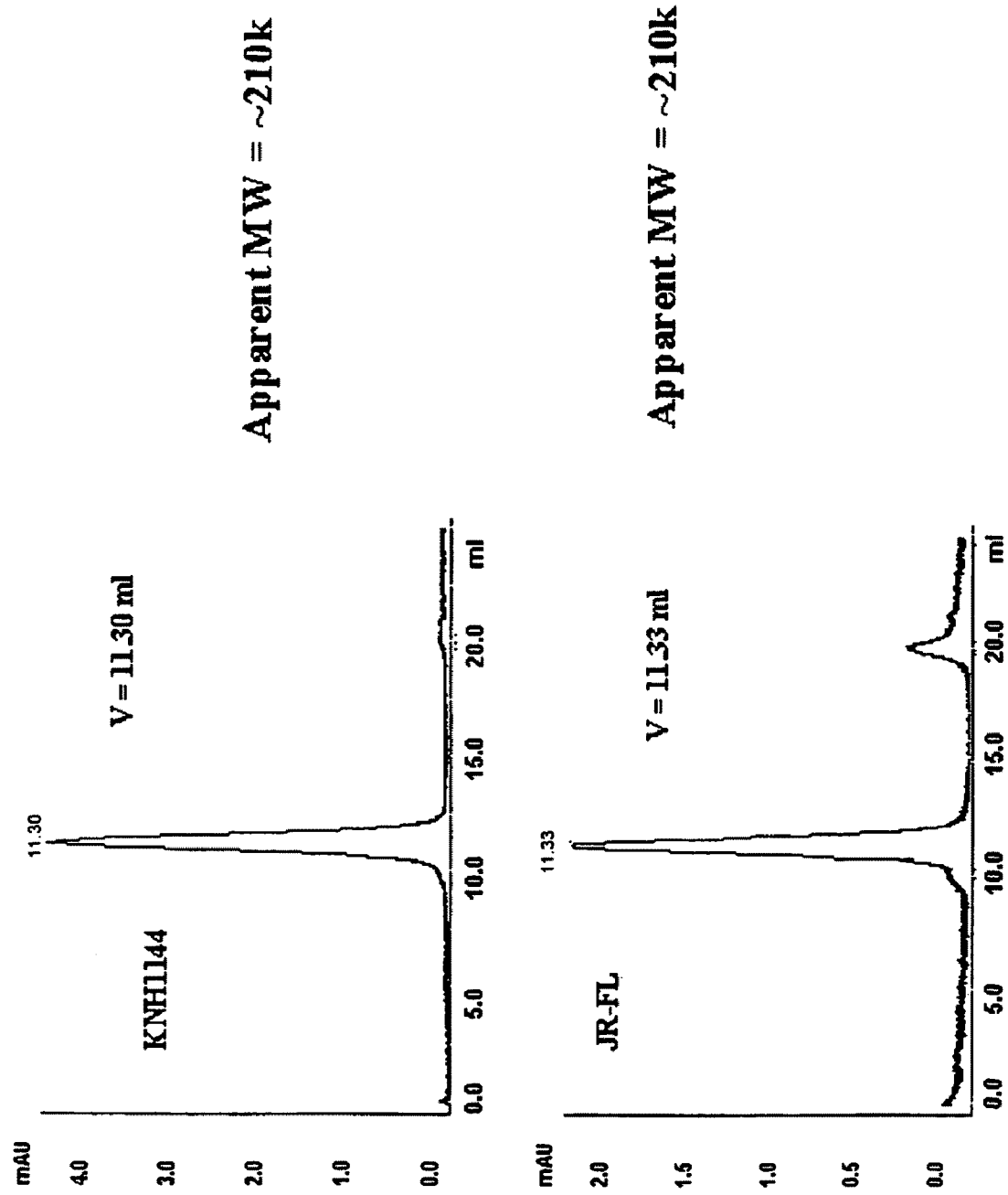

FIG. 20: SEC analysis of KNH1144 gp120 monomer: KNH1144 gp120 monomer was resolved on a Superdex 200 10/300 GL column in TN-500 buffer. The top chromatograph shows its $A_{280}$ protein profile of the run. As a control, JR-FL gp120 monomer was resolved in a similar manner and its $A_{280}$ protein profile is displayed in the bottom chromatograph. The observed retention times for both monomers and their apparent calculated molecular weights are indicated.

Figure 21:
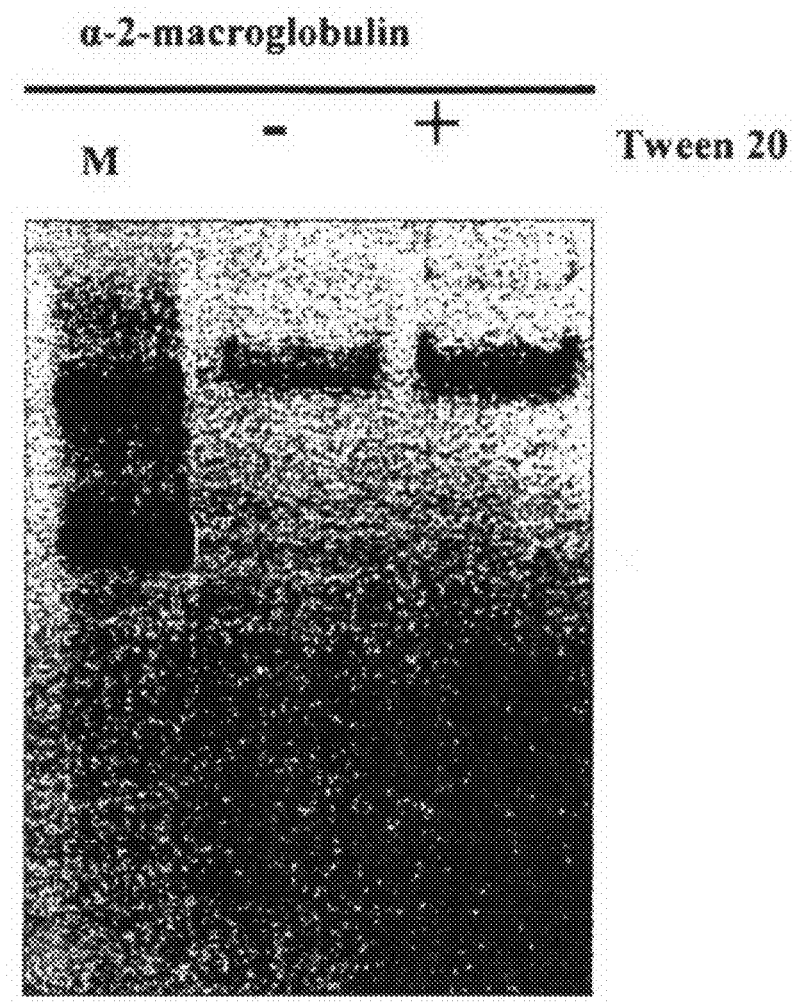

FIG. 21: Tween® 20 effect on $a_2M$: Purified $a_2M$ was incubated with Tween® 20 (+lane) or waa untreated (−lane). Reactions were analyzed by BN-PAGE and Coomassie stain. Arrow indicates $a_2M$ band.

DETAILED DESCRIPTION OF THE INVENTION

Definitions

As used in this application, except as otherwise expressly provided herein, each of the following terms shall have the meaning set forth below.

The following standard abbreviations are used throughout the specification to indicate specific amino acids: A=ala=alanine; R=arg=arginine; N=asn=asparagine; D=asp=aspartic acid; C=cys=cysteine; Q=gln=glutamine; E=glu=glutamic acid; G=gly=glycine; H=his=histidine; I=ile=isoleucine; L=leu=leucine; K=lys=lysine; M=met=methionine; F=phe=phenylalanine; P=pro=proline; S=ser=serine; T=thr=threonine; W=trp=tryptophan; Y=tyr=tyrosine; V=val=valine; B=asx=asparagine or aspartic acid; Z=glx=glutamine or glutamic acid.

An "A492C mutation" refers to a point mutation of amino acid 492, for example, in the HIV-1$_{JRFL}$ isolate gp120 protein, from alanine to cysteine. Because of sequence and sequence numbering variability among different HIV strains and isolates, it will be appreciated that the same amino acid may not reside at position 492 in all other HIV isolates. For example, in the HIV-1 KNH1144 isolate, the corresponding amino acid, or the amino acid position that is equivalent to amino acid position A492 in the JR-FL isolate, is A511; in HIV-1$_{HXB2}$ the corresponding or equivalent amino acid is A501 (Genbank Accession No. AAB50262); and in HIV-1$_{NL4-3}$ such amino acid is A499 (Genbank Accession No. AAA44992). The amino acid may also be an amino acid other than alanine or cysteine which has similar polarity or charge characteristics, for example. This invention encompasses the replacement of such amino acids by cysteine, as may be readily identified in other HIV isolates by those skilled in the art. Thus, the invention encompasses an HIV-1 isolate in which a cysteine residue replaces, or is substituted for, (e.g., by mutation), a non-cysteine amino acid at an amino acid position equivalent to position 492 in the HIV-1 isolate JR-FL. Illustratively, e.g., equivalent amino acid position(s) in other HIV-1 strains or clades may be determined by reference to SEQ ID NO:9, SEQ ID NO:2 and/or SEQ ID NO:22.

"I559P" refers to a point mutation wherein the isoleucine residue at position 559 of a polypeptide chain is replaced by a proline residue. Thus, the invention encompasses an HIV-1 isolate in which a proline residue replaces, or is substituted for, a non-proline (e.g., isoleucine) amino acid at an amino acid position equivalent to position 559 in the HIV-1 isolate KNH1144, for example. Illustratively, e.g., equivalent amino acid position(s) in other HIV-1 strains or clades may be determined by reference to SEQ ID NO:1, SEQ ID NO:5 and/or SEQ ID NO:18.

A "T596C mutation" refers to a point mutation of an amino acid at amino acid position 596 in the HIV-1$_{JRFL}$ isolate gp41 ectodomain from threonine to cysteine. Because of sequence and sequence numbering variability among different HIV strains and isolates, it will be appreciated that this amino acid will not be at position 596 in all other HIV isolates. For example, in HIV-1 KNH1144 isolate, the corresponding amino acid is T605; in HIV-1$_{HXB2}$ the corresponding amino acid is T605 (Genbank Accession No. AAB50262); and in HIV-1$_{NL4-3}$ the corresponding amino acid is T603 (Genbank Accesion No. AAA44992). The amino acid may also be an amino acid other than threonine or cysteine which has similar polarity or charge characteristics, for example. This invention encompasses cysteine mutations in such amino acids, which can be readily identified in other HIV isolates by those skilled in the art. This invention encompasses the replacement, or substitution, of such amino acids by cysteine, as may be readily identified in other HIV isolates by those skilled in the art. Thus, the invention further encompasses an HIV-1 isolate in which a cysteine residue replaces, or is substituted for, a non-cysteine amino acid at an amino acid position equivalent to position 596 in the HIV-1 isolate JR-FL. Similarly, the invention encompasses an HIV-1 isolate in which a cysteine residue replaces, or is substituted for, a non-cysteine amino acid at an amino acid position equivalent to position 492 in the HIV-1 isolate JR-FL.

"HIV" refers to the human immunodeficiency virus. HIV includes, without limitation, HIV-1. HIV may be either of the two known types of HIV, i.e., HIV-1 or HIV-2. The HIV-1 virus may represent any of the known major subtypes or clades (e.g., Classes A, B, C, D, E, F, G, J, and H) or outlying subtype (Group O). Also encompassed are other HIV-1 subtypes or clades that may be isolated.

"gp140 envelope" refers to a protein having two disulfide-linked polypeptide chains, the first chain comprising the amino acid sequence of the HIV gp120 glycoprotein and the second chain comprising the amino acid sequence of the water-soluble portion of HIV gp41 glycoprotein ("gp41 portion"). HIV gp140 protein includes, without limitation, proteins wherein the gp41 portion comprises a point mutation such as I559P. gp140 envelope comprising such mutation is encompassed by the terms "HIV SOS gp140", as well as "HIV gp140 monomer" or "SOSIP gp140".

"gp41" includes, without limitation, (a) the entire gp41 polypeptide including the transmembrane and cytoplasmic domains; (b) gp41 ectodomain (gp41$_{ECTO}$); (c) gp41 modified by deletion or insertion of one or more glycosylation sites; (d) gp41 modified so as to eliminate or mask the well-known immunodominant epitope; (e) a gp41 fusion protein; and (f) gp41 labeled with an affinity ligand or other detectable marker. As used herein, "ectodomain" means the extracellular region of a transmembrane protein exclusive of the transmembrane spanning and cytoplasmic regions.

"Host cells" include, but are not limited to, prokaryotic cells, e.g., bacterial cells (including gram-positive cells), yeast cells, fungal cells, insect cells and animal cells. Suitable animal cells include, but are not limited to HeLa cells, COS cells, CVI cells and various primary mammalian cells. Numerous mammalian cells can be used as hosts, including, but not limited to, mouse embryonic fibroblast NIH-3T3 cells, CHO cells, HeLa cells, L(tk−) cells and COS cells. Mammalian cells can be transfected by methods well known in the art, such as calcium phosphate precipitation, electroporation and microinjection. Electroporation can also be performed in vivo as described previously (see, e.g., U.S. Pat. Nos. 6,110,161; 6,262,281; and 6,610,044).

"Immunizing" means generating an immune response to an antigen in a subject. This can be accomplished, for example, by administering a primary dose of an antigen, e.g., a vaccine, to a subject, followed after a suitable period of time by one or more subsequent administrations of the antigen or vaccine, so as to generate in the subject an immune response against the antigen or vaccine. A suitable period of time between administrations of the antigen or vaccine may readily be determined by one skilled in the art, and is usually on the order of several weeks to months. Adjuvant may or may not be co-administered.

"Nucleic acid" refers to any nucleic acid or polynucleotide, including, without limitation, DNA, RNA and hybrids thereof. The nucleic acid bases that form nucleic acid molecules can be the bases A, C, T, G and U, as well as derivatives thereof. Derivatives of these bases are well known in the art and are exemplified in PCR Systems, Reagents and Consumables (Perkin-Elmer Catalogue 1996-1997, Roche Molecular Systems, Inc., Branchburg, N.J., USA).

A "vector" refers to any nucleic acid vector known in the art. Such vectors include, but are not limited to, plasmid vectors, cosmid vectors and bacteriophage vectors. For example, one class of vectors utilizes DNA elements which are derived from animal viruses such as animal papilloma virus, polyoma virus, adenovirus, vaccinia virus, baculovirus, retroviruses (RSV, MMTC or MOMLV), Semliki Forest virus or SV40 virus. The eukaryotic expression plasmid PPI4 and its derivatives are widely used in constructs described herein. However, the invention is not limited to derivatives of the PPI4 plasmid and may include other plasmids known to those skilled in the art.

In accordance with the invention, numerous vector systems for expression of recombinant proteins may be employed. For example, one class of vectors utilizes DNA elements which are derived from animal viruses such as bovine papilloma virus, polyoma virus, adenovirus, vaccinia virus, baculovirus, retroviruses (RSV, MMTV or MOMLV), Semliki Forest virus or SV40 virus. Additionally, cells which have stably integrated the DNA into their chromosomes may be selected by introducing one or more markers which allow for the selection of transfected host cells. The marker may provide, for example, prototropy to an auxotrophic host, biocide (e.g., antibiotic) resistance, or resistance to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements include those described by (Okayama and Berg, 1983).

"Pharmaceutically acceptable carriers" are well known to those skilled in the art and include, but are not limited to, 0.01-0.1M and preferably 0.05M phosphate buffer, phosphate-buffered saline (PBS), or 0.9% saline. Additionally, such pharmaceutically acceptable carriers may include, but are not limited to, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers, diluents and excipients include water, alcoholic/aqueous solutions, emulsions or suspensions, saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. Preservatives and other additives, such as, for example, antimicrobials, antioxidants, chelating agents, inert gases, and the like may also be included with all the above carriers.

Adjuvants are formulations and/or additives that are routinely combined with antigens to boost immune responses. Suitable adjuvants for nucleic acid based vaccines include, but are not limited to, saponins, Quil A, imiquimod, resiquimod, interleukin-12 delivered in purified protein or nucleic acid form, short bacterial immunostimulatory nucleotide sequences such as CpG-containing motifs, interleukin-2/Ig fusion proteins delivered in purified protein or nucleic acid form, oil in water micro-emulsions such as MF59, polymeric microparticles, cationic liposomes, monophosphoryl lipid A, immunomodulators such as Ubenimex, and genetically detoxified toxins such as *E. coli* heat labile toxin and cholera toxin from Vibrio. Such adjuvants and methods of combining adjuvants with antigens are well known to those skilled in the art.

Adjuvants suitable for use with protein immunization include, but are not limited to, alum; Freund's incomplete adjuvant (FIA); saponin; Quil A; QS-21; Ribi Detox; monophosphoryl lipid A (MPL) adjuvants such as Enhanzyn™; nonionic block copolymers such as L-121 (Pluronic; Syntex SAF); TiterMax Classic adjuvant (block copolymer, CRL89-41, squalene and microparticulate stabilizer; Sigma-Aldrich); TiterMax Gold Adjuvant (new block copolymer, CRL-8300, squalene and a sorbitan monooleate; Sigma-Aldrich); Ribi adjuvant system using one or more of the following: monophosphoryl lipid A, synthetic trehalose, dicorynomycolate, mycobacterial cell wall skeleton incorporated into squalene and polysorbate-80; Corixa); RC-552 (a small molecule synthetic adjuvant; Corixa); Montanide adjuvants (including Montanide IMSlllX, Montanide IMS131x, Montanide IMS221x, Montanide IMS301x, Montanide ISA 26A, Montanide ISA206,Montanide ISA 207, Montanide ISA25, Montanide ISA27, Montanide ISA28, Montanide ISA35, Montanide ISA50V, Montanide ISA563,. Montanide ISA70, Montanide ISA 708, Montanide ISA740, Montanide ISA763A, and Montanide ISA773; Seppic Inc., Fairfield, N.J.); and N-Acetylmuramyl-L-alanyl-D-isoglutamine hydrate (Sigma-Aldrich). Methods of combining adjuvants with antigens are well known to those skilled in the art.

Because current vaccines depend on generating antibody responses to injected antigens, commercially available adjuvants have been developed largely to enhance these antibody responses. To date, the only FDA-approved adjuvant for use with human vaccines is alum. However, although alum helps boost antibody responses to vaccine antigens, it does not enhance T cell immune responses. Thus, adjuvants that are able to boost T cell immune responses after a vaccine is administered are also contemplated for use.

It is also known to those skilled in the art that cytotoxic T lymphocyte and other cellular immune responses are elicited when protein-based immunogens are formulated and administered with appropriate adjuvants, such as ISCOMs and micron-sized polymeric or metal oxide particles. Certain microbial products also act as adjuvants by activating macrophages, lymphocytes and other cells within the immune system, and thereby stimulating a cascade of cytokines that regulate immune responses. One such adjuvant is monophosphoryl lipid A (MPL) which is a derivative of the gram-negative bacterial lipid A molecule, one of the most potent immunostimulants known. The Enhanzyn™ adjuvant (Corixa Corporation, Hamilton, Mont.) consists of MPL, mycobacterial cell wall skeleton and squalene.

Adjuvants may be in particulate form. The antigen may be incorporated into biodegradable particles composed of polylactide-co-glycolide (PLG) or similar polymeric material. Such biodegradable particles are known to provide sustained release of the immunogen and thereby stimulate long-lasting immune responses to the immunogen. Other particulate adjuvants include, but are not limited to, micellular particles comprising Quillaia saponins, cholesterol and phospholipids known as immunostimulating complexes (ISCOMs; CSL Limited, Victoria AU), and superparamagnetic particles. Superparamagnetic microbeads include, but are not limited to, μMACS™ Protein G and μMACS™ Protein A microbeads (Miltenyi Biotec), Dynabeads® Protein G and Dynabeads® Protein A (Dynal Biotech). In addition to their adjuvant effect, superparamagnetic particles such as μMACS™ Protein G and Dynabeads® Protein G have the important advantage of enabling immunopurification of proteins.

A "prophylactically effective amount" is any amount of an agent which, when administered to a subject prone to suffer from a disease or disorder, inhibits or prevents the onset of the disorder. The prophylactically effective amount will vary with the subject being treated, the condition to be treated, the agent delivered and the route of delivery. A person of ordinary skill in the art can perform routine titration experiments to determine such an amount. Depending upon the agent delivered, the prophylactically effective amount of agent can be delivered continuously, such as by continuous pump, or at periodic intervals (for example, on one or more separate occasions). Desired time intervals of multiple amounts of a particular agent can be determined without undue experimentation by one skilled in the art.

"Inhibiting" the onset of a disorder means either lessening the likelihood of the disorder's onset, preventing the onset of the disorder entirely, or in some cases, reducing the severity of the disease or disorder after onset. In the preferred embodiment, inhibiting the onset of a disorder means preventing its onset entirely.

"Reducing the likelihood of a subject's becoming infected with HIV-1" means reducing the likelihood of the subject's becoming infected with HIV-1 by at least two-fold. For example, if a subject has a 1% chance of becoming infected with HIV-1, a two-fold reduction in the likelihood of the subject becoming infected with HIV-1 would result in the subject having a 0.5% chance of becoming infected with HIV-1. In the preferred embodiment of this invention, reducing the likelihood of the subject's becoming infected with HIV-1 means reducing the likelihood of the subject's becoming infected with the virus by at least ten-fold.

"Subject" means any animal or artificially modified animal. Animals include, but are not limited to, humans, non-human primates, cows, horses, sheep, goats, pigs, dogs, cats, rabbits, ferrets, rodents such as mice, rats and guinea pigs, and birds and fowl, such as chickens and turkeys. Artificially modified animals include, but are not limited to, transgenic animals or SCID mice with human immune systems. In the preferred embodiment, the subject is a human.

"Exposed" to HIV-1 means contact or association with HIV-1 such that infection could result.

A "therapeutically effective amount" is any amount of an agent which, when administered to a subject afflicted with a disorder against which the agent is effective, causes the subject to be treated. "Treating" a subject afflicted with a disorder shall mean causing the subject to experience a reduction, diminution, remission, suppression, or regression of the disorder and/or its symptoms. In one embodiment, recurrence of the disorder and/or its symptoms is prevented. Most preferably, the subject is cured of the disorder and/or its symptoms.

"HIV-1 infected" means the introduction of viral components, virus particles, or viral genetic information into a cell, such as by fusion of cell membrane with HIV-1. The cell may be a cell of a subject. In the preferred embodiment, the cell is a cell in a human subject.

EMBODIMENTS OF THE INVENTION

The present invention encompasses HIV envelope (Env) glycoprotein complexes, which comprise non-covalently-associated surface gp120 and transmembrane gp41 glycoprotein subunits, and soluble forms thereof. The HIV envelope (Env) glycoprotein complexes of the invention are more structurally stable than native Env complexes, which are characteristically more labile or unstable in order to be capable of efficiently undergoing conformational changes during the process of virus-cell fusion.

In accordance with the present invention, the structural instability of the native HIV Env complex, or soluble forms thereof, is overcome by the introduction of amino acid sequence changes designed to stabilize inter-subunit interactions between gp120 and gp41, or between the gp41 components of a trimer. Such changes according to this invention include not only the introduction of a disulfide bond between gp120 and gp41; an additional change in gp41 that promotes trimer stability after gp120 and gp41 are cleaved into separate subunits during Env processing, and additional changes at the cleavage site between gp120 and gp41 to promote proteolytic processing, but also include amino acid changes, namely, five amino acid changes, in the highly conserved Leucine-zipper (LZ)-like motif near the N-terminus (NT) of gp41. The five amino acid changes, as described herein, were found to contribute to trimer stability by reducing the prevalence of monomeric, dimeric, or aggregated forms of gp140. Consequently, the present invention provides trimer stability enhancing amino acids which, when present in the NT of gp41 in an HIV isolate, allow the generation of more stable trimer complexes comprised of gp120 and gp41 envelope polypeptides. The invention thus provides a reduction in the qualitative heterogeneity of the Env glycoprotein, which is beneficial for the production of anti-HIV vaccines and immunogens designed to mimic the native trimeric form of viral Env.

In an embodiment, the invention encompasses envelope trimers for the production of virus like particles (VPLS) and pseudoparticles for use as VLP-based immunogens, to generate neutralizing antibodies, for example, and VLP-based vaccines against which a subject can mount a potent immune response against HIV. In accordance with the invention, gp120/gp41 trimers comprising the stabilizing N-terminal gp41 mutations of the invention, as well as gp120/gp41 trimers comprising other stabilizing mutations in gp120 and gp41 and the N-terminal gp41 mutations as described herein, are used to generate VPLs and pseudovirions having reduced monomer, dimer and tetramer forms and enhanced trimer forms of gp120/gp41 Env. The N-terminal stabilizing mutations in the context of HIV-1 virus as described herein can yield trimer forms of Env (gp120/gp41) on VLP and pseudovirions, to the virtual exclusion of monomer, dimer and tetramer forms, thus allowing for an immunogen that more closely resembles native HIV envelope trimers.

This invention provides a modified gp140 envelope polypeptide of an HIV-1 isolate comprising a gp120 polypeptide portion comprising consecutive amino acids, and a gp41 ectodomain polypeptide portion comprising consecutive amino acids, said gp41 ectodomain polypeptide portion being modified to comprise isoleucine (I) at amino acid position 535 (I535); glutamine (Q) at amino acid position 543 (Q543);

serine (S) at amino acid position 553 (S553); lysine (K) at amino acid position 567 (K567); and arginine (R) at amino acid position 588 (R588), wherein the amino acid positions are numbered by reference to the HIV-1 isolate KNH1144. (e.g., SEQ ID NO:1, SEQ ID NO:5 and/or SEQ ID NO:18). In one embodiment, the isoleucine (I) at amino acid position 535 is the result of an M535I mutation. In another embodiment, the glutamine (Q) at amino acid position 543 is the result of an L543Q mutation. In another embodiment, the serine (S) at amino acid position 553 is the result of an N553S mutation. In yet another embodiment, the lysine (K) at amino acid position 567 is the result of a Q567K mutation. In another embodiment, the arginine (R) at amino acid position 588 is the result of a G588R mutation.

Because the amino acid positions of different HIV-1 isolates may not be identical with those of the HIV-1 isolate KNH1144, the invention further provides a modified gp140 envelope polypeptide of an HIV-1 isolate comprising a gp120 polypeptide portion comprising consecutive amino acids, and a gp41 ectodomain polypeptide portion comprising consecutive amino acids, said gp41 ectodomain polypeptide portion being modified to comprise isoleucine (I) at an amino acid position equivalent to amino acid position 535 (I535); glutamine (Q) at an amino acid position equivalent to amino acid position 543 (Q543); serine (S) at an amino acid position equivalent to amino acid position 553 (S553); lysine (K) at an amino acid position equivalent to amino acid position 567 K567); and arginine (R) at an amino acid position equivalent to amino acid position 588 (R588), wherein the amino acid positions are numbered by reference to the HIV-1 isolate KNH1144.

The invention also provides a modified gp140 envelope polypeptide of an HIV-1 isolate comprising a gp120 polypeptide portion comprising consecutive amino acids and a gp41 ectodomain polypeptide portion comprising consecutive amino acids, said gp41 ectodomain polypeptide portion being modified to comprise glutamine (Q) at an amino acid position equivalent to amino acid position 543 (Q543); serine (S) at an amino acid position equivalent to amino acid position 553 (S553); and lysine (K) at an amino acid position equivalent to amino acid position 567 (K567); and optionally being modified to comprise isoleucine (I) at an amino acid position equivalent to amino acid position 535 (I535) and arginine (R) at an amino acid position equivalent to amino acid position 588 (R588); wherein the amino acid positions are numbered by reference to the HIV-1 isolate KNH1144.

This invention further provides a modified gp140 envelope polypeptide of an HIV-1 isolate, wherein a first portion of the gp140 polypeptide corresponds to a modified gp120 polypeptide and a second portion of the gp140 polypeptide corresponds to a modified gp41 ectodomain polypeptide, wherein the modified gp120 polypeptide comprises a cysteine (C) at an amino acid position equivalent to amino acid position 492 of the HIV-1 isolate JR-FL (e.g., SEQ ID NO:9), and the modified gp41 ectodomain polypeptide comprises (i) a cysteine (C) at an amino acid position equivalent to amino acid position 596 of the HIV-1 isolate JR-FL (e.g., SEQ ID NOS:2 and 22); and (ii) at least one of isoleucine (I) at an amino amino acid position equivalent to amino acid position 535 (I535); glutamine (Q) at an amino acid position equivalent to amino acid position 543 (Q543); serine (S) at an amino acid position equivalent to amino acid position 553 (S553); lysine (K) at an amino acid position equivalent to amino acid position 567 (K567); and arginine (R) at an amino acid position equivalent to amino acid position 588 (R588), wherein the amino positions of (ii) are numbered by reference to the HIV-1 isolate KNH1144. In one embodiment, the modified gp140 envelope polypeptide further comprises proline (P) at an amino acid position equivalent to amino acid position 559, numbered by reference to the HIV-1 isolate KNH1144. In another embodiment, the gp41 ectodomain polypeptide portion of the modified gp140 envelope polypeptide is modified to comprise glutamine (Q) at an amino acid position equivalent to amino acid position 543 (Q543); serine (S) at an amino acid position equivalent to amino acid position 553 (S553); and lysine (K) at an amino acid position equivalent to amino acid position 567 (K567); and is optionally modified to comprise isoleucine (I) at an amino acid position equivalent to amino acid position 535 (I535) and arginine (R) at an amino acid position equivalent to amino acid position 588 (R588), wherein the 543, 553, 567, 535 and 588 amino acid positions are numbered by reference to the HIV-1 isolate KNH1144.

In another embodiment, the gp41 ectodomain polypeptide portion of the modified gp140 envelope polypeptide is modified to comprise glutamine (Q) at an amino acid position equivalent to amino acid position 543 (Q543); serine (S) at an amino acid position equivalent to amino acid position 553 (S553); lysine (K) at an amino acid position equivalent to amino acid position 567 (K567); isoleucine (I) at an amino acid position equivalent to amino acid position 535 (I535); and arginine (R) at an amino acid position equivalent to amino acid position 588 (R588), wherein the 543, 553, 567, 535 and 588 amino acid positions are numbered by reference to the HIV-1 isolate KNH1144.

This invention provides a modified gp140 envelope polypeptide of an HIV-1 isolate, wherein a first portion of the gp140 polypeptide corresponds to a modified gp120 polypeptide and a second portion of the gp140 polypeptide corresponds to a modified gp41 ectodomain polypeptide, wherein the modified gp120 polypeptide comprises a cysteine (C) at an amino acid position equivalent to amino acid position 492 of the HIV-1 isolate JR-FL, and the modified gp41 ectodomain polypeptide comprises (i) a cysteine (C) at an amino acid position equivalent to amino acid position 596 of the HIV-1 isolate JR-FL; (ii) a proline (P) at an amino acid position equivalent to amino acid position 559 of the HIV-1 isolate KNH1144 (e.g., SEQ ID NO:6; SEQ ID NO:19); and (iii) one or more of isoleucine (I) at an amino amino acid position equivalent to amino acid position 535 (I535); glutamine (Q) at an amino acid position equivalent to amino acid position 543 (Q543); serine (S) at an amino acid position equivalent to amino acid position 553 (S553); lysine (K) at an amino acid position equivalent to amino acid position 567 (K567); and arginine (R) at an amino acid position equivalent to amino acid position 588 (R588), wherein the amino positions of (iii) are numbered by reference to the HIV-1 isolate KNH1144.

In an embodiment, the gp41 ectodomain polypeptide portion of the modified gp140 envelope polypeptide is modified to comprise glutamine (Q) at an amino acid position equivalent to amino acid position 543 (Q543); serine (S) at an amino acid position equivalent to amino acid position 553 (S553); and lysine (K) at an amino acid position equivalent to amino acid position 567 (K567); and is optionally modified to comprise isoleucine (I) at an amino acid position equivalent to amino acid position 535 (I535) and arginine (R) at an amino acid position equivalent to amino acid position 588 (R588), wherein the 543, 553, 567, 535 and 588 amino acid positions are numbered by reference to the HIV-1 isolate KNH1144.

In another embodiment, the gp41 ectodomain polypeptide portion of the modified gp140 envelope polypeptide is modified to comprise glutamine (Q) at an amino acid position equivalent to amino acid position 543 (Q543); serine (S) at an amino acid position equivalent to amino acid position 553

(S553); lysine (K) at an amino acid position equivalent to amino acid position 567 (K567); isoleucine (I) at an amino acid position equivalent to amino acid position 535 (I535); and arginine (R) at an amino acid position equivalent to amino acid position 588 (R588), wherein the 543, 553, 567, 535 and 588 amino acid positions are numbered by reference to the HIV-1 isolate KNH1144. In another embodiment, the isoleucine (I) at an amino acid position equivalent to amino acid position 535 is the result of an M535I mutation; the glutamine (Q) at an amino acid position equivalent to amino acid position 543 is the result of an L543Q mutation; the serine (S) at an amino acid position equivalent to amino acid position 553 is the result of an N553S mutation; the lysine (K) at an amino acid position equivalent to amino acid position 567 is the result of a Q567K mutation; and the arginine (R) at an amino acid position equivalent to amino acid position 588 is the result of a G588R mutation, wherein the 543, 553, 567, 535 and 588 amino acid positions are numbered by reference to the HIV-1 isolate KNH1144.

In another embodiment, the invention provides a modified gp140 envelope polypeptide of an HIV-1 isolate, wherein a first portion of the gp140 polypeptide corresponds to a modified gp120 polypeptide and a second portion of the gp140 polypeptide corresponds to a modified gp41 ectodomain polypeptide, wherein the modified gp120 polypeptide comprises an A→C mutation at amino acid position 492, numbered by reference to the HIV-1 isolate JR-FL, and the modified gp41 ectodomain polypeptide comprises (i) a T→C mutation at amino acid position 596, numbered by reference to the HIV-1 isolate JR-FL; and (ii) isoleucine (I) at amino acid position 535; glutamine (Q) at amino acid position 543; serine (S) at amino acid position 553; lysine (K) at amino acid position 567; and arginine (R) at amino acid position 588, wherein the 535, 543, 553, 567 and 588 amino acid positions are numbered by reference to the HIV-1 isolate KNH1144. In an embodiment this modified gp140 envelope polypeptide further comprises an I→P mutation at amino acid position 559, numbered by reference to the HIV-1 isolate KNH1144.

This invention provides a modified gp41 ectodomain polypeptide which comprises the consecutive amino acid sequence as set forth in any one of SEQ ID NO:1, SEQ ID NO:18, SEQ ID NO:2, SEQ ID NO:22, SEQ ID NO:3, SEQ ID NO:25, or SEQ ID NO:28. The invention further provides a modified gp41 ectodomain polypeptide which comprises the consecutive amino acid sequence as set forth in any one of SEQ ID NO:20, SEQ ID NO:21, SEQ ID NO:24, SEQ ID NO:27, or SEQ ID NO:30.

This invention provides a modified gp160 polypeptide which comprises the consecutive amino acid sequence as set forth in SEQ ID NO:7, SEQ ID NO:8, SEQ ID NO:9, SEQ ID NO:12, or SEQ ID NO:15. The invention further provides a modified gp160 polypeptide which comprises the consecutive amino acid sequence as set forth in any one of SEQ ID NO:5, SEQ ID NO:11, SEQ ID NO:14, or SEQ ID NO:17. Also embraced by the invention are the sequences of the gp120 and gp41 portions of the gp160 polypeptides described herein.

In one embodiment, the HIV-1 isolate represents a subtype selected from the group consisting of clades A, B, C, D, E, F, G, H, J and O. In another embodiment, the HIV-1 isolate is a lade A subtype. In another embodiment, the HIV-1 isolate is a lade B subtype. Additionally, the HIV isolate that is modified to contain the trimer stabilizing amino acid residues of the invention may be a strain or a lade other than those particularly specified.

This invention provides a trimeric complex which comprises a noncovalent oligomer of three identical modified HIV-1 gp140 envelope polypeptides of the invention. The invention further provides a trimeric complex which comprises a noncovalent oligomer of three identical modified gp41 ectodomain polypeptides of the invention.

This invention provides a composition comprising the modified polypeptide of the invention and a pharmaceutically acceptable carrier, excipient, or diluent.

This invention also provides a composition comprising the trimeric complex of the invention and a pharmaceutically acceptable carrier, excipient, or diluent. In one embodiment, the composition further comprises an adjuvant. In one embodiment, the composition further comprises an antiretroviral agent.

This invention provides an isolated nucleic acid encoding a modified form of an HIV-1 gp120 and gp41 polypeptide complex, wherein the modification in gp120 comprises a mutation of the amino acid at a position equivalent to amino acid position 492 of the HIV-1 isolate JR-FL to cysteine (C); and the modifications in gp41 comprise (i) a mutation of the amino acid at a position equivalent to amino acid position 596 of the HIV-1 isolate JR-FL to cysteine (C); (ii) a mutation of the amino acid at a position equivalent to amino acid position 543 of the HIV-1 isolate KNH1144 to glutamine (Q); (iii) a mutation of the amino acid at a position equivalent to amino acid position 553 of the HIV-1 isolate KNH1144 to serine (S); (iv) a mutation of the amino acid at a position equivalent to amino acid position 567 of the HIV-1 isolate KNH1144 to lysine (K); and optionally, (v) a mutation of the amino acid at a position equivalent to amino acid position 535 of the HIV-1 isolate KNH1144 to isoleucine and (vi) a mutation of the amino acid at a position equivalent to amino acid position 588 of the HIV-1 isolate KNH1144 to arginine (R). In an embodiment, the modifications in gp41 further comprise a mutation to proline of a non-proline amino acid at a position equivalent to amino acid position 559, as numbered by reference to the HIV-1 isolate KNH1144 (e.g., SEQ ID NOS:1, 18 and/or 19). In an embodiment, the modifications in gp41 further comprise a mutation to isoleucine of a non-isoleucine amino acid at a position equivalent to amino acid position 535, as numbered by reference to the HIV-1 isolate KNH1144. In an embodiment, the modifications in gp41 further comprise a mutation to methionine of a non-methionine amino acid at a position equivalent to amino acid position 535, as numbered by reference to the HIV-1 isolate KNH1144 (e.g., SEQ ID NO:20; SEQ ID NO:21). In one embodiment, the isolated nuceic acid is DNA. In another embodiment, the isolated nucleic acid is cDNA. In another embodiment, the isolated nucleic acid is RNA.

This invention provides a vector comprising the isolated nucleic of the invention. This invention also provides a host cell comprising the vector or expression cassette of the invention. The host cell may be a eukaryotic cell or a prokaryotic cell.

This invention further provides a method for eliciting an immune response against HIV-1 or an HIV-1 infected cell in a subject comprising administering to the subject an amount of the compositions of the invention effective to elicit the immune response in the subject. In some embodiments, the composition is administered in a single dose or in multiple doses. In another embodiment, the composition is administered as part of a heterologous prime-boost regimen.

This invention provides a method for preventing a subject from becoming infected with HIV-1, comprising administering to the subject an amount of the compositions of the invention effective to prevent the subject from becoming infected with HIV-1.

This invention provides a method for reducing the likelihood of a subject becoming infected with HIV-1, comprising administering to the subject an amount of the compositions of the invention effective to reduce the likelihood of the subject becoming infected with HIV-1. In one embodiment, the subject has been exposed to HIV-1.

This invention also provides a method for delaying the onset of, or slowing the rate of progression of, an HIV-1-related disease in an HIV-1-infected subject, which comprises administering to the subject an amount of the compositions of the invention effective to delay the onset of, or slow the rate of progression of, the HIV-1-related disease in the subject.

This invention provides the trimeric complexes of the invention, or the composition of the invention, further comprising a non-ionic detergent. In one embodiment, the non-ionic detergent is a polyethylene type detergent. In another embodiment, the non-ionic detergent is a polyethylene type detergent. In another embodiment, the polyethylene type detergent is poly(oxyethylene) sorbitan monolaureate. In another embodiment, the poly(oxyethylene) sorbitan monolaureate is poly(oxyethylene) (20) sorbitan monolaureate. In another embodiment, the polyethylene type detergent is poly (oxyethylene) sorbitan monooleate.

In one embodiment, the non-ionic detergent is present in an amount of from 0.01% to 1%. In another embodiment, the non-ionic detergent is present in an amount of from 0.01% to 0.05%.

This invention further provides a method of stabilizing HIV-1 trimer complexes which comprise non-covalently associated gp120 and gp41 envelope polypeptides, which polypeptides comprise consecutive amino acids, said method comprising: introducing into the gp41 ectodomain polypeptide a glutamine (Q) at an amino acid position equivalent to amino acid position 543 of the HIV-1 isolate KNH1144; a serine (S) at an amino acid position equivalent to amino acid position 553 of the HIV-1 isolate KNH1144; a lysine (K) at an amino acid position equivalent to amino acid position 567 of the HIV-1 isolate KNH1144; and optionally, an isoleucine (I) at an amino acid position equivalent to amino acid position 535 of the HIV-1 isolate KNH1144 and an arginine (R) at an amino acid position equivalent to amino acid position 588 of the HIV-1 isolate KNH1144. In one embodiment, the method further comprises introducing a cysteine (C) at an amino acid position equivalent to amino acid position 492 of the gp120 polypeptide of the HIV-1 isolate JR-FL, and a cysteine (C) at an amino acid position equivalent to amino acid position 596 of the gp41 ectodomain polypeptide of the HIV-1 isolate JR-FL. In another embodiment, the method further comprises introducing a proline (P) at an amino acid position equivalent to amino acid position 559 of the gp41 ectodomain polypeptide of the HIV-1 isolate KNH1144.

This invention further provides a method of stabilizing HIV-1 trimer complexes which comprise non-covalently associated gp120 and gp41 envelope polypeptides, which polypeptides comprise consecutive amino acids, said method comprising: introducing into the gp41 ectodomain polypeptide a glutamine (Q) at an amino acid position equivalent to amino acid position 543 of the HIV-1 isolate KNH1144; a serine (S) at an amino acid position equivalent to amino acid position 553 of the HIV-1 isolate KNH1144; a lysine (K) at an amino acid position equivalent to amino acid position 567 of the HIV-1 isolate KNH1144; an isoleucine (I) at an amino acid position equivalent to amino acid position 535 of the HIV-1 isolate KNH1144; and an arginine (R) at an amino acid position equivalent to amino acid position 588 of the HIV-1 isolate KNH1144. In one embodiment, the method further comprises introducing a cysteine (C) residue at an amino acid position equivalent to amino acid position 492 in the gp120 polypeptide of the HIV-1 isolate JR-FL, and a cysteine (C) at an amino acid position equivalent to amino acid position 596 in the gp41 ectodomain polypeptide of the HIV-1 isolate JR-FL. In another embodiment, the method further comprises introducing a proline (P) at an amino acid position equivalent to amino acid position 559 of the gp41 ectodomain polypeptide of the HIV-1 isolate KNH1144.

This invention provides a chimeric gp140 polypeptide comprising (i) a gp120 envelope polypeptide of a clade B subtype of an HIV-1 isolate and (ii) a gp41 ectodomain polypeptide of the HIV-1 isolate KNH1144, said polypeptides comprising consecutive amino acids, wherein the KNH1144 gp41 ectodomain polypeptide comprises isoleucine (I) at amino acid position 535; glutamine (Q) at amino acid position 543; serine (S) at amino acid position 553; lysine (K) at amino acid position 567; and arginine (R) at amino acid position 588.

This invention further provides a chimeric gp140 polypeptide comprising (i) a gp120 envelope polypeptide of a clade B subtype of an HIV-1 isolate and (ii) a gp41 ectodomain polypeptide of the HIV-1 isolate KNH1144, said polypeptides comprising consecutive amino acids, wherein the KNH1144 gp41 ectodomain polypeptide comprises an amino acid sequence as set forth in SEQ ID NO:1, SEQ ID NO:18, SEQ ID NO:20, SEQ ID NO:21, or the gp41 polypeptide portion of the gp160 polypeptide as set forth in any one of SEQ ID NOS:5-8.

In embodiments of the invention, the HIV-1 isolate is an $HIV-1_{JR-FL}$, $HIV-1_{Ba-L}$, $HIV-1_{5768}$, $HIV-1_{DH123}$, $HIV-1_{GUN-1}$, $HIV-1_{89.6}$, or $HIV-1_{HXB2}$ isolate.

In an embodiment, the present invention encompasses a method for treating or preventing human immunodeficiency viral (HIV) infection in a subject by administering to the subject a therapeutically or prophylactically effective amount of a pharmaceutical composition that includes one or more gp160, gp120, gp41 polypeptides or a combination of gp160, gp120, gp41 polypeptides. In some embodiments, the composition contains a trimeric complex of three gp120 proteins and three gp41 subunits, which have been modified for enhanced stability in accordance with the invention.

In another embodiment, the present invention provides a method for treating or preventing human immunodeficiency viral infection (HIV) in a subject by administering an amount of a pharmaceutical composition that includes one or more gp160, gp120, gp41 polypeptides, or a combination of gp160, gp120, gp41 polypeptides, using a dosing and resting regimen to effectively treat or prevent at least 70% of subjects in a population of at least ten subjects. Cure or prevention rates of the present invention include, but are not limited to, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% of subjects having human immunodeficiency viral infection effectively treated, e.g., by reducing viral load, reducing or eliminating viral nucleic acid, or increasing CD4+ cells, in a population of at least 100 subjects.

Compositions and immunogenic preparations, including vaccine compositions, comprising the polypeptides of the present invention capable of inducing an immunological reaction (including protective immunity) in a suitably treated animal or human, and a suitable carrier therefore, are provided. Immunogenic compositions are those which result in specific antibody production or in cellular immunity when injected into a human or an animal. Such immunogenic compositions or vaccines are useful, for example, in immunizing an animal, including a human, against infection and/or damage caused by HIV.

The vaccine preparations comprise an immunogenic amount of one or more of the polypeptides of the invention. By "immunogenic amount" is meant an amount capable of eliciting the production of antibodies directed against the retrovirus in a mammal into which the vaccine has been administered. The route of administration and the immunogenic composition may be designed to optimize the immune response on mucosal surfaces, for example, using nasal administration (via an aerosol) of the immunogenic composition.

In some embodiments, the methods and compositions of the invention also include use of another antiviral agent in addition to the one or more of the present gp160, gp120, gp41 polypeptides, or a combination of gp160, gp120, gp41 polypeptides as described herein. Thus, other antiretroviral agents or compounds, which can be administered in addition to the polypeptides and compositions of the invention include, without limitation, protease inhibitors, retroviral polymerase inhibitors, azidothymidine (AZT), didanoside (DDI), soluble CD4, a polysaccharide sulfates, T22, bicyclam, suramin, antisense oliogonulceotides, ribozymes, rev inhibitors, protease inhibitors, glycolation inhibitors, interferon and the like. Examples include acyclovir, 3-aminopyridine-2-carboxyaldehyde thiosemicarbazone (3-AP, Triapine™) and 3-amino-4-methylpyridine-2-carboxaldehyde thiosemicarbazone (3-AMP), thiamine disulfide, thiamine disulfide nitrate, thiamine disulfide phosphate, bisbentiamine, bisbutytiamine, bisibutiamine, alitiamine, fursultiamine and octotiamine.

Recombinant Production of Polypeptides

Polypeptides of the invention can be made recombinantly using convenient vectors, expression systems and host cells. The invention therefore provides expression cassettes, vectors and host cells useful for expressing a peptide of the invention, for example, any of the gp160, gp120 and/or gp41 polypeptides as described herein.

The expression cassettes of the invention include a promoter. Any promoter able to direct transcription of an encoded peptide or polypeptide may be used. Accordingly, many promoters may be included within the expression cassette of the invention. Some useful promoters include constitutive promoters, inducible promoters, regulated promoters, cell specific promoters, viral promoters, and synthetic promoters. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

For expression of a polypeptide in a bacterium, an expression cassette having a bacterial promoter is used. A bacterial promoter is any DNA sequence capable of binding bacterial RNA polymerase and initiating the downstream (3') transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173 (1984)). Regulated expression may therefore be positive or negative, thereby either enhancing or reducing transcription.

Sequences encoding metabolic pathway enzymes provide particularly useful promoter sequences. Illustrative examples include promoter sequences derived from sugar metabolizing enzymes, such as galactose, lactose (lac) (Chang et al., *Nature*, 198:1056 (1977) and maltose. Additional examples include promoter sequences derived from biosynthetic enzymes such as tryptophan (Trp) (Goeddel et al., *Nuc. Acids Res.*, 8:4057 (1980); Yelverton et al., *Nuc. Acids Res.*, 9:731 (1981); U.S. Pat. No. 4,738,921; and EPO Publ. Nos. 036 776 and 121 775). The β-lactamase (bla) promoter system (Weissmann, "The cloning of interferon and other mistakes", in: *Interferon* 3 (ed. I. Gresser), 1981). Bacteriophage lambda PL (Shimatake et al., *Nature*, 292:128 (1981)) and T5 (U.S. Pat. No. 4,689,406) promoter systems also provide useful promoter sequences. Another promoter is the Chlorella virus promoter (U.S. Pat. No. 6,316,224).

Synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., *Gene*, 25:167 (1983); de Boer et al., *Proc. Natl. Acad. Sci. USA*, 80:21 (1983)). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189:113 (1986); Tabor et al., *Proc. Natl. Acad. Sci. USA*, 82:1074 (1985)). In addition, a hybrid promoter can also be comprised of a bacteriophage promoter and an *E. coli* operator region (EPO Publ. No. 267 851).

An expression cassette having a baculovirus promoter can be used for expression of a polypeptide in an insect cell. A baculovirus promoter is any DNA sequence capable of binding a baculovirus RNA polymerase and initiating transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an enhancer may be present and is usually distal to the structural gene. A baculovirus promoter may be a regulated promoter or a constitutive promoter. Useful promoter sequences may be obtained from structural genes that are transcribed at times late in a viral infection cycle. Examples include sequences derived from the gene encoding the baculoviral polyhedron protein (Friesen et al., "The Regulation of Baculovirus Gene Expression", in: *The Molecular Biology of Baculoviruses* (ed. Walter Doerfler), 1986; and EPO Publ. Nos. 127 839 and 155 476) and the gene encoding the baculoviral p10 protein (Vlak et al., *J. Gen. Virol.*, 69:765 (1988)).

Promoters that are functional in yeast are known to those of ordinary skill in the art. In addition to an RNA polymerase binding site and a transcription initiation site, a yeast promoter may also have a second region called an upstream activator sequence. The upstream activator sequence permits regulated expression that may be induced. Constitutive expression occurs in the absence of an upstream activator sequence. Regulated expression may be either positive or negative, thereby either enhancing or reducing transcription.

Promoters for use in yeast may be obtained from yeast genes that encode enzymes active in metabolic pathways. Examples of such genes include alcohol dehydrogenase (ADH) (EPO Publ. No. 284 044), enolase, glucokinase, glucose-6-phosphate isomerase, glyceraldehyde-3-phosphatedehydrogenase (GAP or GAPDH), hexokinase, phosphofructokinase, 3-phosphoglyceratemutase, and pyruvate kinase (PyK). (EPO Publ. No. 329 203). The yeast PHO5 gene, encoding acid phosphatase, also provides useful promoter sequences. (Myanohara et al., *Proc. Natl. Acad. Sci. USA,* 80:1 (1983)).

Synthetic promoters that do not occur in nature may also be used for expression in yeast. For example, upstream activator sequences from one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters are known in the art. (Cohen et al., *Proc. Natl. Acad. Sci. USA,* 77:1078 (1980); Henikoff et al., *Nature,* 283:835 (1981); Hollenberg et al., *Curr. Topics Microbiol. Immunol.,* 96:119 (1981)); Hollenberg et al., "The Expression of Bacterial Antibiotic Resistance Genes in the Yeast *Saccharomyces cerevisiae"*, in: *Plasmids of Medical, Environmental and Commercial Importance* (eds. K. N. Timmis and A. Puhler), 1979; (Mercerau-Puigalon et al., *Gene,* 11:163 (1980); Panthier et al., *Curr. Genet.,* 2:109 (1980)).

Many mammalian promoters as known in the art that may be used in conjunction with the expression cassette of the invention. Mammalian promoters often have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: *Molecular Cloning: A Laboratory Manual,* 2nd ed., 1989).

Mammalian viral genes are often highly expressed and have a broad host range; therefore sequences encoding mammalian viral genes often provide useful promoter sequences. Nonlimiting examples include the SV40 early promoter, mouse mammary tumour virus LTR promoter, adenovirus major late promoter (Ad MLP), and Herpes Simplex Virus promoter. In addition, sequences derived from non-viral genes, such as the murine metallothionein gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., *Science,* 236:1237 (1987); Alberts et al., *Molecular Biology of the Cell,* 2nd ed., 1989). Enhancer elements derived from viruses are often times useful, because they usually have a broad host range. Nonlimiting examples include the SV40 early gene enhancer (Dijkema et al., *EMBO J.,* 4:761 (1985)) and the enhancer/promoters derived from the long terminal repeat (LTR) of the Rous Sarcoma Virus (Gorman et al., *Proc. Natl. Acad. Sci. USA,* 79:6777 (1982b)) and from human cytomegalovirus (Boshart et al., *Cell,* 41:521 (1985)). Additionally, some enhancers are regulatable and become active only in the presence of an inducer, such as a hormone or metal ion (Sassone-Corsi and Borelli, *Trends Genet.,* 2:215 (1986); Maniatis et al., *Science,* 236:1237 (1987)).

It is understood that many promoters and associated regulatory elements may be used within the expression cassette of the invention to transcribe an encoded polypeptide. The promoters described above are provided merely provided as examples and are not to be considered as a complete list of promoters that are included within the scope of the invention.

The expression cassette of the invention may contain a nucleic acid sequence for increasing the translation efficiency of an mRNA encoding a polypeptide of the invention. Such increased translation serves to increase production of the polypeptide. The presence of an efficient ribosome binding site is useful for gene expression in prokaryotes. In bacterial mRNA, a conserved stretch of six nucleotides, the Shine-Dalgarno sequence, is usually found upstream of the initiating AUG codon. (Shine et al., *Nature,* 254:34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: *Biological Regulation and Development: Gene Expression* (ed. R. F. Goldberger), 1979)). Such a ribosome binding site, or operable derivatives thereof, are included within the expression cassette of the invention.

A translation initiation sequence can be derived from any expressed *Escherichia coli* gene and can be used within an expression cassette of the invention. Preferably the gene is a highly expressed gene. A translation initiation sequence can be obtained via standard recombinant methods, synthetic techniques, purification techniques, or combinations thereof, which are all well known. (Ausubel et al., *Current Protocols in Molecular Biology,* Green Publishing Associates and Wiley Interscience, NY. (1989); Beaucage and Caruthers, *Tetra. Letts.*, 22:1859 (1981); VanDevanter et al., *Nucleic Acids Res.*, 12:6159 (1984). Alternatively, translational start sequences can be obtained from numerous commercial vendors. (Operon Technologies; Life Technologies Inc, Gaithersburg, Md.). In some embodiments, the T7 translation initiation sequence is used. The T7 translation. initiation sequence is derived from the highly expressed T7 Gene 10 cistron and can have a sequence that includes tctagaaataattttgtttaactttaagaaggagatata (SEQ ID NO:4). Other examples of translation initiation sequences include, but are not limited to, the maltose-binding protein (Mal E gene) start sequence (Guan et al., *Gene*, 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989, *Protocols in Molecular Biology*, Chapter 16, Green Publishing Associates and Wiley Interscience, NY).

Eucaryotic mRNA does not contain a Shine-Dalgarno sequence. Instead, the selection of the translational start codon is usually determined by its proximity to the cap at the 5' end of an mRNA. The nucleotides immediately surrounding the start codon in eucaryotic mRNA influence the efficiency of translation. Accordingly, one skilled in the art can determine what nucleic acid sequences will increase translation of a polypeptide encoded by the expression cassette of the invention. Such nucleic acid sequences are within the scope of the invention.

The invention therefore provides an expression cassette that includes a promoter operable in a selected host and a nucleic acid encoding a polypeptide having a sequence of the invention. In embodiments of the invention, the encoded polypeptide comprises SEQ ID NO:1, SEQ ID NO:2, SEQ ID NO:3, SEQ ID NO:9, SEQ ID NO:12, SEQ ID NO:15, SEQ ID NO:18, SEQ ID NO:22, SEQ ID NO:25, or SEQ ID NO:28, modified to contain HIV trimer stabilizing amino acids as described herein. In other embodiments, the encoded polypeptide comprises SEQ ID NO:5, SEQ ID NO:7, SEQ ID NO:8, SEQ ID NO:11, SEQ ID NO:14, SEQ ID NO:17, SEQ ID NO:20, SEQ ID NO:21, SEQ ID NO:24, SEQ ID NO:27, or SEQ ID NO:30, comprising HIV trimer stabilizing amino acid modifications as described herein. The expression cassette can also have other elements, for example, termination signals, origins of replication, enhancers, and the like as described herein. The expression cassette can also be placed in a vector for easy replication and maintenance.

Recombinant expression of the peptides and polypeptides of the invention avoids degradation frequently observed for short peptides within a cell in which they are expressed when the peptides and polypeptides are expressed and stored within inclusion bodies present within the host cells. Hence, the peptides can readily be purified from inclusion bodies. In an embodiment, recombinant peptides are expressed in *E. coli* strain BL21(DE3)/pLysS (Novagen). Cells were grown at 37° C. in LB medium to an optical density of 0.8 at 600 nm and were induced with isopropylthio-β-D-galactoside for 3-4 hr at 37° C. The cells are centrifuged, frozen at −80° C., resuspended in 50 mM Tris-HCl (pH 8.0) and 1 mM EDTA plus 25% sucrose, and disrupted by sonication. Inclusion bodies of the cell lysate are isolated and washed three times with Triton buffer (20 mM Tris-HCl [pH 8.0], 1 mM EDTA, and 1% Triton X-100). The inclusion bodies are then solubilized in 50 mM Tris-HCl (pH 8.5) plus 8 M urea. Insoluble debris is removed by centrifugation (18,000 g, 1 hr, 4° C.); the supernatant is loaded on a DEAE Sepharose column (Amersham Pharmacia Biotech) equilibrated with buffer A (50 mM Tris-HCl [pH 8.5] plus 3 M urea). The soluble peptide is eluted with a linear salt gradient (0-500 mM NaCl in buffer A). The peptide solution is dialyzed into 5% acetic acid overnight at 4° C. Peptides from the soluble fraction are purified to homogeneity by reverse-phase high-performance liquid chromatography (Waters, Inc.) on a Vydac C-18 preparative column (Hesperia, Calif.), using a water-acetonitrile gradient in the presence of 0.1% trifluoroacetic acid, and lyophilized.

The isolation of the peptides and polypeptides is enhanced because they are present in inclusion bodies that can readily be separated from other cellular components. Such inclusion bodies are more or less soluble under defined conditions that include, but are not limited to, pH, temperature, salt concentration, and protein concentration. Thus, an inclusion body can be insoluble in water but soluble in the presence of urea, acid, guanidinium chloride, and other agents. Hence, after recombinant expression of the present peptides and polypeptides in a host cell, the host cells can be isolated and lysed, and inclusion bodies can be collected, for example, by centrifugation. The inclusion bodies can be rinsed with dilute buffer and then solubilized in urea or other agent. Insoluble debris can be removed by centrifugation and the solubilized peptides can be further purified, for example, by ion exchange chromatography or reverse-phase HPLC.

Antibodies and Binding Entities

The invention is also directed to binding entities and antibodies that can bind to a trimeric gp120/gp41 polypeptide complex stabilized as described herein. The binding domains of such antibodies, for example, the CDR regions of these antibodies, can also be transferred into or utilized with any convenient binding entity backbone.

The HIV-1 envelope glycoprotein is the major target for neutralizing antibodies during the course of natural infection and has been extensively employed as an immunogen in vaccine studies (Burton et al., *Nature Med.* 4, 495-498 (1998); Letvin, *Science* 280, 1875-1880 (1998); Burton, *Proc. Natl. Acad. Sci. USA* 94, 10018-10023 (1997); Burton et al., *J. Acquir. Immune Defic. Syndr.* 11 (Suppl A), 587-598 (1997); Montefiori et al., *AIDS Res. Hum. Retroviruses* 15, 689-698 (1999); Wyatt et al., *Science.* 280, 1884-1888 (1998); Parren et al., *AIDS.* 13 (Suppl A), S137-S162 (1999)). Because of the chronic nature of HIV-1 infection, the envelope glycoprotein has evolved to minimize the potential impact of neutralizing antibodies on viral infection. Broad-spectrum neutralization epitopes on the envelope glycoprotein complex appear to be rare and poorly immunogenic.

Notwithstanding, all the monoclonal antibodies (MAbs) that neutralize HIV-1 are able to bind the trimeric envelope glycoprotein spike (Sattentau et al., *J. Exp. Med.* 182, 185-196 (1995); Sullivan et al., *J. Virol.* 69, 4413-4422 (1995); Moore et al., *J. Virol.* 69, 101-109 (1995); Fouts et al., *J. Virol.* 71, 2779-2785 (1997); Parren et al., *J. Virol.* 72, 3512-3519 (1998)). Because the native, trimeric envelope glycoprotein complex is unstable, a major challenge in vaccine research has been to preserve the envelope trimer conformation in vaccine preparations (see, e.g., Sanders et al., *J. Virol.* 76, 8875-8889 (2002)). Thus, by providing a stabilized gp41/gp120 trimeric conformation, the present invention affords a solution to the problem(s) of reproducibly providing stable HIV immunogens that can be used to generate an anti-HIV immune response and potent, neutralizing anti-HIV antibodies.

Antibody molecules belong to a family of plasma proteins called immunoglobulins. The heavy and light chains of an antibody consist of different domains. Each light chain has one variable domain (VL) and one constant domain (CL), while each heavy chain has one variable domain (VH) and three or four constant domains (CH). See, e.g., Alzari, P. N. et al., (1988). Three-dimensional structure of antibodies. *Annu. Rev. Immunol.* 6:555-580. Each domain, consisting of about 110 amino acid residues, is folded into a characteristic β-sandwich structure formed from two β-sheets packed against each other, the immunoglobulin fold. The VH and VL domains each have three complementarity determining regions (CDR1-3) that are loops, or turns, connecting β-strands at one end of the domains. The variable regions of both the light and heavy chains generally contribute to antigen specificity, although the contribution of the individual chains to specificity is not always equal. Antibody molecules have evolved to bind to a large number of molecules by using six randomized loops (CDRs).

Immunoglobulins can be assigned to different classes depending on the amino acid sequences of the constant domain of their heavy chains. There are at least five (5) major classes of immunoglobulins: IgA, IgD, IgE, IgG and IgM. Several of these may be further divided into subclasses (isotypes), for example, IgG1, IgG2 (IgG2a and IgG2b), IgG3 and IgG4; IgA1 and IgA2. The heavy chain constant domains that correspond to the IgA, IgD, IgE, IgG and IgM classes of immunoglobulins are called alpha (a), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

Variability in antibody variable domains is concentrated in three segments called complementarity determining regions (CDRs), also known as hypervariable regions in both the light chain and the heavy chain variable domains. The more highly conserved portions of variable domains are called framework (FR) regions. The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from another chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody portion or fragment, such as Fv, Fab, Fab'2, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific peptide sequence described herein or a derivative thereof. However, in some embodiments, the antibody binds with specificity to a polypeptide with any of the polypeptide sequences disclosed herein, or a combination or complex thereof.

Moreover, the binding regions, or CDRS, of antibodies can be placed within the backbone of any convenient binding entity polypeptide. In some embodiments, in the context of methods described herein, an antibody, binding entity, or portion or fragment thereof is used that is immunospecific for any of the polypeptides described herein, as well as the derivatives thereof, including crosslinked derivatives thereof.

The term "antibody fragment" refers to a portion of a full-length antibody, generally the antigen binding or variable region. Examples of antibody fragments include Fab, Fab', F(ab')$_2$ and Fv fragments. Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site. As used herein, "functional fragment" with respect to antibodies, refers to Fv, F(ab) and F(ab')$_2$ fragments.

Additional fragments can include diabodies, linear antibodies, single-chain antibody molecules and multispecific antibodies formed from antibody fragments. Single chain antibodies are genetically engineered molecules containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun, in The *Pharmacology of Monoclonal Antibodies*, vol. 113, Rosenburg and Moore eds. Springer-Verlag, N.Y., pp. 269-315 (1994).

The term "diabodies" refers to a small antibody fragments with two antigen-binding sites, where the fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., *Proc. Natl. Acad Sci. USA* 90:6444-6448 (1993).

Antibody portions or fragments contemplated by the invention are therefore not full-length antibodies. However, such antibody fragments can have similar or improved immunological properties relative to a full-length antibody. Such antibody fragments may be as small as about 3-4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more.

In general, an antibody fragment of the invention can have any upper size limit as long as it has similar or improved immunological properties relative to an antibody that binds with specificity to a polypeptide described herein. For example, smaller binding entities and light chain antibody fragments can have less than about 200 amino acids, less than about 175 amino acids, less than about 150 amino acids, or less than about 120 amino acids if the antibody fragment is related to a light chain antibody subunit. Moreover, larger binding entities and heavy chain antibody fragments can have less than about 425 amino acids, less than about 400 amino acids, less than about 375 amino acids, less than about 350 amino acids, less than about 325 amino acids or less than about 300 amino acids if the antibody fragment is related to a heavy chain antibody subunit.

Antibodies directed against various immunogens or disease markers can be made by a number of known procedures. Methods for preparing polyclonal antibodies are practiced by those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

Monoclonal antibodies, which are highly specific and directed against a single epitopic site or determinant on an antigen (or immunogen), are also embraced by this invention. As used herein, monoclonal antibodies herein specifically include "chimeric" antibodies in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass. Fragments of such antibodies can also be used, so long as they exhibit the desired biological activity. See U.S. Pat. No. 4,816,567; Morrison et al. *Proc. Natl. Acad Sci. USA.* 81, 6851-55 (1984). The monoclonal antibodies herein also specifically include those made from different animal species, including mouse, rat, human and rabbit.

The preparation of monoclonal antibodies is conventional in the art. (See, for example, Kohler & Milstein, *Nature,* 256:495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. (See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992)).

Methods of in vitro and in vivo manipulation of antibodies are understood by those skilled in the art. For example, the monoclonal antibodies to be used in accordance with the present invention may be made by the hybridoma method as described above, or they may be made by recombinant methods, e.g., as described in U.S. Pat. No. 4,816,567. Monoclonal antibodies may also be isolated from phage antibody libraries using the techniques described, for example, in Clackson et al. *Nature.* 352:624-628 (1991), as well as in Marks et al., *J. Mol Biol.* 222:581-597 (1991).

Methods of making antibody fragments are also known in the art (see for example, Harlow and Lane, Antibodies: *A Laboratory Manual*, Cold Spring Harbor Laboratory, New York, (1988), incorporated herein by reference). Antibody fragments of the present invention can be prepared by proteolytic hydrolysis of the antibody or by expression of nucleic acids encoding the antibody fragment in a suitable host. Antibody fragments can be obtained by pepsin or papain digestion of whole antibodies conventional methods. For example, antibody fragments can be produced by enzymatic cleavage of antibodies with pepsin to provide a 5S fragment described as $F(ab')_2$. This fragment can be further cleaved using a thiol reducing agent, and optionally using a blocking group for the sulfhydryl groups resulting from cleavage of disulfide linkages, to produce 3.5S Fab' monovalent fragments.

Alternatively, enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated by reference in their entireties.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent, or the variable chains can be linked by an intermolecular disulfide bond, or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., *Science.* 242:423-426 (1988); Ladner, et al, U.S. Pat. No. 4,946,778; and Pack, et al., *Bio/Technology.* 11:1271-77 (1993).

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*. Vol.2, page 106 (1991).

The invention also encompasses human and humanized forms of non-human (e.g., murine) antibodies (monoclonal antibodies). Such humanized antibodies are chimeric immunoglobulins, immunoglobulin chains or fragments thereof (such as Fv, Fab, Fab', $F(ab')_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the human recipient antibody are replaced by residues from the CDRs of a nonhuman species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., *Nature*. 321, 522-525 (1986); Reichmann et al., *Nature*. 332, 323-329 (1988); Presta, *Curr. Op. Struct. Biol.* 2, 593-596 (1992); Holmes, et al., *J. Immunol.,* 158:2192-2201 (1997) and Vaswani, et al., *Annals Allergy, Asthma & Immunol.,* 81:105-115 (1998).

While standardized procedures are available and useful to generate antibodies, the size of antibodies, the multi-stranded structure of antibodies and the complexity of six binding loops present in antibodies constitute a hurdle to the improvement and the manufacture of large quantities of antibodies. Hence, the invention further encompasses the use of binding entities, which comprise polypeptides that can recognize and bind to gp41 and/or gp120 polypeptides having the three dimensional structures provided herein.

A number of proteins can serve as protein scaffolds to which binding domains can be attached and thereby form a suitable binding entity. The binding domains bind or interact with the polypeptide sequences of the invention while the protein scaffold merely holds and stabilizes the binding domains so that they can bind. A number of protein scaffolds can be used, for example, phage capsid proteins. See Review in Clackson & Wells, *Trends Biotechnol.* 12:173-184 (1994). Phage capsid proteins have been used as scaffolds for displaying random peptide sequences, including bovine pancreatic trypsin inhibitor (Roberts et al., *PNAS USA*. 89:2429-2433 (1992)), human growth hormone (Lowman et al., *Biochemistry.* 30:10832-10838 (1991)), Venturini et al., *Protein Peptide Letters*. 1:70-75 (1994)), and the IgG binding domain of *Streptococcus* (O'Neil et al., *Techniques in Protein Chemistry V* (Crabb, L,. ed.) pp. 517-524, Academic Press, San Diego (1994)). These scaffolds have displayed a single randomized loop or region that can be modified to include binding domains for gp41 and/or gp120 polypeptides with the structures described herein.

The small 74 amino acid a-amylase inhibitor Tendamistat has also been employed as a presentation scaffold on the filamentous phage M13. (McConnell, S. J., & Hoess, R. H., *J. Mol. Biol.* 250:460-470 (1995)). Tendamistat is a β-sheet protein derived from *Streptomyces tendae*. It has a number of features that make it an attractive scaffold for binding entities, including its small size, stability, and the availability of high resolution NMR and X-ray structural data. The overall topology of Tendamistat is similar to that of an immunoglobulin domain, with two β-sheets connected by a series of loops. In contrast to immunoglobulin domains, the β-sheets of Tendamistat are held together with two rather than one disulfide bond, accounting for the considerable stability of the protein. The loops of Tendamistat can serve a function similar to the CDR loops of immunoglobulins and can be easily randomized by in vitro mutagenesis. Tendamistat may be antigenic in humans. Hence, binding entities that employ Tendamistat are preferably employed in vitro.

Fibronectin type III domain has also been used as a protein scaffold to which binding entities can be attached. Fibronectin type III is part of a large subfamily (Fn3 family or s-type Ig family) of the immunoglobulin superfamily. Sequences, vectors and cloning procedures for using such a fibronectin type III domain as a protein scaffold for binding entities (e.g. CDR peptides) are provided, for example, in U.S. Patent Application Publication 20020019517. See also, Bork, P. & Doolittle, R. F. (1992) *Proc. Natl. Acad. Sci. USA.* 89, 8990-8994; Jones, E. Y. (1993) The immunoglobulin superfamily. *Curr. Opinion Struct. Biol.* 3, 846-852; Bork, P. et al., (1994) *J. Mol. Biol.* 242, 309-320; and Campbell, I. D. & Spitzfaden, C. (1994) *Structure.* 2, 233-337.

In the immune system, specific antibodies are selected and amplified from a large library (affinity maturation). The combinatorial techniques employed in immune cells can be mimicked by mutagenesis and the generation of combinatorial libraries of binding entities. Variant binding entities, antibody fragments and antibodies therefore can also be generated through display-type technologies. Such display-type technologies include, for example, phage display, retroviral display, ribosomal display, and other techniques. Techniques available in the art can be used for generating libraries of binding entities and for screening those libraries; the selected binding entities can be subjected to additional maturation, such as affinity maturation. Wright and Harris, supra., Hanes and Plucthau *PNAS USA* 94:4937-4942 (1997) (ribosomal display), Parmley and Smith, *Gene.* 73:305-318 (1988) (phage display), Scott *TIBS.* 17:241-245 (1992), Cwirla et al. *PNAS USA.* 87:6378-6382 (1990), Russel et al. *Nucl. Acids Res.* 21:1081-1085 (1993), Hoganboom et al. *Immunol. Reviews.* 130:43-68 (1992), Chiswell and McCafferty *TIBTECH.* 10:80-84 (1992), and U.S. Pat. No. 5,733,743.

The invention therefore also provides methods of mutating antibodies, CDRs, or binding domains to optimize their affinity, selectivity, binding strength and/or other desirable properties. A mutant binding domain refers to an amino acid sequence variant of a selected binding domain (e.g., a CDR). In general, one or more of the amino acid residues in the mutant binding domain is different from what is present in the reference binding domain. Such mutant antibodies necessarily have less than 100% sequence identity or similarity with the reference amino acid sequence. In general, mutant binding domains have at least 75% amino acid sequence identity or similarity with the amino acid sequence of the reference binding domain. Preferably, mutant binding domains have at least 80%, more preferably at least 85%, even more preferably at least 90%, and most preferably at least 95% amino acid sequence identity or similarity with the amino acid sequence of the reference binding domain.

For example, affinity maturation using phage display can be utilized as one method for generating mutant binding domains. Affinity maturation using phage display refers to a process, such as is described in Lowman et al., *Biochemistry.* 30(45): 10832-10838 (1991) and in Hawkins et al., *J. Mol Biol.* 254: 889-896 (1992). While not strictly limited to the following description, this process can be described briefly as involving mutation of several binding domains or antibody hypervariable regions at a number of different sites with the goal of generating all possible amino acid substitutions at each site. The binding domain mutants thus generated are displayed in a monovalent fashion from filamentous phage particles as fusion proteins. Fusions are generally made to the gene III product of M13. The phage expressing the various mutants can be cycled through several rounds of selection for the trait of interest, e.g. binding affinity or selectivity. The mutants of interest are isolated and sequenced. Such methods are described in more detail in U.S. Pat. Nos. 5,750,373,6, 290,957 and in Cunningham, B. C. et al., *EMBO J.* 13(11), 2508-2515 (1994).

In one embodiment, the invention provides methods of manipulating binding entity or antibody polypeptides or the nucleic acids encoding them to generate binding entities, antibodies and antibody fragments with improved binding properties that recognize and bind to gp41, gp120 and/or gp41/gp120 stabilized trimer complexes.

Such methods of mutating portions of an existing binding entity or antibody involve fusing a nucleic acid encoding a polypeptide that encodes a binding domain for an antigen, immunogen, or disease marker to a nucleic acid encoding a phage coat protein to generate a recombinant nucleic acid encoding a fusion protein, mutating the recombinant nucleic acid encoding the fusion protein to generate a mutant nucleic acid encoding a mutant fusion protein, expressing the mutant fusion protein on the surface of a phage, and selecting phage that bind to the gp41 and/or gp120 polypeptides comprising a stabilized trimer.

Accordingly, the invention provides antibodies, antibody fragments, and binding entity polypeptides that can recognize and bind to a gp140 or a gp41-gp120 stabilized trimer complex (e.g., polypeptides having any of the sequences provided herein or combinations thereof). The invention further provides methods of manipulating those antibodies, antibody fragments, and binding entity polypeptides to optimize their binding properties or other desirable properties (e.g., stability, size, ease of use).

Administration

The polypeptides, binding entities and antibodies of the invention, including their salts, are administered so as to achieve a reduction in at least one symptom associated with an infection, indication or disease, or a decrease in the amount of antibody associated with the indication or disease.

To achieve the desired effect(s), the binding entities, antibodies, polypeptides (e.g. having any of the sequences disclosed here, or combinations thereof), variants thereof, a combination thereof, or compositions comprising any of these may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the polypeptide, binding entity or antibody chosen, the disease, the weight, the physical condition, the health, the age of the mammal, whether prevention or treatment is to be achieved, and if the polypeptide, binding entity or antibody is chemically modified. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the therapeutic agents of the invention may be essentially continuous over a pre-selected period of time or may be in a series of spaced doses. Both local and systemic administration is contemplated.

To prepare a composition for administration to a subject, polypeptides, binding entities or antibodies are synthesized or otherwise obtained, purified as necessary or desired and then lyophilized and stabilized. Such therapeutic agents can then be adjusted to the appropriate concentration, and optionally combined with other agents. The absolute weight of a given therapeutic agent included in a unit dose can vary widely. For example, about 0.01 to about 2 g, or about 0.1 to about 500 mg, of at least one therapeutic agent of the invention, or a plurality of therapeutic agents can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g. Daily doses of the therapeutic agents of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

In the treatment or prevention of viral infections, an appropriate dosage level will generally be about 0.001 to 100 mg per kg patient body weight per day, which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be about 0.005 to about 0.05, 0.05 to 0.5 or 0.5 to 5 mg/kg per day. For oral administration, the compositions are preferably provided in the form of tablets containing about 1 to 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

Thus, one or more suitable unit dosage forms comprising the therapeutic agents of the invention can be administered by a variety of routes including oral, parenteral (including subcutaneous, intravenous, intramuscular and intraperitoneal), rectal, vaginal, dermal, transdermal, intrathoracic, intrapulmonary and intranasal (respiratory) routes. The therapeutic agents may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The active therapeutic agents may also be presented as a bolus, electuary or paste orally administered therapeutic agents of the invention can also be formulated for sustained release, e.g., the therapeutic agents can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation and that is not deleterious to the recipient thereof. Pharmaceutically acceptable formulations containing the therapeutic agents of the invention can be prepared by procedures known in the art using well-known and readily available ingredients. For example, the therapeutic agents can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They can also contain gums such as xanthan, guar or carbo gum or gum arabic, or alternatively polyethylene glycols, bentones and montmorillonites, and the like.

Illustratively, tablets or caplets containing the therapeutic agents of the invention can include buffering agents, such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more therapeutic agents of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

Thus, the therapeutic agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The therapeutic agents and other ingredients may form suspensions, solutions, or emulsions in oily or aqueous vehicles, and may contain formulatory agents such as suspending, stabilizing and/or dispersing agents. Alternatively, the therapeutic agents and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant selected from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and $\alpha$-tocopherol and its derivatives can be added.

Additionally, the therapeutic agents are well suited to formulation as sustained release dosage forms and the like. The formulations can be so constituted that they release the active therapeutic agents, for example, in a particular part of the intestinal or respiratory tract or within the vagina or rectum, possibly over a period of time. Coatings, envelopes, and protective matrices may be made, for example, from polymeric substances, such as polylactide-glycolates, liposomes, microemulsions, microparticles, nanoparticles, or waxes.

For topical, vaginal or rectal administration, the therapeutic agents may be formulated as is known in the art for direct application to a target area. Forms chiefly conditioned for topical application take the form, for example, of creams, milks, gels, foams, dispersion or microemulsions, lotions thickened to a greater or lesser extent, impregnated pads of tampons, ointments or sticks, aerosol formulations (e.g., sprays or foams), soaps, detergents, lotions or cakes of soap. Other conventional forms for this purpose include wound dressings, coated bandages or other polymer coverings, ointments, creams, foams, lotions, pastes, jellies, sprays, and aerosols. Thus, the therapeutic agents of the invention can be delivered via patches or bandages for dermal administration. Alternatively, the therapeutic agents can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active polypeptides can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agents may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

In general, the dosage forms of the invention comprise an amount of at least one of the agents of the invention effective to treat, reduce the severity of, or prevent the clinical symptoms of a specific infection, indication, condition, or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Therapeutic agents of the present invention can be administered as a dry powder or in an aqueous solution when administered in an aerosol or inhaled form. Other aerosol pharmaceutical formulations may comprise, for example, a physiologically acceptable buffered saline solution containing between about 0.1 mg/ml and about 100 mg/ml of one or more of the polypeptides of the present invention specific for the indication or disease to be treated. Dry aerosol in the form of finely divided solid compound, polypeptide or polypeptide particles that are not dissolved or suspended in a liquid are also useful in the practice of the present invention. Therapeutic agents of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

The therapeutic agents of the invention can also be administered to the respiratory tract. Thus, the present invention also provides aerosol pharmaceutical formulations and dosage forms for use in the methods of the invention. For administration to the upper (nasal) or lower respiratory tract by inhalation, the therapeutic polypeptides of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas.

In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agents may be administered via nose drops, a liquid spray, such as via a plastic bottle atomizer or metered-dose inhaler. Typical of atomizers are the Mistometer (Wintrop) and the Medihaler (Riker).

Also contemplated are combination products that include one or more of the therapeutic agents as active agents, e.g., antibodies and binding proteins, of the present invention and one or more other therapeutic agents, e.g., anti-viral agents, anti-microbial agents, pain relievers, anti-inflammatory agents, anti-bacterial agents, antihistamines, bronchodilators and the like, whether for the condition(s) described or some other condition. Accordingly, other anti-retroviral agents can be included in the compositions of the invention such as protease inhibitors, retroviral polymerase inhibitors, azidothymidine (AZT), didanoside (DDI), soluble CD4, a polysaccharide sulfates, T22, bicyclam, suramin, antisense oliogonulceotides, ribozymes, rev inhibitors, protease inhibitors, glycolation inhibitors, interferon and the like.

The present invention further pertains to a packaged pharmaceutical composition for treating and/or preventing viral (e.g. HIV) infections, such as a kit or other container. The kit or container holds a therapeutically effective amount of a pharmaceutical composition for treating and preventing viral infections and instructions for using the pharmaceutical composition for treating and preventing the viral infection. The pharmaceutical composition can include at least one polypeptide of the present invention, in a therapeutically effective amount such that viral infection is treated or prevented.

In an alternative embodiment, the pharmaceutical composition can include at least one binding entity or antibody of the present invention in a therapeutically effective amount such that the viral infection is treated, reduced, ameliorated, or prevented.

EXPERIMENTAL DETAILS

This invention is illustrated in the Experimental Details sections which follow. The Experimental Details section is set forth to aid in an understanding of the invention but is not intended to, and should not be construed to, limit in any way the invention as set forth in the claims which follow thereafter.

Experimental Details I

Introduction

The HIV-1 envelope glycoprotein is expressed on the viral membrane as a trimeric complex, formed by three gp120 surface glycoproteins non-covalently associated with three membrane-anchored gp41 subunits. The labile nature of the association between gp120 and gp41 hinders the expression of soluble, fully cleaved, trimeric gp140 proteins for structural and immunization studies. Disruption of the primary cleavage site within gp160 allows the production of stable gp140 trimers, but cleavage-defective trimers are antigenically dissimilar from their cleaved counterparts. Soluble, stabilized, proteolytically cleaved, trimeric gp41 proteins can be generated by engineering an intermolecular disulphide bond between gp120 and gp41 (SOS), combined with a single residue change, I559P, within gp41 (SOSIP). SOSIP gp140 proteins based on the subtype A HIV-1 strain KNH1144 form particularly homogenous trimers compared to a prototypic strain (JR-FL, subtype B). Described herein are the determinants of this enhanced stability which are located in the N-terminal region of KNH11144 gp41 and that, when substituted into heterologous Env sequences (e.g., JR-FL and Ba-L) they have a similarly beneficial effect on trimer stability. These stabilized trimers retain the epitopes for several neutralizing antibodies and related agents (CD4-IgG2, b12, 2G12, 2F5 and 4E10) and the CD4-IgG2 molecule, so that the overall antigenic structure of the gp140 protein has not been adversely impaired by the trimer-stabilizing substitutions.

Materials and Methods

Reagents: CD4-IgG2 (PRO 542) (Allaway et al., 1995) and monoclonal antibody (MAb) PA-1 were provided by Dr. William Olson (Progenics Pharmaceuticals, Inc.) Soluble D1D2-CD4 (sCD4-183, 2 domain) (Garlick et al., 1990) was obtained from the NIH AIDS Research and Reference Program. MAb CA13 (ARP3119), from Ms C. Arnold, was provided by the EU Programme EVA Centralized Facility for AIDS Reagents, NIBSC, UK (AVIP Contract Number LSHP-CT-2004-503487). MAbs 2G12 (Calarese et al., 2003; Trkola et al., 1996), 2F5 (Parker et al., 2001; Zwick et al., 2001), 4E10 (Cardoso et al., 2005; Zwick et al., 2001) were obtained from Hermann Katinger, MAb 17b (Thali et al., 1993) from James Robinson and MAb b12 (Burton et al., 1994) from Dennis Burton. The hybridoma for the production of MAb B13 (HIV-1 gp160 Hyb, Chessie 13-39.1) (Abacioglu et al., 1994) was obtained from NIH AIDS Research and Reference Program (donated by George K. Lewis).

Plasmids and Construction of Chimeric and Mutant Env Genes:

Various HIV-1 env genes, cloned into the high-level mammalian expression vector pPPI4, were used for expression of soluble gp140 glycoproteins as previously described. Furin was expressed from pcDNA3.1-Furin (Binley et al., 2000; Sanders et al., 2000). The HIV-1 Env subtype A clone KNH1144 (accession number AF457066) (Beddows et al., 2006) and the subtype B clones JR-FL and Ba-L have been described previously (Binley et al., 2000). In domain-swap experiments, the JR-FL gp41 ectodomain was replaced with the corresponding region of KNH1144 gp41, using EcoRI and HindIII restriction enzymes, followed by repair of the restriction sites and verification of the sequences. Specific amino acid substitutions were made using the QuikChange® II XL site-directed mutagenesis kit (Stratagene Inc., La Jolla, Calif.) and the appropriate primers. The introduced mutations were verified by sequencing.

Transfection and Expression of Soluble gp140 Envelope Glycoproteins:

The human Embryonic Kidney cell line HEK293T was used for expression of the various envelope glycoproteins by transient transfection, as previously described (Binley et al., 2000; Sanders et al., 2000; Sanders et al., 2002). HEK293T cells were grown in Dulbecco's modified Eagle's medium (DMEM, Gibco) supplemented with 10% fetal calf serum, penicillin, streptomycin and L-glutamine. Transient transfections were performed using Polyethylenimine (PEI) (Polysciences Inc., Warrington, Pa.) (Boussif et al., 995; Kirschner et al., 2006). For each small-scale transfection, 7 μg of env DNA and 3.5 μg of furin DNA were used. Five hours post-transfection, the 293T cells were washed and the media replaced with DMEM containing 0.05% bovine serum albumin (BSA), antibiotics (penicillin, streptomycin) and L-glutamine. Forty-eight hours post-transfection, the supernatant was collected and filtered using a 0.45 μm filter. A cocktail of protease inhibitors (Roche Diagnostics, Indianapolis, Ind.) was added before concentration of the supernatant by >20-fold using the Amicon ultracentrifugal filter system (Millipore, Billerica, Mass.). Aliquots of concentrated supernatant were analyzed by sodium-dodecyl sulfate polyacrylamide electrophoresis (SDS-PAGE), or stored at −80° C.

Purification of Soluble Envelope Glycoproteins:

Supernatants (1 L) from transfected HEK293T cells were concentrated by >20-fold then processed by Lectinaffinity chromatography. The column eluate was then size-fractionated using an analytical Superose™ 6 column (GE Amersham Pharmacia, Piscataway, N.J.) equilibrated with phosphate-buffered saline (PBS; 100 mM NaCl, 50 mM sodium phosphate, pH 7.0). The column was calibrated with protein standards of known molecular weights (HMW Gel Filtration Calibration Kit; Amersham Pharmacia, Piscataway, N.J.). Fractions (200 μl) were collected and analyzed using Blue-native polyacrylamide electrophoresis (BN-PAGE) and SDS-PAGE. Quantification of proteins was carried out using the BCA quantification kit (Pierce) with known BSA standards.

BN-PAGE, SDS-PAGE and Western Blot Analysis:

BN-PAGE was performed as described previously by Schulke et al. (2002). Concentrated culture supernatants or purified protein samples were diluted with an equal volume of a loading buffer containing 100 mM 4-(N-morpholino) propane sulfonic acid (MOPS), 100 mM Tris-HCl (pH 7.7), 40% glycerol, 0.1% Coomassie blue, and loaded onto a 4-12% Bis-Tris NuPAGE gel (Invitrogen). Gel electrophoresis was performed at 100 V for 3 h using 50 mM MOPS, 50 mM Tris (pH 7.7) as electrophoresis buffer. SDS-PAGE was performed as described previously by Schulke et al. (2002). Reduced and non-reduced samples were prepared in Laemmli sample buffer (62.5 mM Tris-HCl, pH6.8, 2% SDS, 25% glycerol, 0.01% DTT) and boiled for 5 min in the presence or absence of 50 mM dithiothreitol (DTT), respectively. Western blot analyses were performed as described elsewhere (Schulke et al., 2002). Following transfer, the polyvinylidene difluoride (PVDF) membrane was destained, then probed using anti-Env MAbs CA13 (ARP3119) or B13, followed by horseradish peroxidase-labeled anti-mouse immunoglobulin G (IgG) (Kirkegaard & Perry Labs), at a final concentration of 0.2 μg/ml. The bound MAbs were detected using the Western Blot Chemiluminescence Reagent Plus system (Perkin-Elmer Life Sciences, Boston, Mass.). Protein mixtures containing Thyroglobulin (669 kDa), Ferritin (440 kDa), Catalase (232 kDa), Lactate dehydrogenase (140 kDa) and BSA (66 kDa) (Amersham Biosciences) were used as standard markers for native gels. For denaturing electrophoresis, the MultiMark® multi-colored standard (Invitrogen) was used.

BIAcore Surface Plasmon Resonance (SPR):

The BIAcore X system (BIAcore Inc., Uppsala, Sweden) was used for comparison of the JR-FL WT versus mutant gp140 env binding to various monoclonal antibodies. All assays were performed at 25° C. using HBS-EP buffer (10 mM HEPES, pH 7.4, 150 mM NaCl, 3 mM EDTA, 0.005% [v/v] Surfactant P20; BIAcore, Uppsala, Sweden), which was degassed for 1 h before use. The flow-rate was maintained at 10 μl/minute. A BIAcore streptavidin (SA) chip was used for capturing ~1000 response units (RU) of biotinylated protein G (Pierce) in both the experimental and the control flow-cells. Biotin was then used to block the uncoated streptavidin surface on both flow-cells. In the experimental cell, ~1000 RU of various MAbs were directionally captured onto the surface-attached biotinylated Protein G via their Fc regions. Purified envelope glycoproteins (5 nM) were then injected for analysis of their ligand-binding properties. For study of the CD4-induced binding of MAbs directed to the CD4i-epitope, D1D2-CD4 (at a 6-molar excess concentration) was incubated with the envelope glycoprotein for 1 hour at room temperature before injection. Following each run, the sensor surface was regenerated using two 10 µl injections of 10 mM Glycine-HCl, pH 3.0. For each analyte, association was measured for 180 s, dissociation for a further >500 s. All binding studies were performed three times (n=3) with good reproducibility. The data were analyzed using BIAevaluation software 3.2 (BIAcore Inc). To correct for refractive index changes and instrument noise, the response data from the control flow-cell were subtracted from those obtained from the experimental flow-cell. For comparison of the antigenicity profiles of the wild-type and mutant gp140 proteins, the end-of-injection RU values+/–SD (n=3) are reported.

Results

Specific amino acids in the N-terminal region of $gp41_{ECTO}$ contribute to enhanced oligomerization of cleaved gp140 from KNH1144. Cleaved, SOSIP gp140 proteins from the subtype A strain KNH1144 form unusually stable and homogenous trimers compared to JR-FL SOSIP gp140, which is expressed as both dimers and trimers (Sanders et al., 2002). The SOS gp140 protein from KNH1144 is also more stable than the corresponding JR-FL construct, the latter being expressed as a mixture of trimers, dimers and, predominantly, monomers (Beddows et al., 2006; Binley et al., 2000). On purification, JR-FL SOS gp140 yields mostly monomeric gp140 proteins as a result of the instability of the gp41-gp41 interactions (Binley et al., 2000). The N-terminal region of gp41, particularly around the Heptad Repeat 1 (HR1) region, plays a role in oligomerization of gp140 proteins (Center, Kemp, and Poumbourios, 1997; Center et al., 2004; Poumbourios et al., 1997). When the N-terminal regions of gp41 from KNH144 and JR-FL were aligned, five amino acids were seen to differ at amino acid positions 535, 543, 553, 567 and 588 (FIG. 1). While KNH1144 has isoleucine (I) at amino acid position 535, JR-FL has methionine (M); while KNH1144 has glutamine (Q) at amino acid position 543, JR-FL has leucine (L); while KNH1144 has serine (S) at amino acid position 553, JR-FL has asparagine (N); while KNH1144 has lysine (K) at amino acid position 567, JR-FL has glutamine (Q); and while KNH1144 has arginine (R) at amino acid position 588, JR-FL has glycine (G). To determine, which, if any, of these five differences contributed to the enhanced stability of KNH1144 trimers, each residue in KNH11144 SOSIP gp140 was substituted with the corresponding one from JR-FL; the mutant Env proteins were then expressed and studied on BN-PAGE gels. The wild-type forms of KNH1144 SOS and SOSIP gp140 proteins were also analyzed to allow a comparison with the trimer-stabilizing effect of the I559P substitution in the SOSIP version (FIG. 2A). In general, the amino acid substitutions described below had similar effects whether they were made in the SOS or the SOSIP gp140 background, so only a subset of the results is depicted. The S553N and R588G changes had little or no effect on trimer formation by KNH144 SOSIP gp140 (FIG. 2B, lanes 3 and 5), whereas the I535M substitution enhanced trimer formation (FIG. 2B, lane 1), an observation confirmed in a larger scale expression and purification study. In contrast, substitutions of glutamine and lysine at positions 543 and 567 (Q543L and K567Q) destabilized the KNH1144 SOSIP gp140 trimers (FIG. 2B, lanes 2 and 4). When all five amino acids were substituted in the KNH1144 SOS and SOSIP gp140 templates, the destabilizing effect on trimer formation was pronounced. The extent of the increase in monomer formation, compared to wild-type, was estimated to be ~45% and ~60% for the KNH1144 SOSIP and SOS gp140 mutants, respectively (FIG. 2C, lane 1, SOSIP; lane 2, SOS; compare with FIG. 2A). Hence, the five amino acid differences between the N-terminal regions of KNH1144 and JR-FL gp41 do influence the stability of cleaved gp140 trimers.

Substitution of five amino acids from the N-terminal region of KNH1144 $gp41ECTO$ promotes JR-FL gp140 trimer formation. Both the SOS and SOSIP versions of JR-FL gp140 were used as templates on which to explore the effects of the five amino acid differences in the KNH1144 gp41 ectodomain, to take into account the additional, possibly complicating, influence of the I559P change. In the first construct, a chimera, the JR-FL gp120 subunit was combined with the KNH1144 gp41 ectodomain (JR-FLgp120-1144gp41 ECTO); the second construct was a mutant JR-FL SOS gp140 in which the five varying amino acids (positions 535, 543, 553, 567 and 588) were substituted by the corresponding residues from KNH1144 (JR-FL gp41 NT 1-5); the third was another chimera in which the C-terminal region of $gp41ECTO$ from JR-FL was replaced by the corresponding segment of KNH1144 gp41 (JR-FL-1144 gp41 CT) (FIG. 3A). The various chimeric and mutant envelope glycoproteins were expressed in HEK293T cells and analyzed on BN-PAGE gels (FIG. 3B). JR-FL SOS gp140 was predominantly monomeric, while by contrast, the SOSIP gp140 formed dimers and trimers (FIG. 3B, lanes 1 and 2). The insertion of $gp41_{ECTO}$ from KNH1144 into the JR-FL SOS gp140 template stabilized the trimeric form, with a reduction in the amount of monomers present (FIG. 3B, lane 3). The same change, but made in the JR-FL SOSIP gp140 context, had a lesser effect (FIG. 3B, compare lanes 2 and 4). Swapping the C-terminal region of $gp41_{ECTO}$ in either SOS or SOSIP JR-FL gp140 had no visible effect on oligomerization (FIG. 3B, compare lane 1 to lane 5 and lane 2 to lane 6). In contrast, oligomer formation by JR-FL SOS or SOSIP gp140 was increased by the substitution of the five varying amino acids in $gp41_{ECTO}$ with the corresponding residues from KNH1144 (M535I, L543Q, N553S, Q567K and G588R) (FIG. 3B, compare lane 7 to lane 1 and lane 8 to lane 2). These results confirm that the trimer-promoting determinants of KNH1144 are located in the N-terminal region of gp41. Moreover, the greater stability of KNH1144 gp140 trimers can be conferred upon a heterologous gp140, JR-FL, by altering the specific residues that differ between the two proteins.

Further studies showed that all five changes were necessary for creating an optimally stable and homogenous JR-FL gp140 trimer; various combinations of the five changes had negligible or partial effects. To ascertain whether the chimeric/mutant proteins were fully cleaved, the JR-FLgp120-KNH1144gp41 (ECTO) SOS gp140 chimera and the JR-FL gp41 NT 1-5 SOS gp140 mutant were analyzed using SDS- PAGE (FIG. 3C). Under denaturing conditions, both gp140 proteins were resolved as monomers (lanes 1 and 3). When DTT was added to reduce the SOS disulphide bond, release of the gp120 subunit was complete (lanes 2 and 4), along with gp$41_{ECTO}$ (which is not detectable by the b13 MAb used for blotting). Hence aberrantly linked, uncleaved products do not contribute to the enhanced oligomerization of JR-FL gp140 conferred by substitution of the residues from the KNH1144 gp41 N-terminal region. The stabilized, mutant proteins are fully cleaved.

Figure 4:
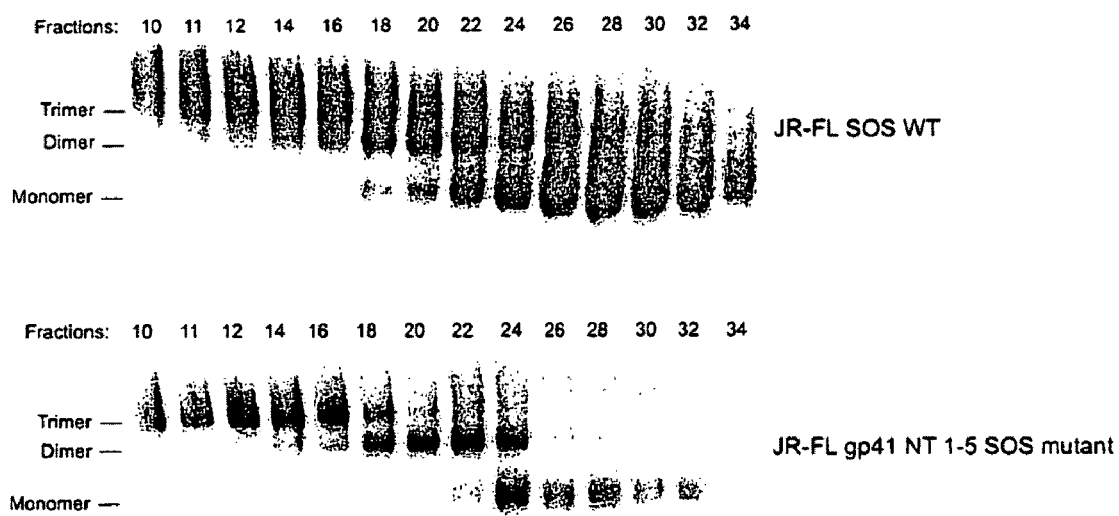

To further assess the formation and stability of JR-FL gp41 NT 1-5 SOS gp140 trimers, this protein and JR-FL SOS gp140 were purified using lectin-affinity and size exclusion chromatography (SEC) techniques. The SEC-fractionated aliquots were then resolved by BN-PAGE (FIG. 4). The JR-FL SOS gp140 protein was predominantly a monomer (FIG. 4A), while a much greater proportion of the Env species present in JR-FL gp41 NT 1-5 SOS migrated as well-resolved trimers (FIG. 4B; compare lanes 11-16 with the corresponding lanes in FIG. 4A). A densitometric analysis of the resolved gp140 trimer, dimer and monomer fractions on BN-PAGE was combined with BCA quantification of the pooled SEC fractions (trimer, dimer and monomer), to estimate the change in each gp140 species. Compared to the wild-type JR-FL SOS gp140 protein, trimer formation by JR-FL gp41 NT 1-5 SOS gp140 was increased by ~20% and dimmer formation by ~10%, whereas the monomer content was reduced by ~50%.

Antigenic Properties of the Wild-Type JR-FL SOS and Stabilized JR-FL gp41 NT 1-5 SOS Mutant gp140s:

To determine whether the antigenicity of the mutant JR-FL gp140 had been altered by the introduction of the trimer-stabilizing substitutions, SPR methods were used to study the binding of various antibodies to the mutant JR-FL gp140, in comparison to the wild-type gp140. In these studies, biotinylated Protein G was immobilized onto a Streptavidin (SA)-coated chip, which was then used to capture various agents via their Fc regions (FIG. 5A). The CD4-IgG2 protein (used as a surrogate for CD4) and the following MAbs were all studied: b12 (neutralizing, anti-CD4BS), 2G12 (neutralizing, high-mannose epitope on the 'silent face'), 2F5, 4E10 (both neutralizing, anti-gp41), PA-1 (nonneutralizing, anti-V3), b6 (non-neutralizing, anti-CD4BS) and 17b (non-neutralizing, CD4-induced epitope). Equal molar amounts of purified wild-type and mutant gp140 trimers (>90% purity) were then injected at 10 µl/min, to react with the immobilized MAbs. Both the wild-type SOS gp140 and the mutant gp41 NT 1-5 SOS gp140 bound CD4-IgG2 similarly (FIG. 5A and Table 1). The reactivities of wild-type SOS gp140 and the mutant gp41 NT 1-5 SOS gp140 with b12 and 2G12 were also similar, with similar response unit (RU) values at the end-of-injection time (t=180 s). The two neutralizing anti-gp41 MAbs, 2F5 and 4E10, also bound similarly to the two gp140 proteins (FIG. 5A and Table 1). In the absence of sCD4 (D1D2-CD4), neither gp140 protein bound efficiently to MAb 17b, but when D1D2-CD4 was added, the 17b epitope was induced on both proteins. The extent of the induction was greater for the stabilized trimer than for the wild-type protein (25-fold compared to 5-fold respectively; FIG. 5A and Table 1). The non-neutralizing MAbs PA-1 and b6 bound less efficiently to the stabilized trimer than to its wild-type counterpart (FIG. 5A and Table 1). To ensure that the MAb binding properties of two trimer variants (wild-type and stabilized) were compared, the injected gp140 samples used in the ligand-binding assays were manually collected from the BIAcore X system and analyzed using BNPAGE. Both gp140 proteins were substantially trimeric, even after passage through the BIAcore system (FIG. 5B).

TABLE 1

SPR binding of various monoclonal antibodies or CD4-IgG2 to WT and mutant forms of trimeric JR-FL gp140 proteins

| Test Agent | WT SOS gp140 Mean RU ± SD (t = 180 s$^a$) | Gp41 NT 1-5 SOS gp140 mutant Mean RU ± SD (t = 180 s$^a$) |
|---|---|---|
| CD4-IgG2 | 212 ± 8$^b$ | 224 ± 13$^b$ |
| b12 | 223 ± 6 | 195 ± 10 |
| 2G12 | 269 ± 7 | 278 ± 15 |
| 2F5 | 191 ± 8 | 216 ± 6 |
| 4E10 | 83 ± 4 | 94 ± 5 |
| PA-1 | 242 ± 11 | 123 ± 10 |
| b6 | 391 ± 14 | 233 ± 11 |
| 17b | 39 ± 5 | 14 ± 2 |
| 17b (+D1D2 CD4) | 237 ± 8 | 399 ± 18 |

$^a$End-of-injection time (t) in seconds (s).
$^b$Mean RU ± SD based on three experiments, all using 5 nM of analyte.

Substitution of Four Amino Acids in N-Terminal Region of gp41 ECTO also Increases the Stability of SOS gp140 from HIV-1 Ba-L:

To test whether the trimer-stabilizing effect of the above five gp41 amino acids was a generalized phenomenon, another subtype B Env protein, Ba-L was studied. Like JR-FL, Ba-L contains Met, Leu, Asn and Gln residues at positions 535, 543, 553 and 567, respectively. However, at position 588, Ba-L contains Arg, as does KNH1144 (FIG. 1). The four non-cognate amino acids from KNH1144 were introduced into the N-terminal region of Ba-L (M535I, L543Q, N553S, Q567K) to construct a mutant Ba-L gp41 NT 1-4 SOS gp140 protein. When expressed in HEK293T cells, the wild-type Ba-L SOS gp140, like JR-FL, was a mixture of monomers, dimers and trimers (FIG. 6A, lane 1). However, the mutant containing the above four amino acid substitutions was predominantly trimeric (FIG. 6A, lane 2), with >40% reduction in monomer formation. No individual substitution had as pronounced an effect as the quadruple combination. The enhanced trimerization of the mutant Ba-L gp41 NT 1-4 SOS gp140 was not attributable to the presence of aberrantly cross-linked proteins, as shown by SDS-PAGE under reducing and non-reducing conditions (FIG. 6B). Thus, under denaturing conditions, in the absence of the reducing agent, the mutant protein resolved as monomeric gp140; in the presence of DTT, reduction of the disulphide bond dissociated the gp140 into its constituent subunits (as in FIG. 3C, only the gp120 component is detected in this analysis). Taken together, these results suggest that modifications of a few selected amino acids in the N-terminal region of gp41 can improve the stability of gp140 trimers and that the finding might be generalizable to diverse HIV-1 genotypes.

Discussion

Described herein are residues in the N-terminal region of the gp41 ectodomain that influence the stability of trimeric forms of the HIV-1 gp140 glycoprotein, particularly the trimers that most, but of course incompletely, resemble the native form of the Env complex. The residues were found by inspection of the sequence of gp$41_{ECTO}$ from a subtype A SOSIP gp140 (KNH1144) that formed stable, cleaved trimers with unusual efficiency. Comparison of this sequence with that of JR-FL, a strain from which homogenous trimers are less easily made, identified five variable residues in a plausibly relevant region of gp$41_{ECTO}$ that lay in and around HR1. Substitution of those five residues in KNH1144 gp140 by the corresponding ones from JR-FL destabilized the resulting gp140 trimers. Conversely, and of more relevance, formation of JR-FL gp140 trimers could be considerably improved when the variable residues from KNH1144 were introduced in place of the JR-FL residues. The same approach also improved trimer formation in the context of the Ba-L sequence, suggesting that the observation is generally relevant for making stable, cleaved gp140 trimers. Substituting naturally variable amino acids may be a less invasive way to promote trimer stabilization than previously described alternatives, such as the use of heterologous trimerization domains (Yang et al., 2000; Yang et al., 2002), or the insertion of the SIV gp41 N-terminal region to make a HIV-SIV chimeric envelope glycoprotein (Center et al., 2004). The effect of substituting the KNH1144 gp41 residues into JR-FL and Ba-L is to reduce the heterogeneity of the oligomeric forms of SOS gp140 proteins when they are expressed as unpurified culture supernatants. Thus, there was a marked decrease in the amount of monomers present, lesser but sill notable decreases in dimers, tetramers and high-molecular weight aggregates and, of most relevance, an increase in the proportion of trimers.

When the stabilized JR-FL SOS gp140 protein was purified by lectin-affinity and size-exclusion chromatography, the amounts of monomers, tetramers and aggregates were reduced, whereas trimers were markedly more abundant and a small increase in the amount of dimers was also apparent. The dimers are likely to be dissociation products of trimers that arise during the purification process. This would not be too surprising, since the increase in trimer-stability is presumably only relative, not absolute, compared to the wild-type protein. Some of the amino acids in the KNH1144 N-terminal region have longer side chains than their JR-FL counterparts (KNH1144 vs. JR-FL: Q543L, K567Q and R588G).

It is also noteworthy that the S553, K567 and R588 residues in KNH1144 have greater α-helix-stabilizing propensities than the corresponding residues, N553, Q567 and G588, in JR-FL. Hence, alterations in the size or the nature of the side chains strengthen localized helix-to-helix packing interactions in a way that stabilizes gp140 oligomers. Both the wild-type JR-FL SOS gp140 and the stabilized JR-FL gp41 NT 1-5 SOS gp140 mutant bound similarly to neutralizing antibodies and proteins (b12, 2G12, 2F5, 4E10 and CD4-IgG2). As shown herein, the overall antigenic structure of the stabilized gp140 trimers was not adversely influenced by the sequence changes introduced into gp41. The stabilized JR-FL trimers bound non-neutralizing antibodies (PA-1, b6 and 17b) to a lesser extent than the corresponding wild type trimers. Stabilizing the conformation of gp140 trimers is advantageous for use of these proteins as vaccine immunogens.

Experimental Details II

To overcome the structural instability of the native Env complex, or soluble forms thereof, various amino acid sequence changes have been designed and introduced into the Env polypeptide to stabilize inter-subunit interactions between gp120 and gp41, or between the gp41 components of a trimer (Binley et al., 2000; Sanders et al., 2002). A disulfide bond was introduced between gp120 and gp41, together with an additional change in gp41 that promotes trimer stability after gp120 and gp41 are cleaved into separate subunits during Env processing (Binley et al., 2000; Sanders et al., 2002). The resulting gp140 proteins are designated SOSIP. Additional changes at the cleavage site between gp120 and gp41 promote proteolytic processing (Binley et al., 2002). As described herein, five amino acid changes in the highly conserved Leucine zipper (LZ)-like motif near the N-terminus of gp41 (i.e., I535, Q543, S553, K567 and R588) have been shown to contribute to trimer stability by reducing the prevalence of monomeric, dimeric, or aggregated forms of gp140. The resulting reduction in the qualitative heterogeneity of Env may be useful for the production of vaccines designed to mimic native trimers. Accordingly, the invention provides less heterogeneous envelope trimers for the production of virus like particles (VPLs) and pseudoparticles for use as VLP-based immunogens and vaccines. In accordance with the invention, gp120/gp41 trimers comprising the stabilizing N-terminal gp41 mutations of the invention, as well as gp120/gp41 trimers comprising other stabilizing mutations in gp120 and gp41 and the N-terminal gp41 mutations as described herein, can be used to generate VPLs and pseudovirions having reduced monomer, dimer and tetramer forms and enhanced trimer forms of gp120/gp41 Env. The N-terminal stabilizing mutations in the context of HIV-1 virus as described herein can serve to restrict VLP and pseudovirion immunogens to the expression of Env trimers and to yield trimer forms of Env (gp120/gp41) on VLP and pseudovirions to the virtual exclusion of monomer, dimer, tetramer, or aggregate forms, thus providing an immunogen and/or vaccine that more closely resembles native HIV envelope trimers.

The beneficial effect of the described amino acid changes in gp41 could potentially be countered if they were found to substantially compromise Env structure by creating a non-native configuration. Even though the sequence changes are in gp41, there is ample precedent that amino acid variation in this subunit may affect the conformation of gp120 and the overall topology and function of the entire Env complex. For example, mutations in or near the LZ region of gp41 are known to affect the binding and action of anti-gp120 antibodies, creating neutralization-resistant viruses. (Back et al., 1993; Klasse et al., 1993; Park et al., 2000; Park and Quinnan, 1999; Park et al., 1998; Thali et al., 1994). Other changes in gp41 affect the sensitivity of HIV-1 to small molecules that bind near the CD4 binding site on gp120 (Guo et al., 2003; Lin et al., 2003). Thus, this set of experimental details examines whether the five amino acid changes in gp41 according to the invention, which promote the stability of gp140 trimers, affect Env expression, antigenic structure, neutralization sensitivity and fusion function when made in the context of fusion-competent proteins from HIV-1 JR-FL. As described further herein, it was found that the altered Env proteins retained their function, albeit with a modest reduction in the rate of fusion. It was also found that the five amino acid changes reduced the proportion of aberrant, non-trimeric Env forms present on the surfaces of virions. These non-functional Env proteins serve as targets for the binding of non-neutralizing antibodies, thereby complicating any analysis of the relationships between the antibody binding and virus neutralization. (Broder et al., 1994; Cavacini and Posner, 2004; Fouts et al., 1997 and 1998; Herrara et al., 2003; Moore et al., 1995 and 2006; Poignard et al., 2003; Sattentau and Moore, 1995; York et al., 2001). Accordingly, the binding of various non-neutralizing antibodies to virions and Env-expressing cells was reduced for the gp41 mutant compared with wild-type JR-FL, without adversely affecting the binding of neutralizing antibodies. The use of the form of Env gp41 containing the five mutations, as well as SOS and SOSIP mutations, may also simplify the analyses of antibody binding and neutralization.

Materials and Methods

Plasmids and DNA Mutagenesis:

The pCI plasmid was used to express full-length WT JR-FL (gp160) Env (JR-FL WT) (Herrera et al., 2005). The JR-FL gp41 NT 1-5 mutant was created by site-directed DNA mutagenesis; five amino acid substitutions (M535I, L543Q, N553S, Q567K and G588R) near the N-terminus (NT) of gp41 were made using the QuikChange® II XL site-directed mutagenesis kit (Stratagene Inc., CA) and the appropriate primers according to the manufacturer's instructions. The introduced mutations were verified by sequencing. The pcDNA3.1-Furin plasmid was used for expressing Furin (Binley et al., 2000).

Antibodies and Cell Lines:

Soluble CD4, CD4-IgG2 (PRO-542) (Allaway et al., 1995) and the anti-V3 (JR-FL) MAb PA1 (Trkola et al., 1996a) were provided by Dr. William Olson (Progenics Pharmaceuticals, Inc., NY). MAb CA13 (ARP3119) directed to a linear epitope in the gp120 C1 region, was provided by the EU Programme EVA Centralized Facility for AIDS Reagents, NIBSC, UK (AVIP Contract Number LSHP-CT-2004-503487). MAbs 2G12 (Buchacher et al., 1994; Scanlan et al., 2002; Trkola et al., 1996b), 2F5 (Buchacher et al., 1992; Muster et al., 1993) and 4E10 (Buchacher et al., 1992; Stiegler et al., 2001; Zwick et al., 2001) were obtained from Hermann Katinger, MAb 17b (Thali et al., 1993) was obtained from James Robinson and MAb b12 (Burton et al., 1991) was obtained from Dennis Burton. MAbs A32 (Moore et al., 1994; Wyatt et al., 1995) and 15e (Robinson et al., 1990) were obtained from the Neutralizing Antibody Consortium (NAC) repository. F425-B4e8 (Cavacini et al., 2003) was obtained through the NIH AIDS Research and Reference Reagent Program, Division of AIDS, NIAID, NIH, from Dr. Marshall Posner and Dr. Lisa Cavacini. The anti-v3 MAb 447-52D was also obtained from the NIH AIDS Research and Reference Reagent Program, Division of AIDS, NIAID, NIH, contributed by S. Zolla-Pazner (Gorny et al., 1992 and 1993). T-20 (Enfuvirtide), (Wild et al., 1994), was a gift from Roche Laboratories, Inc., NJ.

All cell lines were maintained at 37° C. in an atmosphere containing 5% $CO_2$. Human Embryonic Kidney (HEK) 293T cells were grown in Dulbecco's minimal essential medium (DMEM, GIBCO), supplemented to contain 10% fetal calf serum (FCS), 2 mM L-glutamine, antibiotics (100 U/ml penicillin, 100 µg/ml streptomycin) and 0.5 mg/ml of the neomycin analog G-418. U87.CD4.CCR5 and U87.CD4.CXCR4 cells (provided by Dan Littman and available through the NIH AIDS Research and Reference Reagent Program, Division of AIDS, NIAID, NIH, Cat. No. 4035 and 4036, respectively) were cultured under conditions similar to those of the HEK 293T cells, but under selection by 0.3 mg/ml of G-418 and 0.5 mg/ml of puromycin.

Transfection Conditions for Pseudovirus Production and Purification:

To produce luciferase-expressing, Env-pseudotyped viruses, $1 \times 10^8$ HEK 293T cells cultured in growth medium lacking antibotics were co-transfected with plasmid DNA expressing gp160 Envs (WT or gp41 NT 1-5 mutant) and the pNL4-3Env(−)Luc(+) reporter plasmid (Connor et al., 1995 and 1996) using Polyethylenimine (PEI), (Polysciences, Inc., Warrington, Pa.), (Boussif et al., 1995; Kirschner et al., 2006). After sixteen hours, the cells were washed and the medium was replaced with DMEM containing 10% FCS, antibiotics and L-glutamine. Forty-eight hours post-transfection, the virion-containing supernatants were clarified by low speed centrifugation and were filtered through a 0.45-µm membrane. The clarified, filtered supernatants were layered over a 20% sucrose cushion in phosphate buffered saline (PBS) and were centrifuged for 2 hours at 100,000×g. The viral pellet (also referred to as pseudovirions or pseudoviruses herein) was then resuspended in either PBS for biochemical analysis or DMEM for virus infectivity assays and neutralization assays.

For studying cell-surface expression of JR-FL Env, $5 \times 10^6$ HEK 293T cells were transiently transfected with plasmid DNA essentially as described above. pcDNA3.1-Furin was used for Furin co-transfection at a Furin:Env plasmid DNA ratio of 2:1 (Binley et al., 2000). After 24 hours, the cells were washed, and fresh culture medium was added. Forty-eight hours post-transfection, the cell-surface expressed Envs were biotin labeled for polyacrylamide gel electrophoresis (PAGE), or were stained with anti-Env antibodies for FACS analysis as described below.

Biotinylation of Cell Surface-Expressed Env:

Forty-eight hours post-transfection, the cell surface-expressed envelope glycoproteins were biotinylated as described previously (Daniels and Amara, 1998) with minor modifications. Briefly, the Env-expressing cells were washed extensively with ice-cold PBS containing 1.2 mM $CaCl_2$, 1 mM $MgCl_2$ and were incubated with 0.5 mg/ml of EZ-link sulfo-NHS-SS-Biotin (Pierce Biotechnology, Rockford, Ill.) for 1 hour at 4° C. The biotin reaction was quenched using 50 mM ammonium chloride. The cells were then washed extensively and lysed in a buffer containing 25 mM Tris-HCl (pH 8.0), 150 mM NaCl, 1% Triton X-100, 1 mM phenylmethylsulfonyl fluoride (PMSF) and 1×Protease Inhibitors cocktail (Roche Diagnostic GmbH, Mannheim, Del.). The homogenates were centrifuged at 14,000×g for 15 minutes at 4° C. A 50 µl aliquot of the supernatants was removed to measure total protein levels and to analyze the Env content; the remaining supernatant was incubated with 50 µl of NeutrAvidin agarose resin (Pierce Biotechnology, Rockford, Ill.) for 2 hours at 4° C. to precipitate biotin-labeled proteins. The pellets were then washed three times in TSA buffer, one time in 20 mM Tris-HCl (pH 8.0), 500 mM NaCl, and finally in 50 mM Tris-HCl (pH 8.0). Bound proteins were resuspended in 50 µl of 2×SDS-PAGE sample buffer, boiled and resolved on a reduced SDS-PAGE gradient (4-12%) Tris-glycine gel (Invitrogen, Carlsbad, Calif.). After transfer to a PVDF membrane, the samples were immunoblotted with anti-gp120 antibody ARP3119, with anti-CD47 antibody (Santa Cruz Biotechnology) at 0.31 µg/ml, or with anti-GAPDH antibody (Meridian Life Science, Inc.) at 0.1 µg/ml. GAPDH was used as a control for equal loading of proteins in the total cell lysate; cell-surface CD47 expression served a similar purpose for studying cell-surface-expressed Env.

Fluorescence-Activated Cell Sorting (FACS) Assay for MAb Binding to Cell Surface Env:

CD4-IgG2 and MAbs were biotinylated using the EZ-link Sulfo-NHS-LC-Biotinylation kit (Pierce) according to the manufacturer's instructions. Env-expressing, transiently-transfected HEK 293T cells ($0.5 \times 10^6$ cells per analysis) were harvested, washed extensively with. PBS and incubated with 10 µg/ml of biotinylated CD4-IgG2 or MAbs in FACS buffer (PBS containing 5% FCS) for 1 hour at 4° C. The cells were washed repeatedly in FACS buffer and then were incubated with 100 µl of Streptavidin-phycoerthrin (PE), (BD Biosciences), at a 1:250 dilution for 30 minutes at 4° C. The stained cells were then washed, fixed using 2% paraformaldehyde and analyzed. Each binding assay was performed in triplicate. Mean Fluorescence Intensity (MFI) values were derived using the appropriate isotype-matched control MAb. The resulting background signal was subtracted from the experimental results and presented as Mean±Standard Deviation.

BN-PAGE, SDS-PAGE and Western Blotting:

Env that was expressed on the surface of pseudovirions was analyzed under non-denaturing conditions by the use of BN-PAGE (Schulke et al., 2002), with modifications as described elsewhere (Moore et al., 2006; Schagger et al., 1994). To release Env glycoproteins from the pseudovirion surface, an equal volume of solubilization buffer (0.12% Triton X®-100 in 1 mM EDTA/1.5 M aminocaproic acid) and 5 µl of a protease inhibitor cocktail (Sigma-Aldrich) were added, followed by the addition of an equal volume of double-strength sample buffer (100 mM morpholinepropanesulfonic acid (MOPS), 100 mM Tris-HCl, pH 7.7, 40% glycerol, 0.1% Commassie Blue). The extracts were then loaded onto a 4-12% Bis-Tris NUPAGE gel (Invitrogen) and electrophoresed at 4° C. for 3 hours at 100 V. The cathode buffer was 50 mM MOPS/50 mM Tris, pH 7.7, containing 0.002% Coommassie Blue, and the same buffer without Coommassie Blue served as the anode buffer. The gel was then blotted onto a polyvinylidene difluoride (PVDF) membrane, which was then washed with 30% methanol/10% acetic acid, followed by 100% methanol, to remove excess Coommassie Blue dye. Thyroglobulin (669 kDa), Ferritin (440 kDa), Catalase (232 kDa), Lactate dehydrogenase (140 kDa) and BSA (66 kDa) were used as molecular weight markers (Amersham Biosciences, PA). Densitometric analyses were performed using ImageJ software (NIH).

SDS-PAGE analysis of denatured Env glycoproteins was performed as described previously (Schulke et al., 2002). The pseudovirions were lysed by boiling in Laemmli sample buffer (62.5 mM Tris-HCl, pH 6.8, 25% glycerol, 2% SDS, 0.1% bromophenol blue, 10% 2-mercaptoethanol) in the presence of 50 mM DTT, and then were fractionated using either a 4-12% or an 8-16% gel. Overnight blotting onto a PVDF membrane was performed as described previously (Schulke et al., 2002). The membrane was then destained, treated with blocking buffer (4% nonfat milk in PBS) for 30 minutes and probed using 0.5 pg/ml of the anti-gp120 MAb CA13 or 20 µg/ml each of the 4E10 and 2F5 antibodies (anti-gp41 MAb cocktail). The mouse MAb 39/6.14 (Abcam Inc., MA) was used to detect p24. Goat anti-human and/or mouse Fc and Fab'2 alkaline phosphatase conjugates (Jackson Labs) were used at a dilution of 1:3,000, as appropriate, to detect the primary MAbs, followed by the Western blot Chemiluminescence Reagent Plus System (Perkin-Elmer Life Sciences, MA). The MultiMark® multi-colored standard kit (Invitrogen, Calif.) was used as a molecular weight marker.

Assay for gp120 Dissociation from Pseudovirions:

Pseudovirions, in 200 µl of PBS containing 0.5% BSA, were incubated with or without sCD4 for 2 hours at 4° C. or 37° C. (or without sCD4, but at various temperatures), and then were layered over a 1 ml cushion of 20% sucrose and ultracentrifuged at 100,000 g for 1.2 hours. The purified virions were then resuspended in 200 µl of dilution buffer (TMSS: 2% milk powder, 20% sheep serum in Tris-Buffered Saline (TBS)) for analysis of their gp120 content by capture ELISA.

gp120 Capture ELISA:

The gp120 capture ELISA was carried out as previously described (Moore et al., 1992). Briefly, gp120 was captured onto microtiter plate wells by the absorbed sheep antibody D7324 to the C-terminus (Cliniqa Corp.) and detected using either polyclonal HIVIg or CD4-IgG2 (0.1 µg/ml).

Virus Capture Assay:

The virus capture assay was performed as previously described (Poignard et al., 2003). Briefly, ELISA plates were coated with goat anti-mouse IgG (Fc-specific) antibody (Sigma-Aldrich, Mo.), blocked with 3% BSA in PBS, and then incubated with anti-gp120 MAbs at 10 µg/ml in 100 µl of PBS. After washing thoroughly to remove unbound MAbs, 100 µl of medium containing pseudoviruses (0.5-1.5 ng of p24 antigen) was added for 4 hours at room temperature. After washing thoroughly, the captured pseudoviruses were lysed in 200 µl of lysis buffer and their p24 content was determined using an HIV-1 p24 ELISA kit (ZeptoMetrix Corp., NY). Wells that lacked anti-gp120 antibody served as negative controls for background binding of the added pseudoviruses.

Infectivity and Neutralization Assays:

Pseudotyped virions bearing JR-FL envelope glycoproteins (WT and mutant) were produced by cotransfection of selected env clones with a luciferase-expressing reporter vector, pNL4-3Env(−)Luc(+), as described above. To measure infectivity, luciferase-expressing Env-pseudotyped viruses (50 µl) containing normalized amounts of p24 antigen were added to $3 \times 10^3$ U87.CD4.CCR5 cells/well. U87.CD4.CXCR4 cells were used as a negative control. After 4 days, th cells were lysed with 75 µl of 1× Glo lysis buffer (Promega, Calif.) for subsequent quantification of luciferase, which was expressed by the Env-pseudotyped virions that contain the gene for firefly luciferase inserted into the nef gene of HIV-1, using the Bright-Glo™ Luciferase Assay Substrate (Promega, Calif.) and a VICTOR3 1420 multilabel counter (Perkin Elmer Life Sciences, Mass.).

Neutralization of infectivity was performed as described previously (Trkola et al., 1998). The pseudovirions were incubated with an equal volume of various MAbs, CD4-IgG2, or T-20 for 1 hour at 37° C. before the residual infectivity was determined using U87.CD4.CCR5 cells as described above. The concentration of each inhibitor was expressed as the amount present after the inhibitor-virus mixture was added to the cells. The data were analyzed by non-linear regression (variable-slope sigmoidal dose response) to calculate the inhibitor concentrations that caused 50% reductions in luciferase expression (IC50), using the GraphPad Prism 4 software (maximal viral production in the absence of inhibitor was designated as 100%).

Cell-Cell Fusion Assay:

The β-lactamase cell-cell fusion assay was performed in HeLa-CD4/CCR5 cells (RC49) as described previously. (Lineberger et al., 2002; Rucker et al., 1997).

Results

As described in Experimental Details I above, the five amino acids I535, Q543, S553, K567 and R588 located near the N-terminus of HIV-1 gp41 are associated with the formation and/or stability of soluble, trimeric gp140 proteins based on the subtype A strain KNH1144 of HIV-1. Moreover, introducing these residues into HIV-1 subtype B gp140 proteins with different amino acids at the same positions had a beneficial impact on trimer stability. Of the five residues, Q543, S553 and K567 had the greatest effect when introduced in combination, with I535 and R588 perhaps making an additional minor contribution.

An analysis of gp41 sequences in the Los Alamos HIV-1 Sequence Database shows that I535, Q543, S553 and K567, but not R588, were individually and collectively far more prevalent in subtype A viruses than in ones from subtype B. See Table 2. Their frequency in subtype C viruses was similar to subtype A, with the notable exception of K567, which was completely absent. Subtype D frequencies were similar, but not identical, to subtype B. Too few sequences from the individual subtypes F, G, H, J and K are available to warrant a similar analysis, but treating these "minor" subtypes en masse showed that their gp41 residue frequencies were more similar to subtype A than to subtype B. Overall, with respect to these five positions in gp41, subtype B viruses stand out as being different from the other subtypes. (See Table 2 for statistical significance).

TABLE 2

| Subtypes & CRFs | No. of Isolates (n) | I535 | Q543 | S553 | K567 | R588 | All 5 Amino Acids |
|---|---|---|---|---|---|---|---|
| A | 78 | 72 | 94 | 90 | 81 | 33 | 22% |
| B | 200 | 26 | 59 | 10 | 0.5 | 35 | 0% |
| C | 201 | 87 | 95 | 90 | 0 | 12 | 0% |
| D | 54 | 4 | 89 | 4 | 0 | 22 | 0% |
| F-H, J, K | 35 | 91 | 97 | 69 | 86 | 6 | 3% |

P values (subtype B vs. rest): <<0.001 <<0.001 <<0.001 <<0.001 <<0.001 <0.001

Table 2 lists the prevalence (expressed as a percentage) of the five trimer-promoting acids (I535, Q543, S553, K567 and R588), singly or in combination, in gp41 sequences from viruses fo subtypes A, B, C, D and from subtypes F+G+H+J+K treated collectively (too few sequences from subtypes F, G, H, J and K were available to warrant a separate analysis). Note that Env sequences from what was formerly called subtype E are included within subtype A as the "subtype E" env gene is actually from subtype A. The comparatively high collective prevalence of the five amino acids in subtype A sequences is highlighted in gray. The statistical significance (P value) of the prevalence of the five amino acids in subtype B viruses, singly or in combination, relative to the rest of the subtypes is calculated using Fisher's Exact Test.

Effect of gp41 Substitutions of the Quantity and Quality of Env Incorporated into Pseudovirus:

In view of the potential general utility of the gp41 mutation strategy in accordance with this invention for making stabilized gp140 trimers, the effects of the five amino acid substitutions on Env function when these mutations were introduced into full-length, virion-associated envelope glycoproteins were assessed. The subtype B isolate HIV-1 JR-FL was used for infectivity and related studies, since the effect of the five amino acid substitutions on gp140 trimer formation had been studied using this isolate, as described in Experimental Details I.

The full-length, wild type (WT) JR-FL gp160 env gene (JR-FL WT) was mutated at the same five positions to generate the JR-FL gp41 NT 1-5 mutant. Env-pseudotyped virions (pseudovirions) based on the WT and mutant sequences were generated by co-transfecting HEK 293T cell with each individual full-length Env-encoding plasmid and the pNL4-3.Luc.R-E-reporter plasmid (Connor et al., 1996). Pseudovirions from the two virus preparations were pelleted by ultracentrifugation onto a 20% sucrose cushion and were found to contain similar amounts of the p24 antigen (107 pg/ml for WT; 112 pg/ml for the NT 1-5 mutant).

The gp120 and gp41 content of the WT and the NT 1-5 mutant viruses were then determined by SDS-PAGE and Western blotting, followed by densitometric analysis using ImageJ software (FIG. 7). The normalized gp120:p24 ratios for the WT and mutant viruses were 1 and 0.28, respectively. The corresponding gp41:p24 ratios were 1 and 0.4, respectively. Thus, on average, the mutant pseudovirions contained ~3.5-fold less gp120 and 2.5-fold less gp41 than the WT viruses per unit of particulate p24 antigen. Although similar values were obtained in four replicate experiments, the imprecision of this type of analysis makes it hard to judge whether the modestly greater reduction in gp120 content, compared with gp41, for the mutant viruses is genuine. Additional analyses of gp120-shedding from the WT and mutant viruses suggest that the difference may not be real (see below). Overall, it can be concluded that the mutant viruses incorporate and retain ~30-40% of the total Env content of the WT viruses.

The Env content of the purified pseudovirions was studied in more detail by using BN-PAGE to assess the presence of dimeric, trimeric and tetrameric Env forms (FIG. 8A). Consistent with the gel analysis under denaturing conditions, the total Env content of the mutants was ~2.5-fold lower than thet of the WT viruses. However, a densitometric analysis showed that this reduction was entirely attributable to a decrease in the amounts of Env tetramers and dimers that were present on the mutant particles (no monomers were visible in either of the preparations); the trimer contents of the two sets of virions were identical (FIGS. 8A and 8B). Overall, tetramers comprised 58%; trimers comprised 34%, and dimers comprised 8% of the total Env content of the WT viruses, while the corresponding values, respectively, were 35%, 62% and 3% for the mutant viruses. Thus, it can be concluded that the majority of the Env proteins incorporated into JR-FL WT pseudovirions produced on 293T cells are non-trimeric and that the presence of these aberrant Env forms on the viral surface can be significantly reduced ($P<0.05$, Mann-Whitney U Test, one-tailed) by substituting the five amino acids in the N-terminal region of gp41.

Effect of gp41 Substitutions on Soluble CD4- and Temperature-Induced gp120 Shedding from Pseudovirions:

As noted above, there appeared to be a slight reduction in the gp120 content of the mutant pseudoviruses relative to gp41 that could be attributable to an increase in the shedding of gp120 from functional or non-functional spikes. This scenario is plausible, because changes in residues 528 to 562 have been associated with a destabilization of the gp120-gp41 interaction (Cao et al., 1993). To determine whether the WT and mutant pseudoviruses behaved differently in this respect, soluble CD4 (sCD4) and mild heat were used as inducers of gp120 shedding. To provide an external frame of reference, the HxB2 isolate was also studied under the same conditions, as this type of T-cell line-adapted virus is particularly prone to shedding its gp120 content. (Moore et al., 1992).

As a result of this analysis, it was found that neither the WT nor the mutant JR-FL pseudovirus shed gp120 significantly in response to sCD4 concentrations up to 10 μg/ml, at either 4° C. or 37° C. In contrast, HxB2 Env-bearing pseudoviruses lost over half of their gp120 content following treatment with 10 μg/ml of sCD4 at 37° C. (FIG. 9A). Moreover, the two versions of JR-FL pseudoviruses (WT and mutant) behaved similarly in their reactions to elevated temperatures; both lost significant amounts of gp120 only at 50° C. and 65° C., but even lesser amounts than did the HxB2 reference virus (FIG. 9B). Thus, the five amino acid substitutions in the N-terminal region of gp41 in JR-FL do not detectably destabilize the interactions between gp120-gp41.

Effect of gp41 Substitutions on Pseudovirion Infectivity:

Specific substitutions in the highly conserved N-terminal heptad repeat region can impair the function of gp41 and the infectivity of mutant viruses (Cao et al., 1993; Chen et al., 1993; Weng and Weiss, 1998). Therefore, the infectivity of the WT and mutant JR-FL Env-pseudotyped viruses (normalized for p24 content) was assessed in a single cycle assay using U87.CD4.CCR5 target cells and a luciferase reporter gene read-out four days post-infection. The two viruses were found to be equally infectious (FIG. 10). Thus, the five amino acid changes in the gp41 N-terminal region have no impact on JR-FL Env-pseudovirus infectivity. The modestly reduced total Env content of the mutant pseudoviruses is therefore not relevant to the infection process, presumably because the trimer content remains unchanged.

Effect of gp41 Substitutions on the Efficiency and Rate of Env-Mediated Fusion:

Despite the results from the above infectivity experiment, it still could have been possible that the five amino acid substitutions in the NT of gp41 could affect Env function, as assessed in a more direct fusion assay. Some amino acid changes 5 in the gp41 HR1 region can impair fusion efficiency and slow the kinetics of fusion. (Reeves et al., 2005). Therefore, a study of the kinetics of fusion mediated by the WT and mutant Env glycoproteins was undertaken using a cell-cell fusion assay. To this end, HeLa-CD4/CCR5 target cells were loaded with the fluorescent dye CCF2-AM and mixed with effector cells expressing Env glycoproteins and β-lactamase. Cell-cell fusion that leads to cytoplasm mixing allows cleavage of CCF2 by β-lactamase, which causes a change in fluorescence that can be accurately quantified. Using this assay, it was observed that membrane fusion mediated by the mutant Env glycoprotein occurred slightly, but detectably, more slowly than did fusion mediated by the WT Env glycoprotein (FIG. 11A and Table 3). From these results, it could be seen that the changes in gp41 NT do have a modest adverse effect on the fusion function of Env, but not to a degree that impairs pseudovirus infectivity.

TABLE 3

Kinetic parameters of cell-cell fusion mediated by the WT and NT mutant JR-FL Env-pseudotyped virions¥

| Envelope | $Y_{max}$ (% WT)* | $t^{1/2}$ (min)** | B*** |
| --- | --- | --- | --- |
| JR-FL WT | 97.8 ± 2.9 | 48 ± 1 | 12 ± 1 |
| JR-FL gp41 NT 1-5 | 67.6 ± 5.8 | 59 ± 3 | 14.1 ± 2.1 |

¥The kinetic parameters were derived using a β-lactamase reporter assay (See, FIGS. 11A-B). Data derived from three independent experiments were fitted to the equation $Y = Y_{max}/\{1 + \exp[-(t - t^{1/2})/b]\}$. The coefficients extracted from these curves ± standard errors of the mean are shown.
*Fusion expressed as percentage of the maximal fusion mediated by the WT JR-FL Env.
**Time to half-maximal fusion (in minutes).
***Exponential rate constant.

Binding of Neutralizing and Non-Neutralizing Antibodies to the WT and gp41 Mutant Env Glycoproteins on Pseudoviruses, and Correlations with Infection-Inhibition:

Measurements of antibody binding to Env glycoproteins on the surface of virions and Env-expressing cells are compromised by the presence of non-functional forms of Env intermingled with functional, native trimers (Moore et al., 2006; Poignard et al., 2003). This heterogeneity of Env binding sites for antibodies renders it impossible to be sure that a binding event involves a functional spike, and, since only functional spikes are relevant to infectivity neutralization, it has been difficult to draw meaningful conclusions between binding and neutralization events. (Cavacini et al., 1999; Fouts et al., 1997 and 1998; Moore et al., 2006; Nyambi et al., 1998 ; Poignard et al., 2003). The observation that the five amino acid substitutions in the N-terminus of gp41 reduce the abundance of non-native Env forms (e.g., dimers and tetramers) present on virions, without affecting trimeric forms, led to conducting experiments to determine how various antibodies reacted with the mutant Env proteins. Another reason to conduct such experiments was to determine whether the gp41 substitutions could affect the antigenic structure of gp120, in view of reports that other changes in gp41 can have such an effect. (Back et al., 1993; Klasse et al., 1993; Park and Quinnan, 1999; Park et al., 1998; Thali et al., 1994).

To measure Mab-Env interactions, a widely-used virion-binding assay was first employed. This type of assay typically generates results that are highly misleading for judging neutralization mechanisms. (Moore et al., 2006; Poignard et al., 2003). Upon completion of the assay, it was found that there was no difference between the WT and the mutant JR-FL Env-pseudotyped virions in the extent to which they bound the neutralizing MAbs b12, 2G12, 2F5 and 4E10, or the CD4-IgG2 protein (FIG. 12A). However, three non-neutralizing MAbs, i.e., b6 and 15e directed to the CD4BS on gp120, and MAb PA1 directed to the V3 region, captured significantly fewer mutant pseudovirions than WT, compared with the neutralizing anti-V3 MAb F425-B4e8 (P≦0.05 for each, Mann-Whitney U test, one-tailed), (FIGS. 12A and 12B). A modest but not significant decrease in capture of the mutant pseudovirions was also observed with another non-neutralizing, anti-V3 MAb, 447-52D (FIG. 12B). An additional non-neutralizing Mab, A32, directed to the C1-C4 region of gp120, bound minimally, but comparably, to both pseudovirion preparations (FIG. 12B). The non-neutralizing MAb, 17b, captured both pseudovirion preparations weakly in the absence of sCD4, but its binding was increased when sCD4 was also present, which is consistent with the known ability of CD4 to induce the exposure of the 17b epitope on gp120 (Thali et al., 1993). It is noted that the sCD4-induction of the 17b epitope was significantly greater (P=0.04 Mann-Whitney U test, one-tailed) for the mutant pseudovirions than for the WT pseudovirions (FIG. 12A).

For comparision with the Env-binding data and to further assess whether the changes to gp41 affected the native structure of the Env complex, experiments were conducted to measure the sensitivities of the WT and mutant JR-FL Env-pseudovirions to inhibition by MAbs (and to the CD4-IgG2 protein). U87.CD4.CCR5 cells served as targets for infection. The four broadly neutralizing. MAbs (b12, 2G12, 2F5 and 4E10) and CD4-IgG2 all inhibited infection of the two pseudoviruses with comparable potencies, as did the V3 MAb F425-B4e8 (Table 4). By contrast, five MAbs, b6, 15e, A32, PA1 and 17b, that lack neutralizing activity against HIV-1 JR-FL failed to inhibit infection by either pseudovirus. (Table 4). The V3 MAb 447-52D was unable to be tested for neutralization, as it was not available in sufficient quantities; however, this MAb has been reported to lack strong activity against JR-FL Env pseudotyped viruses in a similar assay (Binley et al., 2004).

It was observed that in the presence of sCD4, MAb 17b neutralized the mutant Env-pseudotyped virions ~2-fold more efficiently than the WT virus (IC50 values of 15 and 26 µg/ml, respectively), (Table 4). This finding is consistent with the modestly increased binding of 17b to the mutant pseudoviruses in the presence of sCD4 (FIG. 12A) and suggests that the gp41 substitutions do have a detectable impact on either the conformation of the gp120 component of the native Env complex, or on the way in which that complex changes its configuration after sCD4 binding. The effect of the gp41 NT 1-5 amino acid changes must be modest, however, as there was no difference in the neutralization of the two pseudovirus preparations by any of the other test MAbs. (Table 4).

Sensitivity to T-20 was also studied in the same assay system, because the five amino acid changes are located close to the gp41 HR1 region, which is associated with T-20 resistance (Carmona et al., 2005; Greenberg and Cammack, 2004). The IC50 for T-20 against the WT Env-pseudotyped virus was 2-fold greater than against the mutant, suggesting that one or more of the five amino acid substitutions does modestly affect the binding or antiviral activity of the T-20 peptide against the gp41 NT 1-5 mutant. (Table 4).

TABLE 4

Neutralization of pseudovirus activity by MAbs, CD4-IgG2 and T-20

| Reagent | JR-FL WT | JR-FL gp41 NT 1-5 |
|---|---|---|
| CD4-IgG2 | 0.82 | 0.74 |
| b12 | 0.15 | 0.17 |
| 2G12 | 1.6 | 1.7 |
| b6 | >50 | >50 |
| 15e | >50 | >50 |
| A32 | >50 | >50 |
| PA1 | >50 | >50 |
| F425-B4e8 | 2.94 | 2.64 |
| 447-52D | ND* | ND* |
| 17b | >50 | >50 |
| 17b + sCD4 | 25.9 | 15.2 |
| 2F5 | 6.2 | 5.9 |
| 4E10 | 13.4 | 14.1 |
| T-20 | 24.2 | 11.5 |

The numbers recorded in Table 4 are mean IC50 values in µg/ml for the reagents indicated (in nM for T-20). IC50 values that differ between the WT and mutant viruses are highlighted in bold.
*ND = not done. Not enough of this reagent was able to be procurred for use in neutralization assays. However, MAb 447-52D has been reported to lack potent neutralization activity (IC50 = 32.6 µg/ml) against JR-FL Env-pseudotyped viruses in an assay of comparable design. (Binley et al., 2004).

Binding of Neutralizing and Non-Neutralizing Antibodies to Cells Expressing the WT and gp41 Mutant Env Glycoproteins:

Various studies have shown that structural forms of Env and antibody-binding profiles are different on transfected cells than on infectious virions, probably because over-expression affects Env processing pathways. (Herrera et al., 2003 and 2005; Sattentau and Moore, 1995; Si et al., 2001; York et al., 2001). To address this in view of the WT and gp41 NT 1-5 Env mutant viruses, full-length WT and gp41 mutant Envs were expressed in HEK 293T cells and the binding of various neutralizing and non-neutralizing antibodies was investigated. As seen with the pseudovirions, WT Env was expressed at ~3-fold higher levels than the gp41 mutant Env, both within the transfected cells and on the cell surface (FIG. 13A).

Flow cytometry was used to analyze antibody binding to the surface of Env-expressing cells (FIG. 13B). Each Mab was tested at a concentration of 10 µg/ml. In contrast to what was observed with the pseudovirions, few, if any, differences were detected between the WT and gp41 mutant Envs. A slight decrease in PA1 binding to the mutant Env was marginally significant (P=0.05, Mann-Whitney U test, one-tailed). The differences between what was observed with the cell surface binding assay compared with the pseudovirion capture assay may reflect the greater diversity of Env forms that are present on cells. (Herrera et al., 2003 and 2005; Pancera and Wyatt, 2005).

Discussion:

When the HIV-1 envelope glycoproteins are expressed as recombinant proteins for use as vaccine antigens, for structural studies, or for analysis of neutralization mechanisms, their structural heterogeneity creates problems. Thus, preparations of soluble gp140 proteins can, and often do, contain monomers, dimers, trimers, tetramers and aggregates (Center et al., 2004; Earl et al., 1994; Schulke et al., 2002; Staropoli et al., 2000), and multiple forms of membrane-bound Env are present on pseudovirions and on Env-expressing cells. (Herrera et al., 2005; Moore et al., 2006; Poignard et al., 2003). The degree to which these problems arise from the over-expression of Env, or from the use of non-lymphoid cells, is hard to determine; the Env content of naturally-produced viruses may be less diverse than what arises in transfection-based systems. Nonetheless, transfection systems are widely used experimentally, and the practical production of Env vaccine candidates usually requires the use of non-lymphoid cells. The development of ways to reduce the extent of Env heterogeneity prior to purification of trimers is therefore useful, since it is generally assumed that trimers best mimic the native, virion-associated form of Env.

In accordance with the present invention, the identity of selected residues near the N-terminus of gp41 provides one of the genetic influences on the formation of aberrant forms of Env. The residues associated with increased trimer formation/stabilization are much rarer in HIV-1 subtype B viruses compared with those from other subtypes, particularly HIV-1 subtype A, for reasons that are not completely understood. However, when the relevant residues are inserted into subtype B viruses, they increase the formation and/or stability of trimers. Considering that most vaccine-related studies with soluble gp140 proteins have been carried out using subtype B sequences as templates, it seems possible that the commonly observed Env instability might not be as pronounced with proteins from other subtypes as it is with subtype B. (Jeffs et al., 2004).

The effect of the N-terminal gp41 residues has been studied with the prototypic subtype B primary isolate JR-FL, initially in the context of soluble gp140 proteins and now with full-length gp160 proteins that are the basis of infectious Env-pseudoviruses. These studies were performed to determine whether the gp41 NT substitutions adversely affect the overall structure of Env, which could be problematic for vaccine production and to learn whether the reduction in the formation of aberrant forms of Env could beneficially influence previously problematic analyses of the relationships between antibody binding to Env and the neutralization of virus infectivity.

The introduction of the five amino acid changes into full-length gp160 proteins reduced Env expression overall by ~2-4 fold in different assays, thus implying that they have a modest affect on Env production or degradation. However, all of that reduction was accounted for by the presence of lesser amounts of Env dimers and tetramers; the trimer content was unchanged. Without wishing to be limited by theory, the most likely explanation of this effect is that the trimers are more stable and do not dissociate as readily into dimers and monomers (the tetramers are probably dimers of dimers).

The gp41 amino acid changes in the N-terminal region had no effect on pseudovirion infectivity, and they did not cause any destabilization of the gp120-gp41 linkage. Thus, they seem to be benign from the perspective of the overall topology of the Env complex. Their lack of effect on the overall structure of functional, native Env complexes is further shown by the similar binding of various neutralizing MAbs to both the WT and mutant pseudovirions and their identical neutralization sensitivities. An exception was the slightly greater sensitivity of the mutant viruses to the CD4i MAb 17b in the presence of sCD4, which was associated with a comparable increase in 17b binding in a pseudovirion-capture assay in the presence of sCD4. Presumably, the gp41 NT substitutions do have a modest impact on the exposure of the CD4i epitope post CD4 binding. Broadly similar effects of selected gp41 sequence changes on gp120 topology have been described. (Back et al., 1993; Klasse et al., 1993; Reitz et al., 1988; Thali et al., 1994).

The gp41 changes did have a modest effect on fusion kinetics in a cell-cell fusion assay, but seemingly not enough to affect infectivity when the same Env proteins were present on pseudovirions. Mutational studies of the gp41 HR1 segment have shown that mutations in the "a" and "d" positions, particularly helix-disrupting mutations, impair fusion. (Cao et al., 1993; Chen et al., 1993; Chen, 1994; Dubay et al., 1992). The S553, K567 and R588 residues that were identified are not helix disrupting and occupy the "b" position on the coiled-coil helix, which may explain why their adverse effect is so modest. The NT substitutions also had a slight affect on T-20 sensitivity, decreasing the IC50 by 2-fold. Although the substitutions lie outside the $_{547}$GIV$_{549}$ 'hot spot' associated with T-20 reactivity (Rimsky et al., 1998), natural polymorphisms at position 553 (e.g., N553S) most commonly observed in non-subtype B isolates, have been associated with increased susceptibility to T-20. (Carmona et al., 2005; Whitcomb et al., 2003).

Studies of antibody binding to pseudovirions showed that several non-neutralizing MAbs (i.e., b6, 15e, F425-4e8 and PA1) directed to the CD4BS and V3 epitopes bound to the mutant Env significantly (2-3 fold) less than to the WT Env. The differential binding was not seen, however, with two other MAbs that also lack neutralizing capacity against JR-FL, namely, 447-52D and A32. The decreased binding of the non-neutralizing MAbs to pseudoviruses bearing the mutant Env could, be due to the lesser content of non-trimeric (i.e., non-functional) Env forms present. This explanation would be consistent with the findings of Poignard et al., 2003.

It was notable that when the pseudovirion binding (FIGS. 12A and 12B) and neutralization data (Table 4) were compared, there was no clear relationship between the ability of a MAb to capture pseudoviruses and impair their infectivity, as reported previously. (Moore et al., 2006; Poignard et al., 2003). Thus, some neutralizing MAbs captured pseudoviruses strongly, e.g., b12, 2G12, F425-B4e8, but others did not, e.g., 2F5, 4E10. Additionally, all three V3 MAbs, e.g., PA1, 447-52D and F425-B4e8, captured pseudoviruses efficiently, but only F425-B4e8 was neutralizing. Nonetheless, the introduction of the five NT substitutions in gp41 that reduce (but that do not eliminate) the presence of non-native forms of Env on pseudoviruses did improve the performance of the virion capture assay. For example, the difference between the closely related neutralizing and non-neutralizing CD4BS MAbs b12 and b6 was substantially increased in the virion capture assay when the gp41 NT 1-5 Env mutant pseudoviruses were used (FIG. 12A).

Binding assays involving Env expressed on the surface of transfected cells were less informative, probably because of the multiplicity of Env configurations present on the cells. This further reinforces the problems associated with these types of assays when they are used to assess the relationship between antibody binding and virus neutralization (Gorse et al., 1999; Herrera et al., 2003; Sattentau and Moore, 1995; Si et al., 2001; York et al., 2001).

Thus, from the results presented in Experimental Details II, it can be concluded that the five amino acid changes in gp41 have a generally beneficial effect on the overall configuration of the subtype B gp140 and gp160 Env proteins (as well as on those of subtype A Env proteins as described in Experimental Details I) by reducing the presence of non-native Env forms, i.e., non-trimer forms, without compromising the function of trimers. Accordingly, the present invention encompasses a facilitation of the production of Env trimers for HIV vaccine development and production and for HIV structural and immunogenicity studies.

References for Experimental Details I and II

Abacioglu, Y. H., Fouts, T. R., Laman, J. D., Claassen, E., Pincus, S. H., Moore, J. P., Roby, C. A., Kamin-Lewis, R., and Lewis, G. K. (1994). Epitope mapping and topology of baculovirus-expressed HIV-1 gp160 determined with a panel of murine monoclonal antibodies. *AIDS Res Hum Retroviruses* 10(4), 371-81.

Allaway, G. P., Davis-Bruno, K. L., Beaudry, G. A., Garcia, E. B., Wong, E. L., Ryder, A. M., Hasel, K. W., Gauduin, M. C., Koup, R. A., McDougal, J. S., and et al. (1995). Expression and characterization of CD4-IgG2, a novel heterotetramer that neutralizes primary HIV type 1 isolates. *AIDS Res HumRetroviruses* 11(5), 533-9.

Back, N. K., Smit, L., Schutten, M., Nara, P. L., Tersmette, M. and Goudsmit, J. (1993). Mutations in human immunodeficiency virus type 1 gp41 affect sensitivity to nuetralization by gp120 antibodies. J. Virol. 67(11), 6897-902.

Beddows, S., Kirschner, M., Campbell-Gardener, L., Franti, M., Dey, A. K., Iyer, S. P., Maddon, P. J., Paluch, M., Master, A., Overbaugh, J., Vancott, T., Olson, W. C., and Moore, J. P. (2006). Construction and Characterization of Soluble, Cleaved, and Stabilized Trimeric Env Proteins Based on HIV Type 1 Env Subtype A. *AIDS Res Hum Retroviruses* 22(6), 569-79.

Berger, E. A., Murphy, P. M., and Farber, J. M. (1999). Chemokine receptors as HIV-1 coreceptors: roles in viral entry, tropism, and disease. *Annu Rev Immunol* 17, 657-700.

Binley, J. M., Sanders, R. W., Clas, B., Schuelke, N., Master, A., Guo, Y., Kajumo, F., Anselma, D. J., Maddon, P. J., Olson, W. C., and Moore, J. P. (2000). A recombinant human immunodeficiency virus type 1 envelope glycoprotein complex stabilized by an intermolecular disulfide bond between the gp120 and gp41 subunits is an antigenic mimic of the trimeric virion-associated structure. *J Virol* 74(2), 627-43.

Binley, J. M., Sanders, R. W., Master, A., Cayanan, C. S., Wiley, C. L., Schiffner, L., Travis, B., Kuhmann, S., Burton, D. R., Hu, S. L., Olson, W. C., and Moore, J. P. (2002). Enhancing the proteolytic maturation of human immunodeficiency virus type 1 envelope glycoproteins. *J Virol* 76(6), 2606-16.

Binley, J. M., Wrin, T., Korger, B., Zwick, M. B., Wang, M., Chappey, C., Stiegler, G., Kunert, R., Zolla-Pazner, S., Katinger, H., Petropoulos, C. J. and Burton, D. R. (2004). Comprehensive cross-clade neutralization analysis of a panel of anti-human immunodeficiency virus type 1 monoclonal antibodies. *J Virol* 78(23), 13232-52.

Blacklow, S. C., Lu, M., and Kim, P. S. (1995). A trimeric subdomain of the simian immunodeficiency virus envelope glycoprotein. *Biochemistry* 34(46), 14955-62.

Boussif, O., Lezoualc'h, F., Zanta, M. A., Mergny, M. D., Scherman, D., Demeneix, B., and Behr, J. P. (1995). A versatile vector for gene and oligonucleotide transfer into cells in culture and in vivo: polyethylenimine. *Proc Natl Acad Sci USA* 92(16), 7297-301.

Broder, C. C., Earl, P. L., Long, D., Abedon, S. T., Moss, B. and Domms, R. W. (1994). Antigenic implications of human immunodeficiency virus type 1 envelope quaternary structure: oligomer-specific and -sensitive monoclonal antibodies. *Proc. Natl. Acad. Sci. USA.* 91(24), 11699-703.

Buchacher, A., Predl, R., Strutzenberger, K., Steinfellner, W., Trkola, A., Purtscher, M., Gruber, G., Tauer, C., Steindl, F., Jungbauer, A. and Katinger, H. (1994). Generation of human monoclonal antibodies against HIV-1 proteins; electrofusion and Epstein-Barr virus transformation for peripheral blood lymphocyte immortalization. *AIDS Res. Hum. Retroviruses.* 10, 359-369.

Buchacher, A., Predl, R., Tauer, C., Purtscher, M., Gruber, G., Heider, R., Steindl, F., Trkola, A., Jungbauer, A. and Katinger, H. (1992). Human monoclonal antibodies against gp41 and gp120 as potential agents for passive immunization. *Vaccines.* 92, 191-195.

Burton, D. R., Barbas, C. F., 3rd, Persson, M. A., Koenig, S., Chanock, R. M. and Lerner, R. A. (1991). A large array of human monoclonal antibodies to type 1 human immunodeficiency virus from combinatorial libraries of asymptomatic seropositive individuals. *Proc. Natl. Acad. Sci. USA.* 88(22), 10134-7.

Burton, D. R., Pyati, J., Koduri, R., Sharp, S. J., Thornton, G. B., Parren, P. W., Sawyer, L. S., Hendry, R. M., Dunlop, N., Nara, P. L., and et al. (1994). Efficient neutralization of primary isolates of HIV-1 by a recombinant human monoclonal antibody. *Science* 266(5187), 1024-7.

Calarese, D. A., Scanlan, C. N., Zwick, M. B., Deechongkit, S., Mimura, Y., Kunert, R., Zhu, P., Wormald, M. R., Stanfield, R. L., Roux, K. H., Kelly, J. W., Rudd, P. M., Dwek, R. A., Katinger, H., Burton, D. R., and Wilson, I. A. (2003). Antibody domain exchange is an immunological solution to carbohydrate cluster recognition. *Science* 300(5628), 2065-71.

Cao, J., Bergerson, L., Helseth, E., Thali, M., Repke, H and Sodroski, J. (1993). Effects of amino acid changes in the extracellular domain of the human immunodeficiency virus type 1 gp41 envelope glycoprotein. *J. Virol.* 67(5), 2747-55.

Cardoso, R. M., Zwick, M. B., Stanfield, R. L., Kunert, R., Binley, J. M., Katinger, H., Burton, D. R., and Wilson, I. A. (2005). Broadly neutralizing anti-HIV antibody 4E10 recognizes a helical conformation of a highly conserved fusion-associated motif in gp41. *Immunity* 22(2), 163-73.

Carmona, R. et al. (2005). Natural resistance-associated mutations to Enfuvirtide (T20) and polymorphisms in the gp41 region of different HIV-1 genetic forms from T-20 naive patients. *J. Clin. Virol.* 32(3), 248-53.

Cavacini, L. et al. (2003). Conformational changes in env oligomer induced by an antibody dependent on the V3 loop base. *AIDS.* 17(5), 685-9.

Cavacini, L. and Posner, M. (2004). Native HIV type 1 virion surface structures: relationships between antibody binding and neutralization or lessons from the viral capture assay. *AIDS Res. Hum. Retroviruses.* 20(4), 435-41.

Cavacini, L. et al., (1999). Minimal incidence of serum antibodies reactive with intact primary isolate virions in human immunodeficiency virus type 1-infected individuals. *J. Virol.* 73(11), 9638-41.

Center, R. J., Kemp, B. E., and Poumbourios, P. (1997). Human immunodeficiency virus type 1 and 2 envelope glycoproteins oligomerize through conserved sequences. *J Virol* 71(7), 5706-11.

Center, R. J., Leapman, R. D., Lebowitz, J., Arthur, L. O., Earl, P. L., and Moss, B. (2002). Oligomeric structure of the human immunodeficiency virus type 1 envelope protein on the virion surface. *J Virol* 76(15), 7863-7.

Center, R. J., Lebowitz, J., Leapman, R. D., and Moss, B. (2004). Promoting trimerization of soluble human immunodeficiency virus type 1 (HIV-1) Env through the use of HIV-1/simian immunodeficiency virus chimeras. *J Virol* 78(5), 2265-76.

Center, R. J., Schuck, P., Leapman, R. D., Arthur, L. O., Earl, P. L., Moss, B., and Lebowitz, J. (2001). Oligomeric structure of virion-associated and soluble forms of the simian immunodeficiency virus envelope protein in the prefusion activated conformation. *Proc Natl Acad Sci USA* 98(26), 14877-82.

Chakrabarti, B. K., Kong, W. P., Wu, B. Y., Yang, Z. Y., Friborg, J., Ling, X., King, S. R., Montefiori, D. C., and Nabel, G. J. (2002). Modifications of the human immunodeficiency virus envelope glycoprotein enhance immunogenicity for genetic immunization. *J Virol* 76(11), 5357-68.

Chan, D. C., Fass, D., Berger, J. M., and Kim, P. S. (1997). Core structure of gp41 from the HIV envelope glycoprotein. *Cell* 89(2), 263-73.

Chan, D. C., and Kim, P. S. (1998). HIV entry and its inhibition. *Cell* 93(5), 681-4.

Chen, S. S. (1994). Functional role of the zipper motif region of human immunodeficiency virus type 1 transmembrane protein gp41. *J. Virol.* 68(3), 2002-10.

Chen, S. S. et al. (1993). Mutational analysis of the leucine zipper-like motif of the human immunodeficiency virus type 1 envelope transmembrane glycoprotein. *J. Virol.* 67(6), 3615-9.

Connor, R. I. et al. (1995). Vpr is required for efficient replication of human immunodeficiency virus type 1 in human mononuclear phagocytes. *Virology.* 206(2), 935-44.

Connor, R. I. et al. (1996). Characterization of the functional properties of env genes from long-term survivors of human immunodeficiency virus type 1 infection. *J. Virol.* 70(8), 5306-11.

Daniels, G. M. and Amara, S. G. (1998). Selective labeling of neurotransmitter transporters at the cell surface. *Methods Enzymol.* 296, 307-18.

Doms, R. W., and Moore, J. P. (2000). HIV-1 membrane fusion: targets of opportunity. *J Cell Biol* 151(2), F9-14.

Dubay, J. W. et al. (1992). Mutations in the leucine zipper of the human immunodeficiency virus type 1 transmembrane glycoprotein affect fusion and infectivity. *J. Virol.* 66(8), 4748-56.

Earl, P. L. et al. (1994). Native oligomeric human immunodeficiency virus type 1 envelope glycoprotein elicits diverse monoclonal antibody reactivities. *J. Virol.* 68(5), 3015-26.

Earl, P. L., Moss, B., and Doms, R. W. (1991). Folding, interaction with GRP78-BiP, assembly, and transport of the human immunodeficiency virus type 1 envelope protein. *J Virol* 65(4), 2047-55.

Fields, B. N., Knipe, D. M., Howley, P. M., Chanock, R. M., Melinick, J. L., Monath, T. P., Roizman, B., and Straus, S. E. (1996). "Fields Virology." (P. A. Luciw, Ed.) Lippincott-Raven Publishers, Philadelphia.

Fouts, T. R. et al. (1997). Neutralization of the human immunodeficiency virus type 1 primary isolate JR-FL by human monoclonal antibodies correlates with antibody binding to the oligomeric form of the envelope glycoprotein complex. *J. Virol.* 71(4), 2779-85.

Fouts, T. R. et al. (1998). Interactions of polyclonal and monoclonal anti-glycoprotein gp120 antibodies with oligomeric glycoprotein gp120-glycoprotein 41 complexes of a primary HIV type 1 isolate: relationship to neutralization. *AIDS Res. Hum. Retroviruses.* 14(7), 591-597.

Garlick, R. L., Kirschner, R. J., Eckenrode, F. M., Tarpley, W. G., and Tomich, C. S. (1990). *Escherichia coli* expression, purification, and biological activity of a truncated soluble CD4. *AIDS Res Hum Retroviruses* 6(4), 465-79.

Gorny, M. K. et al. (1992). Neutralization of diverse human immunodeficiency virus type 1 variants by an anti-V3 human monoclonal antibody. *J. Virol.* 66(12), 7538-42.

Gorny, M. K. et al. (1993). Repertoire of human monoclonal antibodies specific for the V3 domain of HIV-1 gp120. *J. Immunol.,* 150(2), 635-43.

Gorse, G. J. et al. (1999) MN and IIIB recombinant glycoprotein 120 vaccine-induced binding antibodies to native envelope glycoprotein of human immunodeficiency virus type 1 primary isolates. National Institute of Allergy and Infectious Disease AIDS Vaccine Evaluation Group, *AIDS Res. Hum. Retroviruses.* 15(10), 921-930.

Greenberg, M. L. and Cammack, N. (2004). Resistance to enfuvirtide, the first HIV fusion inhibitor. *J. Antimicrob. Chemother.*, 54(2), 333-340.

Guo, Q. et al. (2003). Biochemical and genetic characterizations of a novel human immunodeficiency virus type 1 inhibitor that blocks gp120-CD4 interactions. *J. Virol.*, 77(19), 10528-36.

Herrera, C. et al. (2005). The impact of envelope glycoprotein cleavage on the antigenicity, infectivity, and neutralization sensitivity of Env-pseudotyped human immunodeficiency virus type 1 particles. *Virology.* 338(1), 154-72.

Herrera, C. et al. (2003). Nonneutralizing antibodies to the CD4-binding site on the gp120 subunit of human immunodeficiency virus type 1 do not interfere with the activity of a neutralizing antibody against the same site. *J. Virol.* 77(2), 1084-91.

Hunter, E., and Swanstrom, R. (1990). Retrovirus envelope glycoproteins. *Curr Top Microbiol Immunol* 157, 187-253.

Jeffs, S. A. et al. (2004). Expression and characterisation of recombinant oligomeric envelope glycoproteins derived from primary isolates of HIV-1. *Vaccine.* 22(8), 1032-46.

Jones, P. L., Korte, T., and Blumenthal, R. (1998). Conformational changes in cell surface HIV-1 envelope glycoproteins are triggered by cooperation between cell surface CD4 and co-receptors. *J Biol Chem* 273(1), 404-9.

Kirschner, M., Monrose, V., Paluch, M., Techodamrongsin, N., Rethwilm, A., and Moore, J. P. (2006). The production of cleaved, trimeric human immunodeficiency virus type 1 (HIV-1) envelope glycoprotein vaccine antigens and infectious pseudoviruses using linear polyethylenimine as a transfection reagent. *Protein Expr Purif* 48(1), 61-8.

Klasse, P. J. et al., (1993). An immune-selected point mutation in the transmembrane protein of human immunodeficiency virus type 1 (HxB2-Env:Ala582(-->Thr) decreases viral neutralization by monoclonal antibodies to the CD4-binding site. *Virology.* 196(1), 332-7.

Kuznetsov, Y. G. et al. (2003). Atomic force microscopy investigation of human immunodeficiency virus (HIV) and HIV-infected lymphocytes. *J. Virol.* 77(22), 11896-909.

Lin, P. F. et al. (2003). A small molecule HIV-1 inhibitor that targets the HIV-1 envelope and inhibits CD4 receptor binding. *Proc. Natl. Acad. Sci. USA.*, 100(19), 11013-8.

Lineberger, J. E. et al., (2002). Altering expression levels of human immunodeficiency virus type 1 gp120-gp41 affects efficiency but not kinetics of cell-cell fusion. *J. Virol.* 76(7), 3522-33.

Lu, M., Blacklow, S. C., and Kim, P. S. (1995). A trimeric structural domain of the HIV-1 transmembrane glycoprotein. *Nat Struct Biol* 2(12), 1075-82.

Melikyan, G. B., Markosyan, R. M., Hemmati, H., Delmedico, M. K., Lambert, D. M., and Cohen, F. S. (2000). Evidence that the transition of HIV-1 gp41 into a six-helix bundle, not the bundle configuration, induces membrane fusion. *J Cell Biol* 151(2), 413-23.

Moore, J. P., and Doms, R. W. (2003). The entry of entry inhibitors: a fusion of science and medicine. *Proc Natl Acad Sci U S A* 100(19), 10598-602.

Moore, J. P. et al. (1995). Primary isolates of human immunodeficiency virus type 1 are relatively resistant to neutralization by monoclonal antibodies to gp120, and their neutralization is not predicted by studies with monomeric gp120. *J. Virol.* 69(1), 101-9.

Moore, J. P. et al. (1994). Exploration of antigenic variation in gp120 from clades A through F of human immunodeficiency virus type 1 by using monoclonal antibodies. *J. Virol.* 68(12), 8350-64.

Moore, J. P. et al., (1992). Virions of primary human immunodeficiency virus type 1 isolates resistant to soluble CD4 (sCD4) neutralization differ in sCD4 binding and glycoprotein gp120 retention from sCD4-sensitive isolates. *J. Virol.* 66(1), 235-43.

Moore, J. P. et al., (2006). Nature of nonfunctional envelope proteins on the surface of human immunodeficiency virus type 1. *J. Virol.* 80(5), 2515-28.

Muster, T. et al., (1993). A conserved neutralizing epitope on gp41 of human immunodeficiency virus type 1. *J. Virol.* 67(11), 6642-7.

Nyambi, P. N. et al., (1998). Mapping of epitopes exposed on intact human immunodeficiency virus type 1 (HIV-1) virions: a new strategy for studying the immunologic relatedness of HIV-1. J. Virol. 72(11), 9384-91.

Pancera, M and Wyatt, R. (2005). Selective recognition of oligomeric HIV-1 primary isolate envelope glycoproteins by potently neutralizing ligands requires efficient precursor cleavage. *Virology.* 332(1), 145-56.

Pantophlet, R., Ollmann Saphire, E., Poignard, P., Parren, P. W., Wilson, I. A., and Burton, D. R. (2003). Fine mapping of the interaction of neutralizing and nonneutralizing monoclonal antibodies with the CD4 binding site of human immunodeficiency virus type 1 gp120. *J Virol* 77(1), 642-58.

Park, E. J. et al. (2000). A global neutralization resistance phenotype of human immunodeficiency virus type 1 is determined by distinct mechanisms mediating enhanced infectivity and conformational change of the envelope complex. *J. Virol.* 74(9), 4183-91.

Park, E. J., and Quinnan, G. V., Jr. (1999). Both neutralization resistance and high infectivity phenotypes are caused by mutations of interacting residues in the human immunodeficiency virus type 1 gp41 leucine zipper and the gp 120 receptor- and coreceptor-binding domains. *J. Virol.*73(7), 5707-13

Park, E. J., Vujcic, L. K., Anand, R., Theodore, T. S., and Quinnan, G. V., Jr. (1998). Mutations in both gp120 and gp41 are responsible for the broad neutralization resistance of variant human immunodeficiency virus type 1 MN to antibodies directed at V3 and non-V3 epitopes. *J. Virol.* 72(9), 7099-107.

Parker, C. E., Deterding, L. J., Hager-Braun, C., Binley, J. M., Schulke, N., Katinger, H., Moore, J. P., and Tomer, K. B. (2001). Fine definition of the epitope on the gp41 glycoprotein of human immunodeficiency virus type 1 for the neutralizing monoclonal antibody 2F5. *J Virol* 75(22), 10906-11.

Poignard, P., Moulard, M., Golez, E., Vivona, V., Franti, M., Venturini, S., Wang, M., Parren, P. W., and Burton, D. R. (2003). Heterogeneity of envelope molecules expressed on primary human immunodeficiency virus type 1 particles as probed by the binding of neutralizing and nonneutralizing antibodies. *J. Virol.* 77(1)353-65.

Poumbourios, P., Wilson, K. A., Center, R. J., El Ahmar, W., and Kemp, B. E. (1997). Human immunodeficiency virus type 1 envelope glycoprotein oligomerization requires the gp41 amphipathic alpha-helical/leucine zipperlike sequence. *J Virol* 71(3), 2041-9.

Reeves, J. D., Lee, F. H., Miamidian, J. L., Jabara, C. B., Juntilla, M. M., and Doms, R. W. (2005). Enfuvirtide resistance mutations: impact on human immunodeficiency virus envelope function, entry inhibitor sensitivity, and virus neutralization. *J. Virol.* 79(8), 4991-9.

Reitz, M. S., Jr., Wilson, C., Naugle, C., Gallo, R. C., and Robert-Guroff, M. (1988). Generation of a neutralization-resistant variant of HIV-1 is due to selection for a point mutation in the envelope gene. *Cell,* 54(1), 57-63.

Rimsky, L. T., Shugars, D. C., and Matthews, T. J. (1998). Determinants of human immunodeficiency virus type 1 resistance to gp41-derived inhibitory peptides. *J. Virol.* 72(2), 986-93.

Robinson, J. E., Holton, D., Pacheco-Morell, S., Liu, J., and McMurdo, H. (1990). Identification of conserved and variant epitopes of human immunodeficiency virus type 1 (HIV-1) gp120 by human monoclonal antibodies produced by EBV transformed cell lines. *AIDS Res. Hum. Retroviruses.* 6(5), 567-79.

Rizzuto, C. D., Wyatt, R., Hernandez-Ramos, N., Sun, Y., Kwong, P. D., Hendrickson, W. A., and Sodroski, J. (1998). A conserved HIV gp120 glycoprotein structure involved in chemokine receptor binding. *Science* 280(5371), 1949-53.

Rucker, J., BJ., D., Edinger, A., Long, D., Berson, J., and Doms, R. (1997). Cell-cell fusion assay to study role of chemokine receptors in human immunodeficiency virus type 1 entry. "Methods Enzymology", Vol. 288, pp. 118-133.

Sanders, R. W., Schiffner, L., Master, A., Kajumo, F., Guo, Y., Dragic, T., Moore, J. P., and Binley, J. M. (2000). Variable-loop-deleted variants of the human immunodeficiency virus type 1 envelope glycoprotein can be stabilized by an intermolecular disulfide bond between the gp120 and gp41 subunits. *J Virol* 74(11), 5091-100.

Sanders, R. W., Vesanen, M., Schuelke, N., Master, A., Schiffner, L., Kalyanaraman, R., Paluch, M., Berkhout, B., Maddon, P. J., Olson, W. C., Lu, M., and Moore, J. P. (2002). Stabilization of the soluble, cleaved, trimeric form of the envelope glycoprotein complex of human immunodeficiency virus type 1. *J Virol* 76(17), 8875-89.

Sattentau, Q. J., and Moore, J. P. (1991). Conformational changes induced in the human immunodeficiency virus envelope glycoprotein by soluble CD4 binding. *J Exp Med* 174(2), 407-15.

Sattentau, Q. J., and Moore, J. P. (1995). Human immunodeficiency virus type 1 neutralization is determined by epitope exposure on the gp120 oligomer. *J Exp Med.* 182(1), 185-96.

Scanlan, C. N., Pantophlet, R., Wormald, M. R., Ollmann Saphire, E., Stanfield, R., Wilson, I. A., Katinger, H., Dwek, R. A., Rudd, P. M., and Burton, D. R. (2002). The broadly neutralizing anti-human immunodeficiency virus type 1 antibody 2G12 recognizes a cluster of alpha1-->2 mannose residues on the outer face of gp120. *J. Virol.* 76(14), 7306-21.

Schagger, H., Cramer, W. A., and von Jagow, G. (1994). Analysis of molecular masses and oligomeric states of protein complexes by blue native electrophoresis and isolation of membrane protein complexes by two-dimensional native electrophoresis. *Anal. Biochem.* 217(2), 220-30.

Schulke, N., Vesanen, M. S., Sanders, R. W., Zhu, P., Lu, M., Anselma, D. J., Villa, A. R., Parren, P. W., Binley, J. M., Roux, K. H., Maddon, P. J., Moore, J. P., and Olson, W. C. (2002). Oligomeric and conformational properties of a proteolytically mature, disulfide-stabilized human immunodeficiency virus type 1 gp140 envelope glycoprotein. *J Virol* 76(15), 7760-76.

Shugars, D. C., Wild, C. T., Greenwell, T. K., and Matthews, T. J. (1996). Biophysical characterization of recombinant proteins expressing the leucine zipper-like domain of the human immunodeficiency virus type 1 transmembrane protein gp41. *J Virol* 70(5), 2982-91.

Si, Z., Cayabyab, M., and Sodroski, J. (2001). Envelope glycoprotein determinants of neutralization resistance in a simian-human immunodeficiency virus (SHIV HXBc2P 3.2) derived by passage in monkeys. *J. Virol.* 75(9), 4208-18.

Srivastava, I. K., Stamatatos, L., Legg, H., Kan, E., Fong, A., Coates, S. R., Leung, L., Wininger, M., Donnelly, J. J., Ulmer, J. B., and Barnett, S. W. (2002). Purification and characterization of oligomeric envelope glycoprotein from a primary R5 subtype B human immunodeficiency virus. *J Virol* 76(6), 2835-47.

Staropoli, I., Chanel, C., Girard, M., and Altmeyer, R. (2000). Processing, stability, and receptor binding properties of oligomeric envelope glycoprotein from a primary HIV-1 isolate. *J. Biol. Chem.* 275(45), 35137-45.

Stiegler, G., Kunert, R., Purtscher, M., Wolbank, S., Voglauer, R., Steindl, F., and Katinger, H. (2001). A potent cross-clade neutralizing human monoclonal antibody against a novel epitope on gp41 of human immunodeficiency virus type 1. *AIDS Res. Hum. Retroviruses.* 17(18), 1757-65.

Sullivan, N., Sun, Y., Sattentau, Q., Thali, M., Wu, D., Denisova, G., Gershoni, J., Robinson, J., Moore, J., and Sodroski, J. (1998). CD4-Induced conformational changes in the human immunodeficiency virus type 1 gp120 glycoprotein: consequences for virus entry and neutralization. *J Virol* 72(6), 4694-703.

Thali, M., Charles, M., Furman, C., Cavacini, L., Posner, M., Robinson, J. and Sodroski, J. (1994). Resistance to neutralization by broadly reactive antibodies to the human immunodeficiency virus type 1 gp 120 glycoprotein conferred by a gp41 amino acid change. *J. Virol.,* 68(2), 674-80.

Thali, M., Moore, J. P., Furman, C., Charles, M., Ho, D. D., Robinson, J., and Sodroski, J. (1993). Characterization of conserved human immunodeficiency virus type 1 gp120 neutralization epitopes exposed upon gp120-CD4 binding. *J Virol* 67(7), 3978-88.

Thomas, D. J., Wall, J. S., Hainfeld, J. F., Kaczorek, M., Booy, F. P., Trus, B. L., Eiserling, F. A., and Steven, A. C. (1991). gp160, the envelope glycoprotein of human immunodeficiency virus type 1, is a dimer of 125-kilodalton subunits stabilized through interactions between their gp41 domains. *J. Virol.* 65(7), 3797-803.

Trkola, A., Purtscher, M., Muster, T., Ballaun, C., Buchacher, A., Sullivan, N., Srinivasan, K., Sodroski, J., Moore, J. P., and Katinger, H. (1996). Human monoclonal antibody 2G12 defines a distinctive neutralization epitope on the gp120 glycoprotein of human immunodeficiency virus type 1. *J Virol* 70(2), 1100-8.

Trkola, A., Dragic, T., Arthos, J., Binley, J. M., Olson, W. C., Allaway, G. P., Cheng-Mayer, C., Robinson, J., Maddon, P. J., and Moore, J. P. (1996a). CD4-dependent, antibody-sensitive interactions between HIV-1 and its co-receptor CCR-5. *Nature.* 384(6605), 184-7.

Trkola, A., Ketas, T., Kewalramani, V. N., Endorf, F., Binley, J. M., Katinger, H., Robinson, J., Littman, D. R., and Moore, J. P. (1998). Neutralization sensitivity of human immunodeficiency virus type 1 primary isolates to antibodies and CD4-based reagents is independent of coreceptor usage. *J. Virol.* 72(3), 1876-85.

Weng, Y., and Weiss, C. D. (1998). Mutational analysis of residues in the coiled-coil domain of human immunodeficiency virus type 1 transmembrane protein gp41. *J. Virol.* 72(12), 9676-82.

Whitcomb, J. M., Huang, S., Fransen, S., Wrin, T., Paxinos, E., Toma, J., Greenberg, M., Sista, P., Melby, T., Matthews, T., DeMasi, R., Heilek-Snyder, G., Cammack, N., Hellmann, N., and Petropoulos, C. (2003). 10th *Conference on Retroviruses and Opportunistic Infection,* Boston, Mass.

Wild, C. T., Shugars, D. C., Greenwell, T. K., McDanal, C. B., and Matthews, T. J. (1994). Peptides corresponding to a predictive alpha-helical domain of human immunodeficiency virus type 1 gp41 are potent inhibitors of virus infection. *Proc. Natl. Acad. Sci. USA.*, 100(19), 91(21), 9770-4.

Wu, L., Gerard, N. P., Wyatt, R., Choe, H., Parolin, C., Ruffing, N., Borsetti, A., Cardoso, A. A., Desjardin, E., Newman, W., Gerard, C., and Sodroski, J. (1996). CD4-induced interaction of primary HIV-1 gp120 glycoproteins with the chemokine receptor CCR-5. *Nature* 384(6605), 179-83.

Wyatt, R., Moore, J., Accola, M., Desjardin, E., Robinson, J., and Sodroski, J. (1995). Involvement of the V1/V2 variable loop structure in the exposure of human immunodeficiency virus type 1 gp120 epitopes induced by receptor binding. *J. Virol.* 69(9), 5723-33.

Wyatt, R., and Sodroski, J. (1998). The HIV-1 envelope glycoproteins: fusogens, antigens, and immunogens. *Science.* 280(5371), 1884-8.

Yang, X., Florin, L., Farzan, M., Kolchinsky, P., Kwong, P. D., Sodroski, J., and Wyatt, R. (2000). Modifications that stabilize human immunodeficiency virus envelope glycoprotein trimers in solution. *J Virol* 74(10), 4746-54.

Yang, X., Lee, J., Mahony, E. M., Kwong, P. D., Wyatt, R., and Sodroski, J. (2002). Highly stable trimers formed by human immunodeficiency virus type 1 envelope glycoproteins fused with the trimeric motif of T4 bacteriophage fibritin. *J Virol* 76(9), 4634-42.

York, J., Follis, K. E., Trahey, M., Nyambi, P. N., Zolla-Pazner, S., and Nunberg, J. H. (2001). Antibody binding and neutralization of primary and T-cell line-adapted isolates of human immunodeficiency virus type 1. *J. Virol.* 75(6), 2741-52.

Zanetti, G., Briggs, J. A., Grunewald, K., Sattentau, Q. J., and Fuller, S. D. (2006). Cryo-Electron Tomographic Structure of an Immunodeficiency Virus Envelope Complex In Situ. *PLOS Pathog* 2(8).

Zhang, C. W., Chishti, Y., Hussey, R. E., and Reinherz, E. L. (2001). Expression, purification, and characterization of recombinant HIV gp140. The gp41 ectodomain of HIV or simian immunodeficiency virus is sufficient to maintain the retroviral envelope glycoprotein as a trimer. *J Biol Chem* 276(43), 39577-85.

Zhang, W., Canziani, G., Plugariu, C., Wyatt, R., Sodroski, J., Sweet, R., Kwong, P., Hendrickson, W., and Chaiken, I. (1999). Conformational changes of gp120 in epitopes near the CCR5 binding site are induced by CD4 and a CD4 miniprotein mimetic. *Biochemistry* 38(29), 9405-16.

Zhu, P., Chertova, E., Bess, J., Jr., Lifson, J. D., Arthur, L. O., Liu, J., Taylor, K. A., and Roux, K. H. (2003). Electron tomography analysis of envelope glycoprotein trimers on HIV and simian immunodeficiency virus virions. *Proc Natl Acad Sci USA* 100(26), 15812-7.

Zhu, P., Liu, J., Bess, J., Jr., Chertova, E., Lifson, J. D., Grise, H., Ofek, G. A., Taylor, K. A., and Roux, K. H. (2006). Distribution and three-dimensional structure of AIDS virus envelope spikes. *Nature* 441(7095), 847-52.

Zwick, M. B., Labrijn, A. F., Wang, M., Spenlehauer, C., Saphire, E. O., Binley, J. M., Moore, J. P., Stiegler, G., Katinger, H., Burton, D. R., and Parren, P. W. (2001). Broadly neutralizing antibodies targeted to the membrane-proximal external region of human immunodeficiency virus type 1 glycoprotein gp41. *J Virol* 75(22), 10892-905.

Experimental Details III

According to the 2005 World Health Organization AIDS epidemic update, there are over 40 million people infected with the HIV virus worldwide, with close to 5 million newly infected cases just last year (1). Among the hardest hit areas is sub-Saharan Africa, with over 25 million people living with HIV and about 10% dying of AIDS-related illnesses. It has been widely recognized and accepted that prophylactic measures in the form of an HIV vaccine, in addition to therapeutic medicines, need to be implemented to curtail the spread of AIDS globally.

An effective HIV vaccine needs to demonstrate an ability to elicit neutralizing antibodies (NAb) that would be capable of blocking the fusogenic interaction and entry of HIV with the CD4 receptor on $CD4^+$ helper T cells, mediated by the cell surface viral env glycoproteins, gp120 and gp41. Since the genetic polymorphism of the HIV-1 gag and env genes are diverse and constantly evolving due to rapid mutation within individuals (2), the NAbs targeting the gp120 and gp41 envelope proteins on the viral surface need to be capable of blocking the viral interaction with the CD4 receptor and thereby neutralize viruses from a broad range of subtypes, without discrimination.

One logical design of recombinant env vaccine candidates is to base the vaccine sequence on currently existing HIV-1 isolates that are prevalent in the infected population. To this end, several oligomeric env proteins from several different subtypes or "clades" have been described, with subtype B sequences serving as a basis for the majority of those that have been reported (3-11, 29, 31). The oligomeric env protein complex on the surface of the virus is comprised of a gp120-gp41 heterodimer present in a homotrimer configuration (held together via non-covalent interactions), resembling a "spike" structure. These glycoproteins are derived from a gp160 precursor protein, which undergoes processing and cleavage in the cell to result in gp120 and gp41 heterodimers that are then targeted to the surface of the HIV viral envelope (12, 13). Fusion of the virus with the $CD4^+$ cell membrane and oligomerization of the trimer spike is mediated by the gp41 glycoprotein, which is tethered to the virion surface via its transmembrane domain (12, 13).

It has been reasoned that design of a recombinant vaccine should mimic the native trimer spike of the HIV envelope against which NAbs would naturally be generated. Since the native Env trimer is technically challenging to produce in a recombinant form, modified versions of the trimer that could serve as potential vaccine templates have been reported. One typical modification is truncation of the gp41 transmembrane domain from the precursor gp160 to yield gp140 proteins in a soluble form. However, following processing and cleavage, the resulting gp120 and gp41 ectodomain or $gp41_{ECTO}$ (lacking the transmembrane domain) have been shown to form unstable associations and tend to dissociate into their respective monomeric subunits (13, 14). To address these issues, subtype B $HIV_{JR-FL}$ Env was used as a template and a disulfide bond was introduced between $gp^{120}$-$gp^{41}_{ECTO}$ subunits (SOS gp140), followed by a further modification to $gp41_{ECTO}$ (I559P mutation), which successfully allowed for the expression of stable, cleaved and fully processed oligomeric gp140 proteins in a trimeric conformation (SOSIP $gp^{140}$) (8-11, 15-17, and WO 2003/022869). While immunization of rabbits performed with the engineered HIV-$1_{JR-FL}$ SOSIP gp140 elicited antibodies capable of neutralization, the activity was limited primarily to the homologous strain, with only a modest and limited ability to neutralize across different HIV-1 primary isolates (11).

While the SOSIP technology addresses stability and expression, another issue that has limited production and purification of the recombinant trimers has been the spontaneous association of the oligomeric gp140 proteins into aberrant "aggregate" species (3, 9, 11, 18). These aggregate species, typically identified by their reduced mobility on blue native PAGE (BN-PAGE) and non-reduced SDS-PAGE have been difficult to purify from the SOSIP gp140 trimer without compromising yield and/or stability of the trimer. Attempts to fully characterize the aggregate have been limited and their true nature remains elusive.

To explore a wider variety of oligomeric env proteins that could elicit higher breadths of cross-neutralization activity and serve as potential vaccine immunogens, a panel of subtype A sequences from HIV-1 primary isolates in sub-Saharan Africa were studied (19). The env proteins from these sequences were expressed as SOSIP gp140 proteins, with a further engineered mutation at the gp120-gp41$_{ECTO}$ cleavage site (R6) for enhanced furin cleavage (>95% efficiency) to yield soluble, stable and fully processed gp140 trimers. Described herein is the purification and biochemical characterization of KNH1144 SOSIP R6 gp140, derived from a contemporary East African subtype A HIV-1 primary isolate, using methodologies that improve on currently implemented purification procedures. The purified KNH1144 SOSIP R6 gp140 is a trimer based on BN-PAGE and size exclusion chromatography (SEC). In addition, described herein are novel findings of the effects of non-ionic detergents such as Tween 20 on the KNH1144 SOSIP R6 aggregates (19). These findings reveal new insights into the nature of the aggregate species. The effects of non-ionic detergent, e.g., Tween® 20, treatment on the antigenic properties of KNH1144 SOSIP R6 gp140 aggregates and trimers were examined. Finally, digital imaging based on negative stain electron microscopy was performed and revealed the structure of purified KNH1144 SOSIP R6 gp140 as trimeric oligomers.

Materials and Methods

Subtype A KNH1144 SOSIP R6 Transfection and Expression:

The KNH1144 SOSIP R6 envelope and furin DNA plasmids were as described. For a typical 8 L preparation, HEK 293T cells were seeded in triple flasks at a density of 2.5×10$^7$ cells/flask and cultured in DMEM/10% FBS/1% pen-strep with 1% L-glutamine 24 hours prior to transfection. On the day of transfection, 270 ug of KNH1144 SOSIP R6 envelope DNA was mixed with 90 ug of Furin protease DNA plasmid (per flask) in Opti-MEM. Polyethyleneimine (PEI) was added stepwise (2 mg PEI: 1 mg total DNA) and vortexed immediately in between each addition. The PEI/DNA complex solutions were incubated for 20 minutes at room temperature. Complexes were then added to the flasks and incubated for 6 hours at 32° C., 5% CO$_2$. The cells were then washed with warmed PBS and then incubated in exchange media (DMEM/0.05% BSA/1% pen-strep) for 48 hours at 32° C., 5% CO$_2$. After the 48 hour incubation, the supernatants were collected and a cocktail of protease inhibitors was added to minimize protein degradation. Harvested supernatants were then clarified by filtration through a 0.45 um filter and concentrated to 53×. Expression of KNH1144 gp120 monomer has been previously described (1) and typically, 1-2 L of cell culture supernatants from transfected cells were harvested. Supernatants were clarified by filtration and stored at −80° C. without any concentration prior to purification.

Purification of KNH1144 SOSIP R6 gp140 and gp120:

KNH1144 SOSIP R6 gp140 trimer was purified via a four step process starting with an ammonium sulfate precipitation followed by lectin affinity, size exclusion and ion-exchange chromatography. 53X concentrated cell culture supernatant was precipitated with an equal volume of 3.8 M ammonium sulfate to remove contaminant proteins (with the major contaminant being -2-macroglobulin). The ammonium sulfate was added with constant stirring with a stir bar and then was immediately centrifuged at 4000 rpm, 4° C. for 45 minutes. The resulting supernatant was diluted 4-fold with PBS, pH 7.25, and was filtered using a 0.45 um vacuum filter. The sample was then loaded at 0.5-0.8 ml/min onto a *Galanthus nivalis* (GNA) lectin (Vector Laboratories, Burlingame, Calif.) column equilibrated with PBS-pH 7.25. Once the load was finished, the column was washed with PBS pH 7.25 until OD$_{280}$ reached baseline, followed by a second wash with 0.5 M NaCl PBS pH 7.25 at 1 ml/min in order to remove contaminant proteins (mainly BSA). The column was then eluted with 1 M MMP PBS pH 7.25 starting with flowing one half CV through the column at 0.3 ml/min and pausing the purification for a 1 hour incubation in MMP elution buffer. Following the incubation, the flow was restarted at 0.3 ml/min and 0.5-1 ml fractions were collected. All peak fractions were then pooled and concentrated to a final volume of 1 ml using a Vivaspin 100,000 MWCO concentrator (Vivascience, Edgewood, N.Y.) centrifuged at 1000×g. The concentrated lectin elution was applied over a Superdex 200 SEC column (GE Healthcare, Piscataway, N.J.) equilibrated in 20 mM Tris pH 8, 200 mM NaCl (TN-200), injecting 0.5 ml of sample per run and was resolved at 0.4 ml/min, collecting 0.4 ml fractions. The fractions were analyzed by BN-PAGE using a 4-12% Bis-Tris NuPAGE gel (Invitrogen, Carlsbad, Calif.) (10). All trimer containing fractions were pooled and diluted to 75 mM NaCl with 20 mM Tris pH 8. The diluted SEC pool was then applied over a 1 ml HiTrap DEAE FF column (GE Healthcare), equilibrated in 20 mM Tris pH 8, 75 mM NaCl (TN-75). The diluted SEC pool was loaded at 0.5 ml/min. The column was washed with TN-75 at 1 ml/min until the OD$_{280}$ reached baseline. The column was then eluted with 20 mM Tris, 300 mM NaCl pH 8 at 1 ml/min, collecting 0.5 ml fractions.

To maximize trimer yield, the flow-through fraction from the DEAE column was re-applied over the column (equilibrated in TN-75) and typically 20-30% or 30-40% more trimer was recovered in this manner. The fractions were analyzed by BN-PAGE and by reducing and non-reducing SDS-PAGE. Western blot analysis on non-reduced SDS-PAGE gel was performed with the ARP3119 monoclonal antibody. The trimer containing fractions were pooled and trimer concentration was determined through densitometry on a reducing SDS-PAGE gel using JR-FL gp120 as a standard.

KNH1144 gp120 Monomer:

Unconcentrated cell culture supernatants containing secreted gp120 monomer were applied directly over a GNA lectin column equilibrated in 20 mM imidazole pH 7.1 at 1-2 ml/min. Following adsorption, the column was washed with a high salt (PBS containing 1 M NaCl, pH 7.1) wash, followed by a low salt (20 mM imidazole pH 7.1) wash. The column was eluted with 1 M MMP in 20 mM imidazole, 0.2 M NaCl pH 7.1. Peak fractions were pooled and diluted with 20 mM imidazole, pH 7.1, thirteen-fold to a final buffer concentration of 20 mM imidazole, pH 7.1, 15 mM NaCl. The diluted GNA elution was applied over 1 ml HiTrap Q Sepharose FF (GE Healthcare) equilibrated in 20 mM imidazole, pH 7.1. Following binding, the column was washed with 20 mM imidazole, pH 7.1, and was eluted with 20 mM imidazole, 0.2 M NaCl, pH 7.1. The Q elutions were pooled and concentrated and applied over a Superdex 200 column equilibrated in PBS in 0.5 ml volumes and resolved at 0.4 ml/min. Peak fractions were analyzed by 4-12% Bis-tris gels (Invitrogen), followed by Coomassie staining. Fractions containing gp120 were pooled and quantified as described above for the SOSIP R6 gp140 trimers and stored at −80° C.

Tween® 20 Aggregate "Conversion"/"Collapse" Experiments:

Tween® 20 Dose effect: 1 ug of purified KNH1144 SOSIP R6 trimer was incubated with varying concentrations of Tween® 20 (polyoxyethylene sorbitan monolaurate) ranging from 0 to 0.0001% (v/v) and incubated for 1 hour at room temperature. Following incubation, samples were analyzed by BN-PAGE as described above.

Kinetics of Tween® 20 effect: To ascertain the early kinetics of the Tween® 20 effect on aggregate, 1 ug of purified KNH1144 SOSIP R6 trimer was incubated with Tween® 20 at a final concentration of 0.05% (v/v) for 5 minutes and for 10 minutes. A no-detergent control was included separately for each timepoint.

Temperature dependance on Tween® 20 effect: To determine if temperature affected the ability of Tween® 20 to recover trimers from aggregates (i.e., collapse aggregate into trimer), 1 ug of purified KNH1144 SOSIP R6 trimer was incubated with Tween® 20 to a final concentration of 0.05% (v/v) at 0° C. (on ice), room temperature (22-23° C.) at 37° C., or left untreated for 10 minutes. Following the incubation, samples were analyzed by BN-PAGE and Coomassie staining.

Tween® 20 effect on KNH1144 gp120: To test if Tween® 20 had a similar effect on KNH1144 gp120, 1 ug of purified gp120 monomer was either untreated or incubated with Tween® 20 at a final concentration of 0.05% for 10 minutes at room temperature. Following the treatment, samples were analyzed by BN-PAGE and Coomassie staining.

Tween® 20 effect on -2-macroglogulin ($a_2M$): 0.5 ug of purified -2-macroglobulin was either untreated or treated with Tween® 20 at a final concentration of 0.05% for 10 minutes at room temperature. Reactions were analyzed via BN-PAGE, followed by Coomassie staining.

Size Exclusion Chromatography (SEC) Analysis:

All runs were performed at 4° C. on the AKTA FPLC system (GE Healthcare). Each run was performed at least twice.

Molecular weight standards SEC: A Superdex 200 10/300 GL column was equilibrated in 20 mM Tris pH 8, 0.5 M NaCl (TN-500) and calibrated with the following molecular weight standard proteins: thyroglobulin 669,000 Da; ferritin 440,000 Da; BSA 67,000 Da; and RNAse A 13,700 Da. A standard curve was generated by plotting the observed retention volumes of the standard proteins against the log values of their predicted molecular weights.

KNH1144 gp120 SEC analysis: 14 ug of purified KNH1144 gp120 (either untreated or Tween® 20-treated as described above) was applied over the Superdex 200 column equilibrated in TN-500 and resolved at a flow rate of 0.4 ml/min. As a control, 10-14 ug of JR-FL gp120 was also analyzed in a similar manner.

KNH1144 SOSIP R6 gp140 SEC analysis: 8-10 ug of purified KNH1144 SOSIP R6 gp140 was treated with Tween® 20 at a final concentration of 0.05% for 10-30 minutes at room temperature. Treated samples were then applied over the Superdex 200 column equilibrated with TN-500 containing 0.05% Tween® 20 (TNT-500) and resolved at 0.4 ml/min, collecting 0.4 ml fractions. Trimer-containing fractions were then analyzed by BN-PAGE, followed by silver staining. Fractions were also separated by BN-PAGE, followed by Western blot analysis with ARP 3119 antibody.

Blue Native PAGE (BN-PAGE) and SDS-PAGE Analysis:

All SDS-PAGE analysis (reduced and non-reduced) were performed using 4-12% Bis-Tris NuPage gels (Invitrogen). BN-PAGE analysis was performed as described (10). Silver stain analysis was performed with the SilverQuest kit (Invitrogen). Coomassie G-250 stain was performed using either the SimplyBlue SafeStain or Easy-to-Use Coomassie® G-250 Stain (Invitrogen).

Antigenicity Experiments—Lectin ELISA:

Human mAbs b6 (32), b12 (33) and 2G12 (26), HIVIg (40) were obtained from Dr. Dennis Burton (The Scripps Research Institute, La Jolla, Calif.) or Dr. Herman Katinger (University of Natural Resources and Applied Life Sciences, Austria, Vienna). For the lectin based ELISA, anti-Env antibodies 2G12, b6, b12 and HIVIg were used. In addition, the CD4-IgG2 antibody conjugate PRO 542 (39) was also used.

ELISA plates were coated overnight at 4° C. with lentil lectin powder from Lens culinaris (L9267, Sigma) at 10 ug/ml concentration. Plates were washed with PBS twice and blocked with SuperBlock (Pierce) (warmed to RT). Excess blocking agent was washed off with PBS. SEC fractions containing HMW aggregate were either untreated or treated with 0.05% Tween® 20 (v/v, final concentration) for 30 minutes at room temperature (RT) and were added at 0.3 ug/ml (diluted in PBS) and bound to the plates (via the lectin) for 4 hours at RT. Following binding, plates were washed 4 times with PBS and incubated with primary anti-Env antibodies starting at 10 ug/ml in PBS/5% milk. 4× serial dilutions were performed and incubations were performed for 3 hours at RT. Following antibody incubation, plates were washed 6 times and goat anti-human IgG (H+L) alkaline phosphatase conjugate secondary antibody (Jackson ImmunoResearch) was added at 1/4000 concentration in PBS/5% milk. Plates were washed 4 times and ELISAs were developed using the Ampak detection system (Dako Cytomation, Carpinteria, Calif.) as per the manufacturer's instructions.

DEAE Anion Exchange Chromatography of Tween® 20-Treated KNH1144 SOSIP R6 gp140 Trimers:

Purified KNH1144 SOSIP R6 gp140 trimers, treated either with or without 0.05% Tween® 20 (final), containing $a_2M$ contaminant in TN-75 buffer was applied over 1 ml DEAE HiTrap FF column (equilibrated in TN-75) at 0.25 ml/min at RT and flow-through (FT) fractions were collected. Following sample loading, the column was washed with TN-75 at 0.5 ml/min and wash fractions were collected. Finally, the column was eluted with TN-300 and equal amounts from each fraction were analyzed via BN-PAGE, followed by Coomassie G-250 staining.

Electron Microscopy:

EM analysis of the SOSIP trimers was performed by negative stain as previously described (34, 35). Because this technique is incompatible with detergent, 20 l of the original sample (0.5 mg/ml in TN-300) was dialyzed against BSB (0.1 M $H_3BO_3$, 0.025 M $Na_2B_4O_7$, 0.075 M NaCl, pH 8.3) and subsequently depleted of detergent using the Mini Detergent-OUT™ detergent removal kit (Calbiochem, La Jolla, Calif.) as described by the manufacturer. Two microliters of the resulting protein solution, diluted in 200 l BSB, was affixed to carbon support membrane, stained with 1% uranyl formate, and mounted on 600 mesh copper grids for analysis. EMs were recorded at ×100,000 at 100 kV on a JOEL JEM 1200 electron microscope. Measurements were made using the Image-Pro Plus software program. Fifty or more trimers were measured and analyzed statistically. The average diameter of the compact trimers formed by the SOSIP gp140 (e.g., KNH1144.R6 SOSIP) proteins was about 12-13 nm.

Results

Expression and Purification of Trimeric KNH1144 SOSIP R6 gp140:

The purification of KNH1144 SOSIP R6 gp140 trimers typically involved three chromatography steps: GNA lectin affinity, Superdex 200 size exclusion and DEAE weak anion exchange. 53× concentrated cell culture supernatant precipitated with ammonium sulfate was clarified by centrifugation, diluted and applied over the GNA lectin affinity column to capture gp140 proteins via (−1, 3) mannose residues. Analysis of the ammonium sulfate precipitation using different starting concentrations of harvested cell culture supernatant (100× to 40×) revealed that 53× was the optimum condition at which maximum -2-macroglobulin precipitated out, with minimal envelope protein loss. While the GNA lectin column was highly efficient in capture of the gp140 trimer, elution of the protein under even extremely mild conditions, with the competing MMP eluant, caused significant de-stabilization of the trimer and resulted in marked dissociation of the trimer into dimer and monomer species. Attempts to separate the different oligomeric gp140 species via Superdex SEC resulted in efficient separation of the monomer from the dimer and trimer. Superdex 200 SEC of the GNA eluate yielded trimers that were free of monomers, but not of dimers. To resolve trimers away from dimers (and residually co-migrating monomers), a DEAE anion exchange step was incorporated, which led to very efficient separation of dimer from trimer, thereby yielding pure trimers at the end of the purification protocol.

SDS-PAGE analysis under reducing conditions showed that the final preparation was of high purity (at least 90%), with only the gp120 moeity visible on the reduced gel (FIG. 14, left panel, center lane). Common serum contaminants that were detectable by reducing SDS-PAGE were -2-macroglobulin ($a_2M$) and BSA, which typically comprised up to ~10% of the final preparation. The non-reduced gel shows intact gp140 protein on SDS-PAGE (FIG. 14, left panel, right lane). In addition, little to no disulfide-linked aggregate (typically revealed as migrating much slower on a non-reducing gel) was detected. This was confirmed by anti-envelope Western blot analysis on the non-reduced gel (FIG. 14, Anti-Env blot, middle panel). BN-PAGE analysis of the purified trimer revealed the purified trimer to migrate between the 669k thyroglobulin and 440k ferritin marker proteins (FIG. 14, right panel, SOSIP R6). This is consistent with the migration patterns for JR-FL SOSIP gp140 which has been observed to migrate in the lower range of 669k and 440 kDa (9, 10, 11). An additional slower migrating band, typically classified as high molecular weight (HMW) SOSIP aggregates and comprising about 30% of the preparation, was also detected (FIG. 14, right panel, SOSIP R6, −lane). Typical HMW aggregate content ranged from 10 to 40% of the final preparation prior to non-ionic detergent treatment. Treatment of the purified preparation with Tween® 20 at a final concentration of 0.05% converted the HMW aggregate species to trimers, yielding a homogenous trimer preparation (FIG. 14, right panel, SOSIP R6, +lane) (19). It should be noted that treatment with Tween® 20 also caused the treated trimer to migrate slightly more rapidly than the untreated trimer (notice faster mobility of trimer in the +lane).

Purification of the monomeric protein yielded a homogenous preparation as evident by a single band when analyzed by reducing SDS-PAGE (FIG. 14, left panel, left lane) and Superdex 200 SEC. BN-PAGE analysis of the purified monomer, either in the presence or absence of Tween® 20 revealed a single migrating monomeric gp120 species, devoid of any higher order oligomers, consistent with its purity on SDS-PAGE (FIG. 14, right panel, gp120 −/+lanes).

Figure 15:
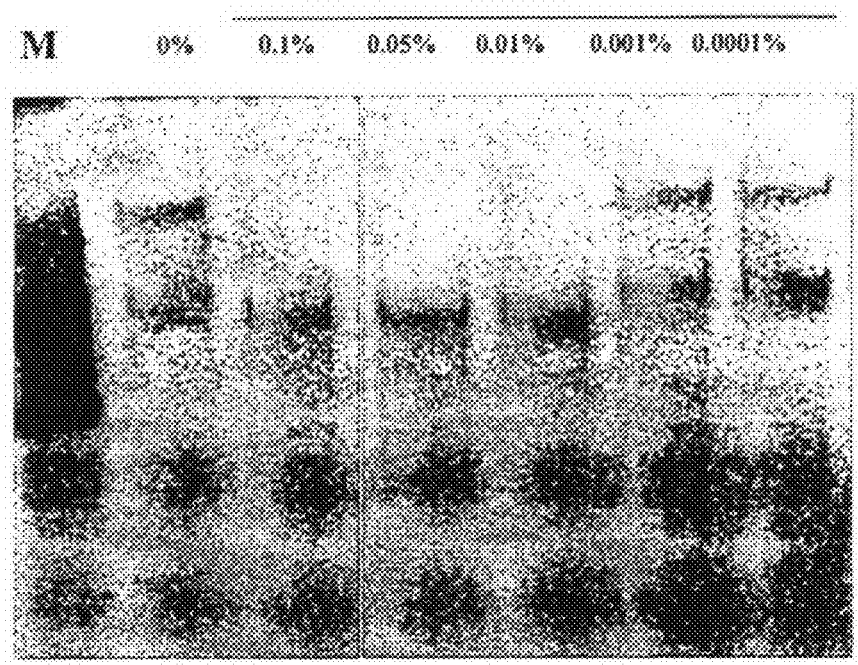
Figure 15:
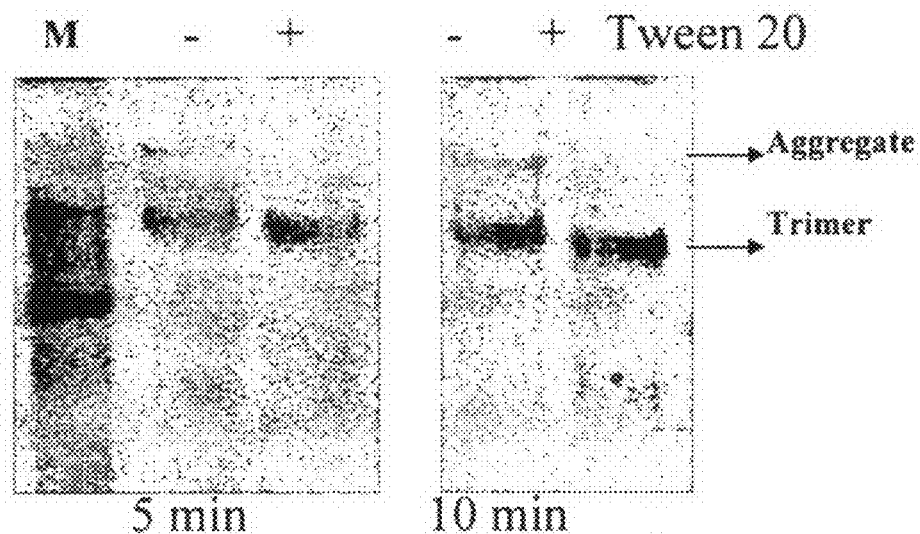
Figure 15:
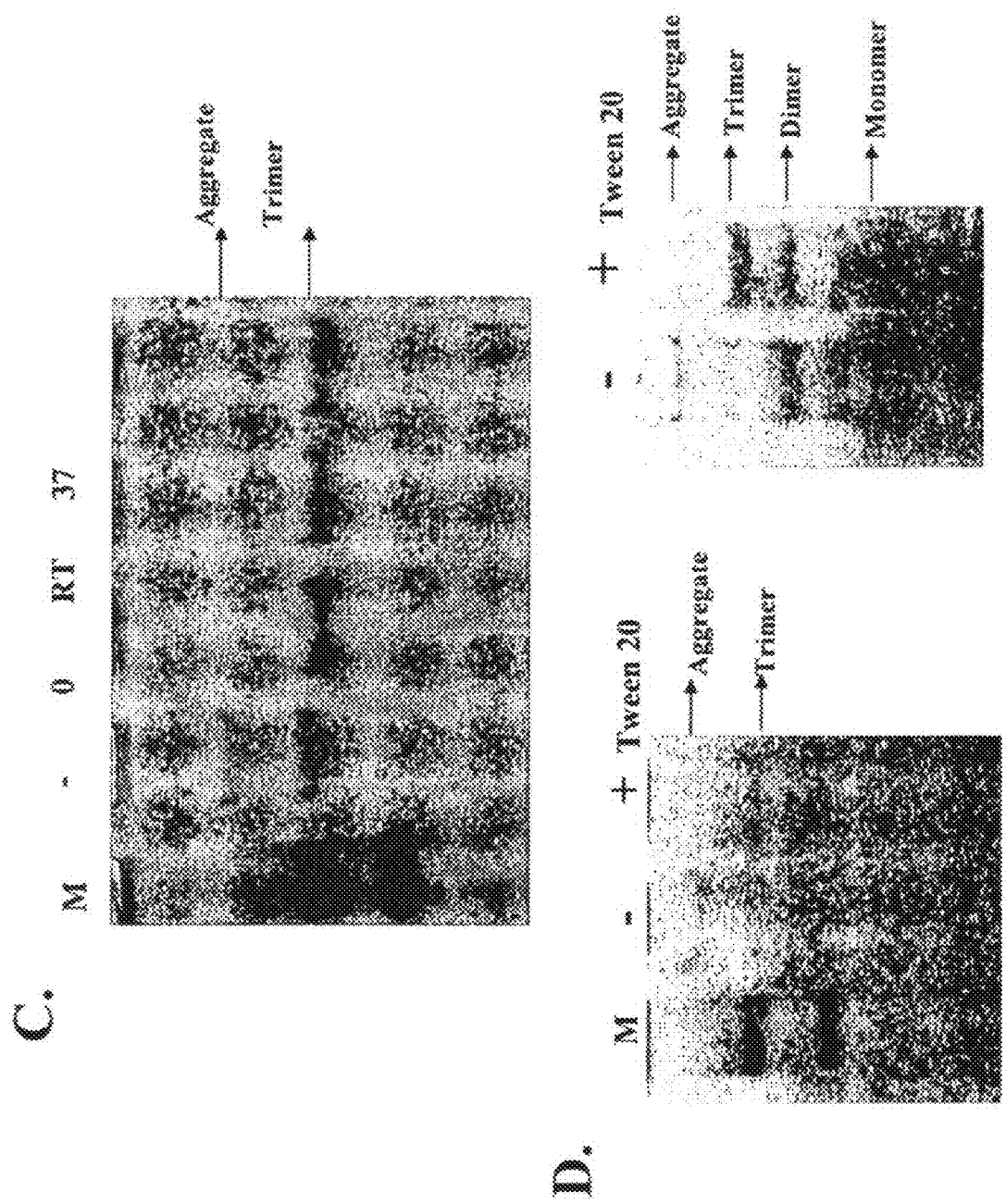

Since Tween® 20 provided a simple and mild means to obtain homogenous trimers, further characterization of the non-ionic detergent effect was performed. A purified trimer preparation containing ~30% aggregates (e.g., monomer, dimmer and trimer) was treated with Tween® 20 at final concentrations of 0.0001% to 0.1% (v/v) (FIG. 15A). The SOSIP R6 aggregates were converted to trimers at concentrations of 0.1% to 0.01% (FIG. 15A, lanes 3-5). No conversion was observed at Tween® 20 concentrations of 0.001 and 0.0001% (FIG. 15A, lanes 6 and 7). Close examination of the 0.01% reaction (lane 5) revealed that traces of aggregate were present, thus indicating that 0.01% Tween® 20 is probably the threshold concentration. To study the kinetics of the conversion, trimer preparations containing ~30% aggregate were incubated with Tween® 20 for 0, 5 and 10 minutes prior to analysis by BN-PAGE. As shown in FIG. 15B, both the 5 minute and 10 minute incubations completely eliminated the aggregate, indicating that the kinetics of the reaction was rapid and within a 5 minute time span.

The effect of temperature on aggregate rearrangement was also examined. Aggregate/trimer preparations were incubated with Tween® 20 either at 0° C. (on ice), room temperature (22-23° C.), or 37° C. As shown in FIG. 15C, conversion of aggregate to trimer occurred at all 3 temperatures, indicating that the Tween® 20 effect on aggregate was independent of temperature over this range. Similar results were obtained when Tween® 80 was used instead of Tween® 20.

Similar Tween® 20 treatment of the gp120 monomer showed that there was no difference observed in its migratory pattern either in the presence or absence of Tween® 20, indicating that Tween® 20 did not affect the gp120 monomer (FIG. 14, right panel, gp120, −/+lanes). In some cases, a mild increase in the staining intensity of the gp120 monomer occurred. To test if the detergent had a collapsive effect on another large multi-subunit protein, -2-macroglobulin ($_2M$), which is an acidic 726 kDa tetrameric glycoprotein comprised of four identical 185 kDa subunits, was incubated with Tween® 20. No change was observed in the migratory pattern of $_2M$ in the presence of Tween® 20, although there was a slight increase in the staining intensity of the protein. (See FIG. 21)

To examine whether Tween® 20 could convert preparations containing predominantly aggregate as the major oligomeric species to resulting trimers, a KNH1144 SOSIP R6 preparation containing >70% HMW aggregate was incubated with Tween® 20 and analyzed by BN-PAGE. As shown in FIG. 15D, Tween® 20 was effective in converting the aggregate rich fraction to trimer (FIG. 19D, left panel). Fractions of less purity containing HMW aggregate, dimers and monomers (FIG. 15D, right panel, −lane, each species denoted by arrows), when treated with Tween® 20 also resulted in collapse of HMW aggregate to resulting trimer (FIG. 15D, right panel, +lane). However, no effect on dimer or monomer migration was observed (FIG. 15D, right panel, +lane, arrows), indicating that the Tween® 20 action was specific to KNH1144 SOSIP R6 HMW aggregate and trimer. Consistent with previous observations, some increase in monomer staining was observed. Thus, these results indicate that Tween® 20 efficiently converts the KNH1144 SOSIP HMW aggregate into trimeric form. According to this invention, Tween® 20 efficiently converted into trimers HMW preparations having greater than 10%, (e.g., greater than 10-40%), aggregate. Greater than 90-99%, or 100%, trimers were able to be recovered from non-ionic detergent-, e.g., Tween® 20, treated HMW aggregates.

SEC Analysis of KNH1144 gp120 Monomer and SOSIP R6 gp140 Trimer:

Size exclusion chromatography (SEC) analysis was performed as a second means to characterize the molecular sizes of KNH1144 gp120 monomer and SOSIP R6 gp140 trimer proteins. A Superdex 200 size exclusion column was calibrated with thyroglobulin (669 kDa), ferritin (440 kDa), BSA (67 kDa) and RNAse A (13.7 kDa) as molecular weight standards. In addition, monomeric JR-FL gp120 was also analyzed as a control. KNH1144 gp120 and JR-FL gp120 were each found to migrate at an apparent molecular weight of 210 kDa (see FIG. 20). These values are consistent with those found for JR-FL gp120 (10).

To further study the oligomeric nature of the KNH1144 SOSIP R6 gp140 trimer, final purified preparations were treated with Tween® 20 prior to analysis on Superdex 200 SEC to yield homogenous and unambiguous trimer samples devoid of HMW aggregate. Initial studies showed re-formation of HMW aggregate when treated trimer samples were resolved in non-detergent TN-500 buffer on the SEC column. The resulting mixed trimer-aggregate fractions, presumably re-formed upon separation of the Tween® 20 from the gp140 oligomers in non-detergent buffer, was considered unsuitable for SEC analysis due to its heterogeneous nature.

In order to maintain homogenous trimers, treated trimer was resolved in the presence of TN-500 containing 0.05% Tween® 20 (TNT-500). As shown in FIG. 16, (bottom panel BN-PAGE), the trimer (thick arrow) migrated from fractions B10 through C2, represented in the major peak, with its peak signal at fraction B12 (vertical arrow). The retention time at this fraction corresponds to an apparent calculated molecular weight of ~518 kDa. The reported apparent molecular weight (MW) of JR-FL SOSIP gp140 trimer calculated via Superdex 200 SEC analysis is ~520 kDa (9); and thus, the calculated apparent MW value for KNH1144 SOSIP R6 gp140 trimer is consistent with MW values of other SOSIP envelope trimers.

Effect of Tween® 20 Treatment on KNH1144 SOSIP R6 Antigenicity:

Studies of the antigenic properties of unpurified KNH1144 SOSIP R6 gp140 (19) showed that it was immunoprecipitated by the neutralizing molecules 2G12, b12, CD4-IgG2, as well as the non-neutralizing mAb b6. The experiments described herein further assessed the effect of the Tween® 20 aggregate collapse on the antigenic properties of KNH1144 SOSIP HMW aggregates to determine if conversion of HMW aggregate into trimer favorably enhanced antigenicity.

SEC fractions containing 80% KNH1144 SOSIP R6 HMW aggregate content (as shown in FIG. 15D, –lane) were either untreated or Tween® 20 treated (typical reaction is represented in FIG. 15D). The antigenicity of the proteins in the presence and absence of Tween® 20 was examined using a lectin based ELISA. These results are shown in FIG. 18A. All the anti-env antibodies and CD4-IgG2, displayed increased binding to the Tween® 20 treated aggregate. The above experiments were performed on Tween® 20 converted trimer, using preps containing >80% HMW aggregate.

To demonstrate that Tween® 20 treatment did not unfavorably disrupt the above antibody epitopes on trimers, similar lectin ELISAs were performed using 2G12, b6, b12 and CD4-IgG2 on SOSIP R6 gp140 trimers that contained low amounts of HMW aggregate (~10-15% content) that were either untreated or treated with Tween® 20. As shown in FIG. 18B, no significant differences were observed in the antigenicity of trimer in presence or absence of Tween® 20. Unfortunately, since the HMW aggregate species is present in very limiting quantities, the Tween® 20 effect was assessed using only the above mentioned mAbs. These results show that Tween® 20 treatment and consequential conversion of HMW aggregate to resulting trimer enhances epitope exposure for Env binding antibodies. Thus Tween® 20 treatment and presence may offer favorable consequences in the context of KNH1144 SOSIP R6 gp140 trimer stability and antibody epitope exposure.

Effect of Tween® 20 Treatment on the Ionic Properties of KNH1144 SOSIP R6 gp140 Trimer:

DEAE anion exchange chromatography was used to examine the effect of Tween® 20 on the ionic properties of SOSIP R6 gp140 and control proteins. Untreated or Tween® 20 treated KNH1144 SOSIP R6 gp140 trimer spiked with $a_2M$ contaminating protein (which is unaffected by Tween® 20 and binds to anion exchange resins) were applied over DEAE anion exchange column (FIG. 18, Load). The column was washed and eluted and fractions were analyzed via BN-PAGE and Coomassie staining and is shown in FIG. 18. As expected, untreated SOSIP R6 gp140 trimer and the $a_2M$ contaminant bound to the DEAE column and were recovered in the elution fraction (FIG. 18, Untreated control, top panel, denoted by asterisks). However, upon treatment with Tween® 20, the KNH1144 SOSIP R6 gp140 trimer was found in the flow-through (FT) fractions of the column (FIG. 18, Tween® 20 treated, bottom panel, FT, denoted by asterisks), indicating that it did not bind to the DEAE, unlike the untreated trimer. Residual trimer is further recovered in the wash fraction (FIG. 18, Wash). In contrast, the $a_2M$ contaminant, which was used as the internal control, bound to the DEAE column and was recovered in the elution, indicating that it was unaffected by the presence of Tween® 20 (FIG. 18, Tween® 20 treated, bottom panel, Elution).

In other similar experiments, in which BSA, another acidic protein was substituted as the contaminant, similar results were obtained. This indicates that Tween® 20 treatment may exert its action on KNH1144 SOSIP R6 HMW aggregate and trimer through a combination of hydrophobic interactions that possibly involve perturbations in inter- and/or intra-subunit charge-charge interactions, as examined by DEAE anion exchange chromatography.

Electron Microscopy and Digital Imaging of KNH1144 SOSIP R6 gp140 Trimers:

Electron microscopy was performed on purified SOSIP R6 preparations employing negative stain EM analysis. The results, shown in FIG. 19, reveal that the majority of the observed structures displayed a regular compact morphology with approximate three-fold symmetry. This tri-lobed configuration is most apparent in preparations with deeper stain (FIG. 19; panel of trimers) that are less subject to the flattening that can occur in thinner staining preparations.

Initially, for the EM studies, it was found that the uranyl formate negative straining technique was not compatible with detergent-containing buffers. However, some trimeric structures of the anticipated dimensions were observed in the poorly staining preparations. Thereafter, the KNH1144 SOSIP preparation was subjected to a detergent removal protocol, which yielded improved staining. Following detergent removal, the majority of the observed structures displayed a regular compact morphology with approximate three-fold symmetry (e.g., FIG. 19). This configuration is most apparent in preparations with deeper stain that are less subject to the flattening that can occur in thinner staining preparations.

In order to calculate diameters of the trimers, 70 spikes in the shallow stain samples were scored and a diameter of 13.5±1.73 nm was calculated. Seventy eight (78) trimers from the deep stain were scored and resulted in a diameter of 11.6 nm±1.75 nm. The shallow stain preparation likely gives a slight overestimation of the size and the deep stain preparation gives a slightly underestimated size. Therefore, the true size is likely to be 12.6±1.74 nm (i.e., and in line with authentic Env spikes measured in situ on both negatively stained, as well as unstained, cryo-EM preparations of SIV (36, 37). Thus the biophysical EM analysis of KNH1144 SOSIP R6 gp140 is in good agreement with the above biochemical data and confirms the oligomeric status of the purified KNH1144 env complex as being trimeric.

Discussion

In the context of identifying and pursuing a variety of HIV-1 Env-based protein vaccines, described herein is the purification and characterizion of a novel subtype A KNH1144 trimeric envelope spike protein and its properties. Several novel insights were gained as a result of these studies, which revealed the biochemical effects of Tween® 20 on the oligomeric conformations of the KNH1144 SOSIP R6 proteins. Until the present invention, only one subtype B envelope, HIV-1 JR-FL has been manipulated to a purified form to mimic as closely as possible the native trimeric structure of the HIV-1 viral surface envelope complex via the SOSIP technology (8-11, 15-17). The present invention provides another clade, clade A KNH1144, for which the SOSIP technology results in purified trimeric envelopes that are stable, soluble, and fully cleaved.

The purification process implemented according to the present invention for the KNH1144 SOSIP trimers provides a marked improvement over that utilized for JR-FL SOSIP gp140 trimers. For the KNH1144 SOSIP, the GNA lectin column provided a significant enrichment of gp140 proteins, but elution off the column significantly destabilized the gp140 trimers, resulting in a compromise of trimer fidelity on the column. As a result, significant dissociation of the trimer to resulting dimer and monomer was noticed. This destabilization could be brought about from *Galanthus Nivalis* lectin binding to 1-3 and 1-6 mannose linkages on the gp140 high mannose chains, which are internal linkages and not terminal linkages (20). During elution, the affinity of the lectin for the mannan is likely much higher than the intersubunit protein-protein affinities of the 3 $gp^{120}$-$gp^{41}{}_{ECTO}$ monomers contributing to trimer formation, resulting in destabilization and dissociation into component dimers and monomers. To alleviate some measure of the destabilization that could be caused due to resulting sheer stresses during elution, a one hour incubation in MMP eluting buffer was included. So while a highly enriching step, the lectin affinity column also decreased the final yield of trimer significantly, due to its dissociation during the elution phase.

The next step in the purification, Superdex 200 SEC, while somewhat efficient in resolving away monomer, was not very effective in resolution of dimer from trimer. The incorporation of a DEAE weak anion exchange chromatography step was very efficient in resolving dimer (and residual monomer) away from trimer, resulting in trimeric KNH1144 SOSIP R6 gp140 of high purity. Notably, binding (and retention) of the trimer occurred under a relatively polar environment (vis-a-vis ion exchange) at 75 mM NaCl, while dimer and monomer flowed through the DEAE column under these conditions.

It is relevant to extrapolate from its behavior on anion exchange chromatography that the nature of the KNH1144 SOSIP R6 g140 trimer is that of an acidic protein, which would be contrary to its predicted basic isoelectric point (pI) of 8.73 calculated for the protein backbone. However, the likely presence of the predicted acidic sialylated complex oligosaccharide chains on the gp140 (21, 22) would contribute to a decrease in the overall charge of the glycoprotein and thus confer on it properties of an acidic protein. Indeed, analysis of purified KNH1144 SOSIP R6 gp140 trimers on isoelectric focusing gels reveal it to migrate at a pI range of 5.9 to 6.1, consistent with the above observations.

The purified trimer was shown to contain variable amounts of HMW aggregate (FIG. 14, right panel, BN-PAGE), which could not be attributed to being formed at any one particular step of the purification, although one possibility might be at the lectin elution step. As mentioned before, one of the key improvements made in this purification protocol is absence of SDS-insoluble aggregates in the final prep, which are formed by abberantly formed disulfide bonds and are visualized by their slow migration on a non-reduced SDS-PAGE. As detected by Coomassie staining and confirmed by anti-envelope Western blot, little to no SDS-insoluble aggregates were observed (FIG. 14, left and middle panels, Non-Red SDS-PAGE and Anti-Env blot). This is in contrast to what was observed with JR-FL SOSIP gp140 (R6 and non-R6 versions), where SDS-insoluble aggregates comprised a significant percentage of the final preparations (9, 10, 11).

Based on observations regarding non-ionic detergent treatments of KNH1144 SOSIP R6 gp140 trimers (19), Tween® 20 was used to address the co-purifying HMW aggregate present in the final trimer preparations. Tween® 20 was chosen because initial observations had shown that Tween® 20 treatment was mild and did not result in any detectable monomer formation, unlike treatment with the other non-ionic detergents NP-40 and Triton X-100, where dimers and monomers were observed upon treatment (19). Tween® 20 treatment of the final purified KNH1144 SOSIP R6 trimer preparation was highly reproducible and resulted in the "conversion" of the HMW aggregate species, as shown in FIG. 14 (right panel, BN-PAGE). Since this resulted in a single, homogenous, oligomeric species of KNH1144 SOSIP R6 gp140 trimers, we routinely incorporated it as the final step in our preparations. Further analysis using reduced SDS-PAGE gels showed that the purified trimer was fully cleaved, with practically undetectable uncleaved protein (as visualized by both Coomassie staining and Western blot analysis) (FIG. 14, left panel, Red SDS-PAGE). The initial purifications were performed using a non-R6 version of KNH1144 SOSIP gp140, which resulted in ~40-50% of uncleaved protein in the final preparation, prompting the development of the R6 version. This also represents another improvement over JR-FL SOSIP R6 gp140 trimers, where cleavage of gp120-$gp41_{ECTO}$ was not as efficient (9, 11).

In order to expand the initial Tween® 20 observations to the stability of HMW aggregates, a variety of experiments were performed to characterize the effect of Tween® 20 and to better understand its mechanism of action. As shown in FIG. 15, the effect of Tween® 20 is dose dependent, time dependent and temperature independent within the parameters that were examined. Its effect is remarkably specific to KNH1144 SOSIP R6 HMW aggregate and trimers and has no effect on gp120 monomers, or KNH1144 SOSIP R6 dimers. In addition, other similar large, macromolecular, acidic proteins such as $a_2M$ are not affected by the detergent. Initially, the hypothesis was that the Tween® 20 specifically interacted with points of gp120-$gp41_{ECTO}$ intersubunit contact within the HMW aggregate, presumably in a hydrophobic manner. In this context, the HMW aggregate would have to be comprised of some multiple of trimer (most likely a dimer of trimers), since detergent treatment specifically results in a "rearrangement" to a trimeric configuration. The specificity of this reaction can further be defined by the observation that dimeric KNH1144 SOSIP R6 gp140 proteins are unaffected and do not undergo the collapse (FIG. 15D). In addition, Tween® 20 treatment would also seem to cause the trimer to assume a more compact configuration, as evident by its slightly more rapid mobility on BN-PAGE (FIG. 14).

While the anti-flocculatory effects of non-ionic detergents on aggregates of macromolecular proteins such as antibodies (immunoglobulins, for example) are well known and documented, the mechanisms of their actions have been realized to be largely by pre-emption of unfavorable hydrophobic interactions by detergent intercalation. Tween® 20, however, would seem to exert its action in a somewhat paradoxical mechanism, since treatment of the KNH1144 SOSIP R6 gp140 trimer with the detergent renders it unable to interact with anion exchange resins such as DEAE (FIG. 18, bottom panel, Tween® 20 treated), indicating that the overall charge of the trimer was being affected by the detergent.

Since the nature of non-ionic detergents is exactly that, i.e., non-ionic, it is difficult to realize how an uncharged molecule such as Tween® 20 would affect the charge status of a large, macromolecular oligomer such as the KNH1144 SOSIP R6 trimer. Furthermore, this effect is highly specific to the trimer, as other such large, highly charged (acidic) oligomeric proteins such as $a_2M$ and even smaller ones such as BSA are unaffected by the detergent. One hypothesis that has emerged from this invention is that perhaps the Tween® 20 was "coating" the trimer in a manner that may cause perturbations in its conformation, resulting in its "compactness". These perturbations would be of a subtle nature which involve the various points of contact between the individual component gp140 monomers, causing disruption and destabilization of interactions that favor the HMW aggregate conformation. A consequence of these perturbations would be "shielding" of ionic charges that would normally be exposed (and contribute to binding to ion exchange resins). It is reasonable to speculate that perhaps the charges that are "shielded" are those on the sialic acid residues of the complex carbohydrate chains, since these would be most likely to be highly exposed at the surface (21, 22). Tween® 20 and Tween® 80 are polyoxyethylene sorbitan esters of fatty acids and thus may likely interact with the sialic acids, causing a charge "neutralization" effect. The involvement of the sialic acid residues can be investigated by mild sialidase treatment (21, 22) and removal of these residues, followed by Tween® 20 treatment, followed by monitoring of binding on ion exchange resins.

To further biochemically characterize the purified KNH1144 monomeric and trimeric envelope proteins, size exclusion chromatography analyses were performed in order to ascertain their apparent molecular masses. These were performed on Tween® 20 treated trimers that were devoid of any HMW aggregates and thus consisted of only one homogeneously oligomeric species, i.e., the trimer, and therefore would yield unambiguous results. The retention times of the KNH1144 SOSIP R6 gp140 trimer resulted in a calculated apparent molecular weight of ~518 kDa. This is consistent with the reported calculated apparent molecular weight of 520 kDa for the other SOSIP gp140 trimer, JR-FL SOSIP gp140 (9). The predicted molecular weight for a trimer such as KNH1144 (and JR-FL) would be ~420 kDa (3×140 kDa monomers). Thus, similar to JR-FL SOSIP gp140, the KNH1144 SOSIP R6 gp140 trimer also exhibits an aberrant migration on SEC, presumably due to interactions of its N-linked glycans with the dextran-(agarose polymer) based matrix of Superdex 200, resulting in a higher than expected apparent molecular mass. In addition, envelope proteins have been shown to be non-globular in shape (10, 23, 24); therefore, gel filtration may not be optimal for determination of their precise molecular masses. This also extends to the KNH1144 gp120 monomer as well. Values of ~210 kDa were obtained for KNH1144 gp120 and the control JR-FL gp120 (see FIG. 20). The reported value for JR-FL gp120 is 200 kDa (10); accordingly, the obtained values are well within the expected range (given that molecular weight determination via SEC is not extremely accurate, unlike other methodologies such as mass spectrometry). Thus, gp120, whose predicted molecular weight ranges from ~95 to ~120 kDa, results in an aberrant migratory pattern on SEC, presumably due to its glycan interactions with the sizing column matrix. It should be noted that unlike the KNH1144 SOSIP R6 gp140 trimer, migration of KNH1144 gp120 (and JR-FL gp120) were not affected by the presence or absence of Tween® 20, consistent with the initial BN-PAGE observations (FIG. 14, right panel, gp120).

While it would seem that the presence of Tween® 20 for KNH1144 SOSIP R6 gp140 proteins would be advantageous, possible Tween® 20 effects on the antigenicity of the HMW aggregate and trimer were examined. Effects on antigenicity was examined by performing lectin ELISAs with the NAbs 2G12, b12, HIVIg, the CD4-IgG2 antibody conjugate PRO 542, as well as the non-neutralizing mAb b6, to gain information on neutralizing/non-neutralizing epitope exposure and accessibility. It was reasoned that trimer preparations containing 10-30% HMW aggregate may not undergo significant enough changes that would be detectable in a non-quantitative assay such as IPs, i.e., subtle changes (20-30% changes) may go undetected in such an assay due to sensitivity. However, samples representing extremes may undergo significantly high changes that should be detectable in an assay format such as ELISA. Therefore, SEC fractions that contained 80% HMW aggregate were used, which would reflect one extreme prior to Tween® 20 treatment and the resulting trimer, which would reflect the other extreme post treatment. A representative reaction of this is illustrated in FIG. 15D.

As shown in FIG. 17A, significant epitope exposures were observed upon Tween® 20 rearrangement of the HMW aggregate to trimer, and these changes were noticed for all of the anti-env agents. These changes indeed were not as apparent in trimer preparations that were predominantly trimer, with low aggregate content (10-15%) (FIG. 21B). Thus the treated, purified trimer displays antigenic properties similar to that which was previously observed with crude, unpurified trimer supernatants, i.e., binding to 2G12, b6, b12 and PRO 542 (19). In the context of HIVIg, which is a low neutralizing polyclonal human antisera directed against gp120 hypervariable loop (40), it can be inferred that this epitope is accessible on the surface of the HMW aggregate, based on its ability to bind the antibody in absence of Tween® 20. Consistent with the other anti-Env agents examined here, HIVIg epitope exposure also significantly increased on the rearranged trimer, upon treatment with Tween® 20. The likely explanation to these increases in epitope exposure is that "disruption/rearrangement" of the aggregate and its subsequent conversion to trimer unshields the above mentioned surfaces and thus, upon conversion, these surfaces are now exposed on their individual trimers and are accessible to the antibodies. From the context of a single HMW aggregate which is likely to be a multimer of trimers, only a small portion of these epitopes are accessible, most probably due to steric hindrance from adjacently "clumped" SOSIP R6 trimers/oligomers. When the single HMW aggregate is then Tween® 20 converted to resulting trimers, antibody epitopes are now exposed on every one of the resulting individual component trimers, resulting in an increase in antibody accessibility and binding. Thus Tween® 20 treatment and its conversion of the aggregate to trimer do not seem to have detrimental effects on antigenicity and may be favorable to the structural properties of the KNH1144 SOSIP R6 gp140 proteins.

Analysis of KNH1144 SOSIP R6 gp140 proteins by negative stain EM further confirmed the biochemical observations that these gp140 proteins were indeed trimeric in nature (FIG. 19). A distinguishing feature of the KNH1144 SOSIP R6 construct, in comparison to other similar constructs of trimerized gp120 and gp140, is its compact nature. Most other constructs show either predominantly loosely associated subunits or a mix of loosely and tightly associated subunits (5, 18, 38). The observation that the KNH1144 SOSIP R6 trimer is compact is associated with anti-Env antibody epitope availability. EM on Tween®-treated trimer which has favorable anti-Env epitope exposure was performed. It is somewhat incongruous from a purely steric standpoint that a "compact" trimer would also have improved epitope exposure, a consequence expected from a "loose" or "elongated" structure. Immunoelectron microscopy analyses with the above mentioned antibodies will further address the exposure of epitopes on trimeric forms.

The present invention expands the panel of trimeric HIV-1 envelope proteins that may be used as protein-based HIV-1 vaccine candidates or serve as a template for future design of Env based protein vaccine candidates, using the SOSIP technology. Immunological studies in rabbits with JR-FL SOSIP R6 gp140 trimers, while effective in eliciting NAbs, were limited in their breadth of neutralization of primary HIV-1 isolates (11). Factors associated with the biochemical nature of the JR-FL SOSIP gp140 and other oligomeric Env proteins that are thought to limit their observed immunological response in animals, such as inefficient furin cleavage of the gp120-gp41$_{ECTO}$ cleavage site giving rise to heterogenous trimers (containing both cleaved and uncleaved trimers), presence of SDS-insoluble aggregates and presence of undesirable gp140 oligomers such as dimers and monomers (5, 6, 9, 10, 11, 27-30) have been issues needing resolution.

The description of the KNH1144 SOSIP R6 gp140 trimers of the present invention addresses most of these issues. Furthermore, the description of the Tween® 20 affects on coverting HMW aggregates to trimeric forms further expands on current knowledge of the aggregate species in HIV-1 biology. Of significance, it was shown for the first time, that oligomeric Env protein complexes designed using the SOSIP technology platform are indeed trimeric from EM images and that the trimers are of a similar diameter as native spikes on the HIV-1 virion (36, 37). Expansion of the panel of potential HIV-1 SOSIP protein vaccine candidates by development of a clade A envelope according to this invention now allows for immunological evaluation of the KNH1144 SOSIP R6 gp140 trimer in small animals, for example. Such evaluations will assist in determining the efficacy of KNH1144 SOSIP R6 gp140 trimers as immunogens capable of eliciting broadly neutralizing immune responses directed against HIV-1.

REFERENCES

1. UNAIDS: AIDS Epidemic Update: December 2005, ISBN 92 9 173439 X.
2. Kijak, G. H., and McCutchan, F. E. (2005) *Curr Infect Dis Rep.* 7, 480-488.
3. Jeffs, S. A., Goriup, S., Kebble, B., Crane, D., Bolgiano, B., Sattentau, Q., Jones, S., and Holmes, H. (2004) *Vaccine.* 22, 1032-1046.
4. Srivastava, I. K., Stamatatos, L., Legg, H., Kan, E., Fong, A., Coates, S. R., Leung, L., Wininger, M., Donnelly, J. J., Ulmer, J. B., and Barnett, S. W. (2002) *J Virol.* 76, 2835-2847.
5. Srivastava, I. K., Stamatatos, L., Kan, E., Vajdy, M., Lian, Y., Hilt, S., Martin, L., Vita, C., Zhu, P., Roux, K. H., Vojtech, L., Montefiori, D. C., Donnelly, J., Ulmer, J. B., and Barnett, S. W. (2003) *J Virol.* 77, 11244-11259.
6. Yang, X., Florin, L., Farzan, M., Kolchinsky, P., Kwong, P. D., Sodroski, J., and Wyatt, R. (2000) *J Virol.* 74, 4746-4754.
7. Grundner, C., Li, Y., Louder, M., Mascola, J., Yang, X., Sodroski, J., and Wyatt R. (2005) *Virology* 331, 33-46.
8. Binley, J. M., Sanders, R. W., Clas, B., Schuelke, N., Master, A., Guo, Y., Kajumo, F., Anselma, D. J., Maddon, P. J., Olson, W. C., and Moore, J. P. (2000) *J Virol.* 74, 627-643.
9. Sanders, R. W., Vesanen, M., Schuelke, N., Master, A., Schiffner, L., Kalyanaraman, R., Berkhout, B., Maddon, P. J., Olson, W. C., Lu, M., and Moore, J. P. (2002) *J Virol.* 76, 8875-8889.
10. Schulke, N., Vesanen, M. S., Sanders, R. W., Zhu, P., Lu, M., Anselma, D. J., Villa, A. R., Parren, P. W., Binley, J. M., Roux, K. H., Maddon, P. J., Moore, J. P., and Olson, W. C. (2002) *J Virol.* 76, 7760-7776.
11. Beddows, S., Schulke, N., Kirschner, M., Barnes, K., Franti, M., Michael, E., Ketas, T., Sanders, R. W., Maddon, P. J., Olson, W. C., and Moore, J. P. (2005) *J Virol.* 79, 8812-8827.
12. Emini, E. A. and Koff, W. C. (2004) *Science* 304, 1913-1914.
13. Poignard, P., Saphire, E. O., Parren, P. W., and Burton, D. R. (2001) *Annu Rev Immunol.* 19, 253-274.
14. Wyatt, R., and Sodroski, J. (1998) *Science* 280, 1884-1888.
15. Sanders, R. W., Schiffner, L., Master, A., Kajumo, F., Guo, Y., Dragic, T., Moore, J. P., and Binley, J. M. (2000) *J Virol.* 74, 5091-5100.
16. Binley, J. M., Sanders, R. W., Master, A., Cayanan, C. S., Wiley, C. L., Schiffner, L., Travis, B., Kuhmann, S., Burton, D. R., Hu, S. L., Olson, W. C., and Moore, J. P. (2002) *J Virol.* 76, 2606-2616.
17. Binley, J. M., Cayanan, C. S., Wiley, C., Schulke, N., Olson, W. C., and Burton, D. R. (2003) *J Virol.* 77, 5678-5684.
18. Pancera, M., Lebowitz, J., Schon, A., Zhu, P., Freire, E., Kwong, P. D., Roux, K. H., Sodroski, J., and Wyatt, R. (2005) *J Virol.* 79, 9954-9969.
19. Beddows, S., Kirschner, M., Campbell-Gardener, L., Franti, M., Dey, A, K., Iyer, S, N., Paluch, M., Master, A., Overbaugh, J., VanCott, T., Olson, W. C., and Moore, J. P. (2006) *AIDS Res Hum Retroviruses* (in press).
20. Botos, I., and Wlodawer, A. (2005) *Prog Biophys Mol Biol.* 88, 233-282.
21. Scanlan, C. N., Pantophlet, R., Wormald, M. R., Ollmann, Saphire, E., Stanfield, R., Wilson, I. A., Katinger, H., Dwek, R. A., Rudd, P. M., and Burton, D. R. (2002) *J Virol.* 76, 7306-7321.
22. Sanders, R. W., Venturi, M., Schiffner, L., Kalyanaraman, R., Katinger, H., Lloyd, K. O., Kwong, P. D., and Moore, J. P. (2002) *J Virol.* 76, 7293-7305.
23. Center, R. J., Earl, P. L., Lebowitz, J., Schuck, P., and Moss, B. (2000) *J Virol.* 74, 4448-4455.
24. Center, R. J., Schuck, P., Leapman, R. D., Arthur, L. O., Earl, P. L., Moss, B., and Lebowitz, J. (2001) *Proc Natl Acad Sci USA.* 98, 14877-14882.
25. Trkola, A., Pomales, A. B., Yuan, H., Korber, B., Maddon, P. J., Allaway, G. P., Katinger, H., Barbas, C. F. 3rd, Burton, D. R., Ho, D. D., and Moore, J. P. (1995) *J Virol.* 69, 6609-6617.
26. Trkola, A., Purtscher, M., Muster, T., Ballaun, C., Buchacher, A., Sullivan, N., Srinivasan, K., Sodroski, J., Moore, J. P., and Katinger, H. (1996) *J Virol.* 70, 1100-1108.
27. Center, R. J., Lebowitz, J., Leapman, R. D., and Moss, B. (2004) *J Virol.* 78, 2265-2276.
28. Chakrabarti, B. K., Kong, W. P., Wu, B. Y., Yang, Z. Y., Friborg, J., Ling, X., King, S. R., Montefiori, D. C., and Nabel, G. J. (2002) *J Virol.* 76, 5357-5368.

29. Zhang, C. W., Chishti, Y., Hussey, R. E., and Reinherz, E. L. (2001) *J Biol Chem.* 276, 39577-39585.
30. Yang, X., Lee, J., Mahony, E. M., Kwong, P. D., Wyatt, R., and Sodroski, J. (2002) *J Virol.* 76, 4634-4642.
31. Lian, Y., Srivastava, I., Gomez-Roman, V. R., Zur Megede, J., Sun, Y., Kan, E., Hilt, S., Engelbrecht, S., Himathongkham, S., Luciw, P. A., Otten, G., Ulmer, J. B., Donnelly, J. J., Rabussay, D., Montefiori, D., van Rensburg, E. J., and Barnett, S. W. (2005) *J Virol.* 79, 13338-13349.
32. Roben, P., Moore, J. P., Thali, M., Sodroski, J., Barbas, C. F. 3rd., and Burton, D. R. (1994) *J Virol.* 68, 4821-4828.
33. Burton, D. R., Pyati, J., Koduri, R., Sharp, S. J., Thornton, G. B., Parren, P. W. H. I., Sawyer, L. S. W., Hendry, R. M., Dunlop, N., Nara, P. L., Lamacchia, M., Garratty, G., Stiehm, E. R., Bryson, Y. J., Cao, Y., Moore, J. P., Ho, D. D., and Barbas, C. F. 3rd. (1994) *Science* 266, 1024-1027.
34. Roux, K. H. (1989) *Methods Enzymol.* 178, 130-144.
35. Roux, K. H. (1996) *Methods* 10, 247-256.
36. Zhu, P., Chertova, E., Bess, J., Jr., Lifson, J. D., Arthur, L. O., Liu, J., Taylor, K. A., and Roux, K. H. (2003) *Proc Natl Acad Sci USA.* 100, 15812-15817.
37. Qiao, Z. S., Kim, M., Reinhold, B., Montefiori, D., Wang, J. H., and Reinherz, E. L. (2005) *J Biol Chem.* 280, 23138-23146.
38. Olson, W. C., and Maddon, P. J. (2003) *Curr Drug Targets Infect Disord.* 3, 255-262.

Experimental Details IV

According to the present invention, the gp41/gp120 trimeric conformation can be stabilized by one or more of the following changes in the gp120 and gp41 sequences:

(1) specific, targeted amino acid sequence changes in the N-terminal region of the gp41 subunit that stabilize the gp120-gp41 trimeric conformation;
(2) an isoleucine to proline substitution at a position equivalent to KNH1144 position 559 (I559P) in the N-terminal heptad region of gp41 ectodomain to promote association between gp41-gp41 association; and
(3) inter-subunit disulfide bonds (SOS) between gp120 and gp41.

Several molecular determinants of enhanced trimer stability are described herein.

Many examples of nucleotide and amino acids for gp160 sequences are available, for example, in the database provided by the National Center for Biotechnology Information (NCBI) (see http://www.ncbi.nlm.nih.gov/).

One example of a gp160 glycoprotein sequence is that of the HIV-1 KNH1144 isolate. A sequence for the KNH1144 gp160 is available at NCBI accession number AAW72237 (gi: 58374202); a nucleotide sequence encoding this gp160 protein is available at accession number AY736812 (gi: 58374201). See website at ncbi.nlm.nih.gov. The amino acid sequence for this KNH1144 gp160 protein is provided below (SEQ ID NO:5).

```
  1 MIVMGTQRNY QHLLRWGTMI LGLIIICSAA DNLWVTVYYG
 41 VPVWKDAETT LFCASDAKAY ETEKHNVWAT HACVPTDPNP
 81 QEIPLENVTE EFNMWKNKMV EQMHTDIISL WDQSLQPCVK
121 LTPLCVTLNC TDATNGTIGN ITDEMKGEIK NCSFNITTEI
161 RDKKQKVYSL FYRLDVVPIE PDSSNSSRNS SEYRLINCNT
201 SAITQACPKV SFEPIPIHYC APAGFAILKC RDKEFNGTGK
241 CKNVSTVQCT HGIKPVVSTQ LLLNGSLAEG EVRIRSENIT
281 NNAKTIIVQL VEPVRINCTR PNNNTRESVR IGPGQAFFAT
321 GDIIGDIRQA HCNVSRSQWN KTLQQVAAQL GEHFKNKAIT
361 FNSSSGGDLE ITTHSFNCGG EFFYCNTSGL FNSTWKANNG
401 TWKANISESN NTEITLQCRI KQIINMWQRT GQAIYAPPIQ
441 GVIRCESNIT GLLLTRDGGE GNNESEIFRP GGGDMRDNWR
481 SELYKYKVVK IEPLGVAPTR ARRRVVGREK RAVGIGAVFL
521 GFLGAAGSTM GAASITLTVQ ARQLLSGIVQ QQSNLLRAIE
561 AQQHMLKLTV WGIKQLQARV LAVERYLRDQ QLLGIWGCSG
601 KLICTTNVPW NSSWSNKSHD EIWNNMTWLQ WDKEISNYTN
641 LIYSLIEESQ NQQEKNEQDL LALDKWASLW NWFDISKWLW
681 YIKIFIMIVG GLIGLRIVFA VLAVIKRVRQ GYSPVSFQIH
721 NPNPGGLDRP GRIEEEGGEP GRGRSIRLVS GFLALAWDDL
761 RNLCLFSYHR LRDFALIVAR TVELLGHSSL KGLRLGWEGL
801 KYLWNLLVYW SQELKTSAIN LVDTIAIAVA GWTDRVIEIG
841 QGIGRAFLHI PRRIRQGLER ALL
```

According to the invention, the KNH1144 HIV gp160 protein gives rise to modified gp120 and gp41 polypeptides that have improved gp41/gp120 trimer stability relative gp41/gp120 trimers from other HIV strains. Such stability is due in part to five amino acids differences between the KNH1144 HIV gp160 protein and other HIV gp160 proteins. These five amino acid differences are found at amino acid positions 535, 543, 553, 567 and 588 of the KNH1144 amino acid sequence. Thus, the modified, stabilized KNH1144 HIV gp160 protein comprises isoleucine at position 535 (I535), glutamine at position 543 (Q543), serine at position 553 (S553), lysine at position 567 (K567) and arginine at position 588 (R588). These "stabilizing" amino acids are highlighted and underlined in the KNH1144 HIV gp160 sequence shown above. Of the foregoing five amino acid residues, Q543, S553 and K567 have the greatest effect when introduced in combination. I535 and R588 make an additional minor contribution. All five of the amino acid residues may be included in an HIV isolate for the production of stable trimers. Alternatively, Q543, S553 and K567 are included, while I535 and R588 may be optionally included, for stabilization in modified HIV-1 isolates. The introduction of these changes did not impair the exposure of various neutralizing antibody epitopes on the resulting gp140 proteins, suggesting the overall antigenic structure of the trimer is not adversely affected.

As provided by the present invention, stabilized gp41/gp120 trimers are formed by modifying an HIV isolate to contain isoleucine at position 535, glutamine at position 543, serine at position 553, and lysine at position 567 and/or arginine at position 588 in any HIV gp160 or gp41 polypeptide. Moreover, according to the invention, a gp41 protein has improved stability if a proline is used at an amino acid position equivalent to amino acid position 559, for example of the below KNH1144 gp160 polypeptide. The KNH1144 gp160 polypeptide typically has isoleucine instead of proline at position 559. The sequence of the I559P mutant polypeptide of the KNH1144 gp160 protein is provided below (SEQ ID NO:6).

```
  1 MIVMGTQRNY QHLLRWGTMI LGLIIICSAA DNLWVTVYYG
 41 VPVWKDAETT LFCASDAKAY ETEKHNVWAT HACVPTDPNP
 81 QEIPLENVTE EFNMWKNKMV EQMHTDIISL WDQSLQPCVK
121 LTPLCVTLNC TDATNGTIGN ITDEMKGEIK NCSFNITTEI
161 RDKKQKVYSL FYRLDVVPIE PDSSNSSRNS SEYRLINCNT
201 SAITQACPKV SFEPIPIHYC APAGFAILKC RDKEFNGTGK
241 CKNVSTVQCT HGIKPVVSTQ LLLNGSLAEG EVRIRSENIT
281 NNAKTIIVQL VEPVRINCTR PNNNTRESVR IGPGQAFFAT
321 GDIIGDIRQA HCNVSRSQWN KTLQQVAAQL GEHFKNKAIT
361 FNSSSGGDLE ITTHSFNCGG EFFYCNTSGL FNSTWKANNG
401 TWKANISESN NTEITLQCRI KQIINMWQRT GQAIYAPPIQ
441 GVIRCESNIT GLLLTRDGGE GNNESEIFRP GGGDMRDNWR
481 SELYKYKVVK IEPLGVAPTR ARRRVVGREK RAVGIGAVFL
521 GFLGAAGSTM GAASITLTVQ ARQLLSGIVQ QQSNLLRAPE
561 AQQHMLKLTV WGIKQLQARV LAVERYLRDQ QLLGIWGCSG
601 KLICTTNVPW NSSWSNKSHD EIWNNMTWLQ WDKEISNYTN
641 LIYSLIEESQ NQQEKNEQDL LALDKWASLW NWFDISKWLW
681 YIKIFIMIVG GLIGLRIVFA VLAVIKRVRQ GYSPVSFQIH
721 NPNPGGLDRP GRIEEEGGEP GRGRSIRLVS GFLALAWDDL
761 RNLCLFSYHR LRDFALIVAR TVELLGHSSL KGLRLGWEGL
801 KYLWNLLVYW SQELKTSAIN LVDTIAIAVA GWTDRVIEIG
841 QGIGRAFLHI PRRIRQGLER ALL
```

In addition, in some embodiments, a KNH1144 gp41 protein has improved stability if methionine is used at position 535 instead of isoleucine. The sequence of this I535M mutant of the KNH1144 gp160 protein is provided below (SEQ ID NO:7).

```
  1 MIVMGTQRNY QHLLRWGTMI LGLIIICSAA DNLWVTVYYG
 41 VPVWKDAETT LFCASDAKAY ETEKHNVWAT HACVPTDPNP
 81 QEIPLENVTE EFNMWKNKMV EQMHTDIISL WDQSLQPCVK
121 LTPLCVTLNC TDATNGTIGN ITDEMKGEIK NCSFNITTEI
161 RDKKQKVYSL FYRLDVVPIE PDSSNSSRNS SEYRLINCNT
201 SAITQACPKV SFEPIPIHYC APAGFAILKC RDKEFNGTGK
241 CKNVSTVQCT HGIKPVVSTQ LLLNGSLAEG EVRIRSENIT
281 NNAKTIIVQL VEPVRINCTR PNNNTRESVR IGPGQAFFAT
321 GDIIGDIRQA HCNVSRSQWN KTLQQVAAQL GEHFKNKAIT
361 FNSSSGGDLE ITTHSFNCGG EFFYCNTSGL FNSTWKANNG
401 TWKANISESN NTEITLQCRI KQIINMWQRT GQAIYAPPIQ
441 GVIRCESNIT GLLLTRDGGE GNNESEIFRP GGGDMRDNWR
481 SELYKYKVVK IEPLGVAPTR ARRRVVGREK RAVGIGAVFL
521 GFLGAAGSTM GAASMTLTVQ ARQLLSGIVQ QQSNLLRAIE
561 AQQHMLKLTV WGIKQLQARV LAVERYLRDQ QLLGIWGCSG
601 KLICTTNVPW NSSWSNKSHD EIWNNMTWLQ WDKEISNYTN
641 LIYSLIEESQ NQQEKNEQDL LALDKWASLW NWFDISKWLW
681 YIKIFIMIVG GLIGLRIVFA VLAVIKRVRQ GYSPVSFQIH
721 NPNPGGLDRP GRIEEEGGEP GRGRSIRLVS GFLALAWDDL
761 RNLCLFSYHR LRDFALIVAR TVELLGHSSL KGLRLGWEGL
801 KYLWNLLVYW SQELKTSAIN LVDTIAIAVA GWTDRVIEIG
841 QGIGRAFLHI PRRIRQGLER ALL
```

Additionally, methionine can be used in any HIV gp160 or gp41 glycoprotein to replace a non-methionine amino acid at an amino acid position equivalent to position 535 of the KNH1144 gp160 protein to stabilize the HIV gp160 or gp41. In addition, the I535M mutation can be used in combination with any of the other mutations or amino acid substitutions contemplated herein. Thus, for example, the I535M mutation can be combined with the I559P mutation described above (see SEQ ID NO:6) to generate the following mutant KNH1144 gp160 protein (SEQ ID NO:8):

```
  1 MIVMGTQRNY QHLLRWGTMI LGLIIICSAA DNLWVTVYYG
 41 VPVWKDAETT LFCASDAKAY ETEKHNVWAT HACVPTDPNP
 81 QEIPLENVTE EFNMWKNKMV EQMHTDIISL WDQSLQPCVK
121 LTPLCVTLNC TDATNGTIGN ITDEMKGEIK NCSFNITTEI
161 RDKKQKVYSL FYRLDVVPIE PDSSNSSRNS SEYRLINCNT
201 SAITQACPKV SFEPIPIHYC APAGFAILKC RDKEFNGTGK
241 CKNVSTVQCT HGIKPVVSTQ LLLNGSLAEG EVRIRSENIT
281 NNAKTIIVQL VEPVRINCTR PNNNTRESVR IGPGQAFFAT
321 GDIIGDIRQA HCNVSRSQWN KTLQQVAAQL GEHFKNKAIT
361 FNSSSGGDLE ITTHSFNCGG EFFYCNTSGL FNSTWKANNG
401 TWKANISESN NTEITLQCRI KQIINMWQRT GQAIYAPPIQ
441 GVIRCESNIT GLLLTRDGGE GNNESEIFRP GGGDMRDNWR
481 SELYKYKVVK IEPLGVAPTR ARRRVVGREK RAVGIGAVFL
521 GFLGAAGSTM GAASMTLTVQ ARQLLSGIVQ QQSNLLRAPE
561 AQQHMLKLTV WGIKQLQARV LAVERYLRDQ QLLGIWGCSG
601 KLICTTNVPW NSSWSNKSHD EIWNNMTWLQ WDKEISNYTN
641 LIYSLIEESQ NQQEKNEQDL LALDKWASLW NWFDISKWLW
681 YIKIFIMIVG GLIGLRIVFA VLAVIKRVRQ GYSPVSFQIH
721 NPNPGGLDRP GRIEEEGGEP GRGRSIRLVS GFLALAWDDL
761 RNLCLFSYHR LRDFALIVAR TVELLGHSSL KGLRLGWEGL
801 KYLWNLLVYW SQELKTSAIN LVDTIAIAVA GWTDRVIEIG
841 QGIGRAFLHI PRRIRQGLER ALL
```

Another example of a gp160 sequence is that of the HIV-1 JR-FL isolate. The JR-FL gp160 amino acid sequence is described as NCBI accession number AAB05604 (gi: 1465781); a nucleotide sequence for this gp160 protein is available at accession number U63632 (gi: 1465777). See website at ncbi.nlm.nih.gov. The amino acid sequence for this JR-FL gp160 protein is provided below (SEQ ID NO:9).

```
  1 MRVKGIRKSY QYLWKGGTLL LGILMICSAV EKLWVTVYYG
 41 VPVWKEATTT LFCASDAKAY DTEVHNVWAT HACVPTDPNP
 81 QEVVLENVTE HFNMWKNNMV EQMQEDIISL WDQSLKPCVK
121 LTPLCVTLNC KDVNATNTTN DSEGTMERGE IKNCSFNITT
161 SIRDEVQKEY ALFYKLDVVP IDNNNTSYRL ISCDTSVITQ
201 ACPKISFEPI PIHYCAPAGF AILKCNDKTF NGKGPCKNVS
241 TVQCTHGIRP VVSTQLLLNG SLAEEEVVIR SDNFTNNAKT
281 IIVQLKESVE INCTRPNNNT RKSIHIGPGR AFYTTGEIIG
321 DIRQAHCNIS RAKWNDTLKQ IVIKLREQFE NKTIVFNHSS
361 GGDPEIVMHS FNCGGEFFYC NSTQLFNSTW NNNTEGSNNT
401 EGNTITLPCR IKQIINMWQE VGKAMYAPPI RGQIRCSSNI
441 TGLLLTRDGG INENGTEIFR PGGGDMRDNW RSELYKYKVV
481 KIEPLGVAPT KAKRRVVQRE KRAVGIGAVF LGFLGAAGST
521 MGAASMTLTV QARLLLSGIV QQQNNLLRAI EAQQRMLQLT
561 VWGIKQLQAR VLAVERYLGD QQLLGIWGCS GKLICTTAVP
601 WNASWSNKSL DRIWNNMTWM EWEREIDNYT SEIYTLIEES
641 QNQQEKNEQE LLELDKWASL WNWFDITKWL WYIKIFIMIV
681 GGLVGLRLVF TVLSIVNRVR QGYSPLSFQT LLPAPRGPDR
721 PEGIEEEGGE RDRDRSGRLV NGFLALIWVD LRSLCLFSYH
761 RLRDLLLTVT RIVELLGRRG WEVLKYWWNL LQYWSQELKN
801 SAVSLLNATA IAVAEGTDRI IEALQRTYRA ILHIPTRIRQ
841 GLERALL
```

According to the invention, the amino acid sequence for this JR-FL gp160 protein can also have a proline instead of an isoleucine at an amino acid position equivalent to the position of isoleucine at amino acid position 559 in the KNH1144 gp160 protein. This mutant JR-FL gp160 protein is provided below (SEQ ID NO:10).

```
  1 MRVKGIRKSY QYLWKGGTLL LGILMICSAV EKLWVTVYYG
 41 VPVWKEATTT LFCASDAKAY DTEVHNVWAT HACVPTDPNP
 81 QEVVLENVTE HFNMWKNNMV EQMQEDIISL WDQSLKPCVK
121 LTPLCVTLNC KDVNATNTTN DSEGTMERGE IKNCSFNITT
161 SIRDEVQKEY ALFYKLDVVP IDNNNTSYRL ISCDTSVITQ
201 ACPKISFEPI PIHYCAPAGF AILKCNDKTF NGKGPCKNVS
241 TVQCTHGIRP VVSTQLLLNG SLAEEEVVIR SDNFTNNAKT
281 IIVQLKESVE INCTRPNNNT RKSIHIGPGR AFYTTGEIIG
321 DIRQAHCNIS RAKWNDTLKQ IVIKLREQFE NKTIVFNHSS
361 GGDPEIVMHS FNCGGEFFYC NSTQLFNSTW NNNTEGSNNT
401 EGNTITLPCR IKQIINMWQE VGKAMYAPPI RGQIRCSSNI
441 TGLLLTRDGG INENGTEIFR PGGGDMRDNW RSELYKYKVV
481 KIEPLGVAPT KAKRRVVQRE KRAVGIGAVF LGFLGAAGST
521 MGAASMTLTV QARLLLSGIV QQQNNLLRAP EAQQRMLQLT
561 VWGIKQLQAR VLAVERYLGD QQLLGIWGCS GKLICTTAVP
601 WNASWSNKSL DRIWNNMTWM EWEREIDNYT SEIYTLIEES
641 QNQQEKNEQE LLELDKWASL WNWFDITKWL WYIKIFIMIV
681 GGLVGLRLVF TVLSIVNRVR QGYSPLSFQT LLPAPRGPDR
721 PEGIEEEGGE RDRDRSGRLV NGFLALIWVD LRSLCLFSYH
761 RLRDLLLTVT RIVELLGRRG WEVLKYWWNL LQYWSQELKN
801 SAVSLLNATA IAVAEGTDRI IEALQRTYRA ILHIPTRIRQ
841 GLERALL
```

As provided by the invention, the amino acid sequence for this JR-FL gp160 protein can also have isoleucine at a position equivalent to position 535 of the KNH1144 gp160 protein, glutamine at a position equivalent position 543 of the KNH1144 gp160 protein, serine at position 553 of the KNH1144 gp160 protein, lysine at position 567 of the KNH1144 gp160 protein and arginine at position 588 of the KNH1144 gp160 protein, as well as a proline at a position equivalent to the position of the KNH1144 gp160 protein. This mutant JR-FL gp160 protein is provided below (SEQ ID NO:11).

```
  1 MRVKGIRKSY QYLWKGGTLL LGILMICSAV EKLWVTVYYG
 41 VPVWKEATTT LFCASDAKAY DTEVHNVWAT HACVPTDPNP
 81 QEVVLENVTE HFNMWKNNMV EQMQEDIISL WDQSLKPCVK
121 LTPLCVTLNC KDVNATNTTN DSEGTMERGE IKNCSFNITT
161 SIRDEVQKEY ALFYKLDVVP IDNNNTSYRL ISCDTSVITQ
201 ACPKISFEPI PIHYCAPAGF AILKCNDKTF NGKGPCKNVS
241 TVQCTHGIRP VVSTQLLLNG SLAEEEVVIR SDNFTNNAKT
281 IIVQLKESVE INCTRPNNNT RKSIHIGPGR AFYTTGEIIG
321 DIRQAHCNIS RAKWNDTLKQ IVIKLREQFE NKTIVFNHSS
361 GGDPEIVMHS FNCGGEFFYC NSTQLFNSTW NNNTEGSNNT
401 EGNTITLPCR IKQIINMWQE VGKAMYAPPI RGQIRCSSNI
441 TGLLLTRDGG INENGTEIFR PGGGDMRDNW RSELYKYKVV
481 KIEPLGVAPT KAKRRVVQRE KRAVGIGAVF LGFLGAAGST
521 MGAASITLTV QARQLLSGIV QQQSNLLRAP EAQQRMLKLT
561 VWGIKQLQAR VLAVERYLRD QQLLGIWGCS GKLICTTAVP
601 WNASWSNKSL DRIWNNMTWM EWEREIDNYT SEIYTLIEES
641 QNQQEKNEQE LLELDKWASL WNWFDITKWL WYIKIFIMIV
681 GGLVGLRLVF TVLSIVNRVR QGYSPLSFQT LLPAPRGPDR
721 PEGIEEEGGE RDRDRSGRLV NGFLALIWVD LRSLCLFSYH
761 RLRDLLLTVT RIVELLGRRG WEVLKYWWNL LQYWSQELKN
801 SAVSLLNATA IAVAEGTDRI IEALQRTYRA ILHIPTRIRQ
841 GLERALL
```

Another example of a sequence for gp160 is the HIV-1 Ba-L gp160 amino acid sequence at NCBI accession number AAT67504 (gi: 49617617); a nucleotide sequence for this gp160 protein is available at accession number AY669732 (gi: 49617616). See website at ncbi.nlm.nih.gov. The amino acid sequence for the HIV-1 Ba-L gp160 protein is provided below (SEQ ID NO:12):

```
  1 MRVTEIRKSY QHWWRWGIML LGXLMICNAE EKLWVTVYYG
 41 VPVWKEATTT LFCASDAKAY DTEVHNVWAT HACVPTDPNP
 81 QEVXXXNVTE NFNMWKNNMV EQMHEDIISL WDQSLKPCVK
121 LTPLCVTLNC TDLRNATXXN XTXTTSSSRG MVGGGEXKNC
161 SFNITTXIRG KVQKEYALFY ELDIVPIDNX IDRYRLISCN
201 TSVITQACPK VSFEPIPIHY CAPAGFAILK CKDKKFNGKG
241 PCXNVSTVQC THGIRPVVST QLLLNGSLAE EEVVIRSXNF
281 XBNAKXIIVQ LNESVEINCT RPNNNTRKSI HIGPGRAFYT
321 TGEIIGDIRQ AHCNLSRAKW NDTLNKIVXK LREQFGNKTI
361 VFKHSSGGDP EIVTHSFNCG GEFFYCNSTQ LFNSTWNVTE
401 ESNNTVENNT ITLPCRIKQI INMWQXVGRA MYAPPIRGQI
441 RCSSNITGLL LTRDGGPEDN KTEVFRPGGG DMRDNWRSEL
481 YKYKVVKIEP LGVAPTKAKR RVVQREKRAV GIGAVFLGFL
521 GAAGSTMGAA SMTLTVQARL LLSGIVQQQN NLLRAIEAQQ
561 HLLQLTVWGI KQLQARVLAV ERYLRDQQLL GIWGCSGKLI
601 CTTAVPWNAS WSNKSLNKIW DNMTWMEWDR EINNYTSIIY
641 SLIEESQNQQ EKNEQELLEL DKWASLWNWF DITXWLWYIK
681 IFIMIVGGLI GLRIVFSVLS IVNRVRQGYS PLSFQTHLPA
721 SRGPDRPGGI EEEGGERDRD RSGPLVNGFL XLIWVDLRSL
761 XLFSYHRLRD LLLIVTRIVE LLGRRGWEVL KYWWXLLQYW
801 SQELKNSAVS LLNXXAXAVA EGTDRVIEVX QRAVRAILHI
841 PRRIRQGLER ALL
```

According to the invention, the amino acid sequence for this Ba-L gp160 protein can also have a proline instead of an isoleucine at an amino acid position equivalent to the amino acid position of the specified isoleucine in the KNH1144 gp160 protein. Such a modified mutant Ba-L gp160 protein is provided below (SEQ ID NO:13):

```
  1 MRVTEIRKSY QHWWRWGIML LGXLMICNAE EKLWVTVYYG
 41 VPVWKEATTT LFCASDAKAY DTEVHNVWAT HACVPTDPNP
 81 QEVXXXNVTE NFNMWKNNMV EQMHEDIISL WDQSLKPCVK
121 LTPLCVTLNC TDLRNATXXN XTXTTSSSRG MVGGGEXKNC
161 SFNITTXIRG KVQKEYALFY ELDIVPIDNX IDRYRLISCN
201 TSVITQACPK VSFEPIPIHY CAPAGFAILK CKDKKFNGKG
241 PCXNVSTVQC THGIRPVVST QLLLNGSLAE EEVVIRSXNF
281 XBNAKXIIVQ LNESVEINCT RPNNNTRKSI HIGPGRAFYT
321 TGEIIGDIRQ AHCNLSRAKW NDTLNKIVXK LREQFGNKTI
```

-continued

```
361 VFKHSSGGDP EIVTHSFNCG GEFFYCNSTQ LFNSTWNVTE
401 ESNNTVENNT ITLPCRIKQI INMWQXVGRA MYAPPIRGQI
441 RCSSNITGLL LTRDGGPEDN KTEVFRPGGG DMRDNWRSEL
481 YKYKVVKIEP LGVAPTKAKR RVVQREKRAV GIGAVFLGFL
521 GAAGSTMGAA SMTLTVQARL LLSGIVQQQN NLLRAPEAQQ
561 HLLQLTVWGI KQLQARVLAV ERYLRDQQLL GIWGCSGKLI
601 CTTAVPWNAS WSNKSLNKIW DNMTWMEWDR EINNYTSIIY
641 SLIEESQNQQ EKNEQELLEL DKWASLWNWF DITXWLWYIK
681 IFIMIVGGLI GLRIVFSVLS IVNRVRQGYS PLSFQTHLPA
721 SRGPDRPGGI EEEGGERDRD RSGPLVNGFL XLIWVDLRSL
761 XLFSYHRLRD LLLIVTRIVE LLGRRGWEVL KYWWXLLQYW
801 SQELKNSAVS LLNXXAXAVA EGTDRVIEVX QRAVRAILHI
841 PRRIRQGLER ALL
```

Additionally, the amino acid sequence for this Ba-L gp160 protein can have isoleucine at a position equivalent to position 535 of the KNH1144 gp160 protein, glutamine at a position equivalent position 543 of the KNH1144 gp160 protein, serine at position 553 of the KNH1144 gp160 protein, lysine at position 567 of the KNH1144 gp160 protein and arginine at position 588 of the KNH1144 gp160 protein, as well as a proline at a position equivalent to the position of the specified isoleucine in the KNH1144 gp160 protein. Such a modified Ba-L gp160 protein is provided below (SEQ ID NO:14):

```
  1 MRVTEIRKSY QHWWRWGIML LGXLMICNAE EKLWVTVYYG
 41 VPVWKEATTT LFCASDAKAY DTEVHNVWAT HACVPTDPNP
 81 QEVXXXNVTE NFNMWKNNMV EQMHEDIISL WDQSLKPCVK
121 LTPLCVTLNC TDLRNATXXN XTXTTSSSRG MVGGGEXKNC
161 SFNITTXIRG KVQKEYALFY ELDIVPIDNX IDRYRLISCN
201 TSVITQACPK VSFEPIPIHY CAPAGFAILK CKDKKFNGKG
241 PCXNVSTVQC THGIRPVVST QLLLNGSLAE EEVVIRSXNF
281 XBNAKXIIVQ LNESVEINCT RPNNNTRKSI HIGPGRAFYT
321 TGEIIGDIRQ AHCNLSRAKW NDTLNKIVXK LREQFGNKTI
361 VFKHSSGGDP EIVTHSFNCG GEFFYCNSTQ LFNSTWNVTE
401 ESNNTVENNT ITLPCRIKQI INMWQXVGRA MYAPPIRGQI
441 RCSSNITGLL LTRDGGPEDN KTEVFRPGGG DMRDNWRSEL
481 YKYKVVKIEP LGVAPTKAKR RVVQREKRAV GIGAVFLGFL
521 GAAGSTMGAA SITLTVQARQ LLSGIVQQQS NLLRAPEAQQ
561 HLLKLTVWGI KQLQARVLAV ERYLRDQQLL GIWGCSGKLI
601 CTTAVPWNAS WSNKSLNKIW DNMTWMEWDR EINNYTSIIY
641 SLIEESQNQQ EKNEQELLEL DKWASLWNWF DITXWLWYIK
681 IFIMIVGGLI GLRIVFSVLS IVNRVRQGYS PLSFQTHLPA
721 SRGPDRPGGI EEEGGERDRD RSGPLVNGFL XLIWVDLRSL
761 XLFSYHRLRD LLLIVTRIVE LLGRRGWEVL KYWWXLLQYW
```

```
801 SQELKNSAVS LLNXXAXAVA EGTDRVIEVX QRAVRAILHI

841 PRRIRQGLER ALL
```

Another example of a sequence for gp160 is the amino acid sequence at NCBI accession number AAA76668 (gi: 665491); a nucleotide sequence for this gp160 protein is available at accession number U12032 (gi: 665490). See website at ncbi.nlm.nih.gov. The amino acid sequence for this gp160 protein is provided below (SEQ ID NO:15):

```
  1 MRVKEKYQHL RRWGWRWGTM LLGMLMICSA TEKLWVTVYY

41 GVPVWKEATT TLFCASDAKA YDTEVHNVWA THACVPTDPN

81 PQEVVLVNVT ENFNMWKNDM VEQMHEDIIS LWDQSLKPCV

121 KLTPLCVSLK CTDLKNDTNT NSSSGGMIME KGEIKNCSFN

161 ISTSIRGKVQ KEYAFFYKLD IIPIDNDTTS YTLTSCNTSV

201 ITQACPKVSF EPIPIHYCAP AGFAILKCNN KTFNGTGPCT

241 NVSTVQCTHG IRPVVSTQLL LNGSLAEEEV VIRSANFTDN

281 VKTIIVQLNQ SVEINCTKPN NNTGKRIRIQ RGPGRTFVTI

321 GKIGNMRQAH CNISRAKWNN TLKQIASKLR EQYGNNKTII

361 FKQSSGGDLE IVTHSFNCGG EFFYCNSTQL FNSTWFNSTG

401 SNNTEGSDTI TLPCRIKQII NMWQEVGKAM YAPPISGQIR

441 CSSNITGLLL TRDGGNNNNG SEIFRPGGGD MRDNWRSELY

481 KYKVVKIEPL GVAPTKAKRR VVQREKRAVG IGALFLGFLG

521 AAGSTMGAAS MTLTVQARQL LSGIVQQQNN LLRAIEAQQH

561 LLQLTVWGIK QLQARILAVE RYLKDQQLLG IWGCSGKLIC

601 TTAVPWNASW SNKSLERIWN HTTWMEWDRE INNYTSLIHS

641 LIEESQNQQE KNEQELLELD KWASLWNWFN ITNWLWYVKI

681 FIMIVGGLVG LRIVFAVLSI VNRVRQGYSP LSFQTHLPTP

721 GGPDRPEGIE EEGGERDRDR SIRLVNGS
```

According to the invention, the amino acid sequence for this gp160 protein can also be modified to include a proline instead of an isoleucine at an amino acid position equivalent to the amino acid position of the specified isoleucine in the KNH1144 gp160 protein. This mutant gp160 protein is provided below (SEQ ID NO:16):

```
  1 MRVKEKYQHL RRWGWRWGTM LLGMLMICSA TEKLWVTVYY

41 GVPVWKEATT TLFCASDAKA YDTEVHNVWA THACVPTDPN

81 PQEVVLVNVT ENFNMWKNDM VEQMHEDIIS LWDQSLKPCV

121 KLTPLCVSLK CTDLKNDTNT NSSSGGMIME KGEIKNCSFN

161 ISTSIRGKVQ KEYAFFYKLD IIPIDNDTTS YTLTSCNTSV

201 ITQACPKVSF EPIPIHYCAP AGFAILKCNN KTFNGTGPCT

241 NVSTVQCTHG IRPVVSTQLL LNGSLAEEEV VIRSANFTDN

281 VKTIIVQLNQ SVEINCTKPN NNTGKRIRIQ RGPGRTFVTI

321 GKIGNMRQAH CNISRAKWNN TLKQIASKLR EQYGNNKTII

361 FKQSSGGDLE IVTHSFNCGG EFFYCNSTQL FNSTWFNSTG

401 SNNTEGSDTI TLPCRIKQII NMWQEVGKAM YAPPISGQIR

441 CSSNITGLLL TRDGGNNNNG SEIFRPGGGD MRDNWRSELY

481 KYKVVKIEPL GVAPTKAKRR VVQREKRAVG IGALFLGFLG

521 AAGSTMGAAS MTLTVQARQL LSGIVQQQNN LLRAPEAQQH

561 LLQLTVWGIK QLQARILAVE RYLKDQQLLG IWGCSGKLIC

601 TTAVPWNASW SNKSLERIWN HTTWMEWDRE INNYTSLIHS

641 LIEESQNQQE KNEQELLELD KWASLWNWFN ITNWLWYVKI

681 FIMIVGGLVG LRIVFAVLSI VNRVRQGYSP LSFQTHLPTP

721 GGPDRPEGIE EEGGERDRDR SIRLVNGS
```

Further, as provided by the invention, the amino acid sequence for this gp160 protein can also have isoleucine at a position equivalent to position 535 of the KNH1144 gp160 protein, glutamine at a position equivalent position 543 of the KNH1144 gp160 protein, serine at position 553 of the KNH1144 gp160 protein, lysine at position 567 of the KNH1144 gp160 protein and arginine at position 588 of the KNH1144 gp160 protein, as well as a proline at a position equivalent to the position of the specified isoleucine in the KNH1144 gp160 protein. Such a modified gp160 protein is provided below (SEQ ID NO:17):

```
  1 MRVKEKYQHL RRWGWRWGTM LLGMLMICSA TEKLWVTVYY

41 GVPVWKEATT TLFCASDAKA YDTEVHNVWA THACVPTDPN

81 PQEVVLVNVT ENFNMWKNDM VEQMHEDIIS LWDQSLKPCV

121 KLTPLCVSLK CTDLKNDTNT NSSSGGMIME KGEIKNCSFN

161 ISTSIRGKVQ KEYAFFYKLD IIPIDNDTTS YTLTSCNTSV

201 ITQACPKVSF EPIPIHYCAP AGFAILKCNN KTFNGTGPCT

241 NVSTVQCTHG IRPVVSTQLL LNGSLAEEEV VIRSANFTDN

281 VKTIIVQLNQ SVEINCTKPN NNTGKRIRIQ RGPGRTFVTI

321 GKIGNMRQAH CNISRAKWNN TLKQIASKLR EQYGNNKTII

361 FKQSSGGDLE IVTHSFNCGG EFFYCNSTQL FNSTWFNSTG

401 SNNTEGSDTI TLPCRIKQII NMWQEVGKAM YAPPISGQIR

441 CSSNITGLLL TRDGGNNNNG SEIFRPGGGD MRDNWRSELY

481 KYKVVKIEPL GVAPTKAKRR VVQREKRAVG IGALFLGFLG

521 AAGSTMGAAS ITLTVQARQL LSGIVQQQSN LLRAPEAQQH

561 LLKLTVWGIK QLQARILAVE RYLRDQQLLG IWGCSGKLIC

601 TTAVPWNASW SNKSLERIWN HTTWMEWDRE INNYTSLIHS

641 LIEESQNQQE KNEQELLELD KWASLWNWFN ITNWLWYVKI

681 FIMIVGGLVG LRIVFAVLSI VNRVRQGYSP LSFQTHLPTP

721 GGPDRPEGIE EEGGERDRDR SIRLVNGS
```

Another example of an amino acid sequence for a HIV gp160 protein is available in the NCBI database at accession number AAA76666 (gi: 665487); the nucleotide sequence for this HIV gp160 protein can be found at accession number U12030 (gi: 665486). See website at ncbi.nlm.nih.gov. Many more sequences for HIV gp160 are available, for example, at the ncbi.nlm.nih.gov website.

The gp120 protein derived from the gp160 precursor directs target-cell recognition and viral tropism through interaction with the cell-surface receptor CD4 and one of several co-receptors that are members of the chemokine receptor family. (Broder, C. C. et al., *Pathobiology.* 64:171-179 (1996); D'Souza, M. P. et al., *Nature Medicine.* 2:1293-1300 (1996); Wilkinson, D., *Current Biology.* 6:1051-1053 (1996)). The membrane-spanning gp41 subunit then promotes fusion of the viral and cellular membranes, a process that results in the release of viral contents into the host cell.

Binding of gp120/gp41 complexes to cellular receptors (e.g., CD4 and a chemokine receptor such as CCR5 or CXCR4) triggers a series of structural rearrangements in the envelope glycoprotein. A transient species arises, termed the prehairpin intermediate, in which gp41 exists as a membrane protein simultaneously in both the viral and cellular membranes. This extended gp41 prehairpin intermediate ultimately collapses into a trimer-of-hairpins structure that provides sufficient tension to drive membrane fusion. The core of the HIV-1 trimer-of-hairpins is a bundle of six α-helices from three gp41 ectodomains. Three α-helices derived from the N-terminal HR1 regions form a central, trimeric coiled coil, around which three a-helices derived from the C-terminal HR2 regions pack in an anti-parallel manner into hydrophobic grooves on the surface of the coiled coil. Thus, formation of the timer-of-hairpins structure is believed to bring the membranes into close apposition necessary for the fusion event.

The gp120 and gp41 envelope glycoproteins can, of course, have a variety of sequences, depending upon the strain, clade, or type of HIV. For example, the KNH1144 gp41 protein can have the following sequence (SEQ ID NO:18):

```
508                         REK RAVGIGAVFL

521 GFLGAAGSTM GAASITLTVQ ARQLLSGIVQ QQSNLLRAIE

561 AQQHMLKLTV WGIKQLQARV LAVERYLRDQ QLLGIWGCSG

601 KLICTTNVPW NSSWSNKSHD EIWNNMTWLQ WDKEISNYTN

641 LIYSLIEESQ NQQEKNEQDL LALDKWASLW NWFDISKWLW

681 YIKIFIMIVG GLIGLRIVFA VLAVIKRVRQ GYSPVSFQIH

721 NPNPGGLDRP GRIEEEGGEP GRGRSIRLVS GFLALAWDDL

761 RNLCLFSYHR LRDFALIVAR TVELLGHSSL KGLRLGWEGL

801 KYLWNLLVYW SQELKTSAIN LVDTIAIAVA GWTDRVIEIG

841 QGIGRAFLHI PRRIRQGLER ALL
```

A modified KNH1144 gp41 protein can include a proline rather than an isoleucine at position 559, as indicated in the following sequence (SEQ ID NO:19):

```
508                               REK RAVGIGAVFL
521 GFLGAAGSTM GAASITLTVQ ARQLLSGIVQ QQSNLLRAPE
561 AQQHMLKLTV WGIKQLQARV LAVERYLRDQ QLLGIWGCSG
601 KLICTTNVPW NSSWSNKSHD EIWNNMTWLQ WDKEISNYTN
641 LIYSLIEESQ NQQEKNEQDL LALDKWASLW NWFDISKWLW
681 YIKIFIMIVG GLIGLRIVFA VLAVIKRVRQ GYSPVSFQIH
721 NPNPGGLDRP GRIEEEGGEP GRGRSIRLVS GFLALAWDDL
```

-continued

```
761 RNLCLFSYHR LRDFALIVAR TVELLGHSSL KGLRLGWEGL
801 KYLWNLLVYW SQELKTSAIN LVDTIAIAVA GWTDRVIEIG
841 QGIGRAFLHI PRRIRQGLER ALL
```

In some embodiments, a KNH1144 gp41 protein has improved stability if an isoleucine is used at position 535 instead of a methionine residue. The amino acid sequence of this M535I mutant of the KNH1144 gp41 protein is provided below (SEQ ID NO:20).

```
                                  REK RAVGIGAVFL
521 GFLGAAGSTM GAASITLTVQ ARQLLSGIVQ QQSNLLRAIE
561 AQQHMLKLTV WGIKQLQARV LAVERYLRDQ QLLGIWGCSG
601 KLICTTNVPW NSSWSNKSHD EIWNNMTWLQ WDKEISNYTN
641 LIYSLIEESQ NQQEKNEQDL LALDKWASLW NWFDISKWLW
681 YIKIFIMIVG GLIGLRIVFA VLAVIKRVRQ GYSPVSFQIH
721 NPNPGGLDRP GRIEEEGGEP GRGRSIRLVS GFLALAWDDL
761 RNLCLFSYHR LRDFALIVAR TVELLGHSSL KGLRLGWEGL
801 KYLWNLLVYW SQELKTSAIN LVDTIAIAVA GWTDRVIEIG
841 QGIGRAFLHI PRRIRQGLER ALL
```

Additionally, the M535I mutation can be included in combination with any of the other mutations or amino acid substitutions contemplated herein. Thus, for example, the M535I mutation can be combined with the I559P mutation described above (see SEQ ID NO:19) to generate the following modified or mutant KNH1144 gp41 protein (SEQ ID NO:21):

```
                                  REK RAVGIGAVFL
521 GFLGAAGSTM GAASITLTVQ ARQLLSGIVQ QQSNLLRAPE
561 AQQHMLKLTV WGIKQLQARV LAVERYLRDQ QLLGIWGCSG
601 KLICTTNVPW NSSWSNKSHD EIWNNMTWLQ WDKEISNYTN
641 LIYSLIEESQ NQQEKNEQDL LALDKWASLW NWFDISKWLW
681 YIKIFIMIVG GLIGLRIVFA VLAVIKRVRQ GYSPVSFQIH
721 NPNPGGLDRP GRIEEEGGEP GRGRSIRLVS GFLALAWDDL
761 RNLCLFSYHR LRDFALIVAR TVELLGHSSL KGLRLGWEGL
801 KYLWNLLVYW SQELKTSAIN LVDTIAIAVA GWTDRVIEIG
841 QGIGRAFLHI PRRIRQGLER ALL
```

Another example of a gp41 amino acid is that of the HIV-1 JR-FL isolate. The amino acid sequence for the HIV-1 JR-FL gp41 protein is provided below (SEQ ID NO:22):

```
499                    RE KRAVGIGAVF LGFLGAAGST
521 MGAASMTLTV QARLLLSGIV QQQNNLLRAI EAQQRMLQLT
561 VWGIKQLQAR VLAVERYLGD QQLLGIWGCS GKLICTTAVP
601 WNASWSNKSL DRIWNNMTWM EWEREIDNYT SEIYTLIEES
641 QNQQEKNEQE LLELDKWASL WNWFDITKWL WYIKIFIMIV
```

```
681 GGLVGLRLVF TVLSIVNRVR QGYSPLSFQT LLPAPRGPDR

721 PEGIEEEGGE RDRDRSGRLV NGFLALIWVD LRSLCLFSYH

761 RLRDLLLTVT RIVELLGRRG WEVLKYWWNL LQYWSQELKN

801 SAVSLLNATA IAVAEGTDRI IEALQRTYRA ILHIPTRIRQ

841 GLERALL
```

According to the invention, the amino acid sequence for the JR-FL gp41 protein may also include a proline instead of an isoleucine at an amino acid position equivalent to amino acid position 559 of the KNH1144 gp41 protein. This modified or mutant JR-FL gp41 protein is provided below (SEQ ID NO:23):

```
499                    RE KRAVGIGAVF LGFLGAAGST

521 MGAASMTLTV QARLLLSGIV QQQNNLLRAP EAQQRMLQLT

561 VWGIKQLQAR VLAVERYLGD QQLLGIWGCS GKLICTTAVP

601 WNASWSNKSL DRIWNNMTWM EWEREIDNYT SEIYTLIEES

641 QNQQEKNEQE LLELDKWASL WNWFDITKWL WYIKIFIMIV

681 GGLVGLRLVF TVLSIVNRVR QGYSPLSFQT LLPAPRGPDR

721 PEGIEEEGGE RDRDRSGRLV NGFLALIWVD LRSLCLFSYH

761 RLRDLLLTVT RIVELLGRRG WEVLKYWWNL LQYWSQELKN

801 SAVSLLNATA IAVAEGTDRI IEALQRTYRA ILHIPTRIRQ

841 GLERALL
```

As further provided by the invention, the amino acid sequence for the modified HIV-1 JR-FL gp41 protein may also include isoleucine at an amino acid position equivalent to amino acid position 535 of the KNH1144 gp160 protein, glutamine at an amino acid position equivalent amino acid position 543 of the KNH1144 gp160 protein, serine at an amino acid position equivalent to amino acid position 553 of the KNH1144 gp160 protein, lysine at an amino acid position equivalent to amino acid position 567 of the KNH1144 gp160 protein and arginine at an amino acid position equivalent to amino acid position 588 of the KNH1144 gp160 protein, as well as proline at an amino acid position equivalent to amino acid position 559 of the KNH1144 gp160 protein. This modified or mutant JR-FL gp41 protein is provided below (SEQ ID NO:24):

```
                       RE KRAVGIGAVF LGFLGAAGST

521 MGAASITLTV QARQLLSGIV QQQSNLLRAP EAQQRMLKLT

561 VWGIKQLQAR VLAVERYLRD QQLLGIWGCS GKLICTTAVP

601 WNASWSNKSL DRIWNNMTWM EWEREIDNYT SEIYTLIEES

641 QNQQEKNEQE LLELDKWASL WNWFDITKWL WYIKIFIMIV

681 GGLVGLRLVF TVLSIVNRVR QGYSPLSFQT LLPAPRGPDR

721 PEGIEEEGGE RDRDRSGRLV NGFLALIWVD LRSLCLFSYH

761 RLRDLLLTVT RIVELLGRRG WEVLKYWWNL LQYWSQELKN

801 SAVSLLNATA IAVAEGTDRI IEALQRTYRA ILHIPTRIRQ

841 GLERALL
```

Another example of a sequence for gp41 is the HIV-1 Ba-L gp41 amino acid sequence. The amino acid sequence for the HIV-1 Ba-L gp41 protein is provided below (SEQ ID NO:25):

```
505                    REKRAV GIGAVFLGFL

521 GAAGSTMGAA SMTLTVQARL LLSGIVQQQN NLLRAIEAQQ

561 HLLQLTVWGI KQLQARVLAV ERYLRDQQLL GIWGCSGKLI

601 CTTAVPWNAS WSNKSLNKIW DNMTWMEWDR EINNYTSIIY

641 SLIEESQNQQ EKNEQELLEL DKWASLWNWF DITXWLWYIK

681 IFIMIVGGLI GLRIVFSVLS IVNRVRQGYS PLSFQTHLPA

721 SRGPDRPGGI EEEGGERDRD RSGPLVNGFL XLIWVDLRSL

761 XLFSYHRLRD LLLIVTRIVE LLGRRGWEVL KYWWXLLQYW

801 SQELKNSAVS LLNXXAXAVA EGTDRVIEVX QRAVRAILHI

841 PRRIRQGLER ALL
```

According to the invention, the amino acid sequence for a modified Ba-L gp41 protein may include proline instead of an isoleucine at an amino acid position equivalent to the position of the proline amino acid in the KNH1144 gp41 protein. This mutant Ba-L gp41 protein is provided below (SEQ ID NO:26):

```
505                    REKRAV GIGAVFLGFL

521 GAAGSTMGAA SMTLTVQARL LLSGIVQQQN NLLRAPEAQQ

561 HLLQLTVWGI KQLQARVLAV ERYLRDQQLL GIWGCSGKLI

601 CTTAVPWNAS WSNKSLNKIW DNMTWMEWDR EINNYTSIIY

641 SLIEESQNQQ EKNEQELLEL DKWASLWNWF DITXWLWYIK

681 IFIMIVGGLI GLRIVFSVLS IVNRVRQGYS PLSFQTHLPA

721 SRGPDRPGGI EEEGGERDRD RSGPLVNGFL XLIWVDLRSL

761 XLFSYHRLRD LLLIVTRIVE LLGRRGWEVL KYWWXLLQYW

801 SQELKNSAVS LLNXXAXAVA EGTDRVIEVX QRAVRAILHI

841 PRRIRQGLER ALL
```

As provided by the invention, the amino acid sequence for the modified HIV-1 Ba-L gp41 protein can also include isoleucine at an amino acid position equivalent to amino acid position 535 of the KNH1144 gp160 protein, glutamine at an amino acid position equivalent to amino acid position 543 of the KNH1144 gp160 protein, serine at an amino acid position equivalent to amino acid position 553 of the KNH1144 gp160 protein, lysine at an amino acid position equivalent to amino acid position 567 of the KNH1144 gp160 protein and arginine at an amino acid position equivalent to amino acid position 588 of the KNH1144 gp160 protein, as well as a proline at a position equivalent to the position of the specified isoleucine in the KNH1144 gp160 protein. Such a mutant or modified Ba-L gp41 protein is provided below (SEQ ID NO:27):

```
                       REKRAV GIGAVFLGFL

521 GAAGSTMGAA SITLTVQARQ LLSGIVQQQS NLLRAPEAQQ

561 HLLKLTVWGI KQLQARVLAV ERYLRDQQLL GIWGCSGKLI
```

```
601 CTTAVPWNAS WSNKSLNKIW DNMTWMEWDR EINNYTSIIY

641 SLIEESQNQQ EKNEQELLEL DKWASLWNWF DITXWLWYIK

681 IFIMIVGGLI GLRIVFSVLS IVNRVRQGYS PLSFQTHLPA

721 SRGPDRPGGI EEEGGERDRD RSGPLVNGFL XLIWVDLRSL

761 XLFSYHRLRD LLLIVTRIVE LLGRRGWEVL KYWWXLLQYW

801 SQELKNSAVS LLNXXAXAVA EGTDRVIEVX QRAVRAILHI

841 PRRIRQGLER ALL
```

Another example of a sequence for the envelope gp41 glycoprotein is the amino acid sequence at accession number S21998 (gi: 94245). See website at ncbi.nlm.nih.gov. The amino acid sequence for this gp41 protein is provided below (SEQ ID NO:28):

```
  1 KAKRRVVQRE KRAVGMGAAF FLGFLGAAGS TMGAASLTLT

41 VQARLLLSGI VQQQNNLLRA IEAHEHLLQL TVWGIKQLQA

81 RILAVERYLK DQQLLGIWGC SGKLICTTTV PWNASWSNKS

121 LDKIWNNMTW MEWDREINNY TSLIYTLIEQ SQNQQEKNEQ

161 ELLELDKWAS LWNWFDITQW LWYIKIFIMI VGGLIGLRIV

201 FTVLSIVNRV RQGYSPLSFQ TRRPARRGPD RPEGIEEEGG

241 ERDRDRSGRL VNGFLALIWD DLRSLCLFSY HRLRDLLLIV

281 TRIVELLGRR GWEVLKYLWN LLQYWSQELK NSAVSLLNAT

321 AIAVAEGTDR VIELLQRAFR AILHIPRRXR QGLERALL
```

The gp41 polypeptide of accession number S21998 (gi: 94245) can also have a proline instead of an isoleucine at a position equivalent to that of the KNH1144 gp41. Such a mutant gp41 protein has the following sequence (SEQ ID NO:29):

```
  1 KAKRRVVQRE KRAVGMGAAF FLGFLGAAGS TMGAASLTLT

41 VQARLLLSGI VQQQNNLLRA PEAHEHLLQL TVWGIKQLQA

81 RILAVERYLK DQQLLGIWGC SGKLICTTTV PWNASWSNKS

121 LDKIWNNMTW MEWDREINNY TSLIYTLIEQ SQNQQEKNEQ

161 ELLELDKWAS LWNWFDITQW LWYIKIFIMI VGGLIGLRIV

201 FTVLSIVNRV RQGYSPLSFQ TRRPARRGPD RPEGIEEEGG

241 ERDRDRSGRL VNGFLALIWD DLRSLCLFSY HRLRDLLLIV

281 TRIVELLGRR GWEVLKYLWN LLQYWSQELK NSAVSLLNAT

321 AIAVAEGTDR VIELLQRAFR AILHIPRRXR QGLERALL
```

Moreover, as provided by the invention, the amino acid sequence for the gp41 protein having accession number S21998 (gi: 94245) can also be modified to contain isoleucine at an amino acid position equivalent to amino acid position 535 of the KNH1144 gp160 protein, glutamine at an amino acid position equivalent to amino acid position 543 of the KNH1144 gp160 protein, serine at an amino acid position equivalent to amino acid position 553 of the KNH1144 gp160 protein, lysine at an amino acid position equivalent to amino acid position 567 of the KNH1144 gp160 protein and arginine at an amino acid position equivalent to amino acid position 588 of the KNH1144 gp160 protein, as well as a proline at an amino acid position equivalent to the 559 position of the specified isoleucine in the KNH1144 gp160 protein. This modified or mutant. gp41 protein is provided below (SEQ ID NO:30):

```
  1 KAKRRVVQRE KRAVGMGAAF FLGFLGAAGS TMGAASITLT

41 VQARQLLSGI VQQQSNLLRA PEAHEHLLKL TVWGIKQLQA

81 RILAVERYLR DQQLLGIWGC SGKLICTTTV PWNASWSNKS

121 LDKIWNNMTW MEWDREINNY TSLIYTLIEQ SQNQQEKNEQ

161 ELLELDKWAS LWNWFDITQW LWYIKIFIMI VGGLIGLRIV

201 FTVLSIVNRV RQGYSPLSFQ TRRPARRGPD RPEGIEEEGG

241 ERDRDRSGRL VNGFLALIWD DLRSLCLFSY HRLRDLLLIV

281 TRIVELLGRR GWEVLKYLWN LLQYWSQELK NSAVSLLNAT

321 AIAVAEGTDR VIELLQRAFR AILHIPRRXR QGLERALL
```

As would be appreciated by the skilled practitioner, many more sequences for HIV gp41 polypeptides are available, for example, at the ncbi.nlm.nih.gov website.

According to the invention, in addition to any of the foregoing amino acid changes or substitutions, at least one intermolecular disulfide bond can also be placed between the gp41 and gp120 proteins of the HIV-1 strains. The one or more disulfide bonds are generated by placement of cysteine residues at selected locations in the gp41 and gp120 proteins. Thus, for example, in the gp160 glycoprotein, one cysteine can be placed at any of positions 470 to 505 and another cysteine can be placed at any of positions 570 to 620.

For example, cysteine residues can be placed at positions 492 and 596 in the HIV-1 JR-FL gp160 amino acid sequence (NCBI accession number AAB05604; gi: 1465781). The amino acid sequence for this A492C and T596C double mutant JR-FL gp160 protein is provided below (SEQ ID NO:31):

```
  1 MRVKGIRKSY QYLWKGGTLL LGILMICSAV EKLWVTVYYG

41 VPVWKEATTT LFCASDAKAY DTEVHNVWAT HACVPTDPNP

81 QEVVLENVTE HFNMWKNNMV EQMQEDIISL WDQSLKPCVK

121 LTPLCVTLNC KDVNATNTTN DSEGTMERGE IKNCSFNITT

161 SIRDEVQKEY ALFYKLDVVP IDNNNTSYRL ISCDTSVITQ

201 ACPKISFEPI PIHYCAPAGF AILKCNDKTF NGKGPCKNVS

241 TVQCTHGIRP VVSTQLLLNG SLAEEEVVIR SDNFTNNAKT

281 IIVQLKESVE INCTRPNNNT RKSIHIGPGR AFYTTGEIIG

321 DIRQAHCNIS RAKWNDTLKQ IVIKLREQFE NKTIVFNHSS

361 GGDPEIVMHS FNCGGEFFYC NSTQLFNSTW NNNTEGSNNT

401 EGNTITLPCR IKQIINMWQE VGKAMYAPPI RGQIRCSSNI

441 TGLLLTRDGG INENGTEIFR PGGGDMRDNW RSELYKYKVV

481 KIEPLGVAPT KCKRRVVQRE KRAVGIGAVF LGFLGAAGST

521 MGAASMTLTV QARLLLSGIV QQQNNLLRAI EAQQRMLQLT

561 VWGIKQLQAR VLAVERYLGD QQLLGIWGCS GKLICCTAVP

601 WNASWSNKSL DRIWNNMTWM EWEREIDNYT SEIYTLIEES
```

```
641 QNQQEKNEQE LLELDKWASL WNWFDITKWL WYIKIFIMIV

681 GGLVGLRLVF TVLSIVNRVR QGYSPLSFQT LLPAPRGPDR

721 PEGIEEEGGE RDRDRSGRLV NGFLALIWVD LRSLCLFSYH

761 RLRDLLLTVT RIVELLGRRG WEVLKYWWNL LQYWSQELKN

801 SAVSLLNATA IAVAEGTDRI IEALQRTYRA ILHIPTRIRQ

841 GLERALL
```

Thus, after cleavage of the JR-FL gp160 glycoprotein, a gp120 glycoprotein with a cysteine instead of an alanine at position 492 has the following sequence (SEQ ID NO:32):

```
  1 MRVKGIRKSY QYLWKGGTLL LGILMICSAV EKLWVTVYYG

41 VPVWKEATTT LFCASDAKAY DTEVHNVWAT HACVPTDPNP

81 QEVVLENVTE HFNMWKNNMV EQMQEDIISL WDQSLKPCVK

121 LTPLCVTLNC KDVNATNTTN DSEGTMERGE IKNCSFNITT

161 SIRDEVQKEY ALFYKLDVVP IDNNNTSYRL ISCDTSVITQ

201 ACPKISFEPI PIHYCAPAGF AILKCNDKTF NGKGPCKNVS

241 TVQCTHGIRP VVSTQLLLNG SLAEEEVVIR SDNFTNNAKT

281 IIVQLKESVE INCTRPNNNT RKSIHIGPGR AFYTTGEIIG

321 DIRQAHCNIS RAKWNDTLKQ IVIKLREQFE NKTIVFNHSS

361 GGDPEIVMHS FNCGGEFFYC NSTQLFNSTW NNNTEGSNNT

401 EGNTITLPCR IKQIINMWQE VGKAMYAPPI RGQIRCSSNI

441 TGLLLTRDGG INENGTEIFR PGGGDMRDNW RSELYKYKVV

481 KIEPLGVAPT KCKRRVVQ
```

Similarly, after cleavage of the JR-FL gp160 glycoprotein, a gp41 glycoprotein with a cysteine instead of an threonine at position 596 has the following sequence (SEQ ID NO:33):

```
                 RE KRAVGIGAVF LGFLGAAGST

521 MGAASMTLTV QARLLLSGIV QQQNNLLRAI EAQQRMLQLT

561 VWGIKQLQAR VLAVERYLGD QQLLGIWGCS GKLICCTAVP

601 WNASWSNKSL DRIWNNMTWM EWEREIDNYT SEIYTLIEES

641 QNQQEKNEQE LLELDKWASL WNWFDITKWL WYIKIFIMIV

681 GGLVGLRLVF TVLSIVNRVR QGYSPLSFQT LLPAPRGPDR

721 PEGIEEEGGE RDRDRSGRLV NGFLALIWVD LRSLCLFSYH

761 RLRDLLLTVT RIVELLGRRG WEVLKYWWNL LQYWSQELKN

801 SAVSLLNATA IAVAEGTDRI IEALQRTYRA ILHIPTRIRQ

841 GLERALL
```

Moreover, such cysteine residues can be placed in gp160, gp120 and/or gp41 polypeptides of other HIV-1 isolates at amino acid positions equivalent to the alanine 492 and threonine 596 amino acid positions of the JR-FL glycoprotein. For example, the amino acid sequence for the KNH1144 gp160 protein can be modified to contain cysteines at positions equivalent to the alanine 492 and threonine 596 positions of the JR-FL glycoprotein as provided below (SEQ ID NO:34):

```
  1 MIVMGTQRNY QHLLRWGTMI LGLIICSAA  DNLWVTVYYG

41 VPVWKDAETT LFCASDAKAY ETEKHNVWAT HACVPTDPNP

81 QEIPLENVTE EFNMWKNKMV EQMHTDIISL WDQSLQPCVK

121 LTPLCVTLNC TDATNGTIGN ITDEMKGEIK NCSFNITTEI

161 RDKKQKVYSL FYRLDVVPIE PDSSNSSRNS SEYRLINCNT

201 SAITQACPKV SFEPIPIHYC APAGFAILKC RDKEFNGTGK

241 CKNVSTVQCT HGIKPVVSTQ LLLNGSLAEG EVRIRSENIT

281 NNAKTIIVQL VEPVRINCTR PNNNTRESVR IGPGQAFFAT

321 GDIIGDIRQA HCNVSRSQWN KTLQQVAAQL GEHFKNKAIT

361 FNSSSGGDLE ITTHSFNCGG EFFYCNTSGL FNSTWKANNG

401 TWKANISESN NTEITLQCRI KQIINMWQRT GQAIYAPPIQ

441 GVIRCESNIT GLLLTRDGGE GNNESEIFRP GGGDMRDNWR

481 SELYKYKVVK IEPLGVAPTR CRRRVVGREK RAVGIGAVFL

521 GFLGAAGSTM GAASITLTVQ ARQLLSGIVQ QQSNLLRAIE

561 AQQHMLKLTV WGIKQLQARV LAVERYLRDQ QLLGIWGCSG

601 KLICCTNVPW NSSWSNKSHD EIWNNMTWLQ WDKEISNYTN

641 LIYSLIEESQ NQQEKNEQDL LALDKWASLW NWFDISKWLW

681 YIKIFIMIVG GLIGLRIVFA VLAVIKRVRQ GYSPVSFQIH

721 NPNPGGLDRP GRIEEEGGEP GRGRSIRLVS GFLALAWDDL

761 RNLCLFSYHR LRDFALIVAR TVELLGHSSL KGLRLGWEGL

801 KYLWNLLVYW SQELKTSAIN LVDTIAIAVA GWTDRVIEIG

841 QGIGRAFLHI PRRIRQGLER ALL
```

Thus, after cleavage of the KNH1144 gp160 glycoprotein, a gp120 glycoprotein containing a cysteine at the amino acid position equivalent to amino acid position 492 of the HIV-1 JR-FL strain has the following sequence (SEQ ID NO:35):

```
  1 MIVMGTQRNY QHLLRWGTMI LGLIICSAA  DNLWVTVYYG

41 VPVWKDAETT LFCASDAKAY ETEKHNVWAT HACVPTDPNP

81 QEIPLENVTE EFNMWKNKMV EQMHTDIISL WDQSLQPCVK

121 LTPLCVTLNC TDATNGTIGN ITDEMKGEIK NCSFNITTEI

161 RDKKQKVYSL FYRLDVVPIE PDSSNSSRNS SEYRLINCNT

201 SAITQACPKV SFEPIPIHYC APAGFAILKC RDKEFNGTGK

241 CKNVSTVQCT HGIKPVVSTQ LLLNGSLAEG EVRIRSENIT

281 NNAKTIIVQL VEPVRINCTR PNNNTRESVR IGPGQAFFAT

321 GDIIGDIRQA HCNVSRSQWN KTLQQVAAQL GEHFKNKAIT

361 FNSSSGGDLE ITTHSFNCGG EFFYCNTSGL FNSTWKANNG

401 TWKANISESN NTEITLQCRI KQIINMWQRT GQAIYAPPIQ

441 GVIRCESNIT GLLLTRDGGE GNNESEIFRP GGGDMRDNWR

481 SELYKYKVVK IEPLGVAPTR CRRRVVG
```

Also after cleavage, a KNH1144 gp41 glycoprotein modified to contain a cysteine at the amino acid position equivalent to amino acid position 596 in the HIV-1 JR-FL isolate has the following sequence (SEQ ID NO:36):

```
                                      REK RAVGIGAVFL
521 GFLGAAGSTM GAASITLTVQ ARQLLSGIVQ QQSNLLRAIE

561 AQQHMLKLTV WGIKQLQARV LAVERYLRDQ QLLGIWGCSG

601 KLICCTNVPW NSSWSNKSHD EIWNNMTWLQ WDKEISNYTN

641 LIYSLIEESQ NQQEKNEQDL LALDKWASLW NWFDISKWLW

681 YIKIFIMIVG GLIGLRIVFA VLAVIKRVRQ GYSPVSFQIH

721 NPNPGGLDRP GRIEEEGGEP GRGRSIRLVS GFLALAWDDL

761 RNLCLFSYHR LRDFALIVAR TVELLGHSSL KGLRLGWEGL

801 KYLWNLLVYW SQELKTSAIN LVDTIAIAVA GWTDRVIEIG

841 QGIGRAFLHI PRRIRQGLER ALL
```

In another example, the amino acid sequence for the Ba-L gp160 protein can be modified to contain cysteines at amino acid positions equivalent to amino acid position 492 (alanine) and amino acid position 596 (threonine) of the JR-FL glycoprotein as provided below (SEQ ID NO:37):

```
  1 MRVTEIRKSY QHWWRWGIML LGXLMICNAE EKLWVTVYYG

41 VPVWKEATTT LFCASDAKAY DTEVHNVWAT HACVPTDPNP

81 QEVXXXNVTE NFNMWKNNMV EQMHEDIISL WDQSLKPCVK

121 LTPLCVTLNC TDLRNATXXN XTXTTSSSRG MVGGGEXKNC

161 SFNITTXIRG KVQKEYALFY ELDIVPIDNX IDRYRLISCN

201 TSVITQACPK VSFEPIPIHY CAPAGFAILK CKDKKFNGKG

241 PCXNVSTVQC THGIRPVVST QLLLNGSLAE EEVVIRSXNF

281 XBNAKXIIVQ LNESVEINCT RPNNNTRKSI HIGPGRAFYT

321 TGEIIGDIRQ AHCNLSRAKW NDTLNKIVXK LREQFGNKTI

361 VFKHSSGGDP EIVTHSFNCG GEFFYCNSTQ LFNSTWNVTE

401 ESNNTVENNT ITLPCRIKQI INMWQXVGRA MYAPPIRGQI

441 RCSSNITGLL LTRDGGPEDN KTEVFRPGGG DMRDNWRSEL

481 YKYKVVKIEP LGVAPTKCKR RVVQREKRAV GIGAVFLGFL

521 GAAGSTMGAA SMTLTVQARL LLSGIVQQQN NLLRAIEAQQ

561 HLLQLTVWGI KQLQARVLAV ERYLRDQQLL GIWGCSGKLI

601 CCTAVPWNAS WSNKSLNKIW DNMTWMEWDR EINNYTSIIY

641 SLIEESQNQQ EKNEQELLEL DKWASLWNWF DITXWLWYIK

681 IFIMIVGGLI GLRIVFSVLS IVNRVRQGYS PLSFQTHLPA

721 SRGPDRPGGI EEEGGERDRD RSGPLVNGFL XLIWVDLRSL

761 XLFSYHRLRD LLLIVTRIVE LLGRRGWEVL KYWWXLLQYW

801 SQELKNSAVS LLNXXAXAVA EGTDRVIEVX QRAVRAILHI

841 PRRIRQGLER ALL
```

After cleavage of the HIV-1 Ba-L gp160 glycoprotein, a gp120 glycoprotein modified to contain a cysteine at an amino acid position equivalent to amino acid position 492 of HIV-1 JR-FL has the following sequence (SEQ ID NO:38):

```
  1 MRVTEIRKSY QHWWRWGIML LGXLMICNAE EKLWVTVYYG

41 VPVWKEATTT LFCASDAKAY DTEVHNVWAT HACVPTDPNP

81 QEVXXXNVTE NFNMWKNNMV EQMHEDIISL WDQSLKPCVK

121 LTPLCVTLNC TDLRNATXXN XTXTTSSSRG MVGGGEXKNC

161 SFNITTXIRG KVQKEYALFY ELDIVPIDNX IDRYRLISCN

201 TSVITQACPK VSFEPIPIHY CAPAGFAILK CKDKKFNGKG

241 PCXNVSTVQC THGIRPVVST QLLLNGSLAE EEVVIRSXNF

281 XBNAKXIIVQ LNESVEINCT RPNNNTRKSI HIGPGRAFYT

321 TGEIIGDIRQ AHCNLSRAKW NDTLNKIVXK LREQFGNKTI

361 VFKHSSGGDP EIVTHSFNCG GEFFYCNSTQ LFNSTWNVTE

401 ESNNTVENNT ITLPCRIKQI INMWQXVGRA MYAPPIRGQI

441 RCSSNITGLL LTRDGGPEDN KTEVFRPGGG DMRDNWRSEL

481 YKYKVVKIEP LGVAPTKCKR RVVQ
```

Also after cleavage, a Ba-L gp41 glycoprotein modified to contain a cysteine at an amino acid position equivalent to amino acid position 596 of HIV-1 JR-FL has the following sequence (SEQ ID NO:39):

```
                                     REKRAV GIGAVFLGFL
521 GAAGSTMGAA SMTLTVQARL LLSGIVQQQN NLLRAIEAQQ

561 HLLQLTVWGI KQLQARVLAV ERYLRDQQLL GIWGCSGKLI

601 CCTAVPWNAS WSNKSLNKIW DNMTWMEWDR EINNYTSIIY

641 SLIEESQNQQ EKNEQELLEL DKWASLWNWF DITXWLWYIK

681 IFIMIVGGLI GLRIVFSVLS IVNRVRQGYS PLSFQTHLPA

721 SRGPDRPGGI EEEGGERDRD RSGPLVNGFL XLIWVDLRSL

761 XLFSYHRLRD LLLIVTRIVE LLGRRGWEVL KYWWXLLQYW

801 SQELKNSAVS LLNXXAXAVA EGTDRVIEVX QRAVRAILHI

841 PRRIRQGLER ALL
```

Similarly, any oterh HIV gp120 and gp41 glycoproteins, including any of the gp160, gp120 and/or gp41 polypeptides described herein, can be modified to contain cysteines residues at amino acid positions equivalent to the amino acid positions of the HIV-1 JR-FL isolate, e.g., at amino acid positions equivalent to amino acid positions 492 and 596 in JR-FL. In addition, any of the other "stabilizing" mutations described herein can be combined with the substitution of cysteine at amino acid positions equivalent to the amino acids at positions 492 and 596 in JR-FL.

References for Experimental Details IV

1. Broder, C. C. et al., (1996). *Pathobiology.* 64:171-179.
2. D'Souza, M. P. et al., (1996). *Nature Medicine.* 2:1293-1300.
3. Wilkinson, D., (1996). *Current Biology.* 6:1051-1053.

What is claimed is:

1. A purified, modified HIV-1 gp140 envelope polypeptide comprising (1) a gp120 polypeptide portion comprising consecutive amino acids and (2) a gp41 ectodomain polypeptide portion comprising consecutive amino acids, said gp41 ectodomain polypeptide portion being heterologous to the gp41 ectodomain polypeptide portion of a KNH1144 HIV-1 isolate and being modified to comprise isoleucine (I) at an amino acid position equivalent to amino acid position 535 (I535); glutamine (Q) at an amino acid position equivalent to amino acid position 543 (Q543); serine (S) at an amino acid position equivalent to amino acid position 553 (S553); lysine (K) at an amino acid position equivalent to amino acid position 567 (K567); and arginine (R) at an amino acid position equivalent to amino acid position 588 (R588), wherein the amino acid positions are numbered by reference to the KNH1144 HIV-1 isolate.

2. A purified, modified gp41 ectodomain polypeptide which comprises a consecutive amino acid sequence as set forth in any one of SEQ ID NO:24, SEQ ID NO:27, or SEQ ID NO:30.

3. A purified, modified gp160 polypeptide which comprises a consecutive amino acid sequence as set forth in SEQ ID NO:11, SEQ ID NO:14, or SEQ ID NO:17.

4. A method of producing a stabilized trimeric complex of HIV gp120 and gp41 wherein said gp41 comprises the following mutations numbered by reference to the KNH1144 HIV-1 isolate:

X535I, X543Q, N553S, X567K, and X588R, comprising the steps of:
a) obtaining an expression vector comprising a nucleic acid which encodes a gp120 envelope polypeptide and a gp41 envelope polypeptide;
b) introducing the following mutations into the portion of the nucleic acid which encodes the gp41 envelope polypeptide: X535I, X543Q, N553S, X567K, and X588R;
c) transfecting a cell with the expression vector resulting from step b) under conditions permitting expression of the gp120 envelope polypeptide and the gp41 envelope polypeptide; and
d) purifying the gp120 envelope polypeptides and gp41 envelope polypeptides expressed in step c) under conditions permitting association of gp120 envelope polypeptides and gp41 envelope polypeptides so as to form the stabilized trimeric complex.

5. A composition comprising the purified, modified polypeptide of claim 1 and a pharmaceutically acceptable carrier, excipient, or diluent, and optionally, an adjuvant.

6. A composition comprising the purified, modified polypeptide of claim 2 and a pharmaceutically acceptable carrier, excipient, or diluent, and optionally, an adjuvant.

7. A composition comprising the purified, modified polypeptide of claim 3 and a pharmaceutically acceptable carrier, excipient, or diluent, and optionally, an adjuvant.

8. A trimeric complex which comprises a noncovalent oligomer of three identical purified, modified HIV-1 gp140 envelope polypeptides of claim 1.

9. A trimeric complex which comprises a noncovalent oligomer of three identical purified, modified gp41 ectodomain polypeptides of claim 2.

10. A trimeric complex which comprises a noncovalent oligomer of three identical purified, modified HIV-1 gp140 envelope polypeptides, each gp140 polypeptide comprising a gp120 polypeptide portion and a gp41 ectodomain polypeptide portion derived from the purified, modified gp160 polypeptide of claim 3.

11. A composition comprising the trimeric complex of claim 8, a pharmaceutically acceptable carrier, excipient, or diluent, and optionally, an adjuvant.

12. A composition comprising the trimeric complex of claim 9, a pharmaceutically acceptable carrier, excipient, or diluent, and optionally, an adjuvant.

13. A composition comprising the trimeric complex of claim 10, a pharmaceutically acceptable carrier, excipient, or diluent, and optionally, an adjuvant.

14. The composition of claim 11, further comprising a non-ionic detergent.

15. The composition of claim 12, further comprising a non-ionic detergent.

16. The composition of claim 13, further comprising a non-ionic detergent.

17. The purified, modified HIV-1 gp140 envelope polypeptide of claim 1, wherein the gp41 ectodomain polypeptide portion further comprises a proline (P) at an amino acid position equivalent to amino acid position 559, numbered by reference to the KNH1144 HIV-1 isolate.

18. The purified, modified HIV-1 gp140 envelope polypeptide of claim 1, wherein the gp120 or gp41 ectodomain is derived from a HIV-1 isolate of clade A, B, C, D, E, F, G, H, J or O.

19. The purified, modified HIV-1 gp140 envelope polypeptide of claim 1, wherein the HIV-1 isolate is an HIV-1$_{JR-FL}$, HIV-1$_{Ba-L}$, HIV-1$_{5768}$, HIV-1$_{DH123}$, HIV-1$_{GUN-1}$, HIV-1$_{89.6}$, or HIV-1$_{HXB2}$ isolate.

20. The purified, modified gp140 envelope polypeptide of claim 1, wherein (1) the gp120 polypeptide portion is modified to comprise a cysteine (C) residue at an amino acid position equivalent to amino acid position 492, numbered by reference to the JR-FL HIV isolate, and (2) the gp41 ectodomain polypeptide portion is modified to comprise a cysteine (C) residue at an amino acid position equivalent to amino acid position 596, numbered by reference to the JR-FL HIV-1 isolate.

21. The purified, modified HIV-1 gp140 envelope polypeptide of claim 20, wherein the gp41 ectodomain polypeptide portion further comprises a proline (P) at an amino acid position equivalent to amino acid position 559, numbered by reference to the KNH1144 HIV-1 isolate.

* * * * *